(12) United States Patent
Tang

(10) Patent No.: US 8,529,981 B2
(45) Date of Patent: Sep. 10, 2013

(54) PROTEIN CONCENTRATES AND ISOLATES, AND PROCESSES FOR THE PRODUCTION THEREOF

(75) Inventor: Qingnong Nelson Tang, Saskatoon (CA)

(73) Assignee: Bioexx Specialty Proteins Ltd., Toronto, Ontario (CA)

( * ) Notice: Subject to any disclaimer, the term of this patent is extended or adjusted under 35 U.S.C. 154(b) by 579 days.

(21) Appl. No.: 12/467,227

(22) Filed: May 15, 2009

(65) Prior Publication Data
US 2009/0286961 A1 Nov. 19, 2009

Related U.S. Application Data

(60) Provisional application No. 61/053,858, filed on May 16, 2008, provisional application No. 61/099,783, filed on Sep. 24, 2008.

(51) Int. Cl.
*A23J 1/00* (2006.01)
(52) U.S. Cl.
USPC ............................ 426/656; 530/377; 530/422
(58) Field of Classification Search
USPC ........................................ 426/656; 530/377
See application file for complete search history.

(56) References Cited

U.S. PATENT DOCUMENTS

| | | | |
|---|---|---|---|
| 4,079,048 A | 3/1978 | Chao | |
| 4,889,921 A | 12/1989 | Diosady et al. | |
| 5,844,096 A | 12/1998 | Hinrichs et al. | |
| 6,005,076 A | 12/1999 | Murray | |
| 6,132,795 A | 10/2000 | Holbrook et al. | |
| 6,231,895 B1 * | 5/2001 | Emanuele et al. | 426/2 |
| 6,800,308 B2 | 10/2004 | Maenz et al. | |
| 6,905,713 B2 | 6/2005 | Diosady et al. | |
| 6,992,173 B2 | 1/2006 | Milanova et al. | |
| 7,001,990 B2 | 2/2006 | Hiron et al. | |
| 7,087,720 B2 | 8/2006 | Murray et al. | |
| 7,090,887 B2 | 8/2006 | Newkirk et al. | |
| 7,211,286 B2 | 5/2007 | Hiron | |

(Continued)

FOREIGN PATENT DOCUMENTS

| | | |
|---|---|---|
| CA | 2450388 | 5/2004 |
| WO | WO02/089598 | 11/2002 |
| WO | WO03/075673 | 9/2003 |
| WO | 2008/024840 | 2/2008 |

OTHER PUBLICATIONS

Vioque et al., "Production and Characterization of an Extensive Rapeseed Protein Hydrolysate," Journal of the American Oil Chemists' Society, vol. 76, No. 7 (1999) 819-23.*

(Continued)

*Primary Examiner* — Humera Sheikh
*Assistant Examiner* — Jeffrey Mornhinweg
(74) *Attorney, Agent, or Firm* — Koppel, Patrick, Heybl & Philpott; Michael J. Ram

(57) ABSTRACT

Protein concentrates and protein isolates, in addition to processes for the production of protein concentrates and protein isolates, are disclosed. In particular, the disclosure relates to a process for removing fiber from an oilseed meal, comprising:
i) mixing an oilseed meal with a blending solvent, optionally water, saline solution, polysaccharide solution or protein containing solution, to form a mixture;
ii) optionally adjusting the pH of the protein slurry to a pH of about 2 to about 10; and
iii) separating the mixture to form a protein slurry comprising soluble and insoluble proteins and an insoluble fiber fraction.

20 Claims, 39 Drawing Sheets

(56) References Cited

U.S. PATENT DOCUMENTS

| | | |
|---|---|---|
| 7,211,288 B2 | 5/2007 | Hiron |
| 7,309,773 B2 | 12/2007 | Green et al. |
| 2003/0021884 A1 | 1/2003 | Murray |
| 2003/0109679 A1 | 6/2003 | Green et al. |
| 2003/0124241 A1 | 7/2003 | Westdal |
| 2003/0125526 A1 | 7/2003 | Barker et al. |
| 2004/0005395 A1 | 1/2004 | Hiron et al. |
| 2004/0034200 A1 | 2/2004 | Logie et al. |
| 2004/0039174 A1 | 2/2004 | Barker et al. |
| 2004/0077838 A1 | 4/2004 | Green et al. |
| 2004/0197378 A1 | 10/2004 | Murray |
| 2004/0254353 A1 | 12/2004 | Barker et al. |
| 2005/0031767 A1 | 2/2005 | Schweizer et al. |
| 2005/0042715 A1 | 2/2005 | Murrah et al. |
| 2005/0064086 A1 | 3/2005 | Hiron et al. |
| 2005/0107593 A1 | 5/2005 | Green et al. |
| 2005/0165220 A1 | 7/2005 | Barker et al. |
| 2005/0181112 A1 | 8/2005 | Schweizer et al. |
| 2005/0208021 A1 | 9/2005 | Calos |
| 2005/0226909 A1 | 10/2005 | Westdal |
| 2005/0249828 A1 | 11/2005 | Logie et al. |
| 2005/0249866 A1 | 11/2005 | Murray |
| 2005/0255226 A1 | 11/2005 | Schweizer et al. |
| 2005/0283001 A1 | 12/2005 | Schweizer et al. |
| 2006/0035003 A1 | 2/2006 | McMindes et al. |
| 2006/0073250 A1 | 4/2006 | Mozaffar et al. |
| 2006/0121171 A1 | 6/2006 | Schweizer et al. |
| 2006/0128020 A1 | 6/2006 | Calos |
| 2006/0193965 A1 | 8/2006 | Newkirk et al. |
| 2006/0205929 A1 | 9/2006 | Milanova et al. |
| 2006/0217318 A1 | 9/2006 | Wu |
| 2006/0281904 A1 | 12/2006 | Green |
| 2006/0286281 A1 | 12/2006 | Hiron et al. |
| 2007/0004908 A1 | 1/2007 | Gosnell et al. |
| 2007/0015910 A1 | 1/2007 | Barker et al. |
| 2007/0065567 A1 | 3/2007 | Segall et al. |
| 2007/0098876 A1 | 5/2007 | Hiron |
| 2007/0178566 A1 | 8/2007 | Schweizer et al. |
| 2007/0191593 A1 | 8/2007 | Green et al. |
| 2007/0237877 A1 | 10/2007 | Diosady et al. |
| 2007/0244300 A1 | 10/2007 | Schweizer et al. |
| 2007/0269583 A1 | 11/2007 | McMindes et al. |
| 2008/0125577 A1 | 5/2008 | Gosnell et al. |
| 2008/0166469 A1 | 7/2008 | Schweizer et al. |
| 2008/0299282 A1 | 12/2008 | Schweizer et al. |
| 2008/0319171 A1 | 12/2008 | Barker et al. |
| 2009/0036655 A1 | 2/2009 | Segall et al. |
| 2009/0076252 A1 | 3/2009 | Barker et al. |
| 2009/0081355 A1 | 3/2009 | Murray |
| 2009/0175999 A1 | 7/2009 | Segall et al. |
| 2009/0203880 A1 | 8/2009 | Gosnell et al. |
| 2010/0249378 A1* | 9/2010 | Wanasundara et al. ........ 530/377 |

OTHER PUBLICATIONS

Aider, M. and Barbana, C., "Canola proteins; composition, extraction, functional properties, bioactivity, applications as a food ingredient and allergenicity—A practical and critical review," Trends in Food Science & Technology, 22 (2011) 21-39.*

Bérot et al., "Large scale purification of rapeseed proteins (*Brassica napus* L.)," Journal of Chromatography B, 818 (2005) 35-42.*

Altenbach, S. B., Kuo, C., Staraci, L. C., Pearson, K. W., Wainwright, C., Georgescu, A., and Townsend, J., "Accumulation of a Brazil nut albumin in seeds of transgenic canola results in enhanced levels of seed protein methionine," Plant Molecular Biology 18: 235-245, 1992.*

Tzeng, Y-M. Diosady, L. L., and Rubin, L. J., "Preparation of Rapeseed Protein Isolates Using Ultrafiltration, Precipitation and Diafiltration," Can. Inst. Food Sci. Technol. J., vol. 21, No. 4, pp. 419-424, 1988.*

International Search Report and Written Opinion, International Application No. PCT/CA2009/000668, issued Sep. 30, 2009.

Folawiyo, Y.L. and Apenten, R.K.O., Effect of pH and Ionic Strength on the Heat Stability of Rapeseed 12S Globulin (Cruciferin) by the ANS Fluorescence Method, Journal of Science Food Agric., 1996, pp. 241-246, vol. 70.

McCurdy, S.M. and March, B.E., "Processing of Canola Meal for Incorporation in Trout and Salmon Diets", Jaocs, 1992, pp. 213-220, vol. 69, No. 3.

European Patent Office, Supplementary Search Report, Application No. EP09745349, dated Sep. 13, 2011.

Yoshie-Stark et al., "Chemical Composition, Functional Properties, and Bioactivities of Rapeseed Protein Isolates", Food Chemistry, Elsevier Ltd. NL, vol. 107, No. 1, Oct. 30, 2007, p. 32-39.

Murray, D., "Rapeseed: A Potential Global Source of High Quality Plant Protein", Asia Pacific Food Industry, AP Trade Publications, Singapore, SG, Apr. 1, 2011, p. 30-34.

Vioque, Javier et al., "Partially Hydrolyzed Rapeseed Protein Isolates With Improved Functional Properties", Journal of the American Oil Chemists' Society, vol. 77, No. 4, Apr. 1, 2000, p. 447-450.

Moure, Andres et al., "Functionality of Oilseed Protein Products: A Review", Food Research International, Elsevier Applied Science, Barking, GB, vol. 39, No. 9, Nov. 1, 2006, p. 945-963.

* cited by examiner

PROTEIN CONCENTRATES AND ISOLATES, AND PROCESSES FOR THE PRODUCTION THEREOF

PRIORITY INFORMATION

This application claims the benefit of U.S. Provisional Application Nos. 61/053,858 and 61/099,783 filed on May 16, 2008 and Sep. 24, 2008, respectively, and entitled PROCESS FOR THE PRODUCTION OF PROTEIN CONCENTRATES AND PROTEIN ISOLATES, the contents of which of which are expressly incorporated herein by reference.

FIELD OF THE DISCLOSURE

The present disclosure relates to protein concentrates and protein isolates as well as processes for their production. In particular, the disclosure relates to a process for removing fiber from an oilseed meal to produce edible protein products.

BACKGROUND

Oilseeds typically contain from about 20 percent oil to about 50 percent oil by weight, with the percentages varying with the type of oilseed. Generally, the seed is pressed, with or without a prior heat treatment step, to obtain a pressed oil and a pressed seedcake. Generally, the pressed seedcake is then solvent extracted to remove or reduce the remaining oil. After removal of the solvent from the pressed seedcake and drying of the seedcake, there generally remains a defatted meal, which contains from about 25% to about 55% of protein on a dry weight basis.

Some defatted meals, depending upon the oilseed, contain a high amount of fiber, as well as other antinutritional factors and undesirable compounds, such as glucosinolates, phytic acid or phytates, sinapine and sinigrin. The fiber and antinutritional factors present in the protein render the defatted meal unattractive for commercial uses.

In the case of canola defatted meal, one method of separating the protein from the fiber, antinutritional factors and other undesirable compounds has been to dissolve the canola protein in a high ionic strength (i.e. high salt content) aqueous solution. This results in the canola protein dissolving in the aqueous solution, while the fiber is insoluble. However, the salt is difficult and uneconomical to remove from the resultant canola protein solution. There remains a need for processes to remove fiber that do not affect protein quality.

SUMMARY OF THE DISCLOSURE

Herein, a process for the production of protein concentrates and protein isolates is disclosed. In addition, protein concentrates and protein isolates produced in accordance with the processes of the disclosure are also disclosed. In particular, the disclosure relates to a process for the facile removal of fiber, antinutritional factors and other constituents from an oilseed meal containing such, to produce protein concentrates and protein isolates of high quality.

In an embodiment of processes of the present disclosure, an oilseed is heat treated to a temperature of about 60° C. to about 120° C., optionally about 70° C. to about 100° C., or about 80° C. to about 90° C., or about 80° C.

In another embodiment of the present disclosure, a process for the production of a protein concentrate possessing a protein content of about 70% to about 75% is disclosed.

Accordingly, the disclosure includes a process for the production of a protein concentrate from a defatted or a protein-enriched meal, comprising:

1) removing fiber from the defatted or protein-enriched meal, comprising either:
   i) mixing the defatted meal or protein-enriched meal with a mixing solvent to form a first mixture; and separating fiber from the mixture, optionally by screening the first mixture to remove the fiber; or
   ii) mixing the defatted or protein-enriched meal with water to form a second mixture; and
      optionally adjusting the pH of the second mixture to a pH suitable for enzyme activity, optionally about 3 to about 7, optionally 4 to 6; and
      adding cellulase complex or other enzyme having fiber hydrolysis activity to the second mixture and heating to a temperature suitable for enzyme activity, to hydrolyze the fiber;
2) washing the first or second mixture with an extraction solvent to form an extract and a washed defatted or protein-enriched meal;
3) separating the extract from the washed defatted or protein-enriched meal;
4) optionally repeating steps 2) and 3) at least once; and
5) optionally desolventizing the washed defatted or protein-enriched meal to form a protein concentrate.

In another embodiment, the defatted or protein-enriched meal comprises a canola, rapeseed, mustard seed, broccoli seed, flax seed, cotton seed, hemp seed, safflower seed, sesame seed or soybean meal. In a further embodiment, the protein-enriched meal comprises a canola meal. In an embodiment, the protein-enriched meal comprises a soybean meal. In another embodiment, the protein-enriched meal comprises mustard seed meal. In a further embodiment, the protein-enriched meal comprises flax seed meal.

In another embodiment, the mixing solvent comprises water, methanol, ethanol or isopropanol, and mixtures thereof. In a further embodiment, the solvent is water or ethanol, and mixtures thereof. In an embodiment of the disclosure, the defatted or protein-enriched meal is mixed with a mixing solvent in a ratio of about 3 to about 10 parts solvent to about 1 part of the defatted or protein-enriched meal, optionally about 4 to about 8, or about 4 to about 6, on a weight-to-weight basis.

In another embodiment of the disclosure, the size of the mesh screen is about 10 to about 200 US mesh screen, optionally about 20 to about 200 US mesh screen. In a further embodiment, the mesh screen is a vibratory screen.

In an embodiment of the present disclosure, the defatted or protein-enriched meal is mixed thoroughly with water to form the second mixture. In an embodiment, the mixing of water and the defatted or protein-enriched meal comprises using a wet mill or an inline mixer.

In another embodiment of the present disclosure, the cellulase complex is added to the second mixture in an amount of about 1 gram to about 10 grams for about every 1 kg of dry solids of the defatted or protein-enriched meal (about 0.1% to about 1%). In a further embodiment, the cellulase complex is mixed with the second mixture for about 0.5 hours to about 5 hours. In another embodiment, the cellulase complex is mixed with the second mixture for about 1 to about 3 hours.

In another embodiment of the disclosure, the second mixture with the added cellulase complex is heated to a temperature of about 30° C. to about 60° C., suitably about 40° C. to about 60° C.

In an embodiment, the cellulase complex comprises at least one of endocellulase, exocellulase, cellobiohydrolase, cellobiase, endohemicellulase and exohemicellulase.

In an embodiment of the disclosure, the extraction solvent comprises methanol, ethanol or isopropanol, and mixtures thereof. In a further embodiment, the extraction solvent comprises ethanol or water, and mixtures thereof.

In an embodiment of the present disclosure, the first or second mixture is washed at least once with about 5% to about 100%, optionally about 25% to about 85%, or about 50% to about 85%, or about 60% to about 85%, of the extraction solvent (v/v) in water.

In an embodiment of the present disclosure, the ratio of the extraction solvent to the first or second mixture is about 5% to about 95%, optionally about 10% to about 90%, about 20% to about 70%, or about 40% to about 80% (v/v) (extraction solvent to first or second mixture).

In an embodiment of the present disclosure, the first or second mixture is washed with the extraction solvent at a temperature of about 10° C. to about 90° C. In another embodiment, the first or second mixture is washed with the extraction solvent at a temperature of about 20° C. to about 60° C. In a further embodiment, the first or second mixture is washed with the extraction solvent at a temperature of about 20° C. to about 25° C.

In another embodiment of the present disclosure, the extract is separated from the washed defatted or protein-enriched meal by centrifugation, vacuum filtration, pressure filtration, decantation or gravity draining in an extractor.

In another embodiment of the present disclosure, steps 2) and 3) are repeated at least twice.

In another embodiment of the present disclosure, the process further comprises the step of drying the washed defatted or protein-enriched meal to form the protein concentrate. In a further embodiment, the washed defatted or protein-enriched meal is dried in a vacuum dryer, fluidized bed dryer, ring dryer or spray dryer. In another embodiment, the washed defatted or protein-enriched meal is dried to a moisture content of about 0.5% to about 12%, optionally about 1% to about 10%, about 4% to about 8%. In a further embodiment, the washed defatted or protein-enriched meal is dried to a moisture content of about 6%.

In another embodiment of the present disclosure, the extract is desolventized and dried to form a high sugar fraction. In an embodiment, the extract is desolventized by spray drying, drum drying or vacuum drying.

In an embodiment of the present disclosure, a process for the production of a protein concentrate possessing a protein content of about 75% to about 90% is disclosed.

Accordingly, the disclosure includes a process for the production of a protein concentrate from a defatted or protein-enriched meal, comprising:

removing fiber from the defatted or protein-enriched meal, comprising:
i) mixing the defatted or protein-enriched meal with a mixing solvent to form a mixture;
   separating fiber from the mixture, optionally by screening the mixture to remove fiber,
   optionally adjusting the pH of the mixture to a pH of about 4.5 to about 8.0, optionally about 6.5 to about 7.5, or optionally about 7;
   optionally milling the mixture;
   separating fiber, optionally by centrifuging the mixture, to remove fiber,
   thereby forming a protein slurry; and
ii) separating the protein slurry, optionally by centrifuging the protein slurry, to form a protein precipitate and a soluble protein fraction;
iii) washing the protein precipitate with an extraction solvent at least once and separating, optionally by centrifuging, to form a purified protein precipitate;
iv) optionally drying the purified protein precipitate to form the protein concentrate.

In another embodiment, the defatted or protein-enriched meal comprises a canola, rapeseed, mustard seed, broccoli seed, flax seed, cotton seed, hemp seed, safflower seed, sesame seed or soybean meal. In a further embodiment, the protein-enriched meal comprises a canola meal. In an embodiment, the protein-enriched meal comprises a soybean meal. In another embodiment, the protein-enriched meal comprises mustard seed meal. In a further embodiment, the protein-enriched meal comprises flax seed meal.

In another embodiment of the disclosure, the mixing solvent comprises water, methanol, ethanol, or isopropanol, and mixtures thereof. In a further embodiment, the mixing solvent comprises water or ethanol, and mixtures thereof. In another embodiment, the ratio of defatted or protein-enriched meal to the mixing solvent is about 1:3 to about 1:20. In a further embodiment, the ratio is about 1:6 to about 1:10. In an embodiment, the ratio is about 1:6 to about 1:8.

In another embodiment of the disclosure, the mixture is screened through a mesh screen of typically about 10 to about 200 US mesh size, optionally a mesh screen of about 20 to about 200 US mesh size. In another embodiment, the mesh size is 40 US mesh size.

In another embodiment of the present disclosure, the pH of mixture is adjusted with aqueous sodium hydroxide. In an embodiment, the aqueous sodium hydroxide has a concentration of about 1% to about 40% by weight of sodium hydroxide. In a further embodiment, the concentration of sodium hydroxide is about 5% to about 30% sodium hydroxide.

In another embodiment, the optional milling step comprises using a wet mill.

In an embodiment, the mixture is centrifuged using a decanting centrifuge. In an embodiment, the mixture is centrifuged with a decanting centrifuge at a speed of about 500 rpm to about 6000 rpm. In another embodiment, the speed is about 1500 rpm.

In an embodiment of the disclosure, the protein slurry is centrifuged using a decanter or disc stack centrifuge. In a further embodiment, the protein slurry is centrifuged at a speed of about 2500 rpm to about 8500 rpm.

In another embodiment of the disclosure, the extraction solvent is water, methanol, ethanol or isopropanol, and mixtures thereof. In a further embodiment, the extraction solvent is water or ethanol, and mixtures thereof. In an embodiment, the extraction solvent is water. In an embodiment, the protein precipitate is washed at least twice with the extraction solvent.

In an embodiment of the present disclosure, the washed protein precipitate is centrifuged with a disc stack centrifuge at a speed of about 7500 rpm to about 8500 rpm.

In an embodiment of the disclosure, the purified protein precipitate is dried in a vacuum dryer, fluidized bed dryer, ring dryer or spray dryer to form the protein concentrate. In a further embodiment, the protein concentrate is dried to a moisture content of about 1% to about 10%. In another embodiment, the protein concentrate is dried to a moisture content of about 6%.

In another embodiment of the present disclosure, a process for the production of a protein isolate possessing a protein content of greater than about 90% is disclosed.

Accordingly, the disclosure includes a process for the production of a protein isolate from a defatted or protein-enriched meal, comprising:

removing fiber from the defatted or protein-enriched meal, comprising:
i) mixing the defatted or protein-enriched meal with a mixing solvent to form a mixture;
separating fiber from the mixture to remove fiber, optionally adjusting the pH of the mixture to a pH of about 6.0 to about 8.0, optionally about 6.5 to about 7.5, or optionally about 7;
optionally milling the mixture;
separating fiber, optionally by centrifuging the mixture, to remove fiber,
thereby forming a protein slurry;
ii) separating the protein slurry, optionally by centrifuging the protein slurry, to form a protein precipitate and a soluble protein fraction;
iii) filtering the soluble protein fraction to separate it from protein precipitate; and
iv) optionally drying the soluble protein to form the protein isolate.

In another embodiment, the defatted or protein-enriched meal comprises a canola, rapeseed, mustard seed, broccoli seed, flax seed, cotton seed, hemp seed, safflower seed, sesame seed or soybean meal. In a further embodiment, the protein-enriched meal comprises a canola meal. In an embodiment, the protein-enriched meal comprises a soybean meal. In another embodiment, the protein-enriched meal comprises mustard seed meal. In a further embodiment, the protein-enriched meal comprises flax seed meal.

In another embodiment of the disclosure, the mixing solvent comprises water or a salt solution. In an embodiment, the salt solution comprises less than 5%, optionally about 3% to about 4%, or 3.5% by weight of salt in solution. In a further embodiment, the mixing solvent comprises water. In another embodiment, the ratio of defatted or protein-enriched meal to the mixing solvent is about 1:3 to about 1:20. In a further embodiment, the ratio is about 1:6 to about 1:10. In an embodiment, the ratio is about 1:6 to about 1:8.

In another embodiment of the present disclosure, the pH of mixture is adjusted with aqueous sodium hydroxide. In an embodiment, the aqueous sodium hydroxide has a concentration of about 1% to about 40% by weight of sodium hydroxide. In a further embodiment, the concentration of sodium hydroxide is about 5% to about 30% sodium hydroxide.

In another embodiment of the disclosure, the mixture is screened through a mesh screen of about 10 to about 200 US mesh size, optionally a mesh screen of about 20 to about 200 US mesh size. In an embodiment, the mesh size is 40 US mesh size.

In an embodiment, the mixture is centrifuged using a decanting centrifuge. In an embodiment, the mixture is centrifuged with a decanting centrifuge at a speed of about 500 rpm to about 6000 rpm. In another embodiment, the speed is about 1500 rpm.

In another embodiment, the optional milling step comprises using a wet mill.

In an embodiment of the disclosure, the protein slurry is centrifuged using a disc stack centrifuge. In a further embodiment, the protein slurry is centrifuged at a speed of about 6500 rpm to about 8500 rpm.

In another embodiment of the disclosure, the soluble protein fraction is filtered using an ultrafiltration or diafiltration apparatus. In a further embodiment, the ultrafiltration or diafiltration apparatus comprises a membrane to filter proteins of larger than about 1,000 daltons, optionally 10,000 daltons, optionally about 30,000 daltons, or about 100,000 daltons. In another embodiment, the ultrafiltration or diafiltration is performed at a temperature of about 1° C. to about 60° C., optionally about 40° C. to about 55° C.

In another embodiment of the disclosure, the soluble protein is dried in a vacuum dryer, fluidized bed dryer, ring dryer or spray dryer to form the protein isolate. In an embodiment, the protein isolate is dried to a moisture content of about 1% to about 10%. In a further embodiment, the protein isolate is dried to a moisture content of about 6%.

In another embodiment of the present disclosure, a process for the production of a protein isolate possessing a protein content of greater than about 90% is disclosed.

Accordingly, the disclosure includes a process for the production of a protein isolate from a defatted or protein-enriched meal, comprising:

removing fiber from the defatted or protein-enriched meal, comprising:
i) mixing the defatted or protein-enriched meal with a mixing solvent to form a mixture;
separating fiber from the mixture to remove fiber, optionally adjusting the pH of the mixture to a pH of about 6.0 to about 8.0, optionally about 6.5 to about 7.5, or optionally about 7;
optionally milling the mixture;
separating fiber, optionally by centrifuging the mixture, to remove fiber,
thereby forming a protein slurry; and
ii) separating the protein slurry, optionally by centrifuging the protein slurry, to form a protein precipitate and a soluble protein fraction;
iii) mixing the protein precipitate with water to form a protein precipitate mixture and optionally adjusting the pH to a pH suitable for enzyme activity, optionally about 3 to about 7, optionally about 4 to about 6;
iv) adding cellulase complex or other enzyme having fiber hydrolysis activity to the protein precipitate mixture to hydrolyze fiber, typically residual fiber;
v) washing the protein precipitate mixture with an extraction solvent at least once and separating, optionally by centrifuging, to form a protein isolate.

In another embodiment, the defatted or protein-enriched meal comprises a canola, rapeseed, mustard seed, broccoli seed, flax seed, cotton seed, hemp seed, safflower seed, sesame seed or soybean meal. In a further embodiment, the protein-enriched meal comprises a canola meal. In an embodiment, the protein-enriched meal comprises a soybean meal. In another embodiment, the protein-enriched meal comprises mustard seed meal. In a further embodiment, the protein-enriched meal comprises flax seed meal.

In another embodiment of the disclosure, the mixing solvent comprises water or a salt solution. In an embodiment, the salt solution comprises less than 5%, optionally about 3% to about 4%, or 3.5% by weight of salt in solution. In a further embodiment, the mixing solvent comprises water. In another embodiment, the ratio of defatted or protein-enriched meal to the mixing solvent is about 1:3 to about 1:20. In a further embodiment, the ratio is about 1:6 to about 1:10. In an embodiment, the ratio is about 1:6 to about 1:8.

In another embodiment of the disclosure, the mixture is screened through a mesh screen of about 10 to about 200 US mesh size, optionally a mesh screen of about 20 to about 200 US mesh size. In another embodiment, the mesh size is 40 US mesh size.

In another embodiment of the present disclosure, the pH of mixture is adjusted with aqueous sodium hydroxide. In an embodiment, the aqueous sodium hydroxide has a concentration of about 1% to about 40% by weight of sodium hydroxide. In a further embodiment, the concentration of sodium hydroxide is about 5% to about 30% sodium hydroxide.

In another embodiment, the optional milling step comprises using a wet mill.

In an embodiment, the mixture is centrifuged using a decanting centrifuge. In an embodiment, the mixture is centrifuged with a decanting centrifuge at a speed of about 500 rpm to about 6000 rpm. In another embodiment, the speed is about 1500 rpm.

In an embodiment of the disclosure, the protein slurry is centrifuged using a disc stack centrifuge. In a further embodiment, the protein slurry is centrifuged at a speed of about 6500 rpm to about 8500 rpm.

In another embodiment of the disclosure, the cellulase complex is added to the protein precipitate mixture in an amount of about 0.1% to about 1% by weight of the protein precipitate mixture. In a further embodiment, the cellulase complex is mixed with the protein precipitate mixture for about 0.5 hours to about 5 hours. In another embodiment, the cellulase complex is mixed with the protein precipitate mixture for about 1 to about 3 hours. In a further embodiment, the cellulase complex comprises at least one of endocellulase, exocellulase, cellobiohydrolase, cellobiase, endohemicellulase and exohemicellulase. In an embodiment, the protein precipitate mixture with cellulase complex is heated to a temperature of about 30° C. to about 60° C. optionally about 40° C. to about 60° C.

In another embodiment of the disclosure, the mixing solvent comprises water. In another embodiment, the ratio of defatted or protein-enriched meal to the mixing solvent is about 1:3 to about 1:20. In a further embodiment, the ratio is about 1:6 to about 1:10. In an embodiment, the ratio is about 1:6 to about 1:8.

In another embodiment of the present disclosure, the protein precipitate mixture is centrifuged using a decanter or disc stack centrifuge. In a further embodiment, the protein precipitate mixture is centrifuged at a speed of about 2500 rpm to about 8500 rpm.

In another embodiment of the present disclosure, the protein isolate is subjected to high pressure jet cooking.

In an embodiment of the present disclosure, the protein isolate is hydrolyzed using proteases to form a hydrolyzed protein extract. In a further embodiment, the proteases comprise Alcalase® (serine endopeptidase, typically from *Bacillus subtilis*), or Flavourzyme® (fungal protease/peptidase complex, typically produced from *Aspergillus oryzae* fermentation), both proteases from Novozymes® North America, Inc. In an embodiment, the ratio of Alcalase® to the protein isolate is about 0.1% to about 1%. In another embodiment, the ratio of Alcalase® to the protein isolate is about 0.5%. In a further embodiment, the ratio of Flavourzyme® to the protein isolate is about 0.1% to about 1%. In an embodiment, the ratio of Flavourzyme® to the protein isolate is about 0.5%.

In another embodiment of the disclosure, there is a provided a process for the production of a protein concentrate from an oilseed meal, comprising:
 i) mixing the partially defatted, fully defatted or protein-enriched meal with a mixing solvent to form a mixture;
 ii) optionally adjusting the pH of the mixture to a pH of about 2.0 to about 10.0;
 iii) separating fiber from the mixture to form a protein slurry, wherein the protein slurry comprises a soluble protein fraction and an insoluble protein fraction;
 iv) optionally repeating steps i)-iii) by mixing the protein slurry with additional partially defatted, fully defatted or protein-enriched meal;
 v) mixing the protein slurry with an extraction solvent to form an extract and a washed insoluble protein fraction;
 vi) separating the extract from the washed insoluble protein fraction;
 vii) optionally repeating steps v) and vi) at least once; and
 viii) optionally desolventizing the washed insoluble protein fraction to form a protein concentrate.

In another embodiment of the disclosure, the ratio of partially defatted, fully defatted or protein-enriched meal to mixing solvent is about 1:3 to about 1:30 (w/w). In another embodiment, the ratio of partially defatted, fully defatted or protein-enriched meal to solvent is about 1:5 to about 1:20 (w/w). In a further embodiment, the ratio is about 1:6 to about 1:12 (w/w). In an embodiment, the ratio is about 1:8 to about 1:10 (w/w).

In a further embodiment of the disclosure, the mixing solvent comprises water or an aqueous solution comprising a polysaccharide, a salt, such as sodium chloride, potassium chloride, or calcium chloride, or an alcohol. In an embodiment, the mixing solvent is water. In another embodiment, the polysaccharide is guar gum.

In an embodiment, the pH of the protein slurry is adjusted to a pH of about 6.5 to about 10.0. In a further embodiment, the pH of the protein slurry is adjusted to a pH of about 7.0 to about 9.0.

In another embodiment of the disclosure, the mixture is separated by centrifugation, gravity sedimentation, a gravity table or hydrocyclone to separate the fiber from the mixture and form the protein slurry. In a further embodiment, the mixture is separated by centrifugation to separate the fiber from the mixture and form the protein slurry. In an embodiment, the mixture is centrifuged at a speed of about 1,000 rpm to about 2,000 rpm. In a further embodiment, the mixture is centrifuged centrifuge at a speed of about 1,400 to about 1,600 rpm. In an embodiment, the mixture is centrifuged using a decanter centrifuge.

In another embodiment of the disclosure, mixing the protein slurry with additional partially defatted, fully defatted or protein-enriched meal is repeated at least once. In a further embodiment, mixing the protein slurry with additional partially defatted, fully defatted or protein-enriched meal is repeated at least two to seven times.

In an embodiment of the disclosure, the extraction solvent comprises water, methanol, ethanol, isopropanol, or mixtures thereof. In an embodiment, the extraction solvent comprises ethanol. In another embodiment, the extraction solvent comprises at least about 50% ethanol. In an embodiment, the extraction solvent comprises at least about 70% ethanol. In a further embodiment, the extraction solvent comprises at least about 90% ethanol.

In a further embodiment, the extract is separated from the washed insoluble protein fraction using centrifugation, vacuum filtration, pressure filtration, decantation or gravity draining. In an embodiment, the extract is separated from the washed insoluble protein fraction using centrifugation.

In another embodiment of the disclosure, wherein steps iv) and v) are repeated at least twice.

In a further embodiment, the process further comprises the step of drying the washed insoluble protein fraction to form the protein concentrate. In an embodiment, the protein concentrate is dried in a vacuum dryer, fluidized bed dryer, hot air dryer ring dryer or spray dryer.

In an embodiment of the disclosure, the partially defatted, fully defatted or protein-enriched meal comprises a canola, rapeseed, mustard seed, broccoli seed, flax seed, cotton seed, hemp seed, safflower seed, sesame seed or soybean meal. In another embodiment, the partially defatted, fully defatted or protein-enriched meal comprises a canola meal.

In an embodiment, the protein concentrate comprises a protein content of about 65% to about 90% on a dry weight basis.

In another embodiment of the disclosure, there is also provided a process for the production of a protein isolate from an oilseed meal, comprising:
  i) mixing the partially defatted, fully defatted or protein-enriched meal with a blending solvent, optionally water or alkaline water, to form a mixture;
  ii) optionally adjusting the pH of the mixture to a pH of about 7.0 to about 10.0;
  iii) separating fiber from the mixture to form a first protein slurry, wherein the first protein slurry comprises a soluble protein fraction and an insoluble protein fraction;
  iv) separating the first protein slurry to form a protein solids fraction and a soluble protein fraction;
  v) optionally mixing the protein solids fraction with a second blending solvent, optionally water, to form a second protein slurry;
  vi) optionally separating the second protein slurry to form a second protein solids fraction and a second soluble protein fraction;
  vii) optionally repeating steps v) and vi) at least once;
  viii) separating the soluble protein fractions to form a clarified soluble protein fraction and a residual insoluble protein fraction;
  ix) optionally adjusting the pH of the clarified soluble protein fraction to a pH of about 6 to about 9;
  x) separating the clarified soluble protein fraction, optionally by filtering the clarified soluble protein fraction by membrane filtration; and
  xi) optionally drying the clarified soluble protein fraction.

In another embodiment of the disclosure, the ratio of partially defatted, fully defatted or protein-enriched meal to water or alkaline water is about 1:4 to about 1:30 (w/w). In another embodiment, the ratio of partially defatted, fully defatted or protein-enriched meal to water or alkaline water is about 1:5 to about 1:20 (w/w). In a further embodiment, the ratio is about 1:6 to about 1:12 (w/w). In an embodiment, the ratio is about 1:8 to about 1:10 (w/w).

In an embodiment of the disclosure, the pH of the alkaline water is about 7 to about 12. In another embodiment, the pH of the first protein slurry is adjusted to about 8.0 to about 9.5. In a further embodiment, the pH of the first protein slurry is adjusted to about 8.5 to about 9.0.

In another embodiment of the disclosure, the mixture is separated by centrifugation, gravity sedimentation, a gravity table or hydrocyclone to separate the fiber from the mixture and form the protein slurry. In a further embodiment, the mixture is separated by centrifugation to separate the fiber from the mixture and form the protein slurry. In an embodiment, the mixture is centrifuged at a speed of about 1,000 rpm to about 2,000 rpm. In a further embodiment, the mixture is centrifuged centrifuge at a speed of about 1,400 to about 1,600 rpm. In an embodiment, the mixture is centrifuged using a decanter centrifuge.

In another embodiment, the first protein slurry is centrifuged, optionally using a disc stack centrifuge, to separate the protein solids fraction from the soluble protein fraction. In a further embodiment, the first protein slurry is centrifuged at a speed of about 4,000 rpm to about 8,000 rpm. In a further embodiment, the first protein slurry is centrifuged at a speed of about 6,500 to about 7,500 rpm.

In another embodiment of the disclosure, the ratio of the protein solids fraction to water is about 1.0:0.5 to about 1.0:3.0 (w/w). In a further embodiment, the ratio of the protein solids fraction to water is about 1.0:1.0 to about 1.0:2.0 (w/w).

In an embodiment, the soluble protein fractions are centrifuged to form the clarified soluble protein fraction and the residual insoluble protein fraction. In an embodiment, the soluble protein fractions are centrifuged using a disc stack centrifuge at a speed of about 7,000 rpm to about 10,000 rpm. In a further embodiment, the soluble protein fractions are centrifuged using a disc stack centrifuge at a speed of about 7,500 rpm to about 8,500 rpm.

In another embodiment of the disclosure, the pH of the clarified soluble protein fraction is adjusted with alkali. In a further embodiment, the pH of the clarified soluble protein fraction is adjusted with sodium hydroxide.

In an embodiment, the clarified soluble protein fraction is filtered using an ultrafiltration apparatus. In a further embodiment, the ultrafiltration apparatus comprises a membrane to filter proteins larger than about 10,000 daltons.

In another embodiment of the disclosure, the process further comprises the step of filtering the clarified soluble protein fraction using a diafiltration apparatus.

In another embodiment, the clarified soluble protein fraction is dried in a vacuum dryer, fluidized bed dryer, ring dryer or spray dryer to form the protein isolate.

In an embodiment of the disclosure, the partially defatted, fully defatted or protein-enriched meal comprises a canola, rapeseed, mustard seed, broccoli seed, flax seed, cotton seed, hemp seed, safflower seed, sesame seed or soybean meal. In another embodiment, the partially defatted, fully defatted or protein-enriched meal comprises a canola meal.

In another embodiment of the disclosure, the protein isolate comprises a protein content of greater than about 90% on a dry weight basis.

In another embodiment of the disclosure, there is also provided a process for the production of a hydrolyzed protein concentrate from an oilseed meal, comprising:
  i) mixing the oilseed meal with a blending solvent, optionally water, to form a first mixture;
  ii) optionally adjusting the pH of the first mixture to a pH of about 6.5 to about 10.0;
  iii) separating the first mixture to remove fiber from the first mixture and form a protein slurry and an insoluble fiber fraction, wherein the protein slurry comprises a soluble protein fraction and an insoluble protein fraction and the insoluble fiber fraction comprises insoluble fiber and a second insoluble protein fraction;
  iv) optionally mixing the insoluble fiber fraction with a second blending solvent, optionally water, to form a washed insoluble fiber fraction and an extract;
  v) separating the washed insoluble fiber fraction from the extract;
  vi) optionally mixing the washed insoluble fiber fraction with a blending solvent, optionally water, to form a second mixture; vii) optionally adjusting the pH of the second mixture to a pH suitable for enzymatic activity;
  viii) mixing the second mixture with at least one protease to form a hydrolyzed protein extract;

ix) separating the hydrolyzed protein extract from the second mixture to form the hydrolyzed protein concentrate and a second insoluble fiber fraction; and x) optionally drying the hydrolyzed protein concentrate.

In another embodiment of the disclosure, the ratio of partially defatted, fully defatted or protein-enriched meal to water is about 1:4 to about 1:30 (w/w). In another embodiment, the ratio of partially defatted, fully defatted or protein-enriched meal to water is about 1:5 to about 1:20 (w/w). In a further embodiment, the ratio is about 1:6 to about 1:12 (w/w). In an embodiment, the ratio is about 1:8 to about 1:10 (w/w).

In another embodiment, the pH of the first mixture is adjusted to about 8.0 to about 9.5. In a further embodiment, the pH of the first mixture is adjusted to about 8.5 to about 9.0.

In another embodiment of the disclosure, the first mixture is separated by centrifugation, gravity sedimentation, a gravity table or hydrocyclone to separate the fiber from the first mixture and form the protein slurry. In a further embodiment, the mixture is separated by centrifugation to separate the fiber from the mixture and form the protein slurry. In an embodiment, the first mixture is centrifuged at a speed of about 1,000 rpm to about 2,000 rpm. In a further embodiment, the first mixture is centrifuged centrifuge at a speed of about 1,400 to about 1,600 rpm. In an embodiment, the mixture is centrifuged using a decanter centrifuge.

In another embodiment, the ratio of the insoluble fiber fraction or washed insoluble fiber fraction to water is about 1.0:0.5 to about 1.0:3.0 (w/w). In a further embodiment, the ratio of the insoluble fiber fraction or washed insoluble fiber fraction to water is about 1.0:1.0 to about 1.0:2.0 (w/w).

In another embodiment, the washed insoluble fiber fraction is centrifuged to separate the washed insoluble fiber fraction from extract. In a further embodiment, the washed insoluble fiber fraction is centrifuged at a speed of about 2,000 rpm to about 6,000 rpm. In a further embodiment, washed insoluble fiber fraction is centrifuged at a speed of about 3,000 to about 5,500 rpm.

In another embodiment of the disclosure, the pH of the second mixture is adjusted to about 8.0 to about 9.0.

In an embodiment of the disclosure, the ratio of the second mixture to the protease is about 100:1 to about 5000:1 (w/w).

In an embodiment of the disclosure, the second mixture is mixed with a protease at a temperature of about 40° C. to about 60° C. In another embodiment, the second mixture is mixed with a protease at a temperature of about 45° C. to about 55° C.

In another embodiment, the at least one protease comprises a protease from *Bacillus Licheniformis*.

In a further embodiment, the process further comprises the step of mixing the second mixture with a second protease.

In an embodiment, the ratio of the second mixture to the second protease is about 250:1 to about 5000:1 (w/w).

In another embodiment, the second mixture is mixed with the second protease at a temperature of about 50° C. to about 70° C. In an embodiment, the second mixture is mixed with the second protease at a temperature of about 55° C. to about 65° C.

In a further embodiment, the second protease comprises a fungal protease/peptidase complex from *Aspergillus oryzae*.

In another embodiment, the hydrolyzed protein concentrate is dried in a vacuum dryer, fluidized bed dryer, ring dryer or spray dryer to form the protein isolate.

In an embodiment of the disclosure, the partially defatted, fully defatted or protein-enriched meal comprises a canola, rapeseed, mustard seed, broccoli seed, flax seed, cotton seed, hemp seed, safflower seed, sesame seed or soybean meal. In another embodiment, the partially defatted, fully defatted or protein-enriched meal comprises a canola meal.

In a further embodiment, the hydrolyzed protein concentrate comprises a protein content of about 65% to about 90% on a dry weight basis.

In another embodiment, the process further comprises mixing the hydrolyzed protein extract with water to form a third mixture. In a further embodiment, the process further comprises filtering the third mixture fraction and the filtering comprises ultrafiltration. In an embodiment, the ultrafiltration comprises contacting the third mixture with an ultrafiltration apparatus that comprises a membrane to filter proteins larger than about 1,000 daltons.

In another embodiment, the process further comprises mixing the second insoluble fiber fraction to form a washed hydrolyzed protein extract and a washed second insoluble fiber fraction and separating the form the washed hydrolyzed protein extract from the washed second insoluble fiber fraction. In another embodiment, the washed hydrolyzed protein extract is combined with the hydrolyzed protein extract.

In an embodiment of the disclosure, there is also provided a process for the production of a protein concentrate from an oilseed meal comprising:

i) mixing the oilseed meal with a blending solvent, optionally water, a saline solution or a polysaccharide solution, to form a mixture;

ii) optionally adjusting the pH of the mixture to a pH of about 2.0 to about 10.0;

iii) separating fiber from the mixture to form a protein slurry, wherein the protein slurry comprises a first soluble protein fraction and an insoluble protein fraction;

iv) optionally repeating steps i)-iii) by mixing the protein slurry with additional oilseed meal;

v) separating the soluble protein fraction from the insoluble protein fraction;

vi) washing the insoluble protein fraction with a second blending solvent, optionally water, saline solution or polysaccharide solution, to form a washed insoluble protein fraction and a second soluble protein fraction;

vii) separating the washed insoluble protein fraction and the second soluble protein fraction;

viii) combining and separating the first and second soluble protein fractions to form a protein concentrate, optionally by filtering the first and second soluble protein fractions to form a protein concentrate or isolate;

ix) combining the washed insoluble protein fraction with the protein concentrate to form a combined protein concentrate or isolate; and x) optionally drying the combined protein concentrate.

In another embodiment of the disclosure, the ratio of partially defatted, fully defatted or protein-enriched meal to water is about 1:3 to about 1:30 (w/w). In another embodiment, the ratio of partially defatted, fully defatted or protein-enriched meal to water is about 1:5 to about 1:20 (w/w). In a further embodiment, the ratio is about 1:6 to about 1:12 (w/w). In an embodiment, the ratio is about 1:8 to about 1:10 (w/w).

In an embodiment, the pH of the mixture is adjusted to a pH of about 6.5 to about 10.0. In another embodiment, the pH of the mixture is adjusted to a pH of about 7.0 to about 9.0.

In another embodiment of the disclosure, the mixture is separated by centrifugation, gravity sedimentation, a gravity table or hydrocyclone to separate the fiber from the mixture and form the protein slurry. In a further embodiment, the mixture is separated by centrifugation to separate the fiber from the mixture and form the protein slurry. In an embodiment, the mixture is centrifuged at a speed of about 1,000 rpm to about 2,000 rpm. In a further embodiment, the mixture is centrifuged at a speed of about 1,400 to about 1,600 rpm. In an embodiment, the mixture is centrifuged using a decanter centrifuge.

In another embodiment, the protein slurry is centrifuged to separate the protein solids fraction from the soluble protein fraction. In an embodiment, the protein slurry is centrifuged at a speed of about 6,000 rpm to about 8,500 rpm in a disc stack centrifuge. In another embodiment, the protein slurry is centrifuged at a speed of about 6,500 to about 7,500 rpm.

In another embodiment, the ratio of the insoluble protein fraction to water is about 1.0:0.5 to about 1.0:3.0 (w/w). In a further embodiment, the ratio of the insoluble protein fraction to water is about 1.0:1.0 to about 1.0:2.0 (w/w).

In another embodiment, the washed insoluble protein fraction and the second soluble protein fraction are separated using a centrifuge. In an embodiment, the washed insoluble protein fraction and the second soluble protein fraction are centrifuged at a speed of about 6,000 rpm to about 8,500 rpm in a disc stack centrifuge. In a further embodiment, the washed insoluble protein fraction and the second soluble protein fraction are centrifuged at a speed of about 6,500 to about 7,500 rpm.

In another embodiment, the first and second soluble protein fractions are filtered using an ultrafiltration apparatus. In a further embodiment, the ultrafiltration apparatus comprises a membrane to filter proteins larger than about 10,000 daltons. In an embodiment, the process further comprises the step of filtering the first and second soluble protein fractions using a diafiltration apparatus.

In another embodiment, the combined protein concentrate is dried in a vacuum dryer, fluidized bed dryer, ring dryer or spray dryer to form the dried protein concentrate.

In an embodiment of the disclosure, the partially defatted, fully defatted or protein-enriched meal comprises a canola, rapeseed, mustard seed, broccoli seed, flax seed, cotton seed, hemp seed, safflower seed, sesame seed or soybean meal. In another embodiment, the partially defatted, fully defatted or protein-enriched meal comprises a canola meal.

In a further embodiment, the protein concentrate comprises a protein content of about 65% to about 90% on a dry weight basis.

In an embodiment of the disclosure, there is also provided a process for the production of a protein isolate from an oilseed meal comprising:
i) mixing the oilseed meal with a blending solvent, optionally water, to form a mixture;
ii) optionally adjusting the pH of the mixture to a pH of about 2.0 to about 10.0;
iii) separating fiber from the mixture to form a protein slurry, wherein the protein slurry comprises a soluble protein fraction and an insoluble protein fraction;
iv) washing the fiber with a second blending solvent, optionally water, to form a washed fiber fraction;
vi) separating the washed fiber fraction to form a second protein slurry and washed fiber solids;
vii) combining and separating the first and second protein slurries to form a protein concentrate, optionally by filtering the first and second soluble protein fractions to form a protein concentrate; and
ix) optionally drying the protein concentrate.

In another embodiment of the disclosure, the ratio of partially defatted, fully defatted or protein-enriched meal to water is about 1:3 to about 1:30 (w/w). In another embodiment, the ratio of partially defatted, fully defatted or protein-enriched meal to water is about 1:5 to about 1:20 (w/w). In a further embodiment, the ratio is about 1:6 to about 1:12 (w/w). In an embodiment, the ratio is about 1:8 to about 1:10 (w/w).

In an embodiment, the pH of the mixture is adjusted to a pH of about 6.5 to about 10.0. In another embodiment, the pH of the mixture is adjusted to a pH of about 7.0 to about 9.0.

In another embodiment of the disclosure, the mixture is separated by centrifugation, gravity sedimentation, a gravity table or hydrocyclone to separate the fiber from the mixture and form the protein slurry. In a further embodiment, the mixture is separated by centrifugation to separate the fiber from the mixture and form the protein slurry. In an embodiment, the mixture is centrifuged at a speed of about 1,000 rpm to about 2,000 rpm. In a further embodiment, the mixture is centrifuged centrifuge at a speed of about 1,400 to about 1,600 rpm. In an embodiment, the mixture is centrifuged using a decanter centrifuge.

In another embodiment, the ratio of the fiber fraction to water is about 1.0:0.5 to about 1.0:3.0 (w/w). In a further embodiment, the ratio of the insoluble protein fraction to water is about 1.0:1.0 to about 1.0:2.0 (w/w).

In another embodiment of the disclosure, the washed fiber fraction is separated by centrifugation, gravity sedimentation, a gravity table or hydrocyclone to separate the fiber solids and form second the protein slurry. In a further embodiment, the washed fiber fraction is separated by centrifugation to separate the fiber and form the second protein slurry. In an embodiment, the mixture is centrifuged at a speed of about 1,000 rpm to about 2,000 rpm. In a further embodiment, the fiber fraction is centrifuged centrifuge at a speed of about 1,400 to about 1,600 rpm. In an embodiment, the fiber fraction is centrifuged using a decanter centrifuge.

In another embodiment, the first and second slurries are filtered using an ultrafiltration/microfiltration apparatus. In a further embodiment, the ultrafiltration/microfiltration apparatus comprises a membrane to filter proteins larger than about 10,000 daltons. In an embodiment, the process further comprises the step of filtering the first and second slurries using a diafiltration apparatus.

In another embodiment, the protein concentrate is dried in a vacuum dryer, fluidized bed dryer, ring dryer or spray dryer to form the dried protein concentrate.

In an embodiment of the disclosure, the partially defatted, fully defatted or protein-enriched meal comprises a canola, rapeseed, mustard seed, broccoli seed, flax seed, cotton seed, hemp seed, safflower seed, sesame seed or soybean meal. In another embodiment, the partially defatted, fully defatted or protein-enriched meal comprises a canola meal.

In a further embodiment, the protein concentrate comprises a protein content of about 65% to about 90% on a dry weight basis.

In another embodiment of the disclosure, there is also provided a process for the removal of fiber from a partially defatted, fully defatted or protein-enriched meal, comprising:
i) mixing an oilseed meal with a blending solvent, optionally water, an aqueous solution or protein containing solution, to form a mixture;
ii) optionally adjusting the pH of the protein slurry to a pH of about 2 to about 10; and
iii) separating the mixture to form a protein slurry comprising soluble and insoluble proteins and an insoluble fiber fraction.

In another embodiment of the disclosure, there is also included protein concentrates and protein isolates, produced in accordance with the processes of the disclosure. Accordingly, in an embodiment of the disclosure, there is provided an oilseed protein isolate having a protein content of at least 90%

(w/w), wherein the canola protein isolate has a solubility of at least 85% (w/w), wherein the solubility is measured at a concentration of about 1% and a pH of about 6.5 to about 7.5 in a borate-phosphate buffer solution. In another embodiment, the oilseed protein isolate has a solubility of at least 95% (w/w) in a borate-phosphate buffer solution. In a further embodiment, the oilseed protein isolate has a solubility of at least 99% (w/w) in a borate-phosphate buffer solution. In a further embodiment, the oilseed protein isolate has a solubility of at least 99.5% (w/w) in a borate-phosphate buffer solution.

In another embodiment of the disclosure, the oilseed protein isolate has a solubility of at least 85% (w/w) at a concentration of about 1% and a pH of about 6.5 to about 7.0 in a borate-phosphate buffer solution. In a further embodiment, the oilseed protein isolate has a solubility of at least 85% (w/w) at a concentration of about 1% and a pH of about 6.7 to about 7.0 in a borate-phosphate buffer solution.

In another embodiment of the disclosure, the oilseed protein isolate has a solubility of at least 85% (w/w) at a concentration of about 1% and a pH of about 6.5 to about 7.0 in a borate-phosphate buffer solution at a temperature of about 35° C. to about 45° C. In another embodiment of the disclosure, the oilseed protein isolate has a solubility of at least 85% (w/w) at a concentration of about 1% and a pH of about 6.5 to about 7.0 in a borate-phosphate buffer solution at a temperature of about 38° C. to about 40° C.

In another embodiment, the oilseed protein isolate comprises,
i) a first class of proteins having a molecular weight of about 60 kDa to about 80 kDa, the first class of proteins comprising about 60% to about 90% (w/w) of the oilseed isolate;
ii) a second class of proteins having a molecular weight of about 10 kDa to about 30 kDa, the second class of proteins comprising about 10% to about 30% (w/w) of the oilseed isolate; and
iii) a third class of proteins having a molecular weight of less than about 10 kDa, the third class of proteins comprising about 2% to about 10% (w/w) of the oilseed isolate.

In another embodiment, the oilseed protein isolate comprises,
i) a first class of proteins having a molecular weight of about 60 kDa to about 80 kDa, the first class of proteins comprising about 60% to about 70% (w/w) of the oilseed isolate;
ii) a second class of proteins having a molecular weight of about 10 kDa to about 30 kDa, the second class of proteins comprising about 20% to about 30% (w/w) of the oilseed isolate; and
iii) a third class of proteins having a molecular weight of less than about 10 kDa, the third class of proteins comprising about 5% to about 10% (w/w) of the oilseed isolate.

In a further embodiment, the oilseed protein isolate comprises
i) a first class of proteins having a molecular weight of about 65 kDa to about 75 kDa, the first class of proteins comprising about 60% to about 90% (w/w) of the oilseed isolate;
ii) a second class of proteins having a molecular weight of about 10 kDa to about 20 kDa, the second class of proteins comprising about 10% to about 30% (w/w) of the oilseed isolate; and
iii) a third class of proteins having a molecular weight of less than about 10 kDa, the third class of proteins comprising about 2% to about 10% (w/w) of the oilseed isolate.

In another embodiment, the oilseed protein isolate comprises
i) a first class of proteins having a molecular weight of about 65 kDa to about 70 kDa, the first class of proteins comprising about 60% to about 70% (w/w) of the oilseed isolate;
ii) a second class of proteins having a molecular weight of about 10 kDa to about 20 kDa, the second class of proteins comprising about 20% to about 30% (w/w) of the oilseed isolate; and
iii) a third class of proteins having a molecular weight of less than about 10 kDa, the third class of proteins comprising about 5% to about 10% (w/w) of the oilseed isolate.

In another embodiment of the disclosure, the oilseed protein isolate comprises a canola, rapeseed, mustard seed, broccoli seed, flax seed, cotton seed, hemp seed, safflower seed, sesame seed or soybean oilseed protein isolate. In another embodiment, the oilseed comprises a canola oilseed.

In another embodiment, the oilseed protein isolate has an antinutritional concentration less than about 0.5% (w/w), optionally less than 0.1%. In a further embodiment, the oilseed protein isolate has a threonine content of at least about 4.1% (w/w) and a valine content of at least about 5.1% (w/w).

In another embodiment of the disclosure, there is also included a oilseed protein hydrolyzate having a protein content of about 65% to about 90% and having a protein dispersibility index of at least 95.0% and wherein a 1.0% solution (w/w) in water of the protein hydrolyzate has a visible light transmittance of least 90.0%. In a further embodiment, the oilseed protein hydrolyzate has a protein dispersibility index of at least 99.0%. In an embodiment, the oilseed protein hydrolyzate has a protein dispersibility index of at least 99.8%.

In another embodiment of the disclosure, a 1.0% solution (w/w) of the protein hydrolyzate has a visible light transmittance of least 95.0%. In a further embodiment, a 1.0% solution (w/w) of the protein hydrolyzate has a visible light transmittance of least 97.0%. In an embodiment, the oilseed protein hydrolyzate contains less than 1% by weight of fiber.

In another embodiment, the oilseed protein hydrolyzate has an antinutritional concentration less than about 0.5% (w/w). In a further embodiment, the oilseed protein hydrolyzate has a threonine content of at least about 4.1% (w/w), a valine content of at least about 5.1% (w/w), a methionine content of at least about 1.7% (w/w) and an isoleucine content of at least about 5.0% (w/w).

In another embodiment of the disclosure, there is also included an oilseed protein concentrate having a protein content of about 65% to about 90%, wherein the protein has a methionine content at least 1.90% by weight and a cysteine content at least 1.60% by weight. In an embodiment, the oilseed protein concentrate has a methionine content at least 1.95% by weight. In an embodiment, the oilseed protein concentrate has a methionine content at least 2.02% by weight. In an embodiment, the oilseed protein concentrate has a cysteine content at least 1.65% by weight. In an embodiment, the oilseed protein concentrate has a cysteine content at least 1.68% % by weight.

In another embodiment, the protein concentrate further has a threonine content of at least 4.0% by weight, a valine content of at least 5.1% (w/w) and a luecine content of at least 8.25% (w/w) of the total protein weight. In another embodiment, the oilseed protein concentrate has an antinutritional concentration less than about 0.5% (w/w), optionally less than 0.1%.

In another embodiment, the protein concentrate has a glucosinolate content of less than about 1 μmol/g of the protein concentrate, and optionally less than about 0.5 μmol/g.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

Embodiments of the invention will be described in relation to the drawings in which.

Figure 1:
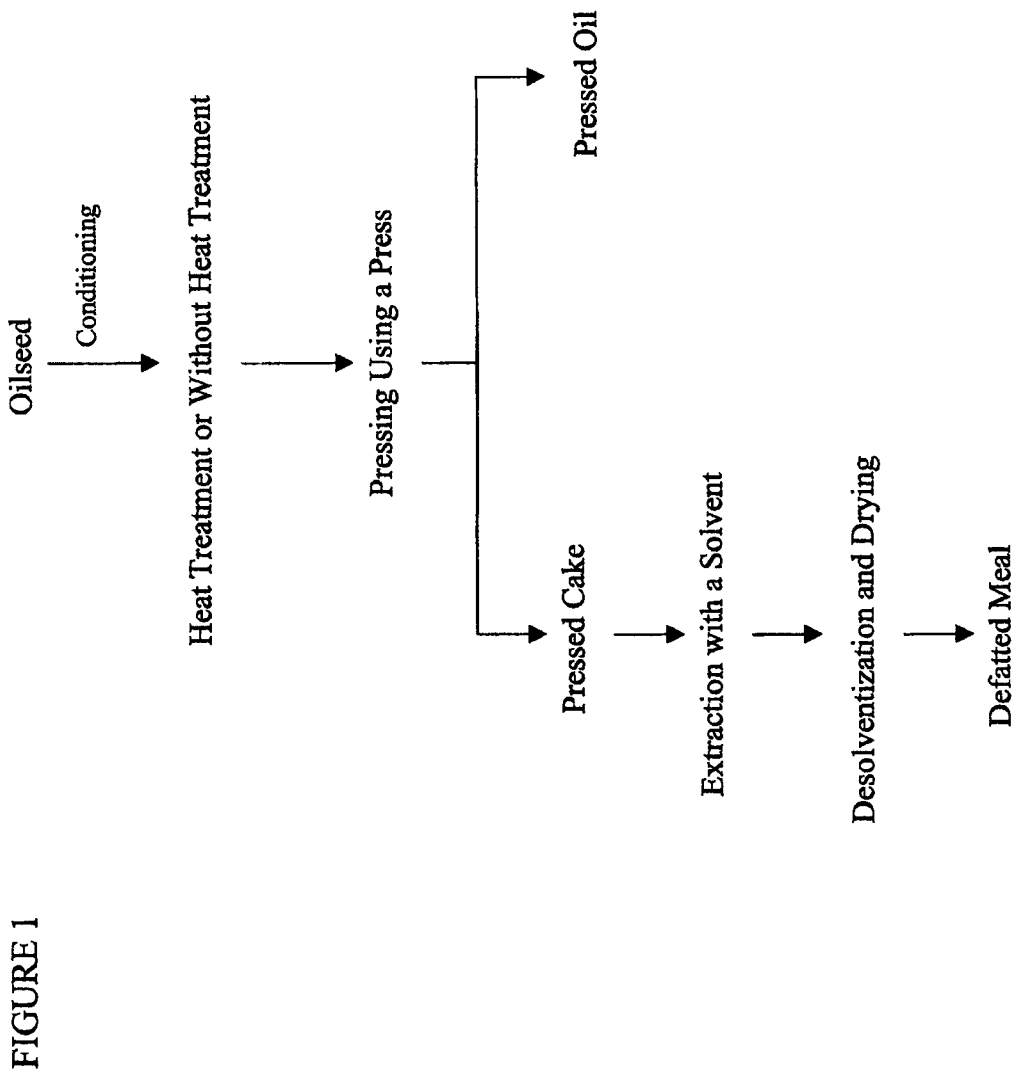
FIG. 1 is a schematic representation showing a preparation of defatted meal of an oilseed.

DETAILED DESCRIPTION OF THE DISCLOSURE (I) Definitions

The term "partially defatted meal" (alternatively called "seedcake" or "presscake") as used herein refers to an oilseed meal in which the oilseed has been pressed to remove the oil contained within. The pressing of the oilseed results in pressed oil and a partially defatted meal, which contains from about 15% to about 50% of protein on a dry weight basis and from about 10% to about 20% oil, optionally about 14% to 16%, on a dry weight basis.

The term "defatted meal" (alternatively called "fully defatted meal") as used herein refers to an oilseed which has been ii) pressed to remove oil, which forms a seedcake and pressed oil, and ii) subjected to solvent extraction, using, for example, hydrophobic and low-boiling solvents, such as butane, pentane, hexane and/or other refrigerants such as iodotrifluoromethane (ITFM) and R134a (1,1,1,2-tetrafluoroethane), to remove or reduce residual oil from the seedcake and form the defatted meal. A defatted meal will typically have a protein content of about 25% to about 55%, optionally 30% to about 50%, suitably about 35% to about 50%, on a dry weight basis, and from about 0% to about 4% oil, optionally about 0.5% to about 4%, optionally about 1% to about 3%, on a dry weight basis.

The term "protein-enriched meal" as used herein refers to a defatted meal as described above, which has subsequently been treated to remove fiber from the defatted meal. Accordingly, the defatted meal is typically subjected to a milling step and a screening step to remove fiber and obtain a protein-enriched meal having a protein content of about 30% to about 60%, optionally 40% to 55%, suitably 50% to 55% on a dry weight basis, and about 5% to about 6.5% fiber, optionally less than about 6%. Collectively, a partially defatted meal, fully defatted meal and a protein-enriched meal may be referred to as "meal".

The term "protein concentrate" as used herein refers to a defatted or protein-enriched meal that has been treated using the processes of the present disclosure to provide an insoluble protein content thereof, when measured at room temperature where the protein concentrate has greater than 65% water insoluble protein content but less than 90% water insoluble protein content on a dry weight basis.

The term "hydrolyzed protein concentrate" as used herein refers to a protein concentrate that has been treated with proteases to hydrolyze the proteins within the protein concentrate into amino acids and smaller peptides.

The term "protein isolate" as used herein refers to a defatted or protein-enriched meal that has been treated using the processes of the present disclosure to provide a soluble protein content thereof, when measured at room temperature where the protein isolate has greater than 90% water soluble protein on a dry weight basis.

The term "hydrolyzed protein isolate" as used herein refers to a protein isolate that has been treated with proteases to hydrolyze the proteins within the protein concentrate into amino acids and smaller peptides.

The term "mixing solvent" as used herein refers to a solvent that forms a protein slurry or mixture when mixed with a partially defatted, fully defatted or protein-enriched meal. In addition, the fiber present in the meal possesses minimal solubility in the mixing solvent (eg. typically less than 1% (w/w) solubility, or about 0% solubility), and suitably, is not soluble in the mixing solvent. Examples of mixing solvents include, but are not limited to, water, alcohols, such as methanol, ethanol or isopropanol, polysaccharide solutions such as guar gum solution, saline solutions, or mixtures of any of the above.

The term "blending solvent" as used herein refers to any aqueous solvent (typically at least: 80%, 85%, 90%, 95%, 98% or 99% water by weight) that forms a slurry or mixture when mixed with a partially defatted, fully defatted or protein-enriched meal. Typically the blending solvent is free from organic solvents, such as methanol, ethanol, propanol, iso-propanol, tetrahydrofuran since these solvents are not desirable as residues in a protein isolate, concentrate or hydrosylate for human consumption, however, if organic solvents are present, they are in the blending solvent in small amount (eg. typically equal to or less than: 20%, 10%, 10%, 5% or 1%) so that their presence in the final product is negligible. Examples of blending solvents include water, acidic water, alkaline water, saline salt solutions (such as sodium chloride, potassium chloride, calcium chloride), polysaccharide solutions (such as guar gum), and aqueous protein solutions.

The invention contemplates using a variety of solvents, which could include blending solvents, mixing solvents or other combinations or alcohols (eg. 80% ethanol), water and/or aqueous solvents. The use of the term blending solvents should not be construed as precluding the use of organic solvents in processes as disclosed herein.

The term "extraction solvent" as used herein refers to a solvent which is capable of solubilizing antinutritional compounds, or other constituents, that are present in the oilseed and which are desirably removed. Examples of antinutritionals include, but are not limited to, glucosinolates, phytic acid, phytates and other compounds that reduce the nutritional or commercial value of the protein concentrate or protein isolate. Antinutritional compounds are compounds that are, for example, not digestible by mammals (e.g humans), have adverse effects, such as toxicity or are bitter tasting, and are desirably removed from the protein product. Accordingly, the concentration of antinutritionals in a protein product produced in accordance with a process of the present disclosure is less than about 1% (w/w), optionally less than about 0.5% (w/w), optionally less than about 0.1% (w/w), and optionally less than about 0.05% (w/w). Examples of other compounds include, but are not limited to, materials that undesirably effect the quality, color, taste, odor, appearance or characteristics of the end product. Examples include compounds that cause a darkening or variation in the color, cause a bitter taste or a pungent odor, such as sinapine or sinigrin, or affect the handling or agglomeration of the end product. While the antinutritionals or other components are not desirable in the protein concentrates or isolates they may constitute commercially valuable side products which can have utility as medicinal or industrial ingredients or end products once separated from the protein concentrate or isolate. Examples of extraction solvents include, but are not limited to, water, alcohols, such as methanol, ethanol, isopropanol, or mixtures of any of the above. Other extractions solvents which are useful include tetrahydrofuran (THF), dimethylformamide (DMF), and ethers, such as methyl t-butyl ether. However, it will be known to those skilled in the art that solvents such as THF, DMF or ethers, as a result of their higher toxicity as compared to, for example, ethanol, require lower limits in the protein product.

The term "homogeneous agitation" as used herein refers to the mixing of a protein meal, such as a partially defatted meal, a fully defatted meal or a protein-enriched meal with a solvent to form a homogenous mixture or suspension. Such agitation is accomplished, for example, by mixing the slurry or mixture at a speed of about 30 rpm to about 300 rpm in a standard mixer.

The term "washed" used herein refers to a protein fraction that has been mixed with an extraction solvent, such as ethanol, to remove antinutritional compounds, or other constituents, from the protein fraction.

The term "protein slurry" as used herein refers to protein, for example, the protein in a defatted or protein-enriched meal, that has been mixed with a mixing solvent to form a suspension of protein, and optionally fiber and other antinutritional compounds, in the mixing solvent.

The terms "soluble protein fraction" and "insoluble protein fraction" as used herein refer to specific protein fractions which are either soluble or insoluble, respectively, in a particular solvent, such as a mixing solvent or an extraction solvent.

The term "water" as used herein refers to any source of water, for example, tap water, distilled water or reverse osmosis water.

The term "alkaline water" as used herein refers to water which has a basic pH of greater than about 7.0, optionally about 7.0 to about 12.0. The alkalinity of the water results from the addition of a base to water, for example, an alkali hydroxide such as sodium hydroxide. For example, a solution of sodium hydroxide at a concentration of about 5% to about 15% (w/w), optionally 11%.

The term "suitable for enzymatic activity" as used herein refers to the pH pH of a solution in which (II) Protein Concentrates and Isolates The present disclosure relates to processes for the production of a protein concentrate or a protein isolate from oilseed. A protein concentrate is an isolated protein extract of pressed oilseed, wherein the extract has greater than 65% protein content but less than 90% protein content on a dry weight basis. A protein concentrate has been treated to separate protein in the oilseed from the fiber and other unwanted antinutritional factors. A protein isolate is an isolated protein extract of pressed oilseed, wherein the extract has greater than or equal to 90% protein content on a dry weight basis. Typically, the protein isolate has up to 98%, 99%, 99.5% or 100% protein content on a dry weight basis. Examples of pressed oilseed include seedcake, defatted meal or protein-enriched meal, as explained below. Typically, the non-protein content includes non-protein compounds such as antinutritional substances, fiber, and other components or impurities such as coloring agents.

In an embodiment, the disclosure provides a process for the removal of fiber, antinutritionals and other constituents, that are present within the oilseed. A person skilled in the art would recognize that antinutritionals include glucosinolates, phytic acid, phytates and other compounds that reduce the nutritional or commercial value of the protein concentrate or protein isolate. For example, antinutritional compounds may not be digestible by mammals (e.g humans), have adverse effects, such as toxicity, and are desirably removed from the protein product. Certain antinutritionals have other undesirable properties, such as undesirable organoleptic properties. Examples of such compounds are sinapine, which has a bitter taste, and sinigrin which has a pungent and very bitter flavor. Further, other antinutritional constituent of oilseeds that are typically removed include, but are not limited to, coloring agents and/or other inert compounds. In an embodiment, the constituents which are removed or are reduced to safe or acceptable levels, are undesirable constituents or impurities using the processes of the present disclosure. A person skilled the art would recognize the safe and/or acceptable levels of particular antinutritionals in the final protein product.

The term protein-enriched meal refers to a meal that possesses a protein content of about 30% to about 60%, optionally 30% to 55%, suitably 50% to 55%, on a dry weight basis. Such protein-enriched meals are useful to prepare the concentrates and isolates of the disclosure, which may be further processed.

In another embodiment of the disclosure, there is also included protein concentrates and protein isolates, produced in accordance with the processes of the disclosure. Accordingly, in an embodiment of the disclosure, there is provided an oilseed protein isolate having a protein content of at least 90%, wherein the canola protein isolate has a solubility of at least 85% (w/w) at a concentration of about 1% and a pH of about 6.5 to about 7.5 in a borate-phosphate buffer solution. In another embodiment, the oilseed protein isolate has a solubility of at least 95% (w/w) in a borate-phosphate buffer solution. In a further embodiment, the oilseed protein isolate has a solubility of at least 99% (w/w) in a borate-phosphate buffer solution. In a further embodiment, the oilseed protein isolate has a solubility of at least 99.5% (w/w) in a borate-phosphate buffer solution.

In another embodiment of the disclosure, the oilseed protein isolate has a solubility of at least 85% (w/w) at a concentration of about 1% and a pH of about 6.5 to about 7.0 in a borate-phosphate buffer solution. In a further embodiment, the oilseed protein isolate has a solubility of at least 85% (w/w) at a concentration of about 1% and a pH of about 6.7 to about 7.0 in a borate-phosphate buffer solution.

In another embodiment of the disclosure, the oilseed protein isolate has a solubility of at least 85% (w/w) at a concentration of about 1% and a pH of about 6.5 to about 7.0 in a borate-phosphate buffer solution at a temperature of about 35° C. to about 45° C. In another embodiment of the disclosure, the oilseed protein isolate has a solubility of at least 85% (w/w) at a concentration of about 1% and a pH of about 6.5 to about 7.0 in a borate-phosphate buffer solution at a temperature of about 38° C. to about 40° C.

In another embodiment, the oilseed protein isolate comprises,
i) a first class of proteins having a molecular weight of about 60 kDa to about 80 kDa, the first class of proteins comprising about 60% to about 90% (w/w) of the oilseed isolate;
ii) a second class of proteins having a molecular weight of about 10 kDa to about 30 kDa, the second class of proteins comprising about 10% to about 30% (w/w) of the oilseed isolate; and
iii) a third class of proteins having a molecular weight of less than about 10 kDa, the third class of proteins comprising about 2% to about 10% (w/w) of the oilseed isolate.

In another embodiment, the oilseed protein isolate comprises,
i) a first class of proteins having a molecular weight of about 60 kDa to about 80 kDa, the first class of proteins comprising about 60% to about 70% (w/w) of the oilseed isolate;
ii) a second class of proteins having a molecular weight of about 10 kDa to about 30 kDa, the second class of proteins comprising about 20% to about 30% (w/w) of the oilseed isolate; and
iii) a third class of proteins having a molecular weight of less than about 10 kDa, the third class of proteins comprising about 5% to about 10% (w/w) of the oilseed isolate.

In a further embodiment, the oilseed protein isolate comprises
i) a first class of proteins having a molecular weight of about 65 kDa to about 75 kDa, the first class of proteins comprising about 60% to about 90% (w/w) of the oilseed isolate;
ii) a second class of proteins having a molecular weight of about 10 kDa to about 20 kDa, the second class of proteins comprising about 10% to about 30% (w/w) of the oilseed isolate; and iii) a third class of proteins having a molecular weight of less than about 10 kDa, the third class of proteins comprising about 2% to about 10% (w/w) of the oilseed isolate.

In another embodiment, the oilseed protein isolate comprises
i) a first class of proteins having a molecular weight of about 65 kDa to about 70 kDa, the first class of proteins comprising about 60% to about 70% (w/w) of the oilseed isolate;
ii) a second class of proteins having a molecular weight of about 10 kDa to about 20 kDa, the second class of proteins comprising about 20% to about 30% (w/w) of the oilseed isolate; and
iii) a third class of proteins having a molecular weight of less than about 10 kDa, the third class of proteins comprising about 5% to about 10% (w/w) of the oilseed isolate.

In an embodiment of the disclosure, the protein isolate produced in accordance with a process of the present disclosure contains greater than 90% protein content (w/w) on a dry weight basis, optionally 90% to about 99% (w/w), optionally 90% to about 98% (w/w), and optionally 90% to about 95% (w/w). In another embodiment, a protein isolate produced in accordance with a process of the present disclosure contains less than about 1% (w/w) fiber, optionally less than about 0.5% (w/w) fiber, and optionally less than about 0.1% (w/w) fiber.

In another embodiment of the disclosure, the oilseed protein isolate comprises a canola, rapeseed, mustard seed, broccoli seed, flax seed, cotton seed, hemp seed, safflower seed, sesame seed or soybean oilseed protein isolate. In another embodiment, the oilseed comprises a canola oilseed.

In an embodiment of the disclosure, oilseed protein isolates, such as a canola protein isolate, produced in accordance with the processes of the present disclosure, have excellent emulsifying and foaming properties. For example, with respect to emulsifying capacity, a 0.5% (w/w) canola protein isolate solution possessed a similar emulsifying capacity as compared to a 5% egg yolk solution. Further, the protein isolates of the present disclosure, such as a canola protein isolate, possess excellent foaming capacity. Further, oilseed protein isolates, such as a canola protein isolate, produced in accordance with the processes of the present disclosure, have excellent properties of gel formation and water immobilization, and therefore, act as stabilizers.

In another embodiment of the disclosure, there is also included a oilseed protein hydrolyzate having a protein content of about 65% to about 90% and having a protein dispersibility index of at least 95.0% and wherein a 1.0% solution (w/w) in water of the protein hydrolyzate has a visible light transmittance of least 90.0%. In a further embodiment, the oilseed protein hydrolyzate has a protein dispersibility index of at least 99.0%. In an embodiment, the oilseed protein hydrolyzate has a protein dispersibility index of at least 99.8%.

In another embodiment of the disclosure, a 1.0% solution (w/w) of the protein hydrolyzate has a visible light transmittance of least 95.0%. In a further embodiment, a 1.0% solution (w/w) of the protein hydrolyzate has a visible light transmittance of least 97.0%. In another embodiment, a protein hydrolyzate produced in accordance with a process of the present disclosure contains less than about 1% (w/w) fiber, optionally less than about 0.5% (w/w) fiber, and optionally less than about 0.1% (w/w) fiber.

In another embodiment of the disclosure, there is also included an oilseed protein concentrate having a protein content of about 65% to about 90%, wherein the protein has a methionine content at least 1.90% by weight and a cysteine content at least 1.60% by weight. In an embodiment, the oilseed protein concentrate has a methionine content at least 1.95% by weight. In an embodiment, the oilseed protein concentrate has a methionine content at least 2.02% by weight. In an embodiment, the oilseed protein concentrate has a cysteine content at least 1.65% by weight. In an embodiment, the oilseed protein concentrate has a cysteine content at least 1.68% % by weight.

In another embodiment of the disclosure, a protein concentrate produced in accordance with a process of the present disclosure, contains less than about 5% (w/w) of fiber, optionally about 0.5% to about 5% (w/w).

In an embodiment, the protein concentrate possessing a protein content of about 60% to about 70% produced in accordance with the processes of the present disclosure are utilized as a protein ingredient in aquafeeds for fish, swine and pet foods.

In another embodiment, the protein concentrate possessing a protein content of about 70% to about 75% produced in accordance with the processes of the present disclosure are useful as a protein ingredient for baked food products such as bread, rolls, cake and pastry products (including mixtures for preparing baked food products), cookies, biscuits, crackers, pancakes, pastries, doughnuts, and other pasta products. In addition, this protein concentrate is useful as a protein ingredient in meat products such as baked meat, hot dogs, bologna, analogs, ham and sausages. Further, this protein concentrate is also useful as a protein ingredient in vegetarian foods. It will be understood by a person skilled in the art that this protein concentrate is also useful for other applications where a lower grade of protein concentrate is sufficient, such as in aquafeeds and pet foods as described above.

In another embodiment, the protein concentrate possessing a protein content of about 75% to less than 90% produced in accordance with the processes of the present disclosure is useful as a protein ingredient in breakfast cereals, and baked goods, as well as meat products such as bologna, frankfurters, luncheon loaves and ham. Further, this protein concentrate is useful in candies, confections, desserts, dietary items, Asian foods, soup mixes, gravies and other similar food items. Again, it will be understood by a person skilled in the art that this protein concentrate is also useful for other applications where a lower grade of protein concentrate is sufficient, such as in aquafeeds, pet foods, bakery products and meat products, as described above.

In another embodiment, the protein isolate possessing a protein content of greater than 90% produced in accordance with the processes of the present disclosure is useful as a protein ingredient in nutritional beverages such as protein fortified soft drinks, sports drinks, fruit juices and other high protein drinks. In addition, this protein isolate is useful as a protein ingredient for nutritional supplements, special diet products, and high protein nutritional tablets. In addition, the protein isolate is useful as a protein ingredient in infant formulas, as well as an ingredient in comminuted and emulsified meats, simulated meats, combination meat products and cured or uncured meat products. Further, the protein isolate is useful as a protein ingredient in pasta (eg. macaroni), bread and other bakery products, pancakes, waffles, crackers, donuts, pie crusts, soups, egg replacements, dried milk replacements and dairy analogs. Again, it will be understood by a person skilled in the art that this protein isolate is also useful for other applications where a lower grade of protein is sufficient, such as in aquafeeds, pet foods, and meat products, as described above.

In another embodiment, the hydrolyzed protein isolate possessing a protein content of greater than 90% produced in accordance with the processes of the present disclosure is useful as a protein ingredient in nutritional beverages such as protein fortified soft drinks, sports drinks, fruit juices and other high protein drinks. In addition, the hydrolyzed protein isolate is useful as a cosmetic ingredient. Further, the hydrolyzed protein isolate is useful as a protein ingredient for healthy food applications to improve absorption and digestibility. Again, it will be understood by a person skilled in the art that this hydrolyzed protein isolate is also useful for other applications where a lower grade of protein is sufficient, such as in aquafeeds, pet foods, bakery products and meat products, as described above.

(III) Processes of the Disclosure

Figure 2:
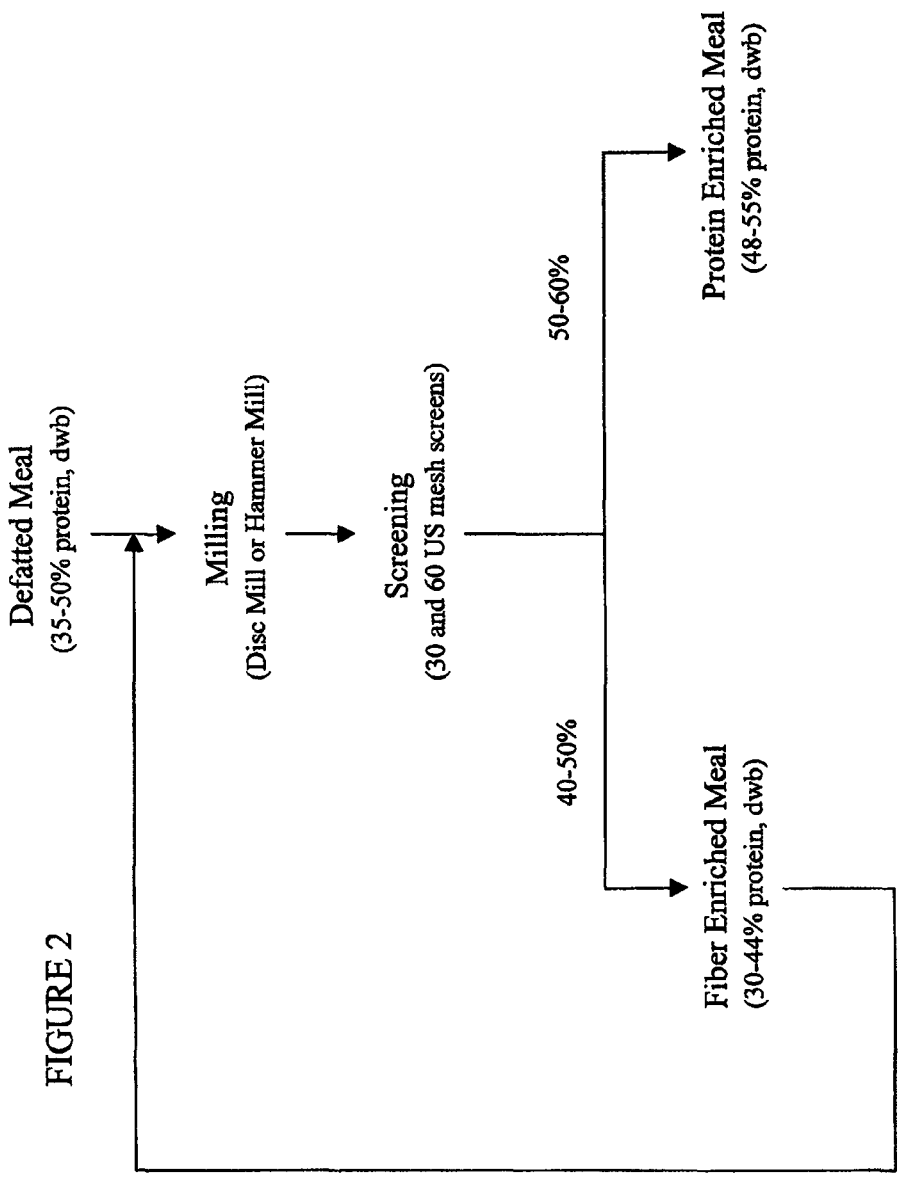
FIG. 2 is a schematic representation showing a preparation of a protein-enriched meal from the defatted meal of an oilseed.

A person skilled in the art would be able to produce a protein-enriched meal using methods that are well known in the art. A general method for obtaining a protein-enriched meal is shown in FIGS. 1 and 2. For example, when beginning with an oilseed, such as canola, rapeseed, mustard seed, broccoli seed, flax seed, cotton seed, hemp seed, safflower seed, sesame seed or soybean meal, in particular canola, the moisture content of the oilseed is adjusted. The moisture adjusted oilseed is optionally exposed to a heat treatment. In an embodiment of the processes of the present disclosure, the oilseed is heat treated to a temperature of about 60° C. to about 120° C., optionally about 70° C. to about 100° C., or about 80° C. to about 90° C., or about 80° C. In another embodiment, the heat treatment is carried out at a temperature of 100° C. The heat treatment of the oilseed results in the inactivation of the enzymes present in the oilseed, for example, myrosinase, lipase, phospholipase. If the oilseed is not heat treated, the enzymes (such as myrosinase, lipase, phospholipase), as a result of their enzymatic action, can degrade the oil and breakdown glucosinolates releasing sulphur into oil. However, a heat treatment can also denature the proteins in the concentrate or isolate. At a temperature of about 75-100° C., the enzymes are deactivated, and are therefore not able to degrade the oil and breakdown glucosinolates releasing sulphur into oil, while the protein within the oilseed is not denatured. The selection of a heat treatment temperature is a compromise between the opposing effects on oil quality, meal quality and economics. Accordingly, in an embodiment, a heat treatment temperature of 75-100° C. results in a reasonably high protein dispersibility index (PDI), lower sulphur, FFA and phosphorus in pressed and butane/R134a extracted oils.

Alternatively, in an embodiment, the oilseed is not exposed to a heat treatment and its moisture content is not adjusted. It will be understood by a person skilled in the art that the moisture content of the seed is typically in the range of about 7% to about 10% for a pressing operation. If the moisture content of the seed is not in this range, the moisture of the seed is optionally adjusted to about 7% to about 10% by adding water or drying, which is followed by blending and tempering.

The oilseed is then pressed to remove the oil from within the oilseed. Generally, an oilseed such as canola, rapeseed, mustard seed, broccoli seed, flax seed, cotton seed, hemp seed, safflower seed, sesame seed or soybean, contains about 15% to about 50% oil (w/w), depending on the particular oilseed. Typically, oil is removed from an oilseed by pressing the oil from the oilseed to form a pressed oilseed. Examples of pressed oilseeds are a seedcake (or a presscake), while a defatted meal or a protein-enriched meal begin from a seed-cake (or presscake), as explained below. It will be understood that a seedcake and a presscake define the same pressed seed meal. Methods of pressing oil from an oilseed are well known in the art. A typical pressing will remove about 30% to about 70% of the oil in the oilseed, and results in pressed oil and a pressed seedcake (or presscake).

In an embodiment, the removal of much of the remaining oil from the seedcake is accomplished by solvent extraction of the seedcake. Solvent extraction is a well known process in the art and utilizes low boiling solvents, such as hexane, methyl pentane or other refrigerants such as ITFM and R134a (1,1,1,2-tetrafluoroethane), to remove residual oil from the seedcake.

The solvent extraction process results in a defatted seedcake meal and a solution of solvent and oil. The oil is separated from the solvent and utilized for other purposes. Generally, depending on the extraction process, the seedcake will contain residual amounts of solvent that are removed from the seedcake. Typically, the removal of the residual solvent from seedcake is accomplished by heating the seedcake in a desolventizer toaster (DT), flash desolventizer (such as a ring dryer) or vacuum oven, which causes the residual solvent to evaporate. The seedcake is subsequently dried. The above process removes much of the oil from the pressed oilseed and leaves material known as defatted meal. In an embodiment, the defatted meal will contain less than about 6% of oil, optionally about 0.5% to about 3% (w/w).

The defatted meal is then subjected to a milling step and a screening step to obtain a pressed oilseed known as a protein-enriched meal.

The defatted meal is typically milled, for example with a disc mill or a hammer mill, to reduce the particle size of the defatted meal. When using a disc mill, the defatted meal is forced through two rotating discs which crush the defatted meal. When a hammer mill is used to reduce the particle size of the defatted meal, the meal is loaded into the hammer mill, wherein the hammers reduce the particle size of the defatted meal.

After the particle size of the defatted meal has been sufficiently reduced, the milled defatted meal is screened through mesh screens, which results in an initial separation of a fiber fraction from the defatted meal, resulting in a protein-enriched meal. Fiber tends to have a larger particle size which is not able to pass through the screen. However, a portion of the fiber will be able to pass through the screen, and as such, only a portion of the fiber is removed by screening. Typically, about a 45 US mesh screen is used for the initial fiber separation. This is a dry screening process which results in a fiber enriched meal, which does not pass through the screen, and the protein-enriched meal, which does pass through the screen. The protein-enriched meal, however, still contains a significant amount of fiber and other antinutritional factors. From the milled defatted material, about a 30% to about 60% by weight protein-enriched meal is typically obtained, while the fiber fraction constitutes about 40% to about 70% of the original weight of the defatted material. The protein-enriched meal possesses a protein content of about 40% to about 60%, optionally 50% to about 55%, while the fiber fraction possesses about 35% to about 48% protein content. In an embodiment of the disclosure, it is this protein-enriched meal that is utilized to produce the protein concentrates and protein isolates of the present disclosure. However, in another embodiment, it will be apparent to those skilled in the art that a seedcake, defatted meal or protein-enriched meal is utilized with the processes of the present disclosure. The use of such a defatted or protein-enriched meal, and processing with a minimum amount of heat during conditioning, pressing, solvent extraction, desolventization and drying, leads to better protein concentrates and protein isolates.

In an embodiment of the present disclosure, there is a process for removing fiber from a partially defatted, fully defatted or protein-enriched meal or "meal"). In particular, the process relates to separating and removing fiber from a meal based on the density and particle size differences between the fiber particles and the protein particles. The separation and removal of fiber is accomplished by using separation methods, at specific speeds, which can separate particles based on their density or particle size such as centrifugation, gravity sedimentation, a gravity table or hydrocyclone to separate the fiber from the mixture and form the protein slurry. In an embodiment, the separation is accomplished using centrifugation. In another embodiment, the separation is accomplished using a decanter centrifuge. In another embodiment, the separation is accomplished using a decanter centrifuge at a speed of about 1,000 rpm to about 2,000 rpm. In another embodiment, the separation is accomplished using a decanter centrifuge at a speed of about 1,500 rpm. In an embodiment, the centrifugation of a meal mixture results in three layers: i) an insoluble fiber layer and a protein slurry on top of the fiber, which is comprised of ii) an insoluble protein fraction and iii) a soluble protein fraction. Separation of the top and middle layers (the soluble protein extract and the insoluble fine protein fraction) from the bottom layer (coarse fiber solids), results in a protein slurry with fiber removed.

Figure 3:
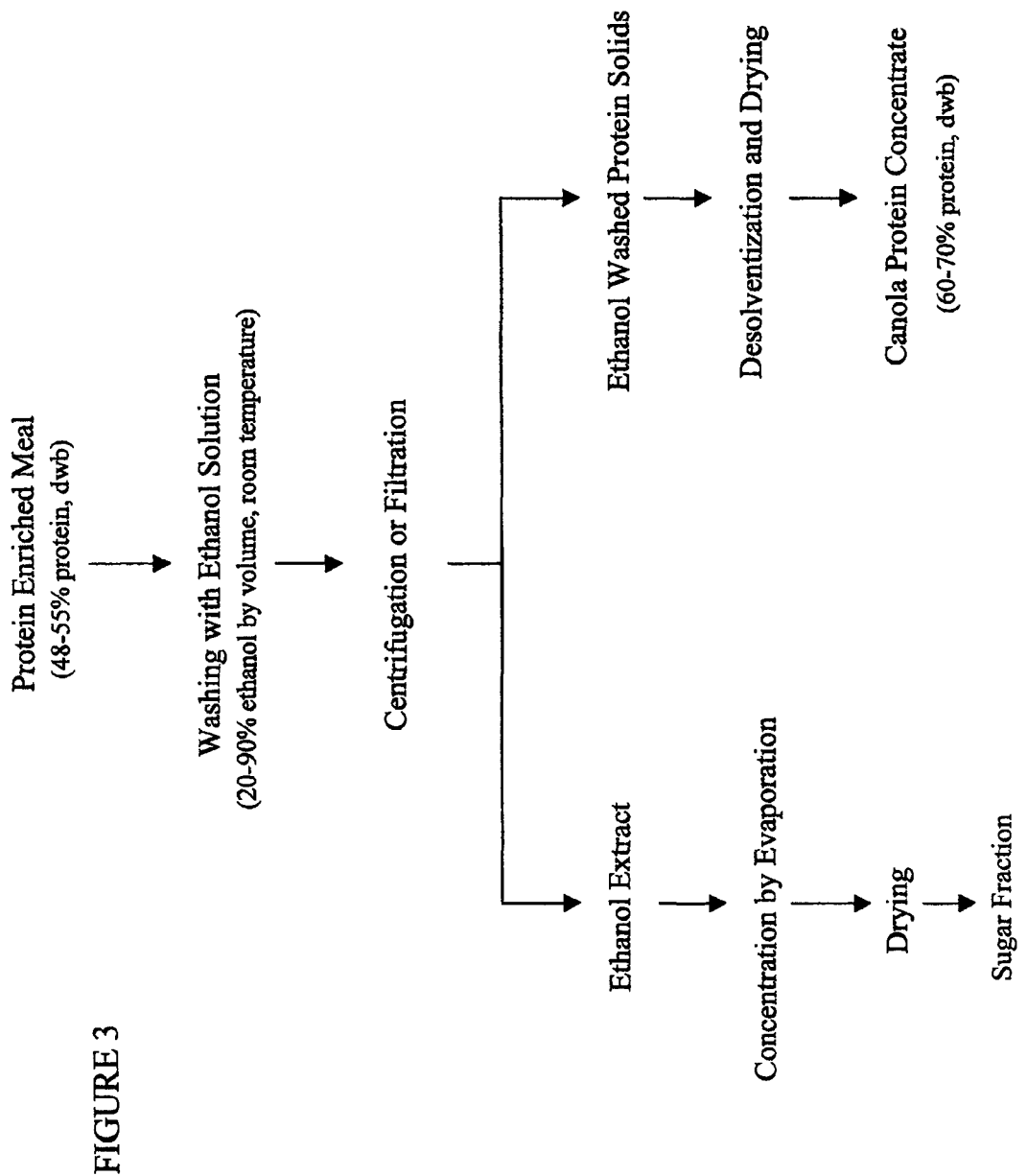
FIG. 3 is schematic representation showing a preparation of a protein concentrate from a protein-enriched meal.
Figure 4:
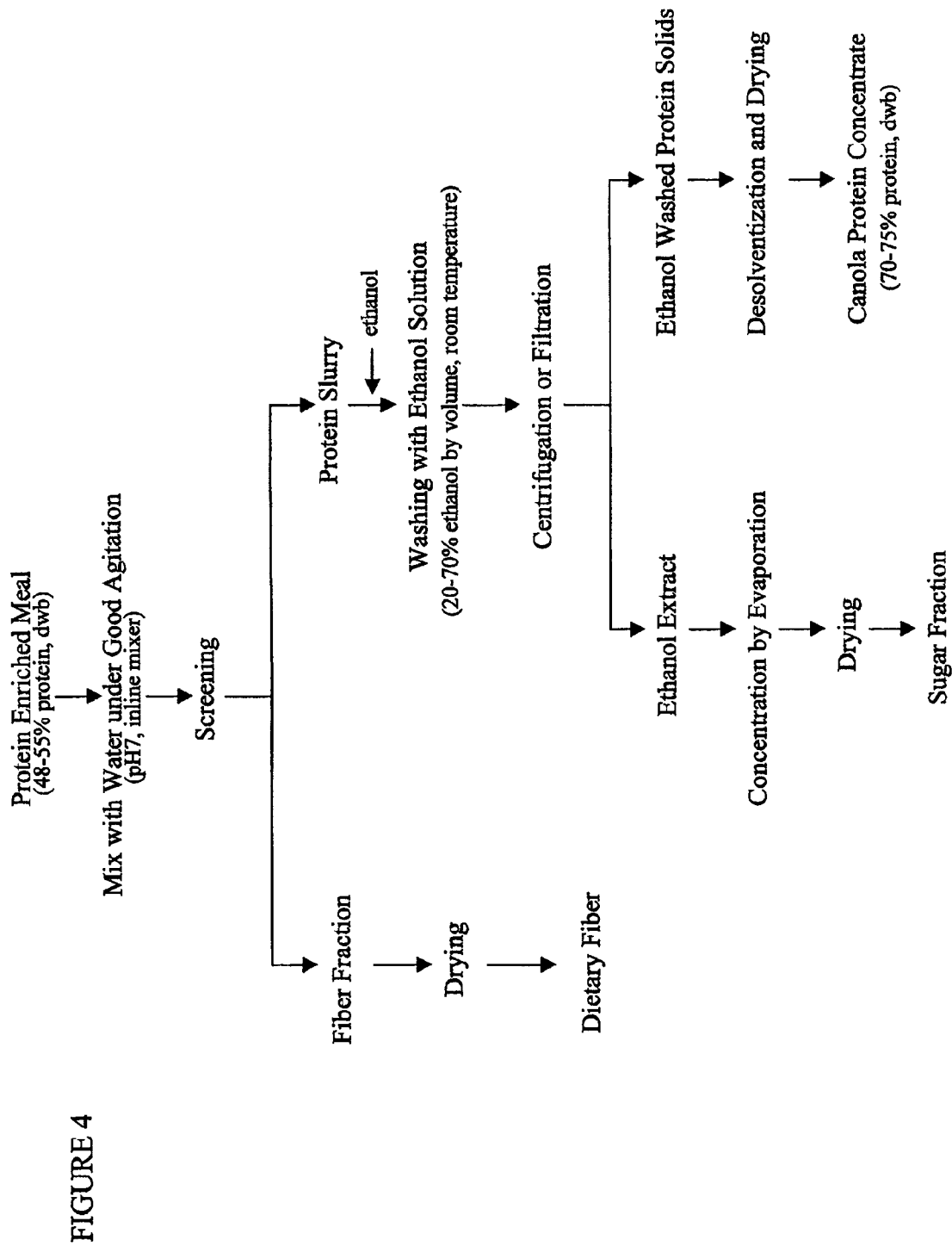
FIG. 4 is a schematic representation showing the removal of fiber during a preparation of a protein concentrate from a protein-enriched meal.
Figure 5:
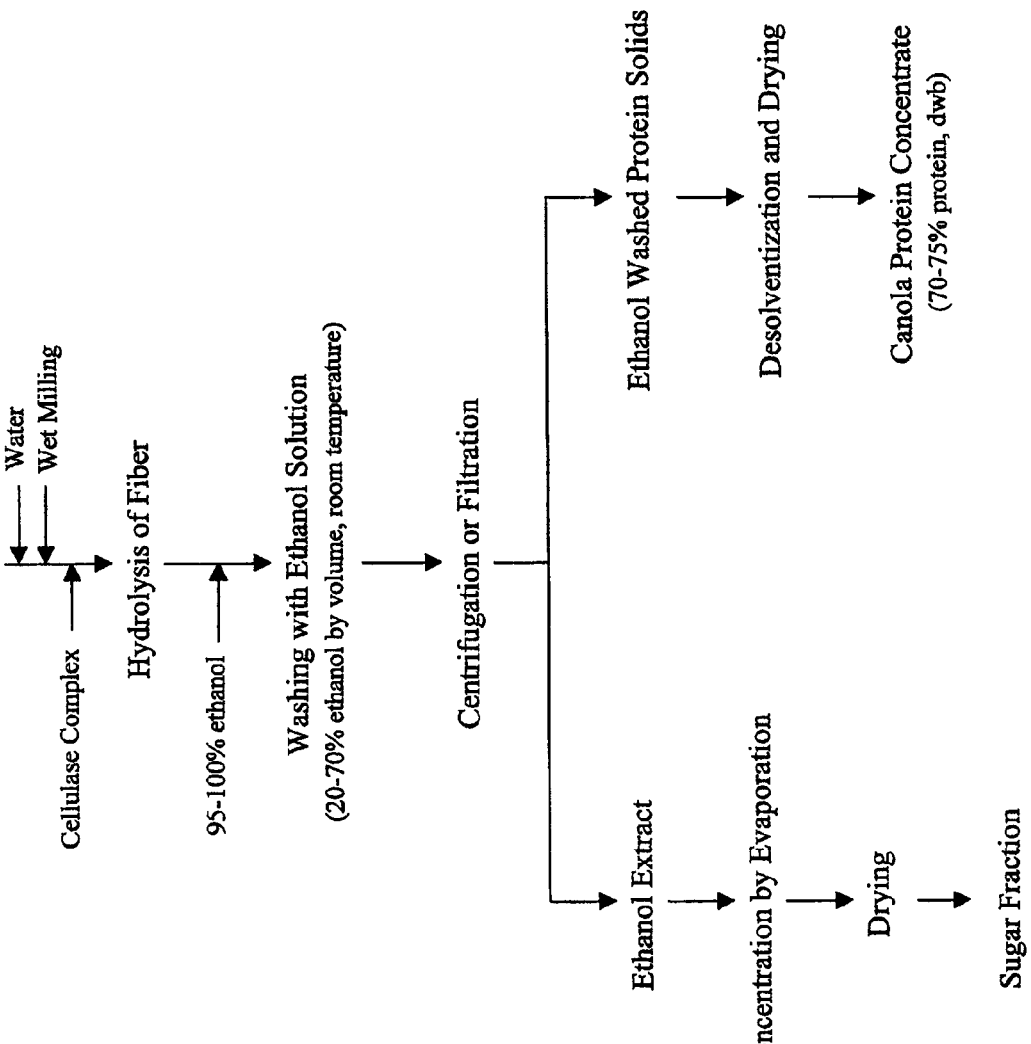
FIG. 5 is a schematic representation showing the removal of fiber during a preparation of a protein concentrate from a protein-enriched meal.
Figure 6:
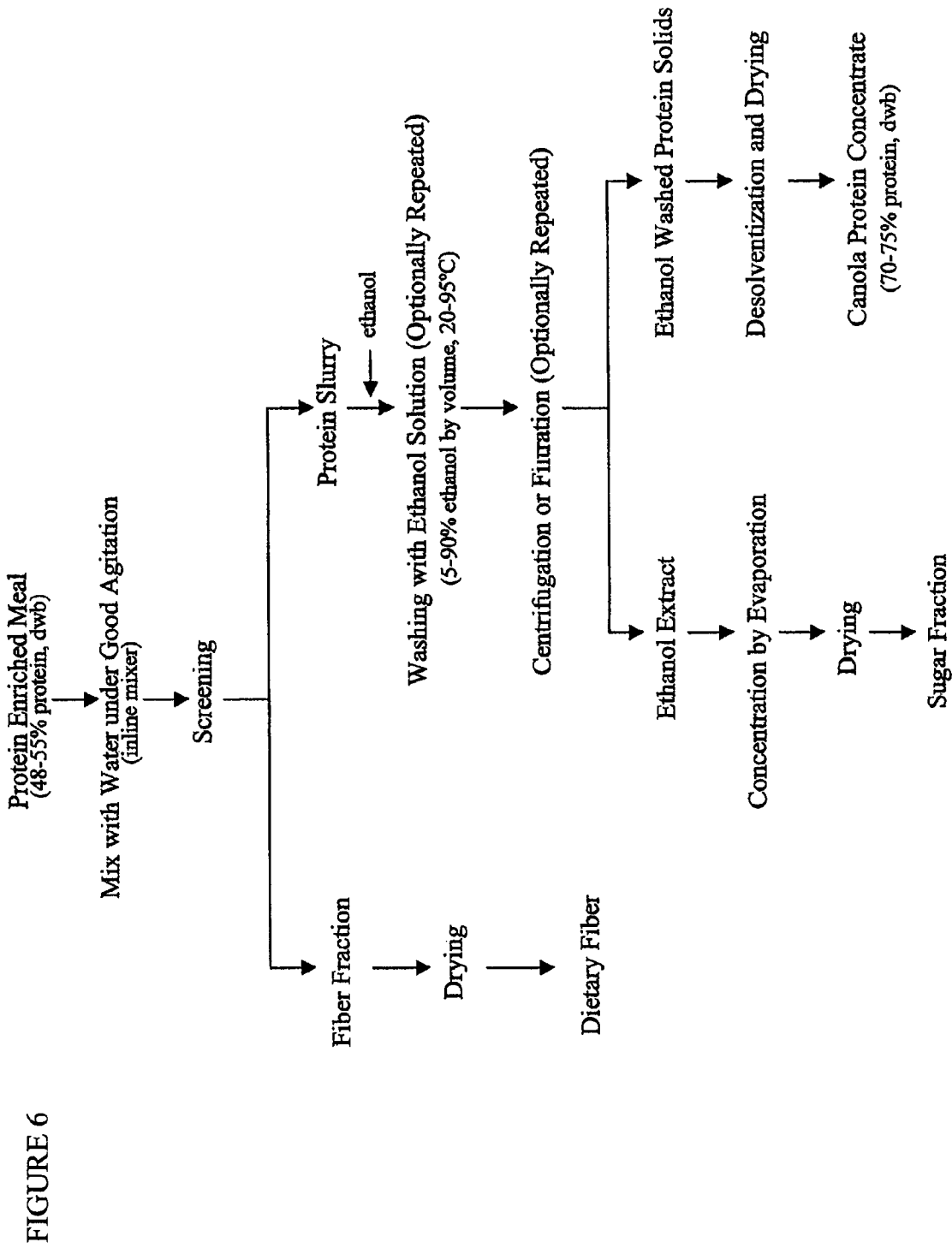
FIG. 6 is a schematic representation showing the removal of fiber during a preparation of a protein concentrate from a protein-enriched meal.
Figure 7:
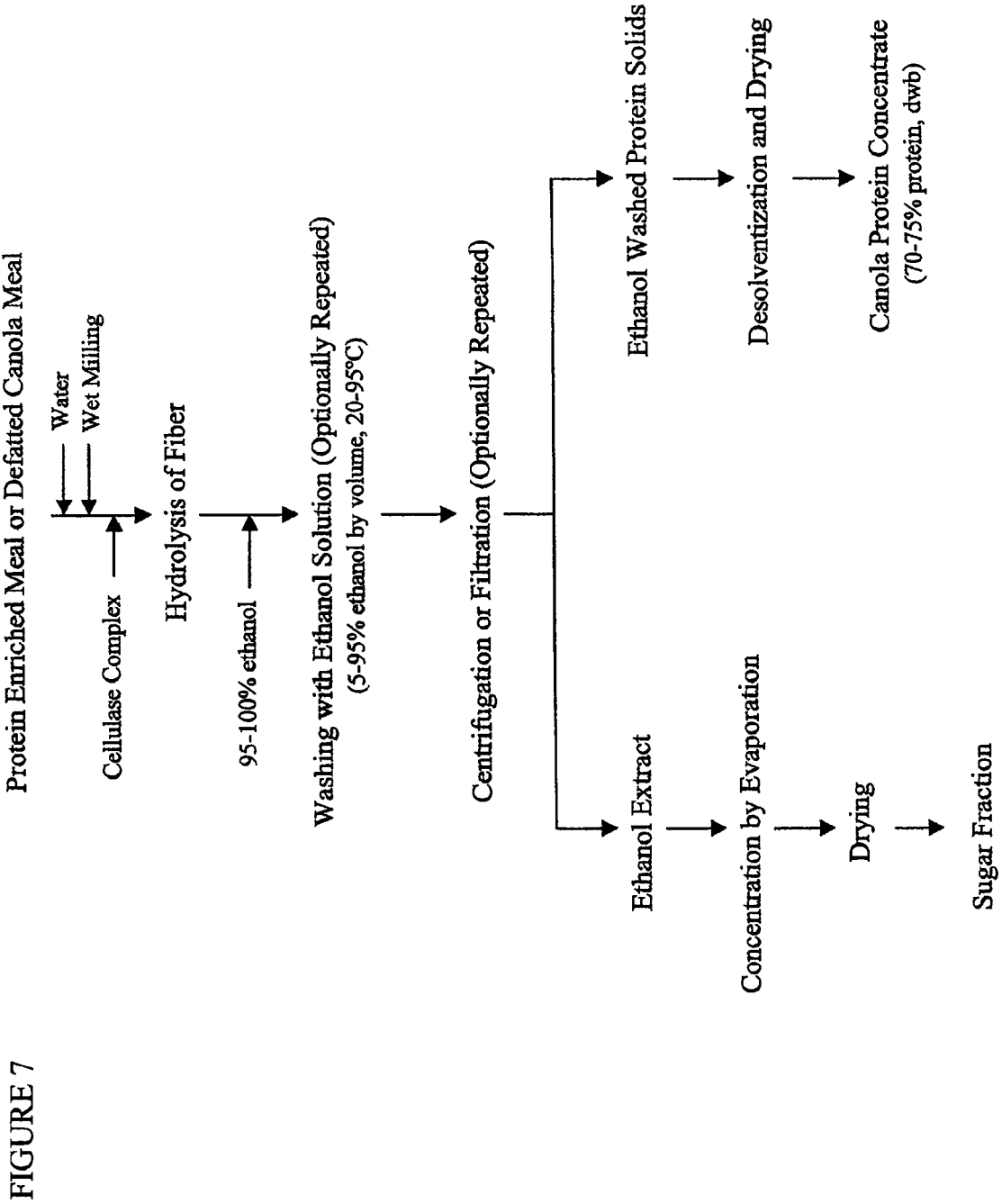
FIG. 7 is a schematic representation showing the removal of fiber during the preparation of a protein concentrate from a protein-enriched meal.

In an embodiment of the present disclosure, a process for the production of a protein concentrate possessing a protein content of about 65% to about 70% is obtained from a defatted or protein-enriched meal. An optional general process for the production of a protein concentrate is illustrated in FIG. 3.

In an embodiment, a defatted or protein-enriched meal is produced by the process above, and is then washed at least once with about 5% to about 100%, optionally about 20% to about 90%, or about 40% to about 80% (v/v) ethanol in water, resulting in an ethanol extract and an ethanol washed defatted or protein-enriched meal. Other alcohols, such as methanol or isopropanol, can be utilized for washing the defatted or protein-enriched meal. In an embodiment, ethanol is used for washing the defatted or protein-enriched meal because it is less toxic than other alcohols, and a higher percentage of ethanol residue is allowed in the final product.

In another embodiment, the defatted or protein-enriched meal is washed once with ethanol, wherein the ratio of ethanol to the protein-enriched meal is about 1:3 to about 1:15, typically about 1:4 to about 1:8, optionally 1:6, on a weight-to-weight basis of protein-enriched meal to ethanol.

In another embodiment, the defatted or protein-enriched meal is washed twice with ethanol, wherein the amount of ethanol added to the protein-enriched meal results in a ratio of about 1:2 to about 1:15, typically about 1:5 to about 1:8, optionally 1:6, on a weight-to-weight basis of protein-enriched meal to ethanol. Typically, washing the defatted or protein-enriched meal at least twice results in the removal of more impurities from the defatted or protein-enriched meal and therefore increases the protein content in the protein concentrate.

In a further embodiment, the defatted or protein-enriched meal is washed in a counter-current extractor. In this embodiment, the defatted or protein-enriched meal is washed about 2 times to about 10 times, wherein the ratio of solvent to the defatted or protein-enriched meal is about 1 to about 10 of meal to about 1 of meal.

In another embodiment, the defatted or protein-enriched meal is washed with ethanol at a temperature of about 10° C. to about 90° C., optionally 20° C. to about 60° C., suitably at a temperature of about 40° C. to about 60° C.

The ethanol extract is optionally separated from the ethanol washed defatted or protein-enriched meal by centrifugation, filtration, vacuum filtration, pressure filtration, sedimentation, decantation or gravity draining. With respect to centrifugation, the ethanol mixture is typically fed to a decanter centrifuge or a basket centrifuge. The ethanol extract is then separated from the ethanol washed defatted or protein-enriched meal by centrifugal force. For the decanter centrifuge, a screw conveyer is contained within a solid bowl and both rotate at high speeds. Solids settling on the bowl are conveyed by the screw conveyer out of the centrifuge. For a basket centrifuge, which consists of a perforated basket rotating inside a stationary housing, the ethanol mixture is fed into the basket and centrifugal force pushes it against the filter liner. The solids are retained by the liner while the liquid passes through. For filtration, the ethanol extract is typically separated from the ethanol washed defatted or protein-enriched meal by draining through a perforated belt or basket in a reactor. For vacuum filtering or pressure filtering, the separation is aided by vacuum or pressure. In an embodiment, the ethanol extract is concentrated by evaporation of the ethanol to form a high sugar fraction, optionally containing antinutritional factors that can be further purified. The antinutritional compounds may be purified into valuable pharmaceutical, medicinal or chemical compounds, such as glucosinolates, phytic acid or phytates, sinapine and sinigrin. In an embodiment, the ethanol extract is heated under vacuum at about 30° C. to about 90° C., which results in the evaporation of ethanol and water, and soluble solids are left behind. Ethanol is further separated from water by distillation and re-used in the process. The concentrated high-sugar fraction is dried by spray drying, rotary drum drying, vacuum drying, flash drying, ring drying, microwave drying, freeze drying or using a fluidized bed dryer.

In another embodiment, the washed defatted or protein-enriched meal is dried to form the protein concentrate, possessing a protein content of about 65% to about 70%. In a further embodiment, the washed protein-enriched meal is dried in a spray dryer, drum dryer, vacuum dryer, fluidized bed dryer or ring dryer to form the protein concentrate possessing a protein content of about 65% to about 70%. These dryers remove the solvent by drying the protein concentrate under a vacuum or at atmospheric pressure at elevated temperatures of about 30° C. to about 100° C.

In an embodiment, the protein concentrate is dried to a moisture content of about 1% to about 10%, optionally about 4% to about 8%.

In another embodiment, the ethanol that is removed through drying is recovered and recycled so it can be used again in further ethanol extractions. The ethanol is recovered through evaporation and distillation.

In another embodiment, the dried protein concentrate possessing a protein content of about 65% to about 70% is further milled into powder form without coarse particles.

In another embodiment of the present disclosure, there is provided a process for producing a protein concentrate possessing a protein content of about 70% to about 75% on a dry weight basis. In an embodiment, a general process for the production of a protein concentrate possessing a protein content of about 70% to about 75% is illustrated in FIGS. 4-7, where the removal of fiber is also detailed. In an embodiment, the use of an extraction solvent, such as ethanol, leads to a protein concentrate or protein isolate having superior organoleptic properties, as well as superior water solubility properties, which therefore possesses better functional properties.

Accordingly, in an embodiment of the present disclosure, a process for the production of a protein concentrate from a defatted or protein-enriched meal is disclosed, comprising:
1) removing fiber from the defatted or protein-enriched meal, comprising either:
   i) mixing the defatted or protein-enriched meal with a mixing solvent to form a first mixture;
      screening the first mixture through a mesh screen of about 10 to about 200 US mesh size to remove the fiber; or
   ii) mixing the defatted or protein-enriched meal with water to form a second mixture;
      optionally adjusting the pH of the second mixture to a pH of about 3 to about 7; and
      adding cellulase complex to the second mixture and heating to a temperature of about 30° C. to about 60° C. to hydrolyze the fiber;
2) washing the first or second mixture with an extraction solvent to form an extract and a washed defatted or protein-enriched meal;
3) separating the extract from the washed defatted or protein-enriched meal;
4) optionally repeating steps 2) and 3) at least one more time; and
5) desolventizing the washed defatted or protein-enriched meal to form a protein concentrate.

In an embodiment of the present disclosure, the mixing solvent is any solvent which forms a slurry with the defatted or protein-enriched meal when mixed together and is able to suspend the protein within the mixture. In another embodiment, the mixing solvent comprises water, methanol, ethanol, or isopropanol, or mixtures thereof. In a further embodiment, the mixing solvent comprises water or ethanol, and mixtures thereof.

In another embodiment, the defatted or protein-enriched meal comprises a canola, rapeseed, mustard seed, broccoli seed, flax seed, cotton seed, hemp seed, safflower seed, sesame seed or soybean meal. In a further embodiment, the protein-enriched meal comprises a canola meal, a soybean meal, a mustard seed meal or a flax seed meal.

In an embodiment of the disclosure, the defatted or protein-enriched meal is mixed with a mixing solvent in a ratio of about 3 to about 10 parts solvent to about 1 part of the defatted or protein-enriched meal, on a weight-to-weight basis.

In an embodiment of the present disclosure, the pH of the first mixture is adjusted to a pH of about 3.0 to about 10.0, optionally about 6.8 to about 7.2 with a solution of an alkali metal base or an acid, such as phosphoric, hydrochloric or sulphuric acid. In a further embodiment, a solution of an alkali metal base comprising about 1% to about 40% by weight, optionally about 5% to about 30%, of the alkali metal base and water is added to the first mixture. In another embodiment, the alkali metal base comprises sodium hydroxide (NaOH).

In another embodiment of the present disclosure, the first mixture is thoroughly agitated. In another embodiment, an inline mixer is used for thorough mixing of the first mixture. Thorough mixing of the first mixture disperses the protein particles and releases natural sugar compounds that are trapped inside the insoluble protein particles in the mixing solvent. In addition, the agitation suspends the solids of the protein-enriched meal in the mixing solvent.

In a further embodiment, the thoroughly mixed first mixture is wet screened resulting in a separation of the fiber from the mixture which contains the protein. In another embodiment of the disclosure, the mesh screen comprises a US mesh screen of about 20 to about 200 US mesh. In a further embodiment, the mesh screen is a vibratory screen. A person skilled in the art would recognize that other screens, for example revolving screens, shaking screens or oscillating screens, could be used in place of vibratory screens to perform substantially the same function of vibrating the mixture which aids in separation of the first mixture from the fiber. In an embodiment of the disclosure, the fiber in the meal swells upon addition of the mixing solvent, increasing the particle size of the fiber. Consequently, the mesh screen prevents the fiber from passing through, while the protein in the first mixture passes through the screen, resulting in a separation of the fiber from the protein. In an embodiment, the fiber fraction is dried and can be used in dietary fiber products. The fiber fraction optionally contains protein and carbohydrates.

In another embodiment of the present disclosure, the defatted or protein-enriched meal is thoroughly mixed with water to form the second mixture. In an embodiment, wet milling is used to mix the second mixture. In another embodiment, an inline mixer is used to thoroughly mix the second mixture. In an embodiment, the mixing of the defatted or protein-enriched meal in water, results in the internal fiber structure being exposed, which allows for the cellulase complex to efficiently hydrolyze the fiber.

In a further embodiment of the disclosure, the pH of the second mixture is optionally adjusted with an acid. In an embodiment, the pH of the second mixture is adjusted to a pH that is suitable for the activity of an enzyme within the second mixture. In an embodiment, the pH of the second mixture is adjusted to a pH of about 3 to about 7. The pH of the second solution is adjusted with an acid solution. In an embodiment, the acid solution is phosphoric acid, hydrochloric acid or sulfuric acid. In an embodiment, the natural pH of the second mixture is about 6.8 to about 7.2, and therefore the pH of the second mixture is not adjusted.

In another embodiment of the present disclosure, the cellulase complex is added to the second mixture in an amount of about 1 to about 10 grams (about 0.1% to about 1%) to about 1 kg of dried solids in the second mixture. In a further disclosure, the cellulase complex is mixed with the second mixture for about 0.5 hours to about 5 hours. In another embodiment, the cellulase complex is mixed with the second mixture for about 1 to about 3 hours. It will be apparent to those skilled in the art that cellulase complex contains different types of cellulase enzyme. For example, cellulase complex contains at least one of endocellulase, exocellulase, cellobiohydrolase, cellobiase, endohemicellulase and exohemicellulase. Cellulase enzymes possess enzymatic activity which are able to hydrolyze the fiber to constituent sugars within the second mixture.

In another embodiment of the present disclosure, the first or second mixture is washed at least once with about 5% to about 100%, optionally about 25% to about 85%, or about 50% to about 85%, or about 60% to about 85%, of the extraction solvent (v/v) in water. The addition of the extraction solvent precipitates proteins in the first or second mixture, while the carbohydrates from the oilseed and from the hydrolyzation of the fiber remain in the extraction solvent, which allows for separation. It will be understood that an extraction solvent will be any solvent which dissolves the carbohydrates and other undesirable compounds, but precipitates the protein. In embodiment, the extraction solvent is water, methanol, ethanol or isopropanol, and mixtures thereof. In another embodiment, the extraction solvent is ethanol. It will be understood by a person skilled in the art that if the extraction solvent comprises 100% extraction solvent, no water will be present in the extraction solvent. For example, the extraction solvent could be 100% ethanol. In another embodiment, the extraction solvent is 60% ethanol in water.

In an embodiment of the present disclosure, the extraction solvent is added in an amount to adjust the ratio of the extraction solvent to the first or second mixture of about 5% to about 95%, optionally about 10% to about 90%, or about 40% to about 80% (v/v) of the extraction solvent.

In an embodiment of the present disclosure, the first or second mixture is washed with an extraction solvent at a temperature of about 10° C. to about 90° C. In another embodiment, the first or second mixture is washed with the extraction solvent at a temperature of about 20° C. to about 60° C. In a further embodiment, the first or second mixture is washed with the extraction solvent at a temperature of about 20° C. to about 25° C.

In another embodiment of the present disclosure, the extract is separated from the washed defatted or protein-enriched meal by centrifugation, vacuum filtration, pressure filtration, decantation or gravity draining. In an embodiment, the extract is concentrated by evaporation of the extraction solvent dried to form a high sugar fraction, as is performed above.

In another embodiment of the disclosure, steps 2) and 3) are optionally repeated at least once. In an embodiment, steps 2) and 3) are repeated at least twice. Repeating steps 2) and 3) results in a protein product containing less impurities, such as fiber and other antinutritional factors.

In another embodiment, the washed defatted or protein-enriched meal is dried to form the protein concentrate, possessing a protein content of about 70% to about 75% on a dry weight basis. In a further embodiment, the washed defatted or protein-enriched meal is dried in a vacuum dryer, fluidized bed dryer, spray dryer or ring dryer to form the protein concentrate possessing a protein content of about 70% to about 75%.

In another embodiment, the washed defatted or protein-enriched meal is dried to a moisture content of about 0.5% to about 12%, optionally about 1% to about 10%, or about 4% to about 8%. In a further embodiment, the washed defatted or protein-enriched meal is dried to a moisture content of about 6%.

In another embodiment of the disclosure, the extraction solvent that is removed through drying is recovered and recycled so it can be used again in further extractions.

In another embodiment, the dried protein concentrate possessing a protein content of about 70% to about 75% is further milled into powder form.

Figure 8:
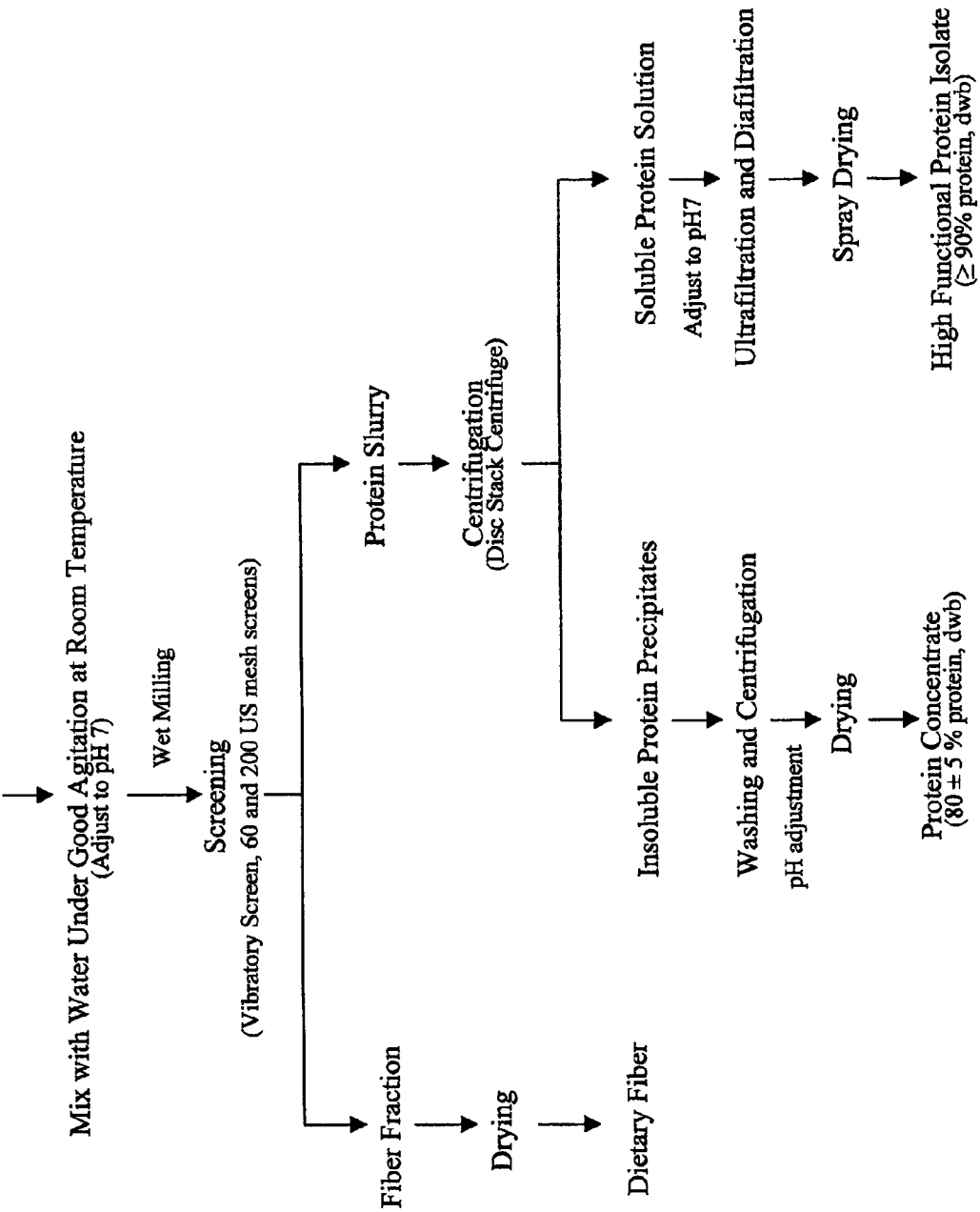
FIG. 8 is a schematic representation showing a preparation of a protein concentrate and a protein isolate from a protein-enriched meal.
Figure 9:
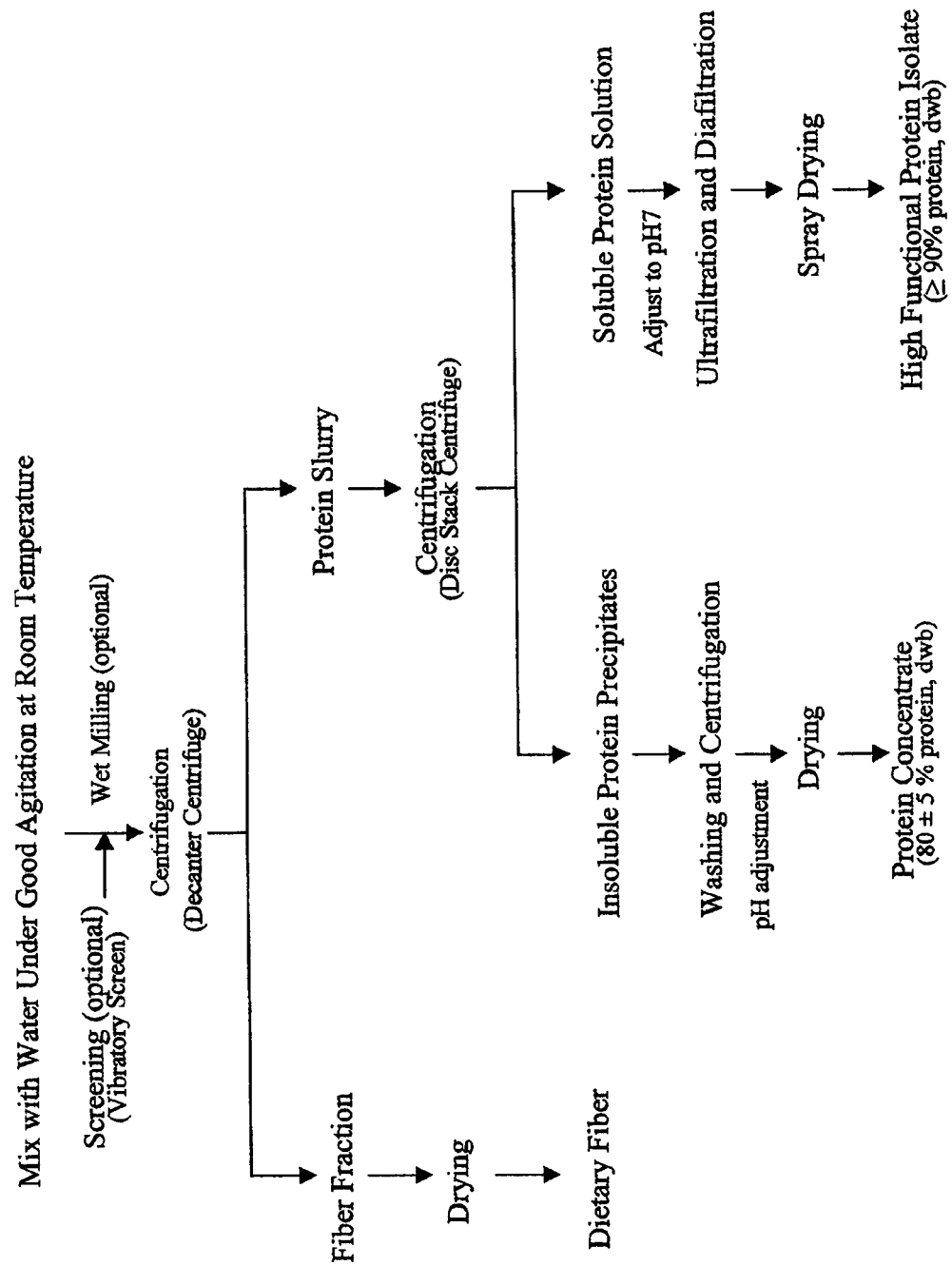
FIG. 9 is a schematic representation showing a preparation of a protein concentrate and a protein isolate from a protein-enriched meal.

In another embodiment of the present disclosure, there is disclosed a process for the production of a protein concentrate comprising a protein content of about 75% to less than 90% on a dry weight basis. In an embodiment, a general process for the production of a protein concentrate possessing a protein content of about 80% and a protein isolate having a protein content greater than 90% is illustrated in FIGS. 8-9.

Accordingly, a process for the production of a protein concentrate from a defatted or protein-enriched meal is disclosed, comprising:

removing fiber from the defatted or protein-enriched meal, comprising:
i) mixing the defatted or protein-enriched meal with a mixing solvent to form a mixture;
optionally screening the mixture through a mesh screen of about 10 to about 200 US mesh size to remove fiber,
optionally adjusting the pH of the mixture to a pH of about 7;
optionally milling the mixture;
centrifuging the mixture to remove fiber, and forming a protein slurry; and
ii) centrifuging the protein slurry to form a protein precipitate and a soluble protein fraction;
iii) washing the protein precipitate with an extraction solvent at least once and centrifuging to form a purified protein precipitate;
iv) drying the purified protein precipitate to form the protein concentrate.

It will be understood by a person skilled in the art that the steps of the process do not have to be followed exactly. For example, a person skilled in the art would recognize that the milling step could be performed before the screening step.

In another embodiment, the defatted or protein-enriched meal comprises a canola, rapeseed, mustard seed, broccoli seed, flax seed, cotton seed, hemp seed, safflower seed, sesame seed or soybean meal. In a further embodiment, the protein-enriched meal comprises a canola meal. In an embodiment, the protein-enriched meal comprises a soybean meal. In another embodiment, the protein-enriched meal comprises mustard seed meal. In a further embodiment, the protein-enriched meal comprises flax seed meal.

In an embodiment of the disclosure, the mixing solvent is any solvent which forms a slurry with the defatted or protein-enriched meal and is able to suspend the protein within the mixture. In another embodiment, the mixing solvent comprises water, methanol, ethanol, or isopropanol, and mixtures thereof. In a further embodiment, the solvent comprises water or ethanol, and mixtures thereof.

In an embodiment, the defatted or protein-enriched meal is mixed with the mixing solvent to form a mixture in a ratio of defatted or protein-enriched meal to mixing solvent of about 1:3 to about 1:20, optionally about 1:6 to about 1:10, or about 1:6 to about 1:8.

In a further embodiment, the mixture is wet screened resulting in a separation of the fiber from the mixture which contains the protein. In another embodiment of the disclosure, the mesh screen comprises a US screen of size about 20 to about 200 mesh. In a further embodiment, the mesh size is 40 US mesh size. In a further embodiment, the mesh screen is a vibratory screen. The mesh screen prevents the fiber from passing through, while the protein in the mixture passes through the screen, resulting in a separation of the fiber from the protein. In an embodiment, the fiber fraction is dried and can be used in dietary fiber products. In an embodiment, protein and carbohydrates are present in the fiber fraction.

In another embodiment, the pH of the mixture is adjusted to about 7 with the addition of aqueous sodium hydroxide. In a further embodiment, the aqueous sodium hydroxide is a solution of about 1% to about 40%, optionally about 5% to about 30%, by weight of sodium hydroxide in water.

In another embodiment, the mixture is optionally milled using a wet milling process. In an embodiment, the wet milling of the mixture results in thorough mixing of the defatted or protein-enriched meal with the mixing solvent. Thorough mixing of the mixture disperses the protein particles and releases natural sugar compounds that are trapped inside the insoluble protein particles in the mixing solvent. In addition, the mixing suspends the solids of the protein-enriched meal in the mixing solvent.

In another embodiment of the present disclosure, the mixture is centrifuged using a decanting centrifuge. In an embodiment, the mixture is centrifuged with a decanting centrifuge at a speed of about 1000 rpm to about 2000 rpm. In another embodiment, the speed is about 1500 rpm.

In another embodiment, the protein slurry is then centrifuged using a disc stack centrifuge to separate insoluble proteins from soluble proteins, forming a protein precipitate and a soluble protein fraction. In an embodiment, the protein slurry is pumped to a disc centrifuge. The centrifuge has a bowl which spins at about 7500 rpm. As the slurry enters the centrifuge bowl, the slurry is brought up to the same speed as the bowl, which results in high centrifugal forces, about 6500 times the force of gravity acting on the mixture. The heavier protein precipitate is forced to the outside of the bowl. The soluble protein fraction is forced towards the axis of the bowl. The heavy precipitate collects around the outside of the bowl which are removed from the bowl periodically or continuously. The protein slurry is fed to the centrifuge continuously while the liquid soluble protein fraction is pumped out continuously. In an embodiment, the disc centrifuge operates at a speed of about 6500 rpm to about 8500 rpm.

In a further embodiment, the protein precipitate is washed with an extraction solvent to purify the protein precipitate and dissolve residual sugars and other non-desirable compounds. It will be understood that an extraction solvent will be any solvent which dissolves the carbohydrates and other non-desirable compounds. In an embodiment, the extraction solvent is water, methanol, ethanol or isopropanol, and mixtures thereof. In another embodiment, the extraction solvent is water or ethanol, and mixtures thereof. In another embodiment, the extraction solvent is water. In an embodiment, the protein precipitate is washed at least twice with the extraction solvent.

In another embodiment, the washed protein precipitate is then centrifuged again with a disc stack centrifuge at a speed of about 6500 rpm to about 8500 rpm to obtain a protein precipitate. In another embodiment, the washing extracts from the centrifugation are added to the soluble protein fraction.

In another embodiment, the washed protein precipitate is dried to form a protein concentrate comprising a protein content of about 75% to about 90% on a dry weight basis. In a further embodiment, the washed protein precipitate is dried in a vacuum dryer, fluidized bed dryer or ring dryer to form the protein concentrate possessing a protein content of about 75% to less than 90%. It will be understood by a person skilled in the art that the washed protein precipitate can be used as a protein isolate without drying. However, the dried protein isolate has a better shelf life as removal of the solvent, for example water, results in a more stable protein isolate.

Figure 10:
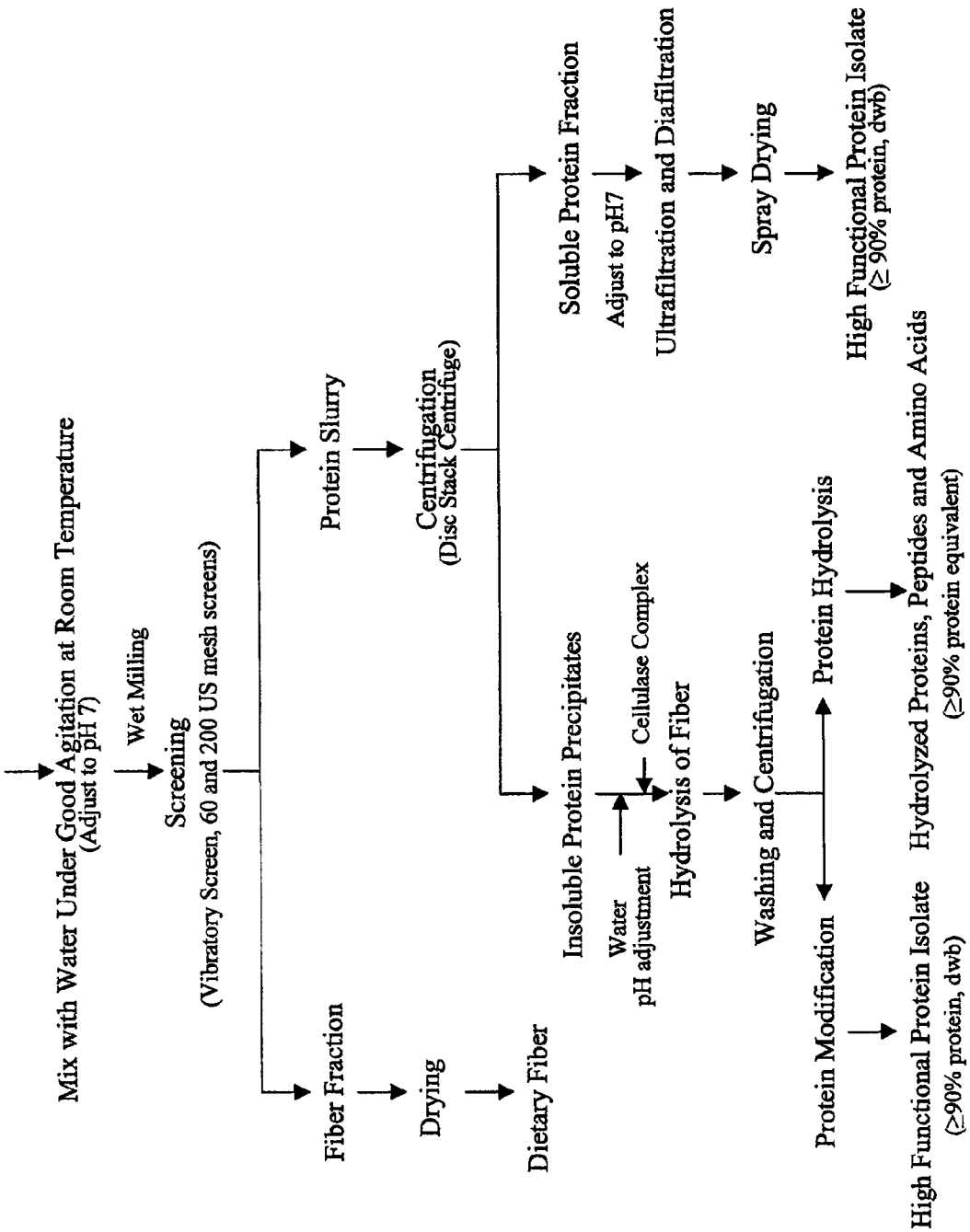
FIG. 10 is a schematic representation showing a preparation of a protein isolate from a protein-enriched meal.
Figure 11:
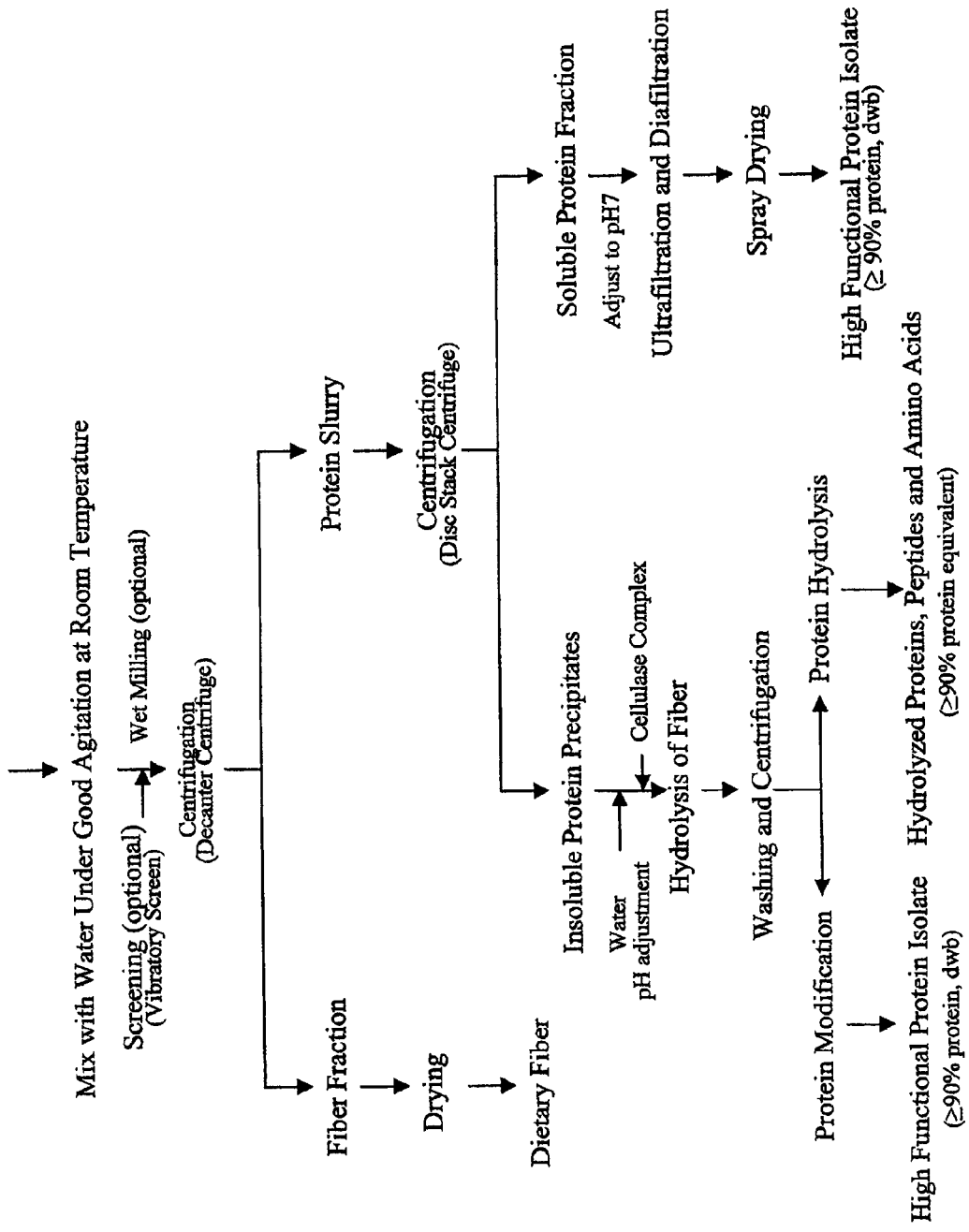
FIG. 11 is a schematic representation showing a preparation of a protein isolate from a protein-enriched meal.

In another embodiment of the present disclosure, there is provided a process for the production of a protein isolate comprising a protein content of greater than 90% on a dry weight basis. In an embodiment, a general process for the production of a protein isolate and hydrolyzed proteins having a protein content greater than 90% is illustrated in FIGS. 10-11.

Accordingly, a process for the production of a protein isolate from a defatted or protein-enriched meal is disclosed, comprising:

removing fiber from the defatted or protein-enriched meal, comprising:
i) mixing the defatted or protein-enriched meal with a mixing solvent to form a mixture;
screening the mixture through a mesh screen of about 10 to about 200 US mesh size to remove fiber,
optionally adjusting the pH of the mixture to a pH of about 7;
optionally milling the mixture; and
centrifuging the mixture to remove fiber,
and forming a protein slurry;
ii) centrifuging the protein slurry to form a protein precipitate and a soluble protein fraction;
iii) filtering the soluble protein fraction; and
iv) drying the soluble protein to form the protein isolate.

In an embodiment, the soluble protein fraction is obtained using the same process as described above.

It will be understood by a person skilled in the art that the steps of the process do not have to be followed exactly. For example, a person skilled in the art would recognize that the milling step could be performed before the screening step.

In another embodiment, the defatted or protein-enriched meal comprises a canola, rapeseed, mustard seed, broccoli seed, flax seed or soybean meal. In a further embodiment, the protein-enriched meal comprises a canola meal. In an embodiment, the protein-enriched meal comprises a soybean meal. In another embodiment, the protein-enriched meal comprises mustard seed meal. In a further embodiment, the protein-enriched meal comprises flax seed meal.

In an embodiment of the disclosure, the mixing solvent comprises water or a salt solution. In an embodiment, the salt solution comprises less than 5%, optionally about 3% to about 4%, or 3.5% by weight of salt in solution. In a further embodiment, the mixing solvent comprises water. In another embodiment, the ratio of defatted or protein-enriched meal to the mixing solvent is about 1:3 to about 1:20. In a further embodiment, the ratio is about 1:6 to about 1:10. In an embodiment, the ratio is about 1:6 to about 1:8.

In an embodiment, the soluble protein fraction is purified by ultrafiltration and diafiltration using a membrane filtration apparatus. In an embodiment, when ultrafiltration is utilized, the soluble protein fraction is heated to a temperature of about 1° C. to about 60° C., optionally 40° C. to about 55° C., before being passed through an ultrafiltration apparatus fitted with membranes to filter proteins larger than about 10,000 daltons, optionally about 30,000, or about 100,000 daltons. The filtered protein is recycled back to the feed tank while the liquid is discarded. The ultrafiltration process is continued until the amount of protein that has been filtered in the feed tank is equal to about 30% to about 40% of its initial weight of the soluble protein fraction.

In a further embodiment, when diafiltration is utilized, it is conducted at about 1° C. to about 60° C., optionally about 40° C. to about 55° C., using the diafiltration unit, which is fitted with the membranes to filter proteins larger than about 10,000 daltons, optionally about 30,000, or about 100,000 daltons. The original volume of soluble protein fraction in the feed tank is held constant by adding water to make up for the removed liquid. The filtered protein is recycled back to the feed tank. The amount of water added to maintain the original volume of protein solution is about 2 times the original volume of soluble protein fraction. For example, if 100 L of soluble protein fraction is used, 200 L of water is added to the soluble protein fraction in the feed tank during the cycle of diafiltration. The volume of the feed tank is kept constant at 100 L with the continued addition of water to the feed tank while the liquid is removed from the system through diafiltration.

In an embodiment, after the soluble protein fraction has been filtered, the filtered soluble protein is spray dried to form a high functional protein isolate comprising a protein content of greater than about 90% on a dry weight basis. It will be understood by a person skilled in the art that spray drying is the transformation of a feed from a fluid state into a dried form by spraying the feed into a circulating hot air medium. Generally, spray drying transforms the filtered protein into many droplets which are then exposed to a fast current of hot air. As a result of the very large surface area of the droplets the water in the protein evaporates almost instantaneously and the droplets are transformed into powdery dry protein particles. In an embodiment, the inlet temperature is about 180° C. to about 220° C. which is the temperature of the hot air entering the spray dryer chamber, the outlet temperature is about 75° C. to about 90° C., which is the temperature of the exhaust, and the feed temperature is about 40° C. to about 50° C. It will be understood by a person skilled in the art that the washed protein precipitate can be used as a protein isolate without drying. However, the dried protein isolate has a better shelf life as removal of the solvent, for example water, results in a more stable protein isolate.

In another embodiment of the present disclosure, there is provided a process for the production of a protein isolate which is subsequently modified or hydrolyzed to form a high functional protein isolate or a mixture of hydrolyzed proteins, peptides and amino acids comprising a protein content of greater than 90% on a dry weight basis.

Accordingly, in an embodiment of the present disclosure, a process for the production of a protein isolate from a defatted or protein-enriched meal is disclosed, comprising:

removing fiber from the defatted or protein-enriched meal, comprising:
i) mixing the defatted or protein-enriched meal with a mixing solvent to form a mixture;
optionally screening the mixture through a mesh screen of about 10 to about 200 US mesh size to remove fiber, optionally adjusting the pH of the mixture to a pH of about 7;
optionally milling the mixture; and
centrifuging the mixture to remove fiber, and forming a protein slurry;
ii) centrifuging the protein slurry to form a protein precipitate and a soluble protein fraction;
iii) mixing the protein precipitate with water to form a protein precipitate mixture and optionally adjusting the pH of the mixture to a pH of about 3 to about 7;
iv) adding cellulase complex to the protein precipitate mixture to hydrolyze residual fiber;
v) washing the protein precipitate with an extraction solvent and centrifuging to form a protein isolate.

It will be understood by a person skilled in the art that the steps of the process do not have to be followed exactly. For example, a person skilled in the art would recognize that the milling step could be performed before the screening step.

In another embodiment, the defatted or protein-enriched meal comprises a canola, rapeseed, mustard seed, broccoli seed, flax seed or soybean meal. In a further embodiment, the protein-enriched meal comprises a canola meal. In an embodiment, the protein-enriched meal comprises a soybean meal. In another embodiment, the protein-enriched meal comprises mustard seed meal. In a further embodiment, the protein-enriched meal comprises flax seed meal.

In another embodiment of the disclosure, the mixing solvent comprises water or a salt solution. In an embodiment, the salt solution comprises less than 5%, optionally about 3% to about 4%, or 3.5% by weight of salt in solution. In a further embodiment, the mixing solvent comprises water. In another embodiment, the ratio of defatted or protein-enriched meal to the mixing solvent is about 1:3 to about 1:20. In a further embodiment, the ratio is about 1:6 to about 1:10. In an embodiment, the ratio is about 1:6 to about 1:8.

In a further embodiment, the mixture is wet screened resulting in a separation of the fiber from the mixture which contains the protein. In another embodiment of the disclosure, the mesh screen comprises a US mesh screen of size about 20 to about 200 mesh. In an embodiment, the mesh screen is of size 40 US mesh size. In a further embodiment, the mesh screen is a vibratory screen. The mesh screen prevents the fiber from passing through, while the protein in the mixture passes through the screen, resulting in a separation of the fiber from the protein. This results in a mixture of protein which passes through the screen and a fiber fraction which is trapped by the screen. In an embodiment, the fiber fraction is dried and can be used in dietary fiber products. In an embodiment, some protein and carbohydrates are present in the fiber fraction.

In another embodiment, the pH of the mixture is optionally adjusted to about 7 with the addition of aqueous sodium hydroxide. In a further embodiment, the aqueous sodium hydroxide is a solution of about 1% to about 40%, optionally about 5% to about 30%, by weight of sodium hydroxide in water.

In another embodiment, the mixture is optionally milled using a wet milling process. In an embodiment, the wet milling of the mixture results in thorough mixing of the defatted or protein-enriched meal with the mixing solvent.

In another embodiment of the present disclosure, the mixture is centrifuged using a decanting centrifuge. In an embodiment, the mixture is centrifuged with a decanting centrifuge at a speed of about 1000 rpm to about 2000 rpm. In another embodiment, the speed is about 1500 rpm.

In another embodiment, the protein slurry is centrifuged using a disc stack centrifuge to separate insoluble proteins from soluble proteins, forming a protein precipitate and a soluble protein fraction. In an embodiment, the soluble protein fraction is filtered as described above. In an embodiment, the disc centrifuge operates continuously at a speed of about 6500 rpm to about 8500 rpm at a temperature of about 1° C. to about 60° C., optionally about 20° C. to about 40° C., or optionally at about 20° C. to about 25° C.

In an embodiment of the disclosure, the precipitated protein is mixed with water and its pH optionally adjusted for the addition of cellulase complex, in a similar manner as described above. This additional enzymatic step hydrolyzes residual fiber and allows the removal of fiber from the protein precipitate.

In another embodiment, after treatment with the cellulase complex, the protein precipitate is washed at least once with an extraction solvent to remove water-soluble sugar compounds as a result of the fiber hydrolyzation by the cellulase complex. In an embodiment, the extraction solvent is water. In an embodiment, the protein precipitate mixture is washed at least twice with the extraction solvent. In an embodiment, the ratio of extraction solvent to the precipitated protein is about 10:1 to about 1:1, optionally about 4:1 to about 2:1. The mixture is then further centrifuged to obtain a protein precipitate that has been further purified.

In an embodiment, the further purified protein precipitate is then subjected to high pressure jet cooking to obtain a high functional protein isolate having a protein content of greater than about 90% on a dry weight basis. In an embodiment, the jet cooking of the protein isolate occurs at a temperature of about 90° C. to about 120° C. for about 1 second to about 2 minutes, optionally about 3 seconds to about 30 seconds. As will be understood by a person skilled in the art, jet cooking involves the injection of steam into the purified protein, and results in the pasteurization of the protein and improves the functional properties of the protein isolate.

In another embodiment, the further purified protein precipitate is hydrolyzed using proteases to form a hydrolyzed protein extract containing hydrolyzed proteins, peptides and amino acids having a protein content of greater than about 90% on a dry weight basis. In an embodiment, the proteases are, for example, Alcalase® and Flavourzyme®. Alcalase® and Flavourzyme® were obtained from Novozymes North America, Inc., Franklinton, N.C. USA. This step hydrolyzes the protein in the protein precipitate into smaller peptides and amino acids, which are soluble in nutritional drinks and are easily adsorbed. In an embodiment, the purified protein precipitate is mixed with water to form a protein slurry, which is optionally followed by pH adjustment to a pH of about 6.0 to about 10.0, optionally about 7.5 to about 8.5. In an embodiment, the Alcalase® is added in a ratio of about 0.5% based on the dry weight of the protein slurry. In a further embodiment, the temperature is adjusted to about 20° C. to about 65° C., optionally about 50° C. to about 60° C., or about 60° C., for about 1 to about 4 hours. The hydrolyzed protein slurry is then cooled to about 30° C. to about 50° C., or about 40° C. to about 50° C., or about 50° C. The pH of the mixture is then adjusted to a pH of about 5.0 to about 7.0, or about 6.0 to about 7.0, or about 6.5, and a protease to form a hydrolyzed protein extract, such as Flavourzyme®, is then added to the mixture. In an embodiment, the protease to form a hydrolyzed protein extract, such as Flavourzyme®, is added in a ratio of about 0.5% based on the dry weight of the protein slurry. In a further embodiment, the mixture is then heated to a temperature of about 20° C. to about 60° C., optionally about 40° C. to about 60° C., or about 45° C. to about 55° C., for about 1 to about 4 hours. The hydrolyzed protein mixture is then centrifuged to separate the hydrolyzed protein extract from the insoluble solids. The soluble hydrolyzed protein extract is then spray dried as described above, while the extract from the centrifugation is added to the soluble protein fraction as described above.

In another embodiment of the disclosure, there is a provided a process for the production of a protein concentrate from a partially defatted, fully defatted or protein-enriched meal, comprising:
i) mixing the partially defatted, fully defatted or protein-enriched meal with a mixing solvent to form a mixture;
ii) optionally adjusting the pH of the mixture to a pH of about 2.0 to about 10.0;
iii) separating fiber from the mixture to form a protein slurry, wherein the protein slurry comprises a soluble protein fraction and an insoluble protein fraction;
iv) optionally repeating steps i)-iii) by mixing the protein slurry with additional partially defatted, fully defatted or protein-enriched meal;
v) mixing the protein slurry with an extraction solvent to form an extract and a washed insoluble protein fraction;
vi) separating the extract from the washed insoluble protein fraction;
vii) optionally repeating steps v) and vi) at least once; and
viii) desolventizing the washed insoluble protein fraction to form a protein concentrate.

In another embodiment of the disclosure, the ratio of partially defatted, fully defatted or protein-enriched meal to mixing solvent is about 1:3 to about 1:30 (w/w). In another embodiment, the ratio of partially defatted, fully defatted or protein-enriched meal to solvent is about 1:5 to about 1:20 (w/w). In a further embodiment, the ratio is about 1:6 to about 1:12 (w/w). In an embodiment, the ratio is about 1:8 to about 1:10 (w/w).

In a further embodiment of the disclosure, the mixing solvent comprises water or an aqueous solution comprising a polysaccharide, a salt or an alcohol. In an embodiment, the mixing solvent is water. In another embodiment, the polysaccharide is guar gum.

In an embodiment, the pH of the protein slurry is adjusted to a pH of about 6.5 to about 10.0. In a further embodiment, the pH of the protein slurry is adjusted to a pH of about 7.0 to about 9.0.

In an embodiment, the mixture is centrifuged to separate the fiber from mixture and form the protein slurry. In an embodiment, the mixture is centrifuged at a speed of about 1,000 rpm to about 2,000 rpm. In a further embodiment, the mixture is centrifuged at a speed of about 1,400 to about 1,600 rpm. In an embodiment, the mixture is centrifuged using a decanter centrifuge.

The centrifugation of the mixture results in three layers: i) an insoluble fiber layer and a protein slurry on top of the fiber, which was comprised of ii) an insoluble protein fraction and iii) a soluble protein fraction. Separation of the top and middle layers (the soluble protein extract and the insoluble fine protein fraction) from the bottom layer (coarse fiber solids), resulted in the protein slurry with fiber removed. In an embodiment, the bird decanter was operated at a low pool depth with a bowl speed of between about 1,000 rpm and about 2,000 rpm, optionally 1,400 to about 1,600 rpm, suitably about 1,500 rpm. It was determined that when the speed of the centrifugation is too high, for example at 5,000 rpm, the insoluble protein fraction settles with the fiber. If the speed of the centrifugation is too low, fiber will remain in the protein slurry. Accordingly, in an embodiment, when the speed of the centrifugation is between about 1,000 rpm and about 2,000 rpm, optionally 1,400 to about 1,600 rpm, suitably about 1,500 rpm, the fiber in the mixture is separated from both the soluble and insoluble protein.

In another embodiment of the disclosure, mixing the protein slurry with additional partially defatted, fully defatted or protein-enriched meal is repeated at least once. In a further embodiment, mixing the protein slurry with additional partially defatted, fully defatted or protein-enriched meal is repeated at least two to seven times. In an embodiment, recycling the protein slurry with additional partially defatted, fully defatted or protein-enriched meal increases the solid content of the meal being processed, and accordingly, reduces the overall processing volume.

In an embodiment of the disclosure, the extraction solvent comprises water, methanol, ethanol, isopropanol, or mixtures thereof. In an embodiment, the extraction solvent comprises ethanol. In another embodiment, the extraction solvent comprises at least about 50% ethanol. In an embodiment, the extraction solvent comprises at least about 70% ethanol. In a further embodiment, the extraction solvent comprises at least about 90% ethanol.

In a further embodiment, the extract is separated from the washed insoluble protein fraction using centrifugation, vacuum filtration, pressure filtration, decantation or gravity draining. In an embodiment, the extract is separated from the washed insoluble protein fraction using centrifugation.

In another embodiment of the disclosure, wherein steps iv) and v) are repeated at least twice.

In a further embodiment, the process further comprises the step of drying the washed insoluble protein fraction to form the protein concentrate. In an embodiment, the protein concentrate is dried in a vacuum dryer, fluidized bed dryer, hot air dryer ring dryer or spray dryer.

In an embodiment of the disclosure, the partially defatted, fully defatted or protein-enriched meal comprises a canola, rapeseed, mustard seed, broccoli seed, flax seed, cotton seed, hemp seed, safflower seed, sesame seed or soybean meal. In another embodiment, the partially defatted, fully defatted or protein-enriched meal comprises a canola meal.

In an embodiment, the protein concentrate comprises a protein content of about 65% to about 90% on a dry weight basis.

In another embodiment of the disclosure, there is also provided a process for the production of a protein isolate from a partially defatted, fully defatted or protein enriched meal, comprising:
i) mixing the partially defatted, fully defatted or protein-enriched meal with alkaline water to form a mixture;
ii) optionally adjusting the pH of the mixture to a pH of about 6.0 to about 10.0;
iii) separating fiber from the mixture to form a first protein slurry, wherein the first protein slurry comprises a soluble protein fraction and an insoluble protein fraction;
iv) separating the first protein slurry to form a protein solids fraction and a soluble protein fraction;
v) mixing the protein solids fraction with water to form a second protein slurry;
vi) separating the second protein slurry to form a second protein solids fraction and a second soluble protein fraction;
vii) optionally repeating steps v) and vi) at least once;
viii) separating the soluble protein fractions to form a clarified soluble protein fraction and a residual insoluble protein fraction;
ix) optionally adjusting the pH of the clarified soluble protein fraction to a pH of about 7;
x) separating the clarified soluble protein fraction, optionally by filtering the clarified soluble protein fraction by membrane filtration; and
xi) optionally drying the clarified soluble protein fraction.

In another embodiment of the disclosure, the ratio of partially defatted, fully defatted or protein-enriched meal to alkaline water is about 1:3 to about 1:30 (w/w). In another embodiment, the ratio of partially defatted, fully defatted or protein-enriched meal to alkaline water is about 1:5 to about 1:20 (w/w). In a further embodiment, the ratio is about 1:6 to about 1:12 (w/w). In an embodiment, the ratio is about 1:8 to about 1:10 (w/w).

In an embodiment of the disclosure, the pH of the alkaline water is about 7 to about 12. In another embodiment, the pH of the first protein slurry is adjusted to about 8.0 to about 9.5. In a further embodiment, the pH of the first protein slurry is adjusted to about 8.5 to about 9.0.

In an embodiment, the mixture is centrifuged to separate the fiber from the protein slurry and form the protein extract. In an embodiment, the mixture is centrifuged at a speed of about 1,000 rpm to about 2,000 rpm. In a further embodiment, the mixture is centrifuged at a speed of about 1,400 to about 1,600 rpm. In an embodiment, the mixture is centrifuged using a decanter centrifuge.

In another embodiment, the first protein slurry is centrifuged to separate the protein solids fraction from the soluble protein fraction. In a further embodiment, the first protein slurry is centrifuged at a speed of about 4,000 rpm to about 8,500 rpm. In a further embodiment, the first protein slurry is centrifuged at a speed of about 5,000 to about 8,500 rpm.

In another embodiment of the disclosure, the ratio of the protein solids fraction to water is about 1.0:0.5 to about 1.0:3.0 (w/w). In a further embodiment, the ratio of the protein solids fraction to water is about 1.0:1.0 to about 1.0:2.0 (w/w).

In an embodiment, the soluble protein fractions are centrifuged to form the clarified soluble protein fraction and the residual insoluble protein fraction. In an embodiment, the soluble protein fractions are centrifuged using a disc stack centrifuge at a speed of about 7,000 rpm to about 10,000 rpm. In a further embodiment, the soluble protein fractions are centrifuged using a disc stack centrifuge at a speed of about 8,400 rpm to about 8,600 rpm.

In another embodiment of the disclosure, the pH of the clarified soluble protein fraction is adjusted with alkali. In a further embodiment, the pH of the clarified soluble protein fraction is adjusted with sodium hydroxide.

In an embodiment, the clarified soluble protein fraction is filtered using an ultrafiltration apparatus. In a further embodiment, the ultrafiltration apparatus comprises a membrane to filter proteins larger than about 10,000 daltons. In another embodiment, the separation of the clarified soluble protein fraction is accomplished by adjusting the pH of the solution to the isoelectric point of the proteins (about pH of 4.5), and consequently, the proteins are precipitated out of solution. In another embodiment, the proteins are cooked to precipitate the proteins from solution.

In another embodiment of the disclosure, the process further comprises the step of filtering the clarified soluble protein fraction using a diafiltration apparatus.

In another embodiment, the clarified soluble protein fraction is dried in a vacuum dryer, fluidized bed dryer, freeze dryer, ring dryer or spray dryer to form the protein isolate.

In an embodiment of the disclosure, the partially defatted, fully defatted or protein-enriched meal comprises a canola, rapeseed, mustard seed, broccoli seed, flax seed, cotton seed, hemp seed, safflower seed, sesame seed or soybean meal. In another embodiment, the partially defatted, fully defatted or protein-enriched meal comprises a canola meal.

In another embodiment of the disclosure, the protein concentrate comprises a protein content of greater than about 90% on a dry weight basis.

In another embodiment of the disclosure, there is also provided a process for the production of a hydrolyzed protein concentrate from a partially defatted, fully defatted or protein-enriched meal, comprising:
i) mixing the partially defatted, fully defatted or protein-enriched meal with water to form a mixture;
ii) optionally adjusting the pH of the mixture to a pH of about 6.0 to about 10.0;
iii) separating the mixture to remove fiber from the mixture and form a first protein slurry, wherein the first protein slurry comprises a soluble protein fraction and an insoluble protein fraction;
iv) optionally adjusting the pH of the first protein slurry to a pH of about 7.0;
v) separating the first protein slurry to form a first protein solids fraction and a first soluble protein fraction;
vi) mixing the first protein solids fraction with water to form a second protein slurry;
vii) separating the second protein slurry to form a second protein solids fraction and a second soluble protein fraction;
viii) mixing the second protein solids fraction with water to form a third protein slurry;
ix) adjusting the pH of the third protein slurry to a pH of about 7.0 to about 9.0;
x) mixing the third protein slurry with at least one protease to form a hydrolyzed protein extract;
xi) separating the hydrolyzed protein extract from the third protein slurry to form the hydrolyzed protein concentrate.

In another embodiment of the disclosure, the ratio of partially defatted, fully defatted or protein-enriched meal to water is about 1:3 to about 1:30 (w/w). In another embodiment, the ratio of partially defatted, fully defatted or protein-enriched meal to water is about 1:5 to about 1:20 (w/w). In a further embodiment, the ratio is about 1:6 to about 1:12 (w/w). In an embodiment, the ratio is about 1:8 to about 1:10 (w/w).

In another embodiment, the pH of the mixture is adjusted to about 8.0 to about 9.0. In a further embodiment, the pH of the mixture is adjusted to about 8.5 to about 9.0.

In an embodiment, the mixture is centrifuged to separate the fiber from the protein slurry and form the protein extract. In an embodiment, the mixture is centrifuged at a speed of about 1,000 rpm to about 2,000 rpm. In a further embodiment, the mixture is centrifuged centrifuge at a speed of about 1,400 to about 1,600 rpm. In an embodiment, the mixture is centrifuged using a decanter centrifuge.

In another embodiment, the first protein slurry is centrifuged to separate the protein solids fraction from the soluble protein fraction. In a further embodiment, the first protein slurry is centrifuged at a speed of about 4,000 rpm to about 8,000 rpm. In a further embodiment, the first protein slurry is centrifuged at a speed of about 5,000 to about 8,500 rpm.

In another embodiment, the ratio of the first and second protein solids fraction to water is about 1.0:0.5 to about 1.0:3.0 (w/w). In a further embodiment, the ratio of the first and second protein solids fraction to water is about 1.0:1.0 to about 1.0:2.0 (w/w).

In another embodiment of the disclosure, the pH of the third protein slurry is adjusted to about 8.0 to about 8.5.

In an embodiment of the disclosure, the ratio of the third protein slurry to the protease is about 100:1 to about 5000:1 (w/w).

In an embodiment of the disclosure, the third protein slurry is mixed with a protease at a temperature of about 50° C. to about 70° C. In another embodiment, the third protein slurry is mixed with a protease at a temperature of about 55 to about 65° C.

In another embodiment, the at least one protease comprises a protease from *Bacillus Licheniformis*.

In a further embodiment, the process further comprises the step of mixing the third protein slurry with a second protease.

In an embodiment, the ratio of the third protein slurry to the second protease is about 100:1 to about 5000:1 (w/w).

In another embodiment, the third protein slurry is mixed with the second protease at a temperature of about 40° C. to about 60° C. In an embodiment, the third protein slurry is mixed with the second protease at a temperature of about 45° C. to about 55° C.

In a further embodiment, the second protease comprises a fungal protease/peptidase complex from *Aspergillus oryzae*.

In an embodiment, the hydrolyzed protein extract is separated using a centrifuge. In a further embodiment, the hydrolyzed protein extract is separated using a decanter centrifuge at a speed of about 3,800 to about 5,200 rpm.

In another embodiment, the clarified soluble protein fraction is dried in a vacuum dryer, fluidized bed dryer, ring dryer or spray dryer to form the protein isolate.

In an embodiment of the disclosure, the partially defatted, fully defatted or protein-enriched meal comprises a canola, rapeseed, mustard seed, broccoli seed, flax seed, cotton seed, hemp seed, safflower seed, sesame seed or soybean meal. In another embodiment, the partially defatted, fully defatted or protein-enriched meal comprises a canola meal.

In a further embodiment, the hydrolyzed protein concentrate comprises a protein content of greater than about 70% on a dry weight basis.

In an embodiment, the use of an extraction solvent, such as ethanol, leads to a protein concentrate or protein isolate having superior organoleptic properties, as well as superior protein solubility properties, which therefore possesses better functional properties. In an embodiment, the use of an extraction solvent, such as ethanol, results in the protein concentrates containing fewer impurities. Consequently, the protein concentrates are generally of higher quality and have better functional properties.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

The following non-limiting examples are illustrative of embodiments of the present disclosure:

EXAMPLES

Reagents and Materials

Canola seeds (*Brassica juncea* and *Brassica napus*) were obtained from Viterra, North Battleford, Saskatchewan, Canada. Commercial methyl pentane was purchased from Univar Canada Ltd., Saskatoon, Saskatchewan, Canada. Enzyme samples of Cellulase (Celluclast® 1.5 L), Cellulase Complex, Alcalase® 2.4 L FG, and Flavourzyme® were obtained from Novozymes North America, Inc., Franklinton, N.C. USA. Pea protein isolate was obtained from Roquette America, Inc., Keokuk, Iowa, USA. Soy protein isolate was obtained from Protient, ABF Ingredients Company, St. Paul, Minn., USA Analysis Mixing of the materials was performed using a Ribbon Blender (Torco Model R-12, Toronto Coppersmithing International Ltd., Scarborough, Ontario, Canada). Heat treatments of seed samples were conducted using an Infra Red Cereal Processing System (Micronizing Company Limited, Framlingham, Sulfolk, England) or a two-tray Simon-Rosedown cooker (Laboratory cooker-press, Simon-Rosedowns Limited, Hull, England). Pressing of the oil seeds is performed using a Gusta Laboratory Screw Press. Ultrafiltration was carried out using a Millipore® Ultrafiltration Unit (Model A60, Millipore® Corporation, Bedford, Mass., USA). Protein content of the samples was determined by the Leco® Protein Analyzer (Model FP-428, Leco® Corporation, ST. Joseph, Mich. U.S.A.) based on AOCS Official Method Ba 4e-93. Moisture content of the samples was determined by drying samples in a 105±2° C. convection oven for 16 hours or to a constant weight based on AOCS Official Method Ba 2a-38. Oil content of the samples was determined based on AOCS Official Method Ba 3-38 with the following changes: (a) 2 g of sample was used instead of 5 g in the analysis; (b) extraction continued for 4 hours, and (c) extraction flask was heated to remove residual petroleum ethers. Ash content of the samples was determined based on AOCS Official Method Ba 5a-49 with the following changes: (a) samples were pre-washed on a hot plate prior to being placed into the muffle furnace; (b) samples were incinerated for 18 hours in muffle furnace; and (c) nitric acid was added if sample remained black. Crude fiber content of the samples was determined based on AOCS Official Method Ba 6-84 with the following changes: (a) samples with oil contents below 3% were not defatted and (b) digest was dried for 2 hours at 130° C. Protein dispersibility index (PDI) of the samples was determined based on A.O.C.S. Official Method Ba 10-65. Free fatty acid (FFA) of the oil samples was determined based on AOCS Official Method Ca 5a-40. Phosphorus and sulphur of the samples were determined based on the modified methods of AOCS Ca20-99 and AOCS Ca 17-01 (modified), respectively. Crude fiber content of the samples was determined based on AOCS Official Method Ba 6-84 with the following changes: (a) samples with oil contents below 3% were not defatted and (b) digest was dried for 2 hours at 130° C. Protein dispersibility index (PDI) of the samples was determined based on A.O.C.S. Official Method Ba 10-65. Glucosinolate content of the samples was determined based on the Method of the Canadian Grain Commission, Grain Research Laboratory (Daun, J. K. and McGregor, D. I., Glucosinolate Analysis of Rapeseed (Canola), Dec. 15, 1981). Solvent residues were determined using GC/MS techniques based on a modified method of A.O.C.S. Official Method, Ba 13-87.

Example 1(a)

Effect of Heat Treatment on Canola Seed (*Brassica juncea*) at Temperatures Between 75° C.-95° C.

Seven samples containing about 4 kg of canola seed (28 kg in total) were adjusted from an original moisture content of about 6.25% to about 11% by adding water to the canola seed in a plastic pail with manual agitation for a few minutes. The canola seed in the pails was then covered and tempered overnight in the laboratory.

After the canola seed had been tempered overnight, six samples containing about 4 kg of the tempered seed (about 24 kg in total) were subjected to individual heat treatments with a combination of high temperatures and short residence times using a lab scale as listed in Table 1. For control, a control sample (about 4 kg) of canola seed was heated in a microwave oven for 2 minutes (heat to 85-95° C.). The canola seed was then covered with an aluminum foil and heated at 95° C. in a forced air oven for 30 minutes (Table 1).

After heat treatment, seven samples (about 4 kg each) of the heat treated canola seeds were flaked using a lab flaking mill and then pressed, resulting in pressed oils and pressed protein cakes. The pressed oils were analyzed for sulfur and free fatty acid (FFA) contents. The pressed cakes were stored in a freezer.

Seven samples (about 1 kg each) of the pressed cakes from the six heat treatment trials and one control were extracted using a solvent mixture of butane and R-134a (1,1,1,2-tetrafluoroethane) to produce extracted oils and defatted canola meals. The press cake was loaded in a column and the solvent mixture under 300 PSI pressure flows through the press cake and fluidizes the press cake particles. The oil was extracted from the cake at 50° C. The solvent mixture with oil in a liquid form was pumped to a low pressure zone and the pressure was released. The solvent mixture turns into gas while the oil remains in a liquid state for the separation of oil from the solvent mixture. The defatted canola meals were analyzed for protein dispersibility index (PDI), the results of which are shown in Table 3. The extracted oil samples were analyzed for sulfur, phosphorus and FFA contents, the results of which are shown in Tables 4-6.

The remaining pressed cakes were extracted with methyl pentane for five hours using a lab Soxhlet system. Approximately 6-8 L of fresh methyl pentane were required for each extraction lot. The extracted oil was recovered by evaporation and desolventization to remove the solvent from the miscella under vacuum at 60° C. The extracted oil was analyzed for sulfur, phosphorus and FFA contents. The methyl pentane extracted meals were desolventized in a laboratory fume hood for three days at room temperature. The moisture and oil contents of the pressed cake are shown in Table 7.

Example 1(b)

Effect of Heat Treatment on Canola Seed (*Brassica juncea*) at Temperatures Between 100° C.-130° C.

Five samples containing about 4 kg (about 20 kg in total) of canola seed were adjusted from an original moisture content of about 6.25% to about 11% by adding water to the canola seed in a plastic pail with manual agitation for a few minutes. The canola seed in the pails was then covered and tempered overnight in the laboratory.

After the canola seed had been tempered overnight, five samples containing about 4 kg of the tempered seed (about 20 kg in total) were subjected to individual heat treatments with a combination of high temperatures and short residence times using a lab scale as listed in Table 2. After heat treatment, the five samples (about 4 kg each) of the heat treated canola seeds were flaked using a lab flaking mill, and then pressed. The pressed oils were analyzed for sulfur, phosphorus and FFA contents. The pressed cakes were stored in a freezer.

Five samples (about 1.5 kg each) of the pressed cakes from the five heat treatment trials were extracted using a solvent mixture of butane and R-134a (1,1,1,2-tetrafluoroethane) to produce extracted oils and defatted canola meals. The extracted oils were analyzed for sulfur and FFA contents. The defatted canola meals were analyzed for protein dispersibility index (PDI).

Discussion

In the heat treatment process, rapid heating makes it possible to expose the canola seed to an increased temperature very quickly and thus to inactivate the enzymes (e.g. myosinase, lipase, phospholipase, etc.) This is a more economical way for consistent inactivation of enzymes without loss of lysine or other heat sensitive amino acids.

As shown in Table 3, the increase in the heat treatment temperature from 75° C. to 100° C. resulted in the gradual decrease in the PDI of the defatted meal. The decrease in PDI of the defatted meal accelerated when the temperature was increased from 105° C. to 130° C. The sharp drop in PDI occurred when the temperature was above 110° C. Typically, the higher the heat treatment temperature, the higher the percentage of protein molecules being denatured and thus the lower the PDI of the defatted meal.

The sulphur content in the pressed oil from canola seed without heat treatment was 46.9 ppm, which decreased sharply to 21.5 ppm and 9.77 ppm with heat treatment at 75° C. and 80° C. for 15 seconds, respectively. Heat treatment at higher temperatures from 80° C. to 130° C. did not have any major effect on the sulphur content in the pressed oil (as shown in Table 4).

The sulphur in the butane/R134a extracted oil decreased from the level of 303 ppm without heat treatment to 99.3 ppm at 75° C. and 101 ppm at 80° C. The sulphur level showed continuous reduction with increase in the temperature of heat treatment except at 85° C.

The sulphur content in the methyl pentane extracted crude oil decreased continuously in relation to the increase in temperature from 222 ppm at 75° C. to 34.5 ppm at 95° C. Methyl pentane extracted oil had higher sulphur levels at 75° C. and 80° C., but lower at 85-95° C. as compared with butane/R134a extracted oils.

The sulphur content in the pressed oil, the butane/R134a and methyl pentane extracted oils of the control samples were high. In the heat treatment of the control samples, the canola seed was covered using an aluminum foil and heated at 95° C. in a forced air oven for 0.5 hour. Because the heat transfer efficiency is low, the temperature of the seed in the oven might have been lower than 95° C. even though the oven temperature was set at that temperature. Therefore, myrosinase was still mostly active, causing the breakdown of glucosinolates and release of the sulphur into the pressed and extracted oils.

The free fatty acid in the pressed oil decreased slightly with the increase in the heat treatment temperature from 75° C. to 95° C. (as shown in Table 5). A sharp drop in FFA occurred at 100° C. and FFA showed little change from 100-130° C. The FFA in the butane/R134a extracted oil showed significant decrease with the increase in temperature from 75-100° C., however a further increase in temperature gained little benefit for the reduction in FFA (Table 5). The FFA in methyl pentane extracted oil also decreased with the increase in temperature from 75 to 95° C. The increase in heat treatment temperature enhanced the degree of inactivation of lipase, which in return reduced the hydrolysis of oil by lipase and thus reduced the FFA content.

The FFA content in the oil is mainly dependent on the quality of seed. Improper handling or storage can cause elevated levels of FFA.

The phosphorus content of butane/R134a extracted oil was very low ranging from 2.93 ppm at 75° C. to 22.8 ppm at 95° C. as listed in seen in Table 6. The phosphorus content of the pressed oil was also low at heat treatment temperatures of 100, 105, 110, and 130° C. The phosphorus content of pressed oil from the heat treatment of 120° C. was 117 ppm.

The selection of a heat treatment temperature is a compromise between the opposing effects on oil quality, meal quality and economics. Accordingly, in an embodiment, a heat treatment temperature of 100° C. results in a reasonably high PDI, lower sulphur, FFA and phosphorus in pressed and butane/R134a extracted oils.

Heat treatment of canola seed above 80° C. reduced the sulphur content in pressed oil to levels below 10 ppm. The pressed oil accounted for about 50-60% of total crude oil from the crushing operation. The heat treatment of canola seed reduced the sulphur content of butane/R134a and methyl pentane extracted oils substantially with an increase in temperature. The high sulphur in the extracted oil is related to high glucosinolates content in the canola seed. The canola seed (*B. juncea*) contained about 22.95 μmoles/g of glucosinolates on a dry weight basis. If canola seed with a glucosinolate content of 12 μmoles/g or lower is used, the sulphur content in the extracted oil can be reduced further using the same heat treatment condition.

For a heat treatment of 100° C. for 15 seconds, the phosphorus content in the pressed and butane/R134a extracted oils was below 50 ppm.

Example 2

Protein Concentrate of about 65% Protein (a) Defatted Meal

Approximately 4 kg of canola seed (*B. juncea*) was adjusted from the original 6.25% moisture to 11% moisture by adding water to canola seed in a plastic pail with manual agitation for a few minutes. The canola seed in the pail was then covered and tempered overnight in the laboratory. The tempered canola seed was then heat treated at 100° C. for 15 seconds.

After heat treatment, the canola seed was flaked using a lab flaking mill and then pressed. The pressed cake was stored in a freezer before solvent extraction. The pressed oil was recovered and stored in a freezer. The pressed cake was extracted with 6-8 liters of methyl pentane at about 58-67° C. for 5 hours using a lab scale Soxhlet system. The extracted oil was recovered by evaporation and desolventization to remove the solvent from the miscella under vacuum at 60° C. The extracted oil was stored in a freezer. The methyl pentane extracted meal or defatted meal was desolventized in a laboratory fume hood for three days at ambient temperature. Approximately 2 kg of defatted meal was produced and stored at ambient temperature before further evaluation.

(b) Protein Enriched Meal

Approximately 2 kg of defatted meal was ground using a coffee grinder for 15-20 seconds. The ground meal was screened through a 60 US mesh screen. Approximately 0.94 kg of fine meal (protein-enriched meal) and 1.06 kg of coarse meal (fiber enriched meal) were obtained.

(c) 65% Protein Concentrate

Approximately 0.94 kg of protein-enriched meal was extracted by mixing with 5.64 kg of 65% (v/v) ethanol at ambient temperature for 1 hour. The mixture was centrifuged at 4,000 g force for 15 minutes to separate the liquid sugar extract from the protein solids using a lab centrifuge. The sugar extracts were combined together and concentrated using a lab Buchi Rotavapor at 80° C., which was followed by freeze drying of the concentrated sugar extract using a lab freeze dryer. The washed protein-enriched meal was desolventized in a lab fume hood, which was followed by drying in a lab forced air oven. Approximately 0.67 kg of protein concentrate containing 65% protein on a dry weight basis and 0.21 kg of dried sugar fraction were produced, respectively. The analysis of the defatted meal, protein-enriched meal and 65% protein concentrate are shown in Table 8.

Example 3

Protein Concentrate of about 70% Protein (a) Ethanol Washing and Screening

The process for preparation of the protein-enriched meal was the same as in Example 2 except for (1) canola seed was cooked at 80° C. for 25 minutes before pressing, and (2) the defatted meal was milled using a disc mill before screening through a 60 US mesh screen as described below.

Approximately 1 kg of protein-enriched meal was mixed under homogeneous agitation with 6 kg of 80% (v/v) ethanol at 50° C.±5° C. for 1 hour, which was followed by screening the mixture through a 40 mesh US screen to remove fiber. The screened mixture was centrifuged at 4,000 g force using a lab centrifuge for 15 minutes to separate the sugar extract from the protein solids. The protein-solids were mixed under homogeneous agitation with 6 kg of 80% (v/v) ethanol at 50° C.±5° C. for 0.5 hour. The washed protein solids was separated from the sugar extract by centrifugation at 4,000 g force for 0.5 hour. The protein solids were again washed 6 kg of 80% (v/v) ethanol for at 50° C.±5° C. 0.5 hour, which was followed by centrifugation at 4,000 g force for 15 minutes. Finally the washed protein solids were dried to give a protein concentrate containing 70% protein on a dry weight basis. The ethanol was recovered from the combined sugar extract through evaporation under vacuum at 80° C. using a lab Buchi Rotavapor. The concentrated sugar extract was spray dried into a dried sugar sample.

Example 4

Canola Protein Concentrate having About 65-70% Protein Content

Three samples of a protein concentrate from *Brassica juncea* were prepared in the following manners (the processing conditions for Samples 1-3 are compared in Table 13):

(1) Sample 1—Moisture Adjustment

Approximately 2,919 kg of canola seed was adjusted from the original about 6.25% moisture content to about 11% moisture by adding 54 kg of water to the canola seed under mixing. The moisture adjustment and mixing were executed as 14 batches due to the capacity constraint of the Ribbon Blender (Table 9). After the moisture adjustment, the canola seed was stored in bins, covered and tempered overnight before pressing.

Pressing

The tempered canola seed was divided into two portions, (i) 300.5 kg of seed for pressing trial without flaking and (ii) the remainder of the tempered seed (2,676 kg) for flaking and pressing.

Approximately 300.5 kg of tempered seed was heat treated using a two-tray cooker. The temperature of the top tray was 50-72° C., while the temperature for the bottom tray was 75-96° C. The resident time for top and bottom trays was 20 minutes, respectively. After heat treatment, the seed was fed into the press and was pressed to produce 181.6 kg of press cake (Sample 1a). Press cake is a term that is synonymous with seed cake.

Approximately 2,676 kg of tempered seed was flaked to produce flaked canola seed with an average thickness of 0.3±0.1 mm using a flaking mill. The flaked canola seed was heat treated using a two-tray cooker. The temperature for the top tray was 50-72° C., while the temperature for the bottom tray was 75-96° C. The resident time for the top and bottom trays was 20 minutes, respectively. After heat treatment, the flaked seed was fed into the press and was pressed to produce 1,566 kg of press cake (Sample 1b). Approximately 945 kg of press oil was produced from the pressing trials of non-flaked and flaked seeds. Approximately 42.9 kg of fine particles (foots) was produced in the pressing trials. Approximately 85.3 kg of canola seed was lost as floor sweeps, which are waste materials that drop on the floor.

Solvent Extraction

Approximately (i) 181.6 kg and (ii) 1,566 kg of press cakes from non-flaked and flaked canola seeds were extracted using a solvent mixture of butane/R124a to produce extracted (defatted) canola meals from the non-flaked press cake (Sample 1c) and the flaked press cake (Sample 1d), in addition to extracted oils. The solvent extraction of the press cakes was conducted at 50° C. for 1.5 hours.

As shown in Tables 10, 11 and 14, the press cake (Sample 1a) from the non-flaking trial contained a high crude oil content of 26.81-32.37% on a dry weight basis.

Milling and Screening

Approximately 1,231 kg of extracted (defatted) meal (Sample 1d) was produced from 1,566 kg of flaked press cake through solvent extraction at 50° C. for 1.5 hours using a solvent mixture of butane and R134a. The extracted meal was milled using a disc mill equipped with #8114 stationary and rotating plates (The Bauer Bros. Co., Springfield, Ohio, U.S.A.) at 0.02" gap, 2340 rpm rotational speed and 200 kg/hr throughput. Only one pass through the disc mill was conducted. Approximately 1,142 kg of milled canola meal was produced. Approximately 88.9 kg of material was lost in the milling operation with a recovery yield of 92.78%. The milled canola meal was screened through a 43-45 US mesh screen using the Rotex® Vibratory Screen (from Rotex®, OH, USA) at a feed rate of 200 kg/hr. Only one pass through the screen was conducted. Approximately 423.66 kg of protein enriched meal (fine fraction) and 717.00 kg of fiber enriched meal (coarse fraction) were produced, respectively. Approximately 1.64 kg of material was lost in the screening operation with a recovery yield of 99.86%. After screening, 37.14% of the total material was protein enriched meal (Sample 1e) and 62.86% was fiber enriched meal (Sample 1f), respectively, as seen in Table 12.

Preparation of Protein Concentrate from Protein Enriched Meal

Approximately 412 kg of protein enriched meal containing 6.90% moisture and 53.92% protein (dwb) was mixed with about 2,400 kg of 80% ethanol (v/v) in two 2600 L stainless steel tanks under homogeneous agitation at room temperature for 1 hour. After extraction, the protein slurry was centrifuged continuously using a decanter centrifuge (Model CA220-21-33, Wesffalia® Separator, GEA Wesffalia Separator® Inc., Northvale, N.J., USA) to separate insoluble protein solids from the sugar extract. The protein solids were mixed with 2,400 kg of 80% ethanol (v/v) under homogeneous agitation at room temperature for 1 hour, which was followed by centrifugation of the protein slurry using the decanter to separate the washed protein solids from the washing sugar extract. Finally, the washed protein solids were mixed with 2,400 kg of 80% ethanol (v/v) under homogeneous agitation at room temperature for 1 hour. The protein slurry was centrifuged using the decanter to separate the final washed protein solids from the washing sugar extract. The final washed protein solids were desolventized and dried at 54±3° C. for 18 hours in a Littleford® vacuum dryer (Littleford Day®, Inc., Florence, Ky., USA) until the moisture content of the dried solids reached 5±1%. The desolventized and dried protein solids were milled using a Fitz mill fitted with a 0.033" screen (The Fitzpatrick Co., Elmhurst, Ill., U.S.A.). The milled protein solids were screened using a Rotex Vibratory Screen (Model 111 A-MS/MS, Rotex Inc., Cincinnati, Ohio, U.S.A.) fitted with a 43-45 US mesh screen (POS #54 screen). Approximately 248.3 kg of protein concentrate containing (Sample 1g) 65.80% protein (dwb) and 5.51% moisture was produced.

(2) Sample 2—Preparation of Defatted Meal

Approximately 4.5 kg of extracted (defatted) canola meal (Sample 2a) was produced from non-flaked press cake through extraction using a solvent mixture of butane and R134a at 50° C. for 2 hours. The non-flaked press cake was produced from canola seed (*B. juncea*) by heat treatment of canola seed at 80° C. for 0.5 hour before pressing in a French Oil Machinery press.

Milling and Screening

Approximately 3.5 kg the defatted meal (Sample 2a) was milled for 1 minute using a lab Waring® Blender, which was followed by manual screening using a 45 US mesh Rotex screen to generate a protein fraction (fine fraction) and a coarse fraction. The coarse fraction was re-milled in the lab Warring Blender for 1 minute. This was followed by manual screening using the 45 US mesh Rotex screen to generate the $2^{nd}$ protein fraction and a coarse fraction. Finally, the coarse fraction was milled in the Warring Blender for 1 minute and the milled material was manually screened using the 45 US mesh Rotex screen to generate the $3^{rd}$ protein fraction and the fiber enriched meal. Approximately, 1.5 kg of combined $1^{st}$, $2^{nd}$ and $3^{rd}$ protein fractions and 2 kg of fiber enriched meal were produced, respectively. Therefore, 42.85% of the total material was the protein enriched meal (Sample 2b) and 57.15% was the fiber enriched meal (Sample 2c), as seen in Table 12.

Preparation of Protein Concentrate from Protein Enriched Meal

Approximately 1.5 kg of protein enriched meal containing 6.16% moisture and 54.77% protein (dwb) was mixed with 9 kg of 80% ethanol (v/v) in a stainless steel pot under homogeneous agitation using an over head stirrer at room temperature for 1 hour. After extraction the slurry was centrifuged batch wise at 4,414 g (4,000 rpm) for 10 minutes to separate insoluble protein solids from the sugar extract. For a second extraction, the protein solids were mixed with 9 kg of 80% ethanol (v/v) under homogeneous agitation at room temperature for 1 hour, which was followed by centrifugation of the protein slurry at 4,414 g (4,000 rpm) for 10 minutes to separate the washed protein solids from the washing sugar extract. Finally, the washed protein solids were extracted for a $3^{rd}$ time with 9 kg of 80% ethanol (v/v) under homogeneous agitation at room temperature for 1 hour. The protein slurry was centrifuged at 4,414 g (4,000 rpm) for 10 minutes to separate the final washed protein solids from the washing sugar extract. The final washed protein solids were desolventized and dried in a lab fume hood for over 3 days, which was followed by drying in a forced air oven at 50° C. for 15 hours to reduce the ethanol residue. The desolventized and dried protein solids were milled twice using a lab pin mill. Approximately 1.1 kg of protein concentrate (Sample 2d) containing 68.69% protein (dwb) and 5.52% moisture was produced.

(3) Sample 3—Preparation of Defatted Meal

Approximately 13.1 kg of defatted canola meal (Sample 3a) was produced from non-flaked press cake through extraction using a solvent mixture of butane and R134a at 50° C. for 1.5 hours. The non-flaked press cake was produced from canola seed (*B. juncea*) by heat treatment of canola seed at 80° C. for 0.5 hour before pressing in a French Oil Machinery press.

Milling and Screening

Approximately 13.1 kg of the defatted meal (Sample 3a) was milled using a disc mill equipped with #8114 stationary and rotating plates (The Bauer Bros. Co., Springfield, Ohio, U.S.A.) at 0.02" gap and a speed of 1150 rpm for the rotating plate. The milled meal was screened using a Rotex Vibratory Screen (Model 111 A-MS/MS, Rotex Inc., Cincinnati, Ohio, U.S.A.) fitted with a 43-45 US mesh screen (POS #54 screen) to generate 4.1 kg of protein enriched meal (fine fraction) and 8.8 kg of coarse fraction. The coarse fraction was fed to the disc mill at 0.015" gap stationary and rotating plates of #8114 and a speed of 1150 rpm for the rotating plate. The milled coarse fraction was screened using a Rotex Vibratory Screen fitted with a 43-45 US mesh screen (POS #54 screen) to generate 1.1 kg of protein enriched meal (fine fraction) and 7.7 kg of fiber enriched meal. After screening, 40.31% of the total material was protein enriched meal (Sample 3b) while 59.69% was fiber enriched meal (Sample 3c) (see Table 12).

Preparation of Protein Concentrate from Protein Enriched Meal

Approximately 3.9 kg of protein enriched meal containing 6.5% moisture and 52.62% protein (dwb) was mixed with 23.4 kg of 80% ethanol (v/v) in a stainless steel pot under homogeneous agitation using an over head stirrer at room temperature for 1 hour. After extraction the slurry was centrifuged batch wise at 4,414 g (4,000 rpm) for 10 minutes to separate the insoluble protein solids from the sugar extract. The protein solids were mixed with 23.4 kg of 80% ethanol (v/v) under homogeneous agitation at room temperature for 1 hour, which was followed by centrifugation of the protein slurry at 4,414 g (4,000 rpm) for 10 minutes to separate washed protein solids from the washing sugar extract. Finally, the washed protein solids were extracted for a $3^{rd}$ time with 23.4 kg of 80% ethanol (v/v) under homogeneous agitation at room temperature for 1 hour. The protein slurry was centrifuged at 4,414 g (4,000 rpm) for 10 minutes to separate the final washed protein solids from the washing sugar extract. The final washed protein solids were desolventized and dried in a lab fume hood for over 3 days. The desolventized and dried protein solids were milled using a lab hammer milled fitted with a 14 US mesh screen, which was followed by further milling through a lab pin mill twice. The milled protein solids were manually screened using a lab Rotex screen fitted with a 60 US mesh screen to obtain 2.38 kg of protein concentrate (Sample 3d) containing 69.6% protein (dwb) and 0.25 kg of coarse fraction containing 59.1% protein (dwb). The protein concentrate was dried in a forced air oven at 50° C. for 15 hours to reduce the ethanol residue.

Vacuum Drying of Samples 1-3

One kilogram samples of Samples 1c, 1d, 2a, 2d, 3a and 3d were loaded into 6 metal trays, which were placed in a freeze dryer (Model 50 SRC-6 Subliminator, Virtis Company, Gardiner, N.Y.). Drying was started at 50° C. and a maximum vacuum attainable (absolute pressure of 150-500 μHg) by the dryer. Drying was continued at 50° C. for 15 hours. After drying, nitrogen was injected into the dryer while vacuum was released slowly. The samples were tested for solvent residues.

Discussion

Figure 12:
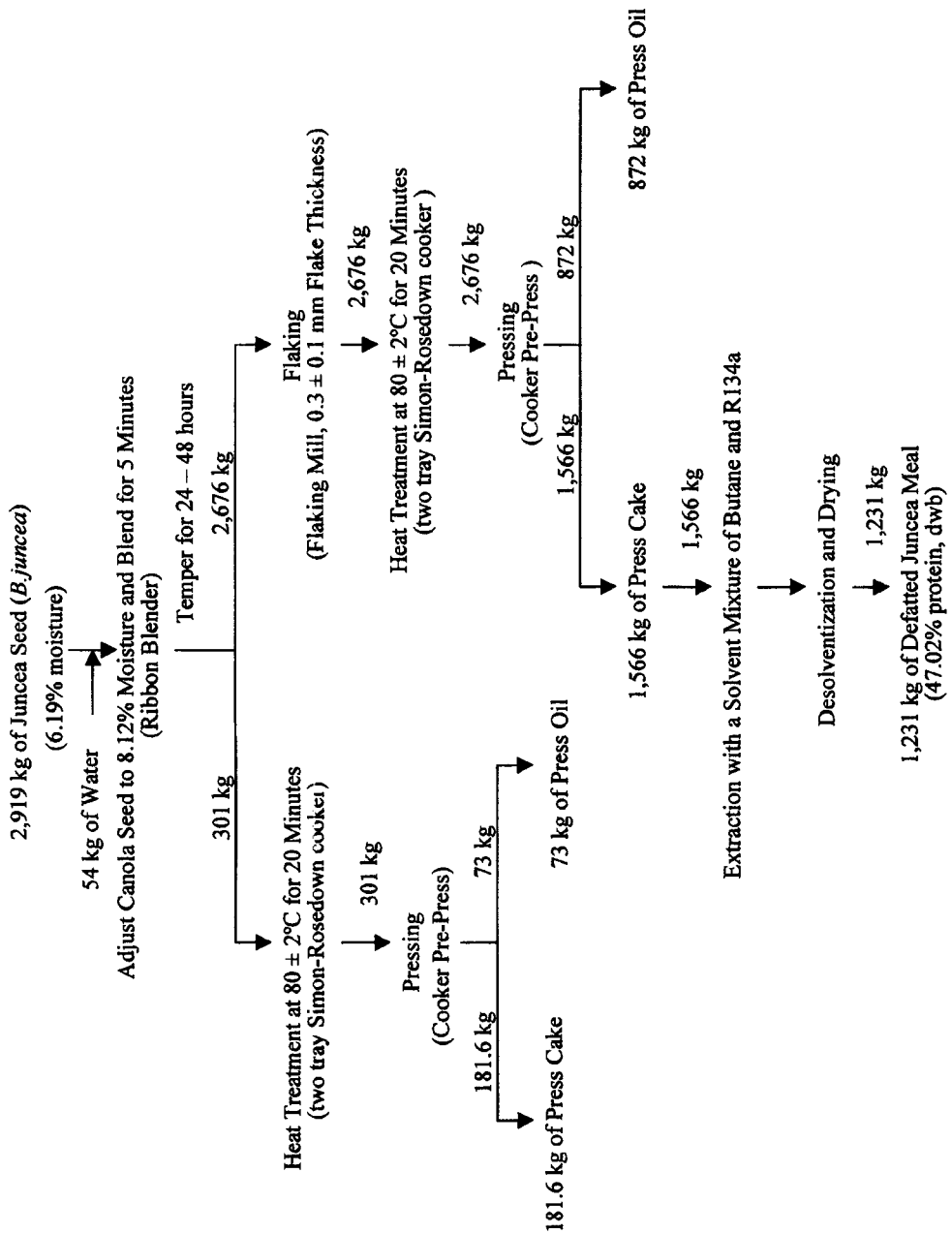
FIG. 12 is a schematic representation for crushing of *Juncea* Seed and preparation of defatted *Juncea* meal.

The mass balance data for flaking and pressing trials for Samples 1a and 1b are shown in Table 10 and FIG. 12, while the proximate analysis results for the Samples are listed in Table 11. Further, the moisture and oil contents of the press cakes of Sample 1 are given in Tables 14 and 15.

The average oil content in the flaked press cake (Sample 1b) as calculated from the results in Table 15 is 15.18% (dwb). The average moisture content in the flaked press cake (Sample 1b) is 7.87%. The oil content in the starting canola seed is 44.39% (dwb) (Table 11). Moreover, 1,566 kg of flaked press cake (Sample 1b) contained 219 kg of crude oil, while the starting 2,676 kg of canola seed after the moisture adjustment contained 1,091 kg of crude oil (see FIG. 12). Approximately 872 kg of crude oil or 79.93% of the total crude oil was pressed out of the flaked seed during the pressing operations.

The average oil content in the non-flaked press cake (Sample 1a) as calculated from the results in Tables 10 and 11 was 29.83% (dwb). The average moisture content in the non-flaked press cake (Sample 1a) was 8.31% (Tables 11 & 14). Moreover, 181.6 kg of non-flaked press cake Sample 1a) contained 49.7 kg of crude oil, while the 301 kg of starting canola seed after the moisture adjustment contained 122.8 kg of crude oil. Approximately 73.1 kg of crude oil or 59.52% of the total crude oil was pressed out of the non-flaked seed during the pressing operation.

Non-flaked press cake (Sample 1a) contained much higher crude oil content than that of flaked press cake (Sample 1b). Higher ratio of press oil was obtained from the flaked seed than from the non-flaked seed in the pressing operation. After solvent extraction, defatted canola meal (Sample 1c) from non-flaked press cake still contained a high oil content of 8.75%-12.73% (dwb) while defatted meal (Sample 1d) from flaked press cake contained less than 3.13% of crude oil (Tables 14 & 16). Visual inspection of the non-flaked press cake showed that it contained many intact seeds, making it difficult for oil extraction by the solvent mixture of butane and R134a. Flaking would be required to rupture the oil cells before pressing to obtain high ratio of press oil in the pressing operation and lower oil content in the solvent extracted meal. Defatted meal (Sample 1d) from flaked press cake was used as the starting material for the preparation of a protein concentrate. Defatted meal from non-flaked press cake was not used for the preparation of protein concentrate due to its high oil content.

The fractions of protein enriched and fiber enriched meals (Samples 1e and 1f) from milling and screening trials are shown in Table 12, while the results of the proximate analysis are given in Table 17. As seen in Table 12 for Sample 1e, approximately 42.33% to 57.23% of the total material was generated as protein enriched fraction and 42.76% to 57.66% as fiber enriched fraction (Sample 1f). From the screening trial of this milled juncea meal, approximately 37.14% was protein enriched meal while 62.86% was fiber enriched meal.

As shown in Table 17, the protein content was increased from 47.02-49.98% (dwb) in the extracted or defatted meals to 52.62-54.77% (dwb) in the protein enriched meals by the milling and screening operation (Samples 1d, 2a and 3a compared to Samples 1e, 2b and 3b). The crude fiber content was reduced from 8.28-9.79% (dwb) in the extracted meals to 4.82-5.49% (dwb) in the protein enriched meals (Samples 1f, 2c and 3c compared to Samples 1e, 2b and 3b). A simple step of dry milling and screening generated a starting material with higher protein and lower fiber contents for protein concentrate preparation.

Figure 13:
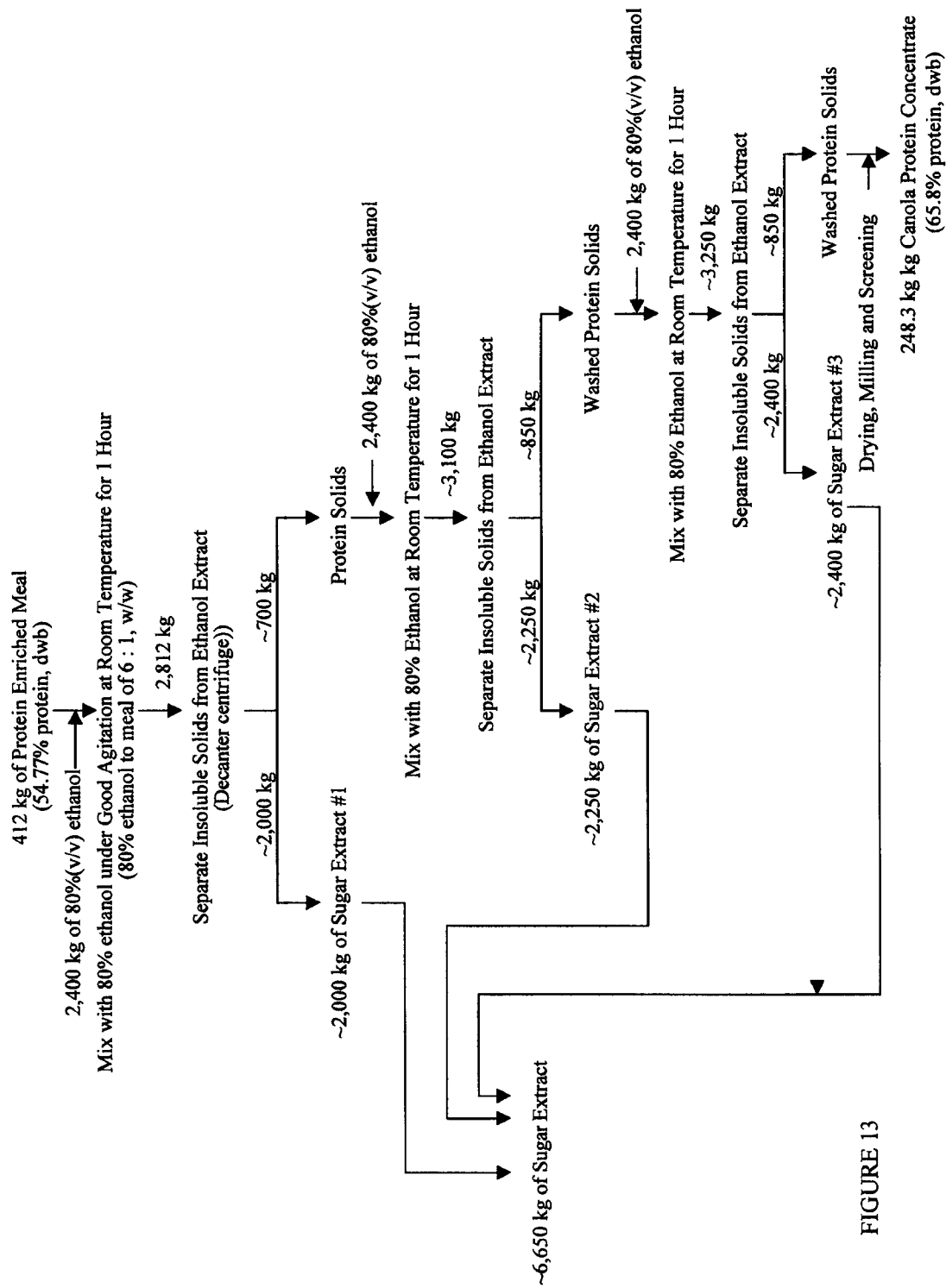
FIG. 13 is a schematic representation showing a preparation of a protein concentrate from a protein enriched meal.
Figure 14:
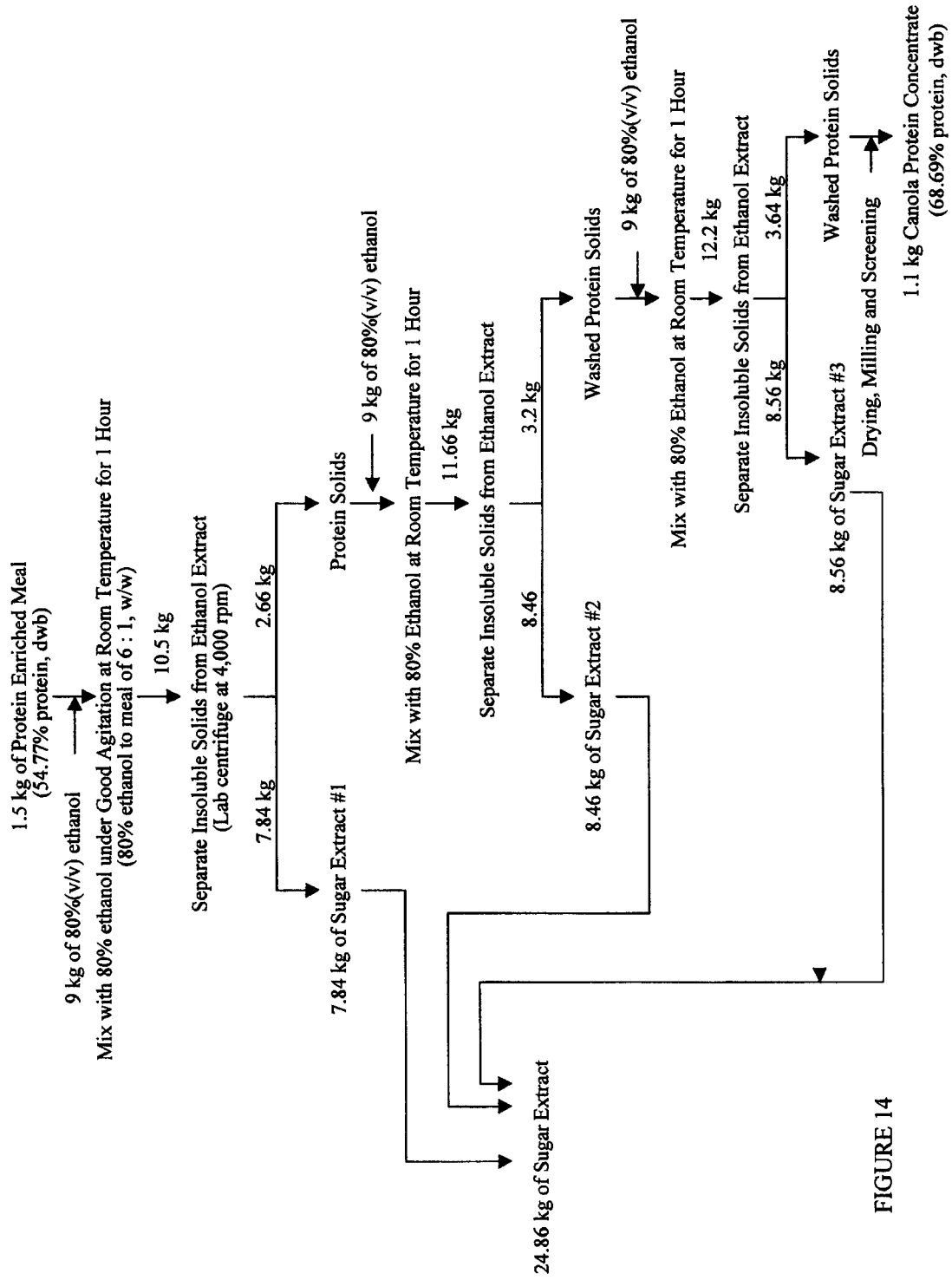
FIG. 14 is a schematic representation showing a preparation of a protein concentrate from a protein enriched meal.
Figure 15:
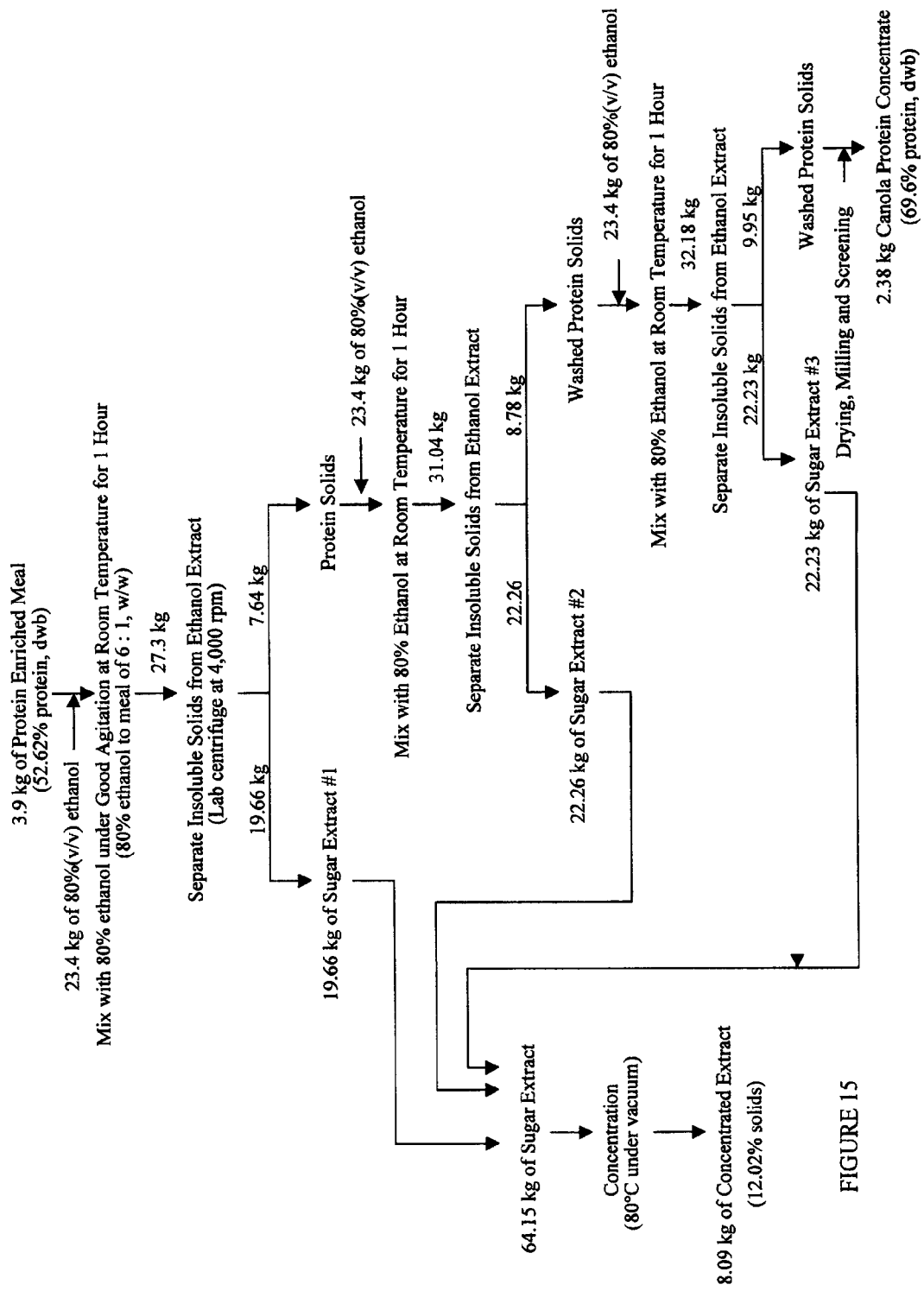
FIG. 15 is a schematic representation showing a preparation of a protein concentrate from a protein enriched meal.

The mass balance flow charts for preparation of protein concentrates (Samples 1g, 2d and 3d) from protein enriched meals are shown in FIGS. 13, 14 and 15. As seen in Table 17, the moisture content of protein concentrates was in the range of 5.32-5.52%, the protein content of protein concentrates (Samples 1g, 2d and 3d) was in the range of 65.80-69.60% (dwb). The crude oil content of protein concentrates was in the range of 0.02-0.41% (dwb) (Samples 1g, 2d and 3d), while the crude fiber content of protein concentrates was in the range of 6.37-7.16% (dwb). The yield of protein concentrates is listed in Table 18. Approximately 0.6-0.733 kg of protein concentrate containing 65.80-69.60% protein (dwb) was produced from 1 kg of protein enriched meal containing 52.62-54.77% protein (dwb).

Protein concentrates from Samples 1g, 2d and 3d contained 65.80%, 68.69% and 69.60% protein (dwb). Protein concentrates contained 6.37-7.16% crude fiber on a dry weight basis (Table 17), which was higher than the crude fiber content of around 3.8-4.5% for soy protein concentrate.

Ethanol extraction was effective to increase the protein content from 52.62-54.77% (dwb) in the protein enriched meals to 65.8-69.6% (dwb) in the protein concentrates (Samples 1g, 2d and 3d). Ethanol washing was also effective in reducing the crude oil content from 0.51-1.49% (dwb) in protein enriched meals to 0.02-0.41% (dwb) in the protein concentrates.

Sample 2d was analyzed for its components and the test results are listed in Table 19. The amino acid profile Sample 2d is given in Table 20. Samples 1d, 2a and 3a; 1f, 2c and 3c; and 1g, 2d and 3d were analyzed. Results are shown in Tables 21, 22 and 23 for the contents of antinutritional factors such as glucosinolates, phytates and sinapines.

The glucosinolate and sinapine contents were reduced significantly by using 80% ethanol washings when protein concentrate (Samples 1g, 2d and 3d) was produced from Samples 1d, 2a and 3a (Tables 21-23).

The results of solvent residues analysis are listed in Table 24. The results of solvent residue analysis after desolventization and drying are shown in Table 25.

Samples 1d, 1f, 2a, 2c, 3a and 3c contained high solvent residues of butane and R134a before vacuum drying. After vacuum drying, the solvent residues of had been reduced significantly. The residues of butane and R134a in Samples 1d, 1f, 2a and 2c were reduced to below the detention limit of 10 ppm respectively. After drying of Samples 2d and 3d at 50° C. for 15 hours in the forced air oven and drying of Sample 1g at 54±3° C. for 18 hour in the Littleford® vacuum dryer, they contained less than 10 ppm of butane and less than 10 ppm of R134a.

In the pressing and extraction trials of Sample 1, non-flaked press cake (Sample 1a) contained much higher crude oil content than that of flaked press cake (Sample 1b). After solvent extraction the defatted canola meal from non-flaked press cake (Sample 1c) contained a high oil content of 8.75%-12.73% (dwb) while the defatted meal from flaked press cake (Sample 1d) contained less than 3.13% (dwb) residual crude oil. Visual inspection of the non-flaked press cake showed that it contained many intact seeds, making it difficult for efficient oil extraction by the solvent mixture of butane and R134a. Flaking would be required to rupture the oil cells before pressing to increase the ratio of press oil and obtain a lower oil content in the solvent extracted meal.

Milling of Sample 1d using a disc mill went smoothly with a throughput of 200 kg per hour. 47.93% protein enriched (Sample 1d) and 52.07% fiber enriched meals (Sample 1f) were produced in lab screening trials of the milled extracted meal using a Rotex screen of 45 US mesh. In these screening trials, up to 57.23% protein enriched meal (Sample 1e) was obtained. 37.14-40.31% protein enriched and 59.69-62.86% fiber enriched meals were produced from the screening of the milled extracted meals. The protein enriched meals (Samples 1e, 2b and 3b) contained 52.62-54.77% protein on a dry weight basis.

Protein concentrates (Samples 1g, 2d and 3d) containing 65.80-69.60% protein on a dry weight basis were prepared from protein enriched meals subjected to three 80% ethanol (v/v) washings. 60.27-73.33% recovery yields for protein concentrates were obtained based on the weight of starting protein enriched meals. Antinutritional factors such as glucosinolates and sinapines were reduced dramatically by 80% ethanol washings of protein enriched meals. Protein concentrates contained 6.37-7.16% crude fiber on a dry weight basis, which was still higher than the crude fiber content of around 3.8-4.5% for soy protein concentrate. A wet separation method was utilized to reduce the crude fiber content to 3.20-4.88% (dwb) in the canola protein concentrates (Samples 1g, 2d and 3d) using a decanter centrifuge to separate the fiber from insoluble and soluble proteins based on the difference in density.

Samples 1d, 2s and 3a, and 1f, 2c and 3c contained high solvent residues of butane and R134a before vacuum drying. After vacuum drying, the solvent residues had been reduced significantly.

Example 5(a)

Figure 16:
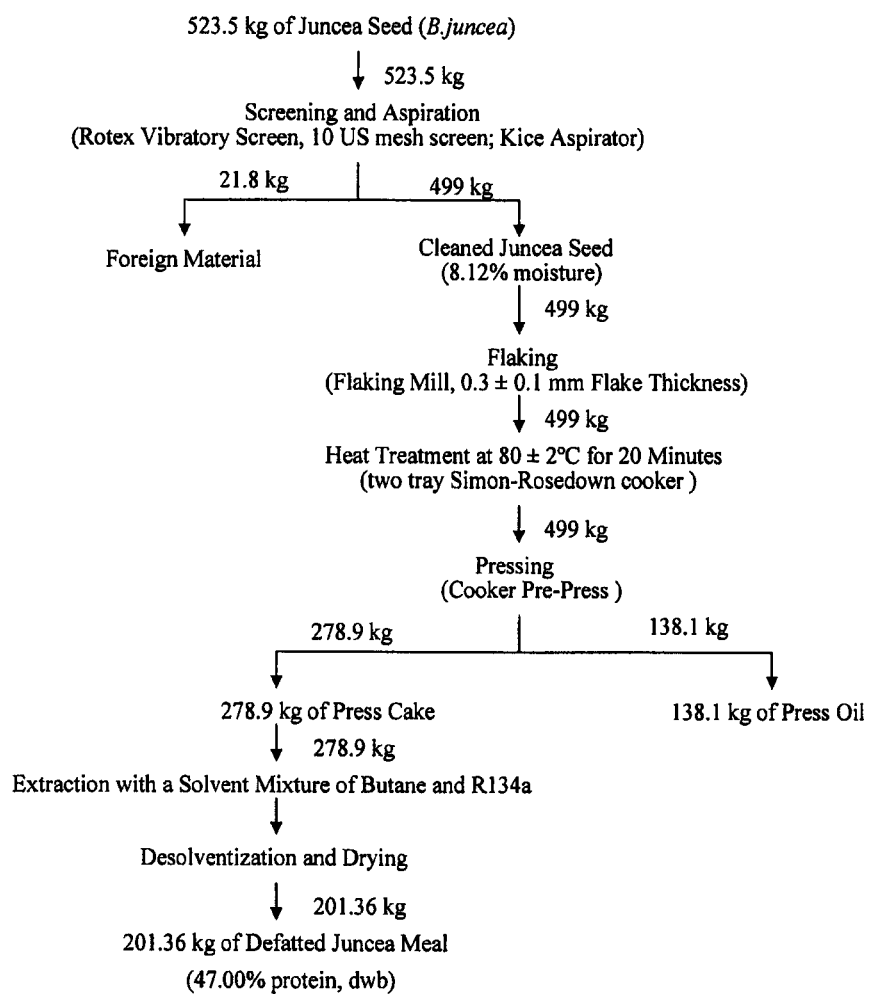
FIG. 16 is a schematic representation showing the crushing of *Juncea* seed and preparation of defatted *Juncea* meal.

Canola Protein Concentrate Having About 70% Protein Content (i) Screening and Aspiration of Canola Seed Approximately 523.5 kg of canola seed (*Brassica juncea*) was screened through a Rotex vibratory Screen (Model 111 A-MS/MS, Rotex Inc., Cincinnati, Ohio, U.S.A.) fitted with a 10 US mesh screen to separate the seed from large size of foreign materials. The screened canola seed was fed to a Kice Aspirator (Kice Metal Products Company Inc., Wichita, Kans., USA) and aspirated into two fractions, the clean seed and the light foreign materials. Approximately 21.8 kg of foreign materials and 499 kg of clean seed were produced from the screening and aspiration operations. The clean seed contained 8.12% moisture. A schematic flowchart for screening and aspiration of canola seed is shown in FIG. 16.

(ii) Screw Pressing of Cleaned Canola Seed

Approximately 499 kg of the cleaned canola seed was flaked to produce flaked seed with an average thickness of 0.3±0.1 mm using a flaking mill (Model S28, Lauhoff Corporation, Detroit, U.S.A.). The flaked canola seed was heat treated using a two tray cooker. The temperature for the top tray was 52-59° C., while the temperature for the bottom tray was 68-90° C. The resident time for the top and bottom trays was 20 minutes, respectively. After heat treatment, the flaked seed was fed into the press and pressed to produce 278.9 kg of press cake and 138.1 kg of press oil.

(iii) Solvent Extraction of Press Cake

Approximately 278.9 kg of press cake was subjected to a solvent extraction which was conducted at 50° C. for 1.5 hours using a solvent mixture of butane and R134a. Approximately 201.4 kg of defatted (extracted) meal containing 47.0% protein on a dry weight basis was produced from 278.9 kg of press cake.

(iv) Milling and Screening of Defatted Meal

Figure 17:
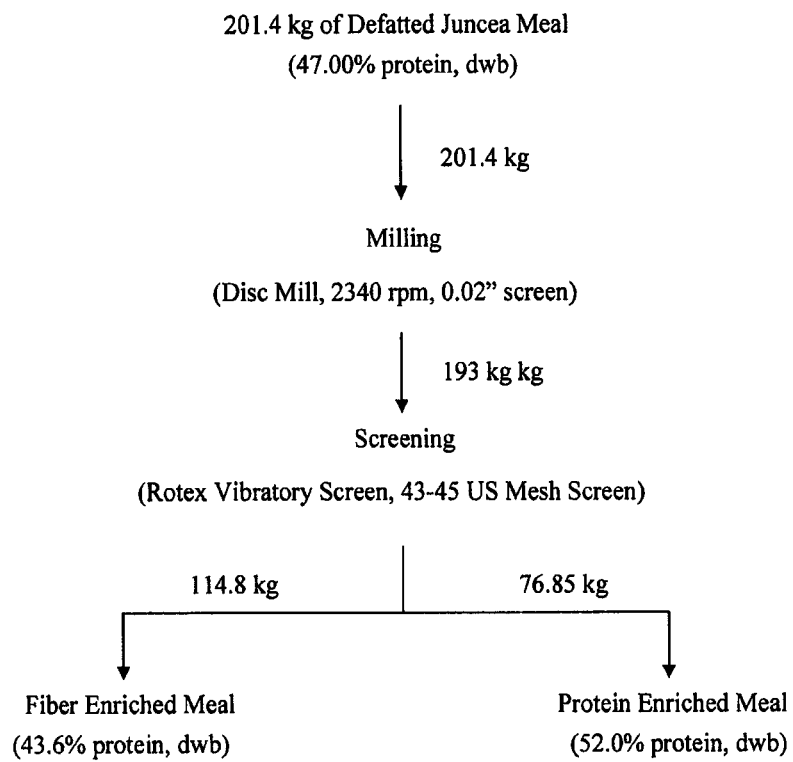
FIG. 17 is a schematic representation showing the milling and screening of defatted *Juncea* meal.

The defatted meal (201.4 kg) was milled using a disc mill equipped with #8114 stationary and rotating plates (The Bauer Bros. Co., Springfield, Ohio, U.S.A.) at 0.02" gap, 2340 rpm rotational speed and 100 kg/h throughput. Only one pass through the disc mill was conducted. A schematic flowchart for milling and screening of the defatted meal is shown in FIG. 17. Approximately 193 kg of milled defatted canola meal was produced. Approximately 8.4 kg of material was lost in the milling operation with a recovery yield of 95.83%.

The milled defatted canola meal was screened through a 45 US mesh screen using the Rotex Vibratory Screen at a feed rate of 100 kg/hr. Only one pass through the screen was conducted. Approximately 76.85 kg of protein enriched meal (fine fraction) and 114.8 kg of fiber-enriched meal (coarse fraction) were produced, respectively. Approximately 1.35 kg of material was lost in the screening operation with a recovery yield of 99.30%. After screening, 40.1% of the total material was protein enriched meal and 59.9% was fiber enriched meal, respectively.

(v) Wet Separation to Remove Fiber

Figure 18:
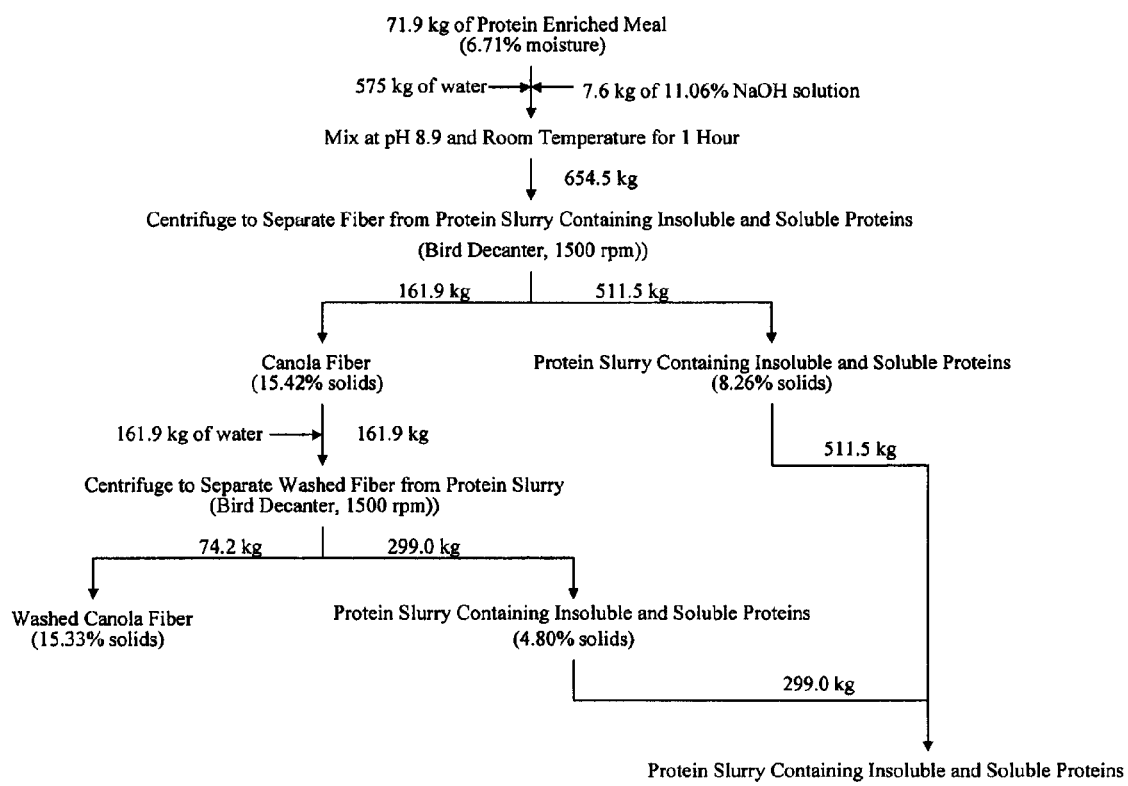
FIG. 18 is a schematic representation illustrating a separation and removal of fiber from a protein slurry containing insoluble and soluble proteins.

Approximately 71.9 kg of protein enriched meal was mixed with 575 kg of tap water at a ratio of about 1 to 8 (by weight) under homogeneous agitation to form a protein slurry. The protein slurry was adjusted to pH 8.9 by slow addition of 7.6 kg of 11.06% NaOH solution under homogeneous agitation. This was followed by centrifugation at room temperature using a Bird Decanter Centrifuge (Bird 6" Continuous Bowl Centrifuge, Bird Machine Company of Canada, Saskatoon, Saskatchewan). The protein slurry was pumped through the Bird Decanter at ambient temperature and a feed rate of 150 kg/h and it was operated at a bowl speed of 1,500 rpm with a low pool depth to separate the coarse fiber solids from the soluble and insoluble protein fractions. Approximately 161.9 kg of wet fiber solids containing 15.42% solids and 511.5 kg of protein slurry containing soluble and insoluble proteins at 8.26% solids were produced, respectively. 161.9 kg of wet fiber solids was mixed with 161.9 kg of water in a tank for 0.5 hour as a second extraction, which was followed by centrifugation at room temperature using the Bird Decanter at a bowl speed of 1,500 rpm and a feed rate of 160 kg/hr. Approximately 74.2 kg of washed wet fiber and 299 kg of protein slurry containing soluble and insoluble proteins were produced. Protein slurries containing soluble and insoluble proteins from these two centrifugations were combined and approximately 810.5 kg of the combined protein slurry was obtained. A schematic flowchart illustrating the wet separation of fiber is shown in FIG. 18.

Discussion

The Bird Decanter can operated at a bowl speed of 1,000-5,000 rpm (100-2130 g) and a pool depth of 5 to 19 mm. A spin down of the protein slurry sample in a centrifuge tube using a bench top centrifuge showed three layers, liquid extract as the top layer, insoluble protein cake of fine protein particles as the middle layer and the coarse fiber solids as the bottom layer. The objective was to separate the top and middle layers (the soluble protein extract and the insoluble fine protein solids) from the bottom layer (coarse fiber solids). The bird decanter was operated at a low pool depth and a bowl speed of 1,000, 1,500, 2,000, 2,500 and 3,000 rpm and the separation efficiency was evaluated by spin down tests of the feed, the fiber fraction and the protein slurry using the bench top centrifuge. Separation of the coarse fiber solids from the insoluble fine protein solids and the soluble protein extract was obtained at a bowl speed of about 1,000 rpm to about 2,000 rpm, optionally about 1,500 rpm (~760 g) and a low pool depth.

(vi) Preparation of Protein Concentrate Containing 70% Protein

Figure 19:
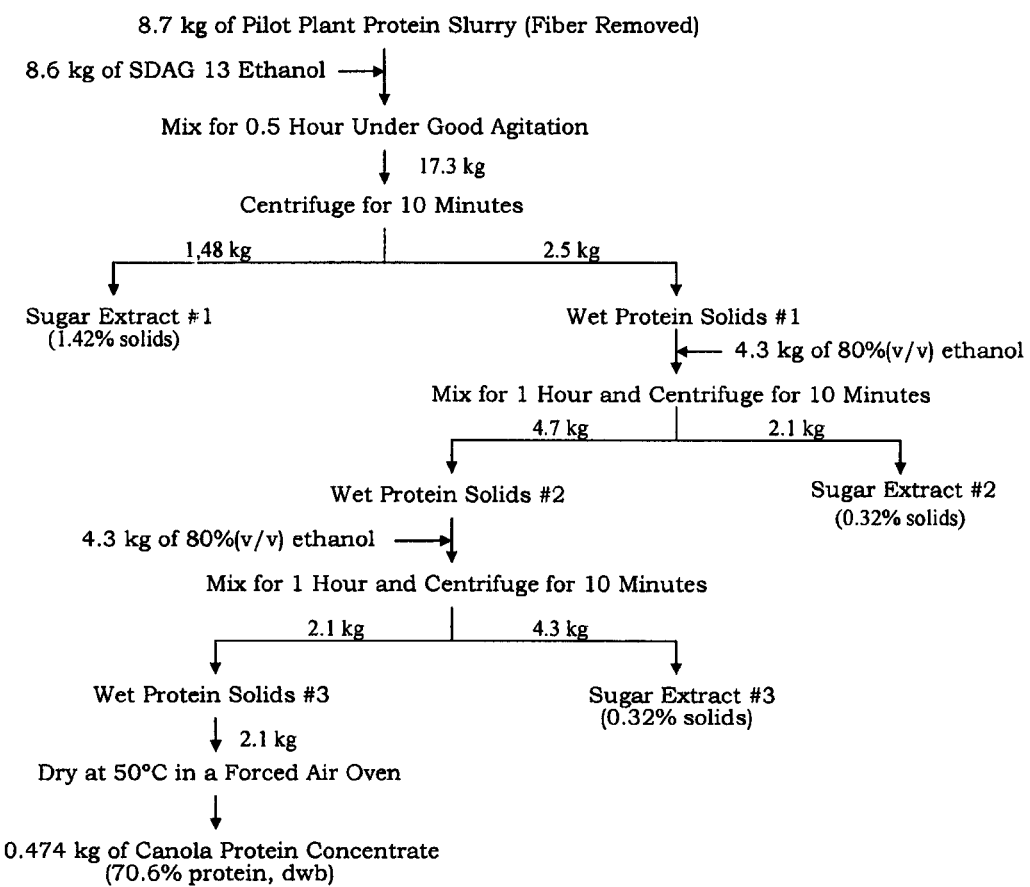
FIG. 19 is a schematic representation illustrating a preparation of a protein concentrate from a protein slurry with fiber removed.

Approximately 8.7 kg of protein slurry containing soluble and insoluble proteins after the fiber removal using the Bird Decanter was mixed with 8.6 kg of SDAG-13 denatured ethanol (containing 99% ethanol and 1% ethyl acetate) for 0.5 hours at room temperature. This was followed by centrifugation for 10 minutes using a lab centrifuge at 4,200 rpm to obtain 14.8 kg of a first sugar extract containing 1.42% solids and 2.5 kg of a first wet protein solid fraction. The wet protein solid fraction (2.5 kg) was further mixed with 4.3 kg of SDAG-13 denatured ethanol for 1 hour at room temperature. This was again followed by centrifugation for 10 minutes using the lab centrifuge at 4,200 rpm to obtain 4.7 kg of a second sugar extract and 2.1 kg of a second wet protein solid fraction. Finally, the wet protein solid fraction (2.1 kg) was mixed with 4.3 kg of SDAG-13 denatured ethanol for 1 hour at room temperature, which was followed by centrifugation for 10 minutes using the lab centrifuge at 4,200 rpm to obtain 4.3 kg of a third sugar extract and 2.1 kg of a third wet protein solid fraction. The wet protein solids were dried in a lab forced air oven at 50° C. until the moisture content was about 6%. The dried protein solids were milled using a lab pin mill to obtain the final protein concentrate containing 70.6% protein on a dry weight basis. A schematic flowchart illustrating the preparation of a protein concentrate containing 70.6% protein is shown in FIG. 19.

Example 5(b)

Canola Protein Isolate

Approximately 770 kg of a protein slurry containing soluble and insoluble proteins prepared in the same manner as in Example 5a(i)-(v) (including fiber removal using the Bird Decanter), was centrifuged using a Westfalia® Decanter (Model CA 225-010, Centrico Inc., Northvale, N.J., USA) at ambient temperature and a bowl speed of 5,200 rpm (3,300 g) to separate the soluble protein extract from insoluble protein solids. Approximately 650 kg of a first protein extract containing soluble proteins and 120 kg of a first protein solid fraction were produced. The first protein solid fraction was mixed with 360 kg of water at room temperature for 0.5 hour under homogeneous agitation, which was followed by centrifugation using the Westfalia® Decanter to obtain 368.5 kg of a second protein extract containing soluble proteins and 91.3 kg of a second protein solids fraction.

The first and second protein extracts were combined together and the combined extract was centrifuged using a Wesffalia® Disc Stack Centrifuge (Model SA14-02-073, Centrico., Northvale, N.J., USA) at ambient temperature and a bowl speed of 8,500 rpm (6,549 g) to remove trace insoluble solids in the soluble protein extract. Approximately 978.5 kg of clarified protein extract and 21.9 kg of a third protein solids fraction were produced.

The clarified protein extract was adjusted to pH 7.0 by addition of 1.8 kg of 11% NaOH solution, which was followed by concentration of the protein extract in the feed tank from 978.5 kg to 140 kg at ambient using a Millipore® Ultrafiltration Unit from Millipore®, MA, USA. The Ultrafiltration Unit (UF) was fitted with three hollow fiber cartridges with a molecular weight cutoff of 10,000 daltons, with each cartridge containing 5 m$^2$ of membrane surface area. The protein extract was pumped through the hollow fiber cartridges at a rate of 800-1000 kg/hr. The retentate was recycled back to the feed tank and the permeate was collected in another tank. The UF unit was operated at an inlet pressure of 25 psi maximum and a retentate back pressure of 15 psi maximum. The flux rate or permeate rate was about 120 kg/hr initially and gradually decreased to about 70 kg/hr and stabilized at that level for a period of time before decreasing further. Back flushing was conducted to increase the flux rate periodically. The ultrafiltration process continued until the amount of protein solution in the feed tank was equal to about 15% of its initial weight.

Approximately 60 kg of water was added into the feed tank and diafiltration was conducted at ambient temperature using the same UF unit fitted with the same three hollow fiber cartridges. The original volume of protein solution in the feed tank was held constant by adding water to make up for the removed permeate. The retentate was recycled back to the feed tank. The amount of water added to maintain the original volume of protein solution was about 2.8 times the original volume of protein solution or 560 kg.

Figure 20:
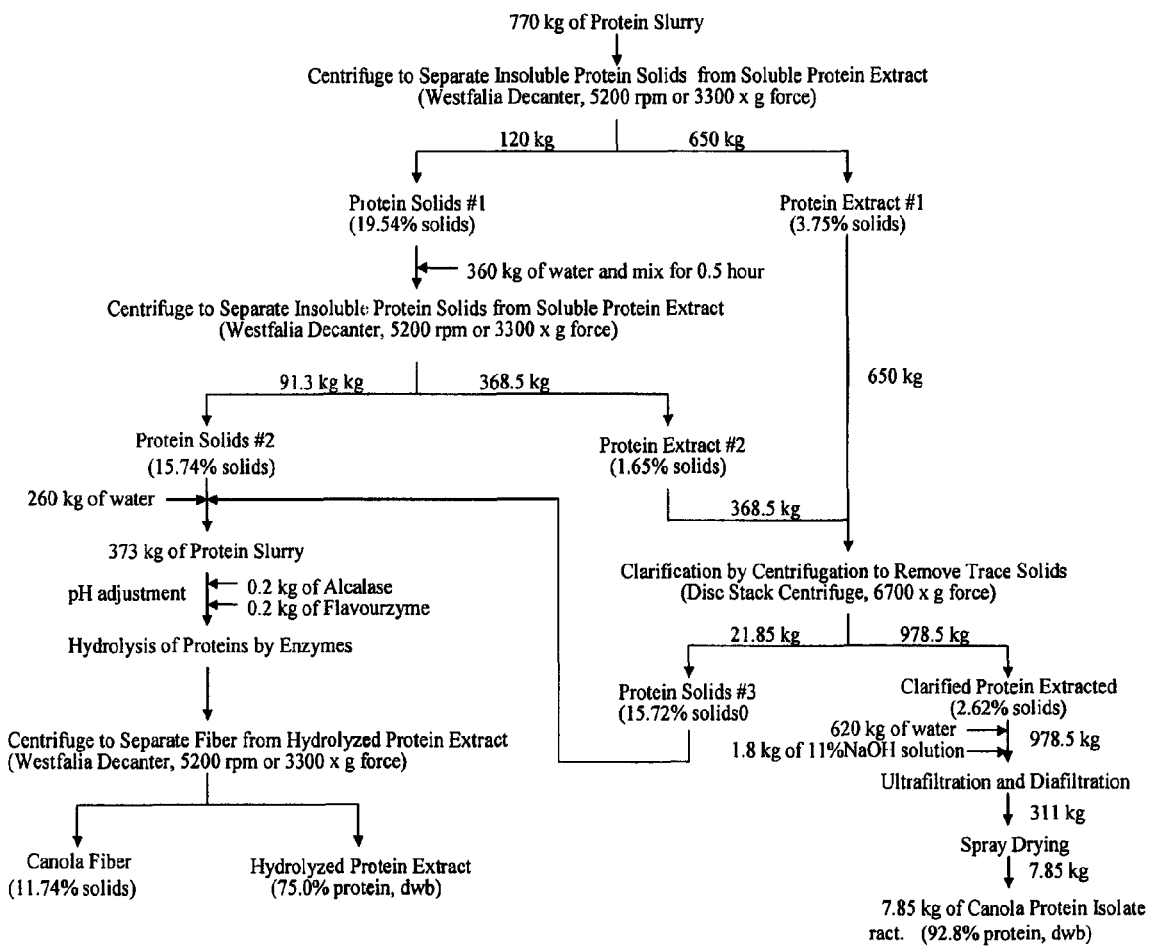
FIG. 20 is a schematic representation illustrating a preparation of a protein isolate and a hydrolyzed protein extract.

Approximately 311 kg of purified protein extract was obtained from the ultrafiltration and diafiltration process. The purified protein extract was heated to 40±10° C. using a heat exchanger prior to being fed to a Komline Sanderson® spray dryer (Komline Sanderson® Ltd., Brampton, Ontario, Canada) by pumping at a feed rate of 150-165 kg per hour. The spray drying operation was conducted at an inlet air temperature of 185±5° C. and an outlet air temperature of 85±5° C. Approximately 7.85 kg of spray dried protein isolate was produced. A schematic flowchart illustrating the preparation of a canola protein isolate is shown in FIG. 20.

Example 5(c)

Preparation of Hydrolyzed Protein Concentrates

Approximately 91.3 kg of the second protein solid fraction and 21.9 kg of the third protein solid fraction (obtained from Example 5(b)) were added to 260 kg of water in a tank, resulting in a slurry of about 5% solids in a 2000 L scraped surface tank. This was followed by pH adjustment to 8.3±0.1 using 8% NaOH solution. Approximately 200 g of a first protease (Alcalase® 2.4 L FG) was added to the slurry. The slurry was then heated to 50±2° C. and held at temperature for 4 hours. The slurry was cooled down to 50±2° C. and 200 g of a second protease (Flavourzyme®) was added to the slurry, which was followed by holding at 50±2° C. for 4 hours. The slurry was centrifuged using the Westfalia® Decanter at 3300×g to separate the hydrolyzed protein extract from the insoluble fiber fraction. The insoluble fiber was washed further with 100 kg of filtered tap water, which was again followed by centrifugation at 3300×g to separate the washed protein extract from the washed fiber solids using the Westfalia® Decanter. A sample of the washed protein extract was taken to analyze the protein content.

Hydrolyzed protein concentrates were also produced from the combined protein slurry after fiber removal using the Bird Decanter (Example 5a(i)-(v)). Approximately 7.48 kg of protein slurry containing soluble and insoluble proteins was adjusted from pH 8.3 to pH 7.0 by addition of 25% phosphoric acid. After pH adjustment, the protein slurry was centrifuged at 4,000 RPM to separate the soluble protein extract from the insoluble solids. Approximately 1.15 kg of insoluble solids was mixed with 3.4 kg of water, which was followed by centrifugation at 4,000 RPM to separate the first washing extract from the first washed solids fraction. Approximately 1.07 kg of the first washed solids was mixed with 3.4 kg of water. This was followed by centrifugation at ambient temperature at 4,000 RPM to separate the second washing extract from the second washed solids fraction.

Figure 21:
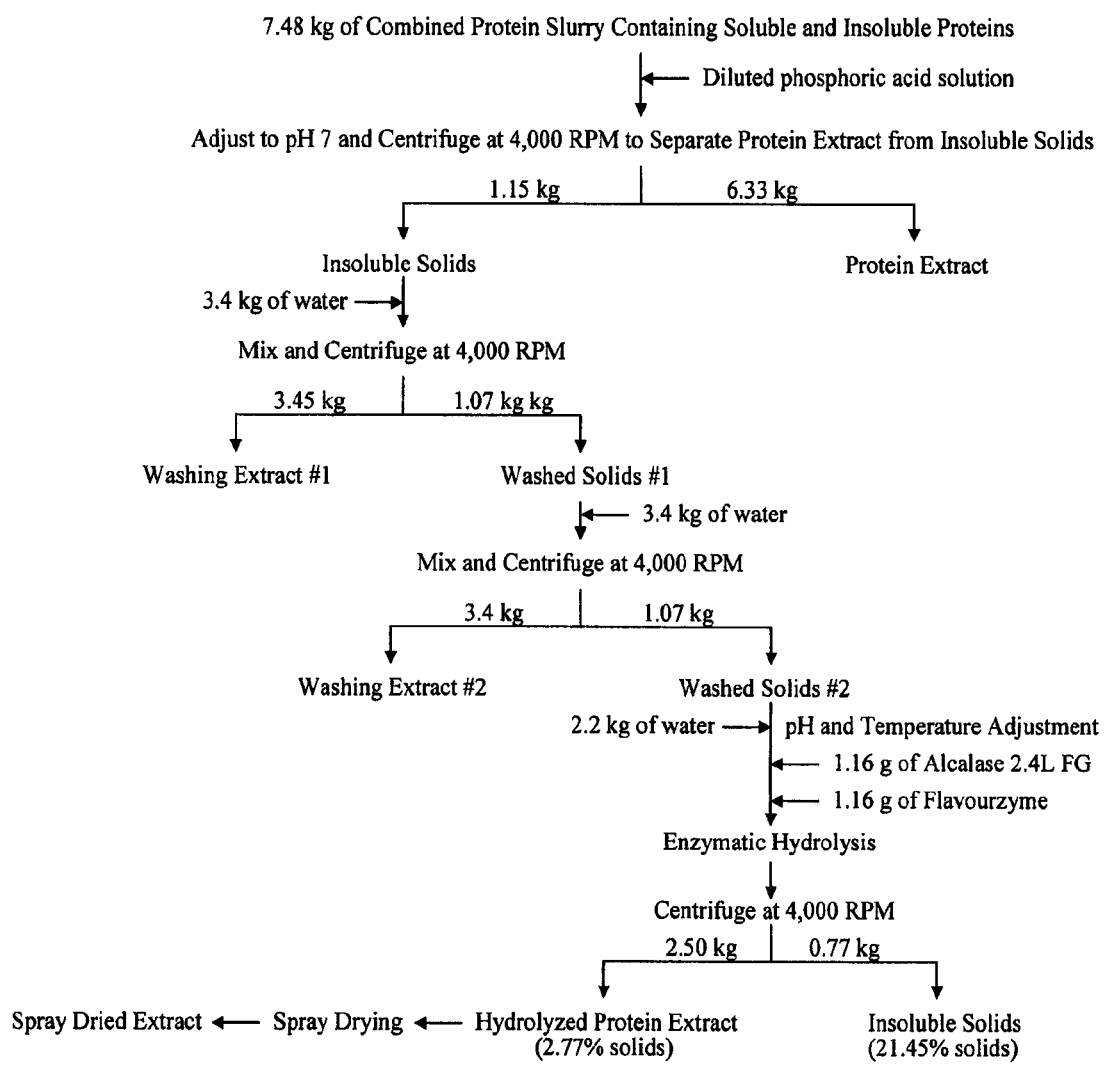
FIG. 21 is a schematic representation illustrating a preparation of a hydrolyzed protein extract.

Approximately 1.07 kg of the second washed solids fraction was mixed with 2.2 kg of water to obtain a slurry, which was followed by pH adjustment to 8.2 with the addition of 1 M NaOH solution. Approximately 1.16 g of a first proteinase (Alcalase® 2.4 L FG) was added to the slurry. The slurry was heated to about 62° C. and held at this temperature for 4 hours. The slurry was cooled down to about 50° C. and approximately 1.16 g of a second proteinase (Flavourzyme®) was added to the slurry, which was followed by holding at 50° C. for 4 hours. Finally, the slurry was centrifuged at 4,000 rpm for 10 minutes to separate the hydrolyzed protein extract from the insoluble fiber fraction. The hydrolyzed protein extract was spray dried into hydrolyzed protein concentrate using a lab spray dryer. A schematic flowchart illustrating the preparation of hydrolyzed protein extract is shown in FIGS. 20 and 21.

Discussion

The results of the proximate analysis for canola seed, press cake, defatted meal, protein enriched meal, fiber enriched meal, protein concentrate, hydrolyzed protein concentrate and protein isolate are shown in Table 26.

As shown in Table 26, dry separation by milling using a disc mill and screening using a vibratory screen of 45 US mesh increased the protein content from 47% in the extracted meal to 52% in the protein enriched meal on a dry weight basis. The fiber content was reduced from 7.75% in the extracted meal to 5.53% in the protein enriched meal by dry separation. Wet separation to remove fiber using the Bird Decanter and to remove sugar compounds by the ethanol extraction process further increased the protein content from 52% in the protein enriched meal to 70.6% in the protein concentrate. The fiber content was reduced from 5.53% in the protein enriched meal to 4.88% in the protein concentrate by wet separation using the bird decanter.

As shown in Table 27, wet separation to remove fiber by the Bird Decanter decreased the crude fiber content from 5.53% in the protein enriched meal (see Table 26) to 3.20% in the protein slurry (see Table 27) after the first fiber removal. The fiber fraction after the first fiber separation contained about 10.2% crude fiber. The fiber fraction was washed with water at a ratio of 1 to 1 by weight, which was followed by centrifugation using the Bird Decanter to separate the washed fiber fraction from the washing protein slurry. The washed fiber fraction contained 12.7% crude fiber. The fiber washing step was able to increase the crude fiber content in the fiber fraction from 10.2% to 12.7% on a dry weight basis. More importantly, the washing step significantly reduced the weight of fiber fraction from 161.9 kg to 74.2 kg or about 54% and thus increased the protein recovery yield in the final protein concentrate. The washed fiber fraction contained 11.34 kg of total dry solids (74.2 kg×15.33% solids=11.34 kg) or 16.91% of starting protein enriched meal on a dry weight basis.

After dry separation by screening, the protein enriched meal produced by this process still contained a high crude fiber content of 5.53% on a dry weight basis (see Table 26). A wet separation process was employed to separate and remove fiber from the soluble protein extract and the insoluble protein particles taking advantage of the difference in density and particle size between the fiber and insoluble protein particles.

Figure 22:
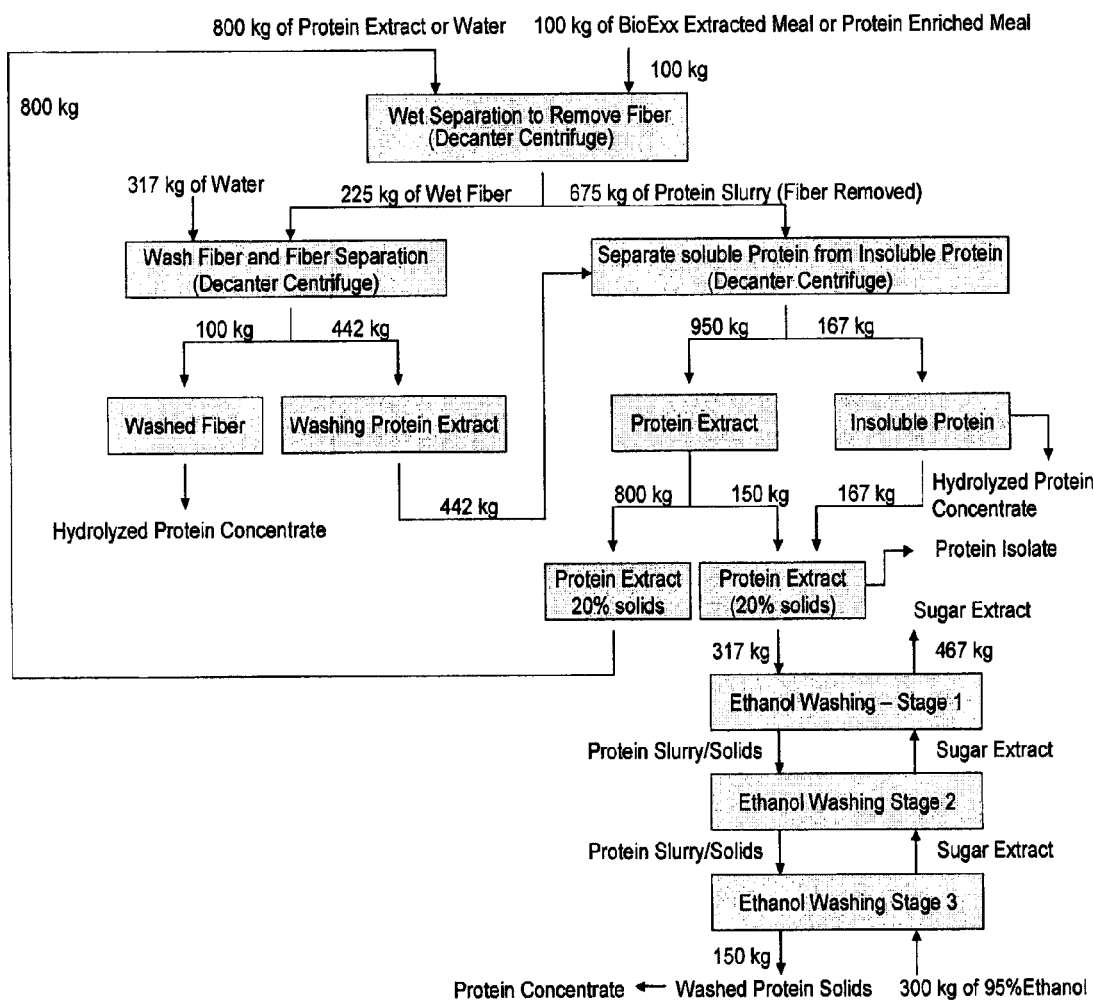
FIG. 22 is a schematic representation illustrating a wet fiber removal process.

Several spin down tests were performed on a protein slurry sample of 10.4% solids in a centrifuge tube in the laboratory using a lab centrifuge, three layers of top liquid layer, the middle protein particle layer and the bottom fiber layer were obtained in the tube. The fiber particles settled faster than the smaller insoluble protein particles. The settling rate was dependent on the g force—the higher the g force, the higher the settling rate. If the decanter centrifuge is run at a full bowl speed of 5,000 rpm or 3000 g force, both fiber and insoluble protein particles settle and would be separated from the liquid extract and be removed by the decanter as the combined insoluble solids. If the decanter is run at a lower bowl speed of 1,500 rpm or a lower g force of 750 g, the large fiber particles settle, but the fine protein particles have not yet had sufficient time to settle, therefore the fiber particles can be separated from the insoluble protein particles and the protein extract. The separation of fiber from protein particles is mainly caused by the difference in density between the insoluble fiber and protein particles. A schematic flowchart for the fiber removal process is illustrated in FIG. 22.

The protein enriched meal was mixed with water at a ratio of 1 to 8 by weight and pH was adjusted to 8.9. After 1 hour of hold time under agitation at room temperature, the protein slurry was centrifuged at a low bowl speed of 1,500 RPM (~750 g force) using the Bird Decanter. Larger fiber particles with higher density were separated from smaller insoluble protein particles with lower density as well as soluble protein solution. The fiber fraction was washed with water at a ratio of 1 to 1, which was followed by centrifugation at 1,500 RPM using the Bird Decanter to separate the large fiber particles with higher density from the insoluble smaller protein particles with lower density as well as protein extract. In an embodiment, the efficiency of a wet fiber separation is affected by viscosity and density of the liquid medium. The soluble protein extract would be cycled and re-used to increase the soluble solid content in order increase the density and viscosity of the liquid medium. This also helps to reduce the volume of water usage.

The results of the amino acid profiles for the canola protein concentrates and isolate on a dry weight basis are shown in Table 28. In addition, a comparison of amino acid profiles for the canola protein concentrate, canola protein isolate and commercially available soy and pea protein isolates is shown in Tables 29 and 30.

From the amino acid profiles as shown in Tables 28, 29 and 30, canola protein compares favorably to that of soy protein or pea protein. Canola protein is of high nutritional quality and capable of providing adequate amounts of all essential amino acids. Canola protein contains much higher sulphur containing amino acids such as methionine and cystine than soy and pea proteins. Canola protein contains 48-72% higher methionine than soy protein and 70-97% higher methionine than pea protein. Usually, cereals tend to be low in lysine but adequate in the sulphur containing amino acid methionine. Legumes are adequate in lysine but low in methionine. Canola protein is unique in that it contains both adequate lysine and sulphur containing amino acid methionine. Therefore, it exhibits a better amino acid balance than cereal proteins and legume proteins (such as pea protein and soy protein). Canola protein has excellent nutritional quality and can be used in applications such as baby formula and foods required for good nutrition.

From the essential amino acid profiles as shown in Table 30, canola protein is very rich in the muscle building essential amino acids such as valine, methionine, leucine and isoleucine. It also contains a much higher content of the essential amino acid threonine, which is important for brain activity. Canola protein concentrate and isolate may be suitable ingredients for sports nutritional supplements.

With respect to the molecular weight and characterization of the canola protein concentrate, the concentrate obtained in Example 5(a) contained three major subunits as listed below:
  (a) 10,000-12,000 dalton molecular weight
  (b) 15,000-20,000 dalton molecular weight
  (c) 25,000-37,000 dalton molecular weight The results obtained using a technique of Gel Permeation Chromatography show that canola protein isolate contains 64.7% of the proteins at molecular weight of 70 kDa, 26.2% at 12 kDa and 9.1% at <10 kDa.

With respect to the functional properties of the canola protein isolate, the emulsifying and foaming properties of the canola protein isolate (obtained in Example 5(b)) as compared to soy and pea protein isolates are shown in Table 31. As seen in Table 31, the canola protein isolate of the present disclosure has much better foaming capacity than soy and pea protein isolates at pH 7.0 and a protein concentration of 0.5%. At pH 7 and concentration of 1.0%, canola protein isolate has slightly lower foaming capacity than soy protein isolate, but much higher foaming capacity than pea protein isolate. The canola protein isolate has a much better foam stability than soy and pea protein isolates. Further, the canola protein isolate has similar emulsifying properties as compared to soy and pea protein isolates at pH 7 and concentrations of 0.5% and 1.0%, and also has similar emulsion stability at pH 7 and concentrations of 0.5% and 1.0%.

The foaming capacity of a protein is characterized by whipping the dissolved protein at 0.5% protein content with a milk foamer (Aeroflott™) at 20° C. for 1 minute. Foam height was determined in a 100 ml scaled cylinder for 1 hour. Additionally, the protein solution at 0.5% protein was heated at 60° C. for 15 minutes and then cooled to 20° C. before foam test The emulsifying capacity of a protein is defined as the maximum amount of oil which can be emulsified with a defined amount of protein forming a stable emulsion. The higher the emulsifying capacity, the higher the effectiveness of the protein substance. The emulsifying capacity is measured by using the following emulsifying conditions:

(1) measuring temperature at 20° C.
(2) protein concentration at 0.5%
(3) stepwise addition of coloured plant oil (starting point at 50%)
(4) Emulsification using Ultra-Turrax (13,000 min$^{-1}$; 60 s)
(5) Evaluation of oil separation 30 minutes after emulsification.

As shown in Table 32, the emulsifying results of a 0.5% canola protein isolate solution were very good as compared to a 5% egg yolk solution. Further, as described in Table 32, the canola protein isolate possesses the functional property of gel formation and water immobilization, and therefore, would act as a stabilizer. The results of gel firmness for canola protein isolate are good and comparable to other vegetable proteins. The results of water immobilization of canola protein isolate gels are good as compared to that of whey protein isolate gels, which is an important parameter for stability and shelf-life of a final product containing canola protein isolate.

Because of its emulsifying and foaming properties, in an embodiment, the canola protein isolate is a suitable protein and functional ingredient in food applications that require good emulsifying and foaming capacity and stability such as in cakes, coffee toppings, and specialty coffee drinks, crèmes, dressings and pastes. In another embodiment, the canola protein isolate is used for laundry and cosmetic products that require good foaming capacity and stability such as in laundry detergents, bath soaps, conditioning shampoos, and cream hand and skin cleansers. In a further embodiment, the canola protein isolate is used for soups, salad dressings, sausages, bologna and other comminuted and emulsified meat products that require good emulsifying capacity.

As seen in Table 33, the solubility of the canola protein isolate, in addition to the solubility for pea and soy protein isolates is shown. The results show that 99.81% of the crude protein canola isolate crude is soluble. The test results demonstrate that the canola protein isolate of the present disclosure has 99.81% soluble crude protein as compared to 25.21% and 18.85% soluble crude protein for soy and pea protein isolates, respectively. Accordingly, in an embodiment, the canola protein isolate is a suitable protein ingredient for nutritional beverages such as protein fortified soft drinks, fruit juices, sports drinks and high protein drinks. In another embodiment, it is also useful for healthy food applications to improve absorption and digestibility.

As shown in Table 34, the concentrations of antinutritional factors in the canola protein isolate obtained in Example 5(b) are illustrated. Accordingly, the canola protein isolate contains very low levels of total glucosinolates, phytic acid and allyl isothiocyanate.

The results of glucosinolates in the canola seed, the canola press cake, the defatted meal, the protein and fiber enriched meals, the protein concentrates and isolate are shown in Table 35. The content of total aliphatic glucosinolates in seed, press cake, extracted meal, protein and fiber enriched meals is high and at similar level on an oil free basis. Dry separation by screening to separate the extracted meal into the protein and fiber enriched meals did not alter the concentration of total aliphatic glucosinolates significantly. Wet separation processing reduced the total aliphatic glucosinolates dramatically from 17.31 µmoles/g in the protein enriched meal to 0.11 µmole/g in canola protein concentrate, 0.23 µmole/g in hydrolyzed protein concentrate and 0.17-0.41 µmole/g in protein isolate.

Accordingly, based on the above described properties of the canola protein concentrates and isolates, the concentrates and isolates have:

(a) Excellent nutritional value and the only vegetable protein product having high lysine and methionine. For example, protein isolates of the present disclosure will typically have greater than 4.5% lysine by weight and 2.0% methionine by weight of the isolate as a whole. Further, protein concentrates of the present disclosure will typically have greater than 5.4% lysine by weight and 1.9% methionine by weight of the concentrate as a whole;
(b) Attractive labeling as GMO free and no food allergies;
(c) Zero or very low fat. Typically, the protein isolates of the present disclosure will have less than 0.2% fat by weight of the protein isolate as a whole, while the protein concentrates will typically have less than 0.5% fat by weight of the protein concentrate as a whole;
(d) Vegetable protein origin and green products;
(e) Gluten free;
(f) Low salt and low sugar contents. Typically, the protein isolates of the present disclosure will have less than 0.5% sugar by weight and less than 0.5% salt by weight of the protein isolate as a whole. Further, the protein concentrates of the present disclosure will have less than 0.5% sugar by weight and about 0% salt by weight of the protein isolate as a whole.

Example 6

Canola Protein Concentrate Having About 70% Protein Content (i) Milling and Screening of Defatted *Juncea* Meal Approximately 458.5 kg of defatted canola meal (prepared as in Example 4) was milled using a disc mill equipped with #8114 stationary and rotating plates (The Bauer Bros. Co., Springfield, Ohio, U.S.A.) at 0.02" gap, 2340 rpm rotational speed and 100 kg/hr throughput. Only one pass through the disc mill was conducted. Approximately 448 kg of milled canola meal was produced. Approximately 10.5 kg of material was lost in the milling operation with a recovery yield of 97.71%.

Figure 23:
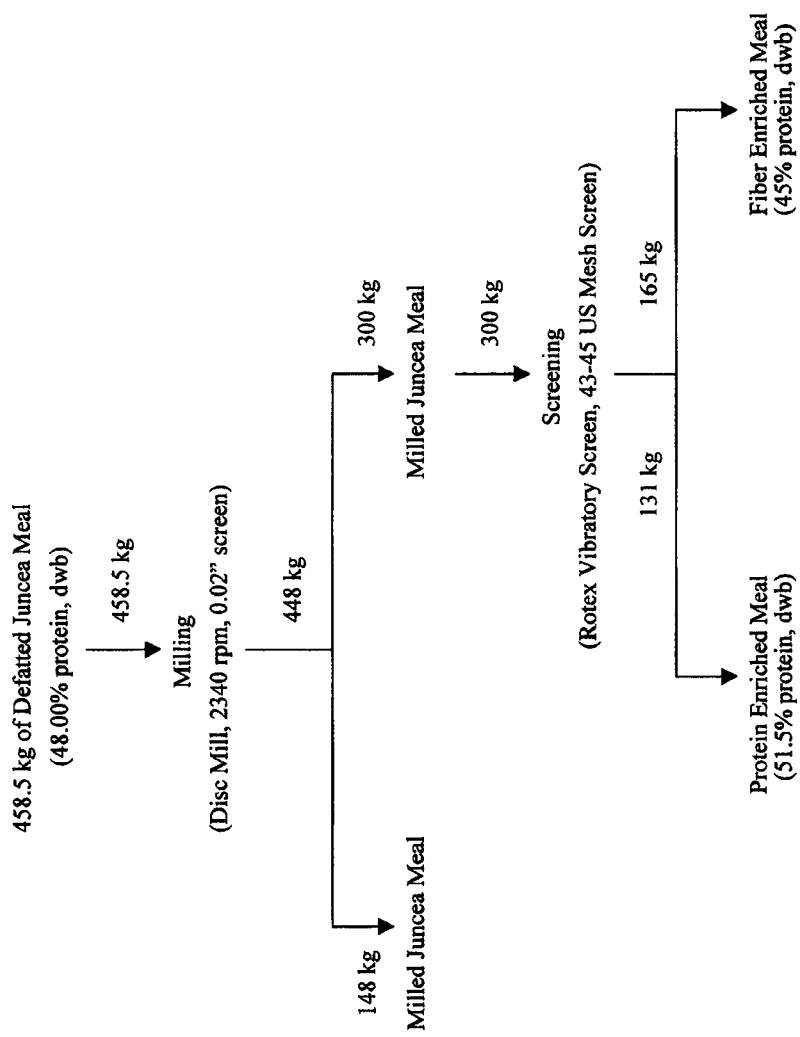
FIG. 23 is a schematic representation illustrating a milling and screening process of defatted *Juncea* meal.

Approximately 300 kg of the milled canola meal was screened through a 45 US mesh screen using the Rotex Vibratory Screen at a feed rate of 100 kg/hr. Only one pass through the screen was conducted. Approximately 131 kg of protein enriched meal (fine fraction) and 165 kg of fiber enriched meal (coarse fraction) were produced, respectively. Approximately 4 kg of material was lost in the screening operation with a recovery yield of 98.67%. After screening, 44.26% of the total material was protein enriched meal and 55.74% was fiber enriched meal, respectively. A schematic representation illustrating milling and screening of defatted *Juncea* meal is shown in FIG. 23.

(ii) Wet Separation to Remove Fiber

Figure 24:
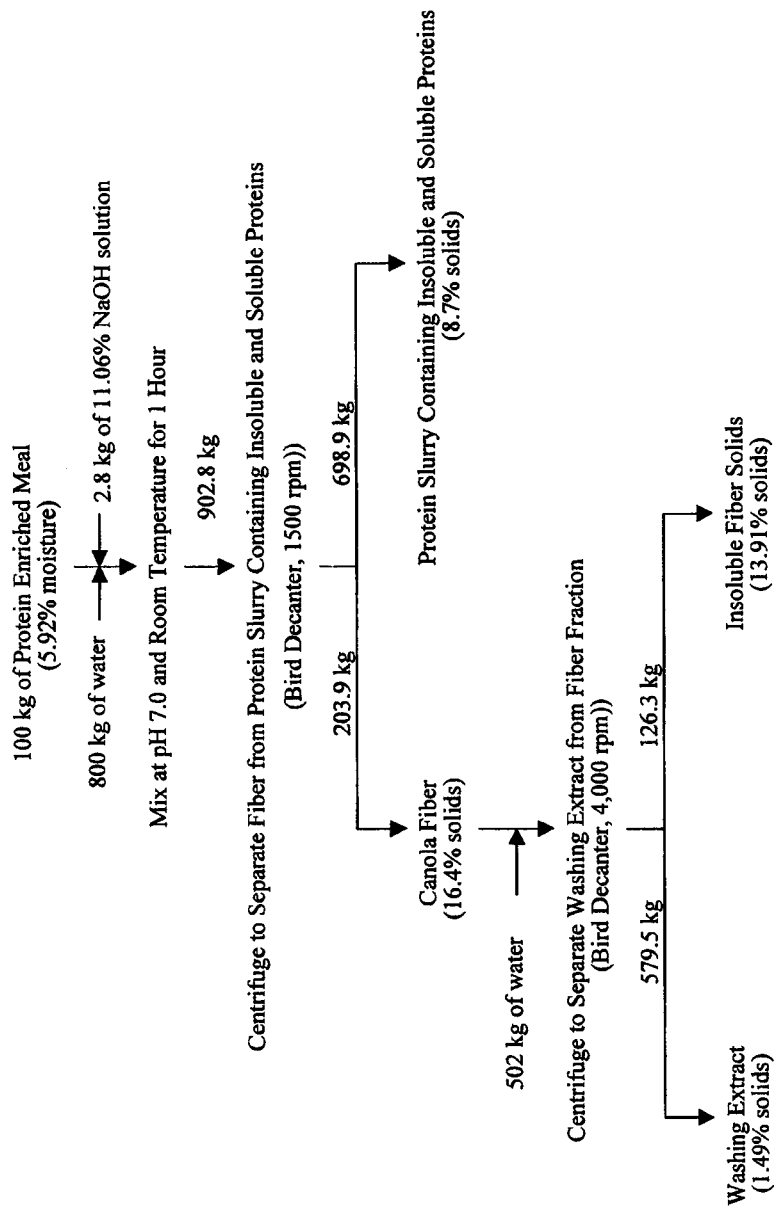
FIG. 24 is a schematic representation illustrating a separation and removal of fiber from a protein slurry containing insoluble and soluble proteins.

Approximately 100 kg of the protein enriched meal was mixed with 800 kg of tap water at a ratio of 1 to 8 (by weight) under homogeneous agitation. The protein slurry was adjusted to about pH 7 by slow addition of 2.8 kg of 11.06% NaOH solution under homogeneous agitation. This was followed by centrifugation at room temperature using a Bird Decanter Centrifuge (Bird 6" Continuous Bowl Centrifuge, Bird Machine Company of Canada, Saskatoon, Saskatchewan) at 1500 rpm bowl speed and a low pool depth. A schematic flowchart illustrating the wet separation and removal of fiber is shown in FIG. 24.

The protein slurry was pumped through the Bird Decanter at ambient temperature and a feed rate of 150 kg/hr and it was operated at a bowl speed of 1,500 rpm and a low pool depth to separate the coarse fiber solids from the soluble and insoluble protein fractions. Approximately 203.9 kg of wet fiber solids containing 16.4% solids and 698.9 kg of protein slurry containing soluble and insoluble proteins at 8.7% solids were produced, respectively. 698.9 kg of protein slurry containing soluble and insoluble proteins would be used to produce protein concentrate.

Approximately 203.9 kg of wet fiber solids was mixed with 502 kg of water in a tank for 0.5 hour, which was followed by centrifugation to separate the soluble liquid extract from the insoluble fiber solids at room temperature using the Bird Decanter at a bowl speed of 4,000 rpm and a feed rate of 350 kg/hr. Approximately 126.3 kg of insoluble fiber solids and 579.5 kg of soluble liquid extract were produced. The insoluble fiber solids are used to produce hydrolyzed protein concentrate.

(iii) Preparation of Protein Concentrate

Figure 25:
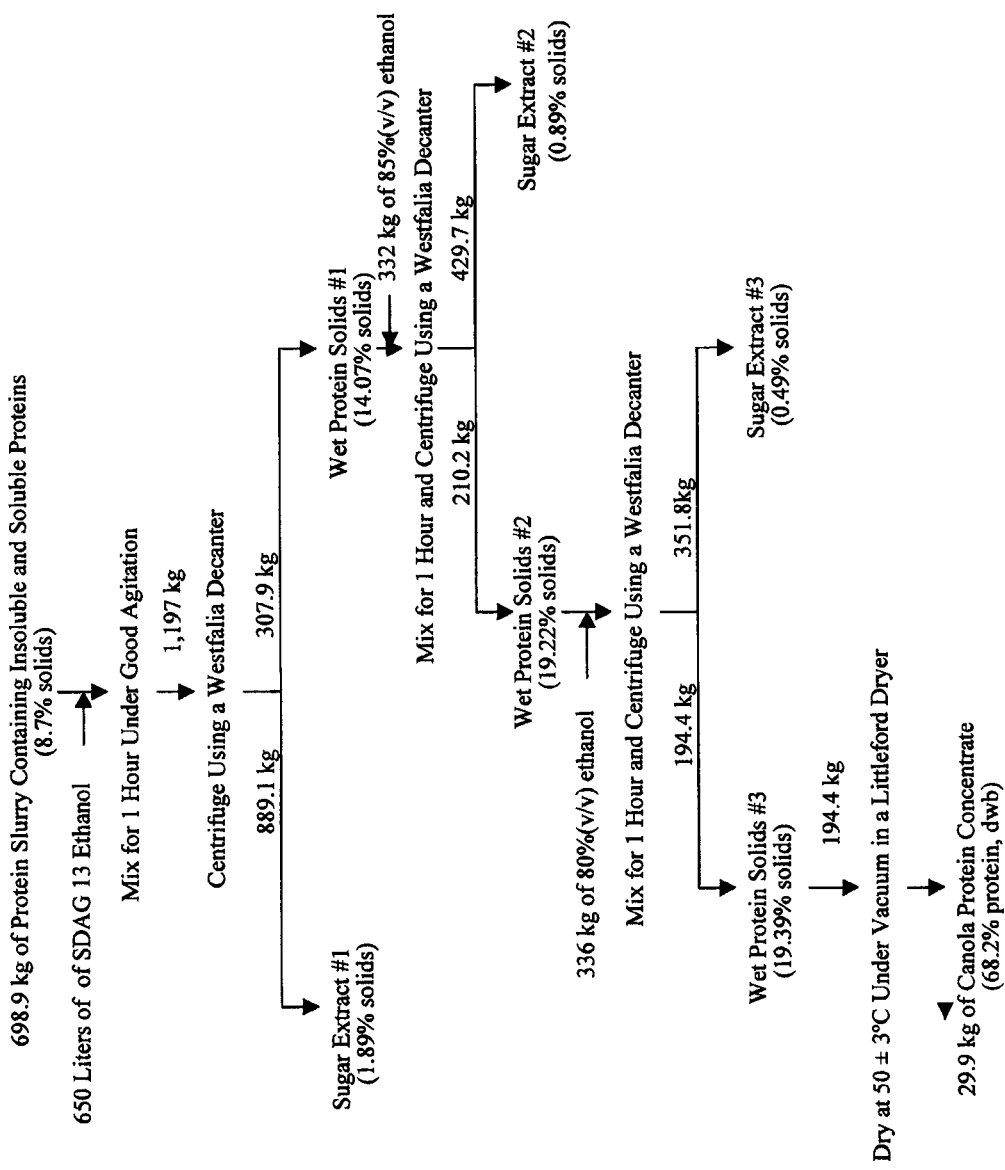
FIG. 25 is a schematic representation illustrating a preparation of a protein concentrate from a protein slurry after the removal of fiber.

Approximately 698.9 kg of protein slurry containing soluble and insoluble proteins after the fiber removal in the using the Bird Decanter was mixed with 650 liters of SDAG 13 denatured ethanol (containing 99% ethanol and 1% ethyl acetate) for 1 hour at room temperature. This was followed by centrifugation using a Westfalia® Decanter to obtain 889.1 kg of a first sugar extract containing 1.89% solids and 307.9 kg of a wet protein solids fraction containing 14.07% solids. The wet protein solids fraction (307.9 kg) was mixed with 332 kg of SDAG 13 denatured ethanol for 1 hour at room temperature. This was again followed by centrifugation using the Westfalia® Decanter to obtain 429.7 kg of a second sugar extract and 210.2 kg of a second wet protein solid fraction. Finally, the wet protein solids (210.2 kg) were mixed with 336 kg of SDAG 13 denatured ethanol for 1 hour at room temperature, which was followed by centrifugation using the Westfalia® Decanter to obtain 351.8 kg of a third sugar extract and 194.4 kg of a third wet protein solid fraction. The wet protein solids fractions were dried at 50±3° C. under vacuum using a Littleford® Dryer until the moisture content was about 7.83%. The protein concentrate contained 68.2% protein on a dry weight basis. A schematic flowchart illustrating the preparation of a protein concentrate is shown in FIG. 25.

(iv) Preparation of Hydrolyzed Protein Concentrate

Figure 26:
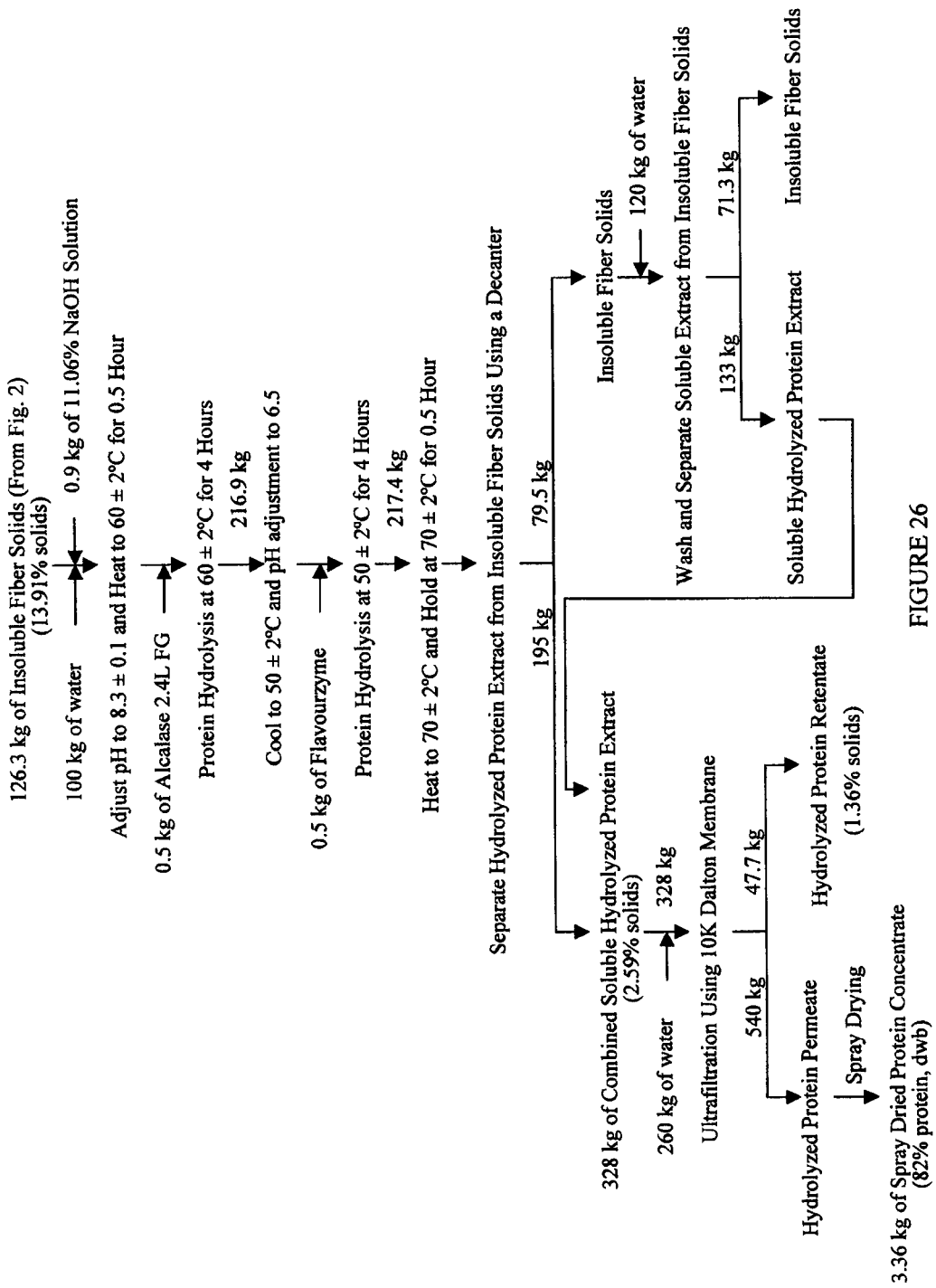
FIG. 26 is a schematic representation illustrating a preparation of a hydrolyzed protein concentrate.

Approximately 126.3 kg of insoluble fiber solids were mixed with 100 kg of water in a tank. This was followed by pH adjustment to 8.3±0.1 using 0.9 kg of 11.06% NaOH solution. Approximately 0.5 kg of a first protease (Alcalase® 2.4 L FG) was added to the slurry. The slurry was then heated to 60±2° C. and held at this temperature for 4 hours. The slurry was cooled down to 50±2° C. and pH adjusted to 6.5. Approximately 0.5 kg of a second protease (Flavouzyme) was added to the slurry, which was followed by holding at 50±2° C. for 4 hours. The slurry was centrifuged using the Westfalia® Decanter at 3300×g to separate the hydrolyzed protein extract from the insoluble fiber fraction. The insoluble fiber was washed further with 120 kg of filtered tap water, which was again followed by centrifugation at 3300×g to separate the wash protein extract from the washed fiber solids using the Westfalia® Decanter. The hydrolyzed protein extract and the wash hydrolyzed protein extract were combined. The combined hydrolyzed protein extract was fed to a Millipore® Ultrafiltration Unit (Model A60, Millipore® Corporation, Bedford, Mass., USA) at ambient temperature. The Ultrafiltration Unit (UF) was fitted with three hollow fiber cartridges with a molecular weight cutoff of 10,000 daltons, with each cartridge containing 5 $m^2$ of membrane surface area. The hydrolyzed protein extract was pumped through the hollow fiber cartridges at a rate of 800-1000 kg/hr. The retentate was recycled back to the feed tank and the permeate was collected in another tank. The UF unit was operated at an inlet pressure of 25 psi maximum and a retentate back pressure of 15 psi maximum. The flux rate or permeate rate was about 190-300 kg/hr throughout the ultrafiltration process. The ultrafiltration process continued until about 40 kg of retentate remained in the feed tank. Approximately 260 kg of water was added continuously into the feed tank and ultrafiltration was conducted at ambient temperature using the same UF unit fitted with the same three hollow fiber cartridges. The original volume of retentate in the feed tank was held constant by adding water to make up for the removed permeate. The retentate was recycled back to the feed tank. The ultrafiltration process continued until all 260 kg of water was added to the retentate. A schematic flowchart illustrating the preparation of a hydrolyzed protein concentrate is shown in FIG. 26.

Approximately 540 kg of permeate and 47.7 kg of retentate were obtained from the ultrafiltration process. The permeate was spray dried to produce hydrolyzed protein concentrate using a Komline Sanderson® spray dryer (Komline Sanderson® Ltd., Brampton, Ontario, Canada). The spray drying operation was conducted at an inlet air temperature of 185±5° C. and an outlet air temperature of 85±5° C. Approximately 3.36 kg of spray dried hydrolyzed protein concentrate containing 82% protein (dwb) was produced.

Discussion

The results of the proximate analysis for defatted canola meal, protein enriched meal, fiber enriched meal, protein concentrate and hydrolyzed protein concentrate are shown in Table 36. As shown in Table 36, dry separation by milling using a disc mill and screening using a vibratory screen of 45 US mesh increased the protein content from 48% in the defatted meal to 51.5% in the protein enriched meal. The fiber content was reduced from 7.75% in the extracted meal to 5.48% in the protein enriched meal by dry separation. Wet separation to remove fiber using the Bird Decanter and to remove sugar compounds by the ethanol extraction process further increased the protein content from 51.5% in the protein enriched meal to 68.2% in the protein concentrate.

The enhancement in the protein content by ethanol washing is shown in Table 37. The protein content in the ethanol washed protein solids was increased to 61.4%, 66.3% and 67.8% in the ethanol precipitation, first and second ethanol washings. The large increase in the protein content was achieved in the $1^{st}$ ethanol washing of the ethanol precipitated protein solids, from 61.4% protein to 66.3% protein.

In order to produce a protein concentrate containing about 70% protein (dwb), it is necessary to separate and remove fiber from the soluble protein extract and the insoluble protein particles taking advantage of the difference in density and particle size between the fiber and insoluble protein particles. The protein enriched meal was mixed with water at a ratio of 1 to 8 by weight and pH was adjusted to 7.0. After 1 hour of holding time under agitation at room temperature, the protein slurry was centrifuged at a low bowl speed of 1,500 RPM (~750 g force) using the Bird Decanter. Larger fiber particles with higher density were separated from smaller insoluble protein particles with lower density as well as soluble protein solution. In an embodiment, the soluble protein extract would be re-cycled and re-used to increase the soluble solid content in order increase the density and viscosity of the liquid medium, which would help to reduce the volume of water usage.

Hydrolyzed protein concentrate containing 82% protein (dwb) was obtained. The hydrolyzed protein concentrate was 100% water soluble and its solution was crystal clear since it was purified by a membrane filtration process. A shown in Table 38, the protein recovery yield through protein hydrolysis and membrane purification was about 85.15% before spray drying, which was calculated based on the hydrolyzed proteins including amino acids and peptides in the permeate of the ultrafiltration divided by the total proteins in the starting material of the insoluble fiber solids before the hydrolysis process (6.88 kg of protein weight in the permeate divided by 8.08 kg of protein weight in the insoluble fiber solids gave 85.15% protein recovery yield). The loss of proteins through membrane filtration is about 3.22% (0.26 kg of protein weight in the retentate divided by 8.08 kg of protein weight in the permeate gives 3.22% protein loss in the UF process).

The hydrolyzed protein concentrate produced in accordance with the processes of the present disclosure contained 82% protein (dwb). It was determined that the protein dispersibility index of the hydrolyzed protein concentrate was 99.8% and its solution was clear and transparent since it was purified by a membrane filtration process. The absorbance and transmittance of 1%, 3% and 5% hydrolyzed protein solutions using distilled water as the control is shown in Table 39. The absorbance and transmittance of 1% soy and pea protein isolate solutions were also determined for comparison. The absorbance and transmittance of the samples were determined at 720 nm wavelength using a Shimadzu® UV-Visible Spectrophotometer (UV-VIS 265, Mandel Scientific® Company Ltd., Guelph, Ontario, Canada).

In spectroscopy, the absorbance A and transmittance $I_{out}/I_{in}$ at 720 nm wavelength are defined as:

$$A_{720\,nm} = -\log_{10}(I_{out}/I_{in}) \quad (I)$$

$I_{out}$ is the intensity of light at 720 nm wavelength that has passed through a sample (transmitted light intensity).

$I_{in}$ is the intensity of the light before it enters the sample.

As shown in Table 39, 97%, 89% and 87% light intensity passed through 1%, 3% and 5% hydrolyzed canola protein concentrate solutions at 720 nm wavelength. These hydrolyzed protein solutions were clear and transparent by visual inspection. In comparison, less than 0.016% light intensity had passed through 1% soy and pea protein isolate solutions. The soy and pea protein isolate solutions were not clear and transparent. The incident light was likely scattered by the dispersed particles in the soy and pea protein isolate solutions.

Example 7

Canola Protein Concentrate Having About 65-75% Protein Content (i) Preparation of Defatted Meal from Regular Canola Seed (*B. napus*)

Approximately 10 kg of regular canola seed (*B. napus*) was adjusted to 9% moisture by adding water to the canola seed in a plastic pail with manual agitation for a few minutes. The canola seed in the pail was then covered and tempered overnight in the laboratory. The moisture adjusted regular canola seed was then heated in a microwave oven for 2 minutes (heat to 85-95° C.). The canola seed was then covered with an aluminum foil and heated at 95° C. in a forced air oven for 30 minutes. After the heat treatment, the regular canola seed was flaked using a lab flaking mill. The flaked and heat treated seed was pressed using a Gusta Laboratory Screw Press. Approximately 3.26 kg of press oil and 6.32 kg of press cake were obtained from the pressing operation.

Approximately 6.32 kg of regular canola press cake was extracted with 16 liters of methyl pentane for 5 hours using a Soxhlet extraction system to obtain an extracted oil and a defatted canola meal. The extracted oil was recovered by evaporation and desolventization to remove the solvent from the miscella under vacuum at 60° C.

The methyl pentane defatted regular canola meal was desolventized in a laboratory fume hood for three days at room temperature. Approximately 5.02 kg of defatted regular canola meal was obtained after desolventization and drying.

(ii) Preparation of Defatted Meal from *Juncea* Seed (*B. juncea*)

Approximately 499 kg of cleaned *Juncea* seed containing 8.12% moisture was flaked to produce flaked seed with an average thickness of 0.3±0.1 mm using a flaking mill (Model S28, Lauhoff Corporation, Detroit, U.S.A.). The flaked canola seed was heat treated using a two tray cooker. The temperature for the top tray was 52-59° C., while the temperature for the bottom tray was 68-90° C. The resident time for the top and bottom trays was 20 minutes, respectively. After heat treatment, the flaked seed was fed into the press and pressed to produce 278.9 kg of press cake and 138.1 kg of press oil.

Approximately 10 kg of canola (*Juncea*) press cake was extracted with 32 liters of methyl pentane for 5 hours using a Soxhlet extraction system to obtain extracted oil and defatted canola meal. The extracted oil was recovered by evaporation and desolventization to remove the solvent from the miscella under vacuum at 60° C. The methyl pentane defatted canola meal was desolventized in a laboratory fume hood for three days at room temperature. Approximately 8.23 kg of defatted canola (*Juncea*) meal was obtained.

(iii) Lab Milling and Screening of Defatted Regular (*napus*) and *Juncea* Meals Approximately 4.01 kg of defatted regular canola meal was milled for 1 minute using a lab Warring Blender, which was followed by manual screening using a 45 US mesh Rotex screen to generate a protein enriched fraction (fine fraction) and a fiber enriched fraction (coarse fraction). The coarse fraction was re-milled in the lab Warring Blender for 1 minute. This was followed by manual screening using the 45 US mesh Rotex screen to generate a second protein enriched fraction and a coarse fraction. Finally, the coarse fraction was milled in the Warring Blender for 1 minute and the milled material was manually screened using the 45 US mesh Rotex screen to generate a third protein enriched fraction and the final fiber enriched meal. Approximately 1.76 kg of combined protein enriched fractions and 2.24 kg of fiber enriched meal were produced, respectively. Therefore, 43.89% of the total material was the protein enriched meal and 56.11% was the fiber enriched meal.

Approximately 3.52 kg of defatted *Juncea* meal was milled for 1 minute using a lab Warring Blender, which was followed by manual screening using a 45 US mesh Rotex screen to generate a protein enriched fraction (fine fraction) and a fiber enriched fraction (coarse fraction). The coarse fraction was re-milled in the lab Warring Blender for 1 minute. This was followed by manual screening using the 45 US mesh Rotex screen to generate a second protein enriched fraction and a coarse fraction. Finally, the coarse fraction was milled in the Warring Blender for 1 minute and the milled material was manually screened using the 45 US mesh Rotex screen to generate a third protein enriched fraction and the final fiber enriched meal. Approximately, 1.53 kg of combined protein enriched fractions and 1.84 kg of fiber enriched meal were produced, respectively. Therefore, 43.71% of the total material was the protein enriched meal and 56.29% was the fiber enriched meal. The mass balance data for preparation of defatted meals, protein and fiber enriched meals are given in Table 40.

(iv) Wet Separation to Remove Fiber

Approximately 0.75 kg regular (*napus*) protein enriched meal was mixed with 6 kg of water at a ratio of 1 to 8 by weight at ambient temperature for 1 hour under homogeneous agitation. The protein slurry was centrifuged at 4,000 rpm for 10 minutes using a lab centrifuge. Three layers of top liquid layer, the middle insoluble protein layer and the bottom insoluble fiber layer were obtained in the centrifuge bottles. The larger fiber particles with higher density settled faster than the smaller insoluble protein particles with lower density. Therefore, the larger fiber particles settled to the bottom of the bottles at first. The smaller insoluble protein particles with lower density settled on the top of the fiber layer. The liquid extract containing soluble proteins was at the top layer. The bottom fiber layer (0.347 kg) was separated manually from the middle insoluble protein layer (1.360 kg) and the top liquid extract layer (5.053 kg). After the fiber removal, the middle insoluble protein layer and the top liquid extract layer were combined and the combined slurry was mixed with 100% SDAG 13 ethanol at a ratio of 1 to 1 by volume for 10 minutes to precipitate proteins. The precipitation slurry was centrifuged at 4,000 rpm for 10 minutes to separate the soluble sugar extract from the insoluble protein solids using the lab centrifuge. The recovered protein solids were mixed with 4.5 kg of 80% ethanol (v/v) at ambient temperature for 1 hour, which was followed by centrifugation at 4,000 rpm for 10 minutes to separate the insoluble protein solids from the washing sugar extract. Finally, the insoluble protein solids were mixed with 4.5 kg of 80% ethanol (v/v) at ambient temperature for 1 hour. The slurry was once again centrifuged at 4,000 rpm to separate the washed protein solids from the soluble sugar extract. The washed protein solids were desolventized in a laboratory fume hood for 3 days before drying to 5.26% moisture at 50° C. using a forced air oven. The dried protein concentrate was milled into powder form using a lab pin mill.

Approximately 1 kg of *Juncea* protein enriched meal was mixed with 8 kg of water at a ratio of 1 to 8 by weight at ambient temperature for 1 hour under homogeneous agitation. The protein slurry was centrifuged at 4,000 rpm for 10 minutes using the lab centrifuge. Three layers of top liquid layer, the middle insoluble protein layer and the bottom insoluble fiber layer were obtained in the centrifuge bottles. The larger fiber particles with higher density settled faster than the smaller insoluble protein particles with lower density. Therefore, the larger fiber particles settled to the bottom of the bottles at first. The smaller insoluble protein particles with lower density settled on the top of the fiber layer. The liquid extract containing soluble proteins was at the top layer. The bottom fiber layer (0.430 kg) was separated manually from the middle insoluble protein layer (2.282 kg) and the top liquid extract layer (6.288 kg). After the fiber removal, the middle insoluble protein layer and the top liquid extract layer were combined and the combined slurry was mixed with 100% SDAG 13 ethanol at a ratio of 1 to 1 by volume for 10 minutes to precipitate proteins. The precipitation slurry was centrifuged at 4,000 rpm for 10 minutes to separate the soluble sugar extract from the insoluble protein solids using the lab centrifuge. The recovered protein solids were mixed with 6 kg of 80% ethanol (v/v) at ambient temperature for 1 hour, which was followed by centrifugation at 4,000 rpm for 10 minutes to separate the insoluble protein solids from the washing sugar extract. Finally, the insoluble protein solids were mixed with 6 kg of 80% ethanol (v/v) at ambient temperature for 1 hour. The slurry was once again centrifuged at 4,000 rpm to separate the washed protein solids from the soluble sugar extract. The washed protein solids were desolventized in a laboratory fume hood for 3 days before drying to 3.9% moisture at 50° C. using a forced air oven. The dried protein concentrate was milled into powder form using a lab pin mill. The mass balance data for the wet separation process to remove fiber and prepare protein concentrate are shown in Table 41.

Discussion

As shown in Table 42, the protein content was increased from 46.8% (dwb) in the defatted regular canola meal to 51.5% (dwb) in the regular protein enriched meal by the milling and screening operation. The crude fiber content was reduced from 9.90% (dwb) in the defatted regular canola meal to 7.09% (dwb) in the regular protein enriched meal. The protein content was increased from 48.7% (dwb) in the defatted *Juncea* meal to 52.8% (dwb) in the Juncea protein enriched meal by the milling and screening operation. The crude fiber content was reduced from 7.44% (dwb) in the defatted *Juncea* meal to 5.36% (dwb) in the *Juncea* protein enriched meal. A simple step of dry milling and screening was able to reduce fiber and increase protein content.

As shown in Table 43, the wet separation process to remove fiber by centrifugation based on the particle size and density difference of insoluble fiber and protein particles as well as to remove sugar compounds by the ethanol extraction process increased the protein content from 51.5% in the regular protein enriched meal to 66.9% in the regular protein concentrate. The protein content was increased from 52.8% in the *Juncea* protein enriched meal to 71.2% in the *Juncea* protein concentrate by the wet fiber separation and ethanol washing process.

The amino acid profile of defatted canola meals and protein concentrates is shown in Table 44. Canola protein concentrates generated from the methyl pentane defatted regular and *Juncea* canola meals contains higher lysine and sulphur containing amino acids methionine and cystine than the canola protein concentrate generated from the defatted *Juncea* meal using a solvent mixture of butane and R134a (see Example 5). From the amino acid profile, canola protein concentrates are of high nutritional quality and capable of providing adequate amounts of all essential amino acids. From the essential amino acid profiles as shown in Table 44, canola protein concentrates are rich in the muscle building essential amino acids such as valine, methionine, leucine and isoleucine. They also contain a high content of the essential amino acid threonine, which is important for brain activity. Both regular and *Juncea* canola protein concentrates generated from methyl pentane defatted meals contain similar content of essential amino acids.

In an embodiment of the disclosure, the canola protein concentrates produced in accordance with the present disclosure, contain about 2% to about 8% crude fiber and 65-75% protein on a dry weight basis. In a further embodiment, the protein concentrates have a minimum 25% soluble protein in a borate-phosphate buffer solution. In a further embodiment of the disclosure, the hydrolyzed canola protein concentrates contains typically less than about 5%, optionally 2% and suitably about 0% crude fiber, and greater than about 75% protein on a dry weight basis. In another embodiment, the hydrolyzed protein concentrate is at least about 95%, optionally about 98%, optionally about 99% and suitably about 100% water soluble. In an embodiment, the hydrolyzed protein concentrate has a 100% water solubility as defined by 100% PDI value (protein dispersibility index). In another embodiment of the disclosure, the canola protein isolates produced in accordance with the present disclosure typically contain about 0% crude fiber and greater than about 90% protein. In another embodiment, the protein isolates have a minimum of about 85% soluble protein in a borate-phosphate buffer solution. In another embodiment, the protein isolates have a typical molecular weigh profile of 64.7% at 70 kDa, 26.2% at 12 kDa and 9.1% at <kDa.

The results of protein solubility test on defatted canola meals and protein concentrates are shown in Table 45. The test results show that the defatted regular and *Juncea* meals have similar protein solubility of 30.36-31.48% while regular and *Juncea* proteins concentrates have protein solubility of 32.27-36.76%. They all have much higher protein solubility than commercially available samples of soy and pea protein isolates.

The results of antinutritional factors in defatted canola meals, canola protein concentrates, canola protein isolate and commercial samples of soy and pea protein isolates are shown in Table 46. The wet separation and ethanol washing process for preparation of canola protein concentrates from defatted meals had significantly reduced the sinapine content. Canola protein concentrates contain similar sinapine content as commercial samples of soy and pea protein isolates. Canola protein concentrates contain higher phytate content than soy and pea protein isolates. Canola protein isolate contains lower phytate content than soy and pea protein isolates.

Example 8

Canola Protein Concentrate Having About 73% Protein Content (i) Preparation of Defatted Meal A press cake was produced from *Juncea* seed (*B. juncea*) using the processing conditions similar to those listed in Example 5. Defatted *Juncea* meal was produced from the press cake through solvent extraction at 50° C. for 1.5 hours using a solvent mixture of butane and R134a. The defatted meal was milled using a disc mill equipped with #8114 stationary and rotating plates (The Bauer Bros. Co., Springfield, Ohio, U.S.A.) at 0.02" gap, 2340 rpm rotational speed and 100 kg/hr throughput. Only one pass through the disc mill was conducted.

Figure 27:
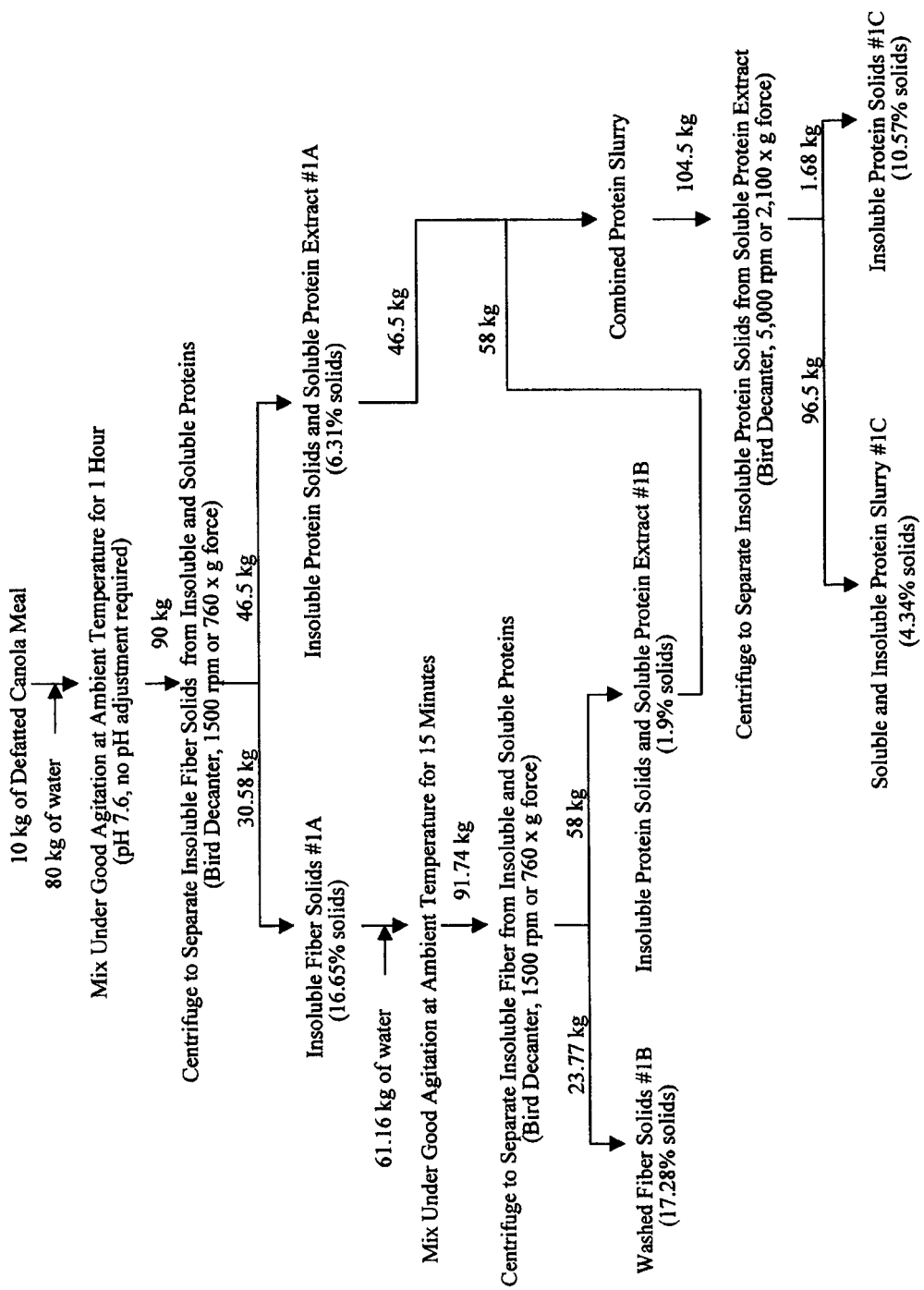
FIG. 27 is a schematic representation illustrating a wet fiber removal process.

(ii) Wet Separation to Remove Fiber (a) A schematic flowchart for wet fiber separation is shown in FIG. 27. Approximately 10 kg of defatted meal was mixed with 80 kg of tap water at a ratio of 1 to 8 (by weight) under homogeneous agitation for 1 hour. The pH of protein slurry was at 7.6 and no further pH adjustment was required. The canola meal slurry was centrifuged at ambient temperature using a Bird Decanter Centrifuge (Bird 6" Continuous Bowl Centrifuge, Bird Machine Company of Canada, Saskatoon, Saskatchewan) at 1500 rpm bowl speed and a low pool depth. The canola meal slurry was pumped through the Bird Decanter at ambient temperature and a feed rate of 150 kg/hr and it was operated at a bowl speed of 1,500 rpm and a low pool depth to separate the coarse fiber solids from the soluble and insoluble protein fractions. Approximately 30.58 kg of wet fiber solids #1A containing 16.65% solids and 46.5 kg of protein slurry #1A containing soluble and insoluble proteins at 6.31% solids were produced, respectively.

The wet fiber solids #1A was mixed with 61.16 kg of water in a tank for 15 minutes, which was followed by centrifugation to separate the washed fiber solids #1B from the insoluble protein solids and soluble protein extract #1B at room temperature using the Bird Decanter at a bowl speed of 1,500 rpm and a feed rate of 150 kg/hr. Approximately 23.77 kg of washed fiber solids #1B containing 17.28% solids and 58 kg of insoluble and soluble protein slurry #1B containing 1.9% solids were produced.

The insoluble protein solids and soluble protein extract #1A and #1B were combined, which was followed by centrifugation using the Bird Decanter at 5,000 rpm to separate the insoluble protein solids #1C from the soluble and insoluble protein slurry #1C. Approximately 1.68 kg of insoluble protein solids #1C containing 10.57% solids and 96.5 kg of soluble and insoluble protein slurry #1C containing 4.34% solids were produced.

Figure 28:
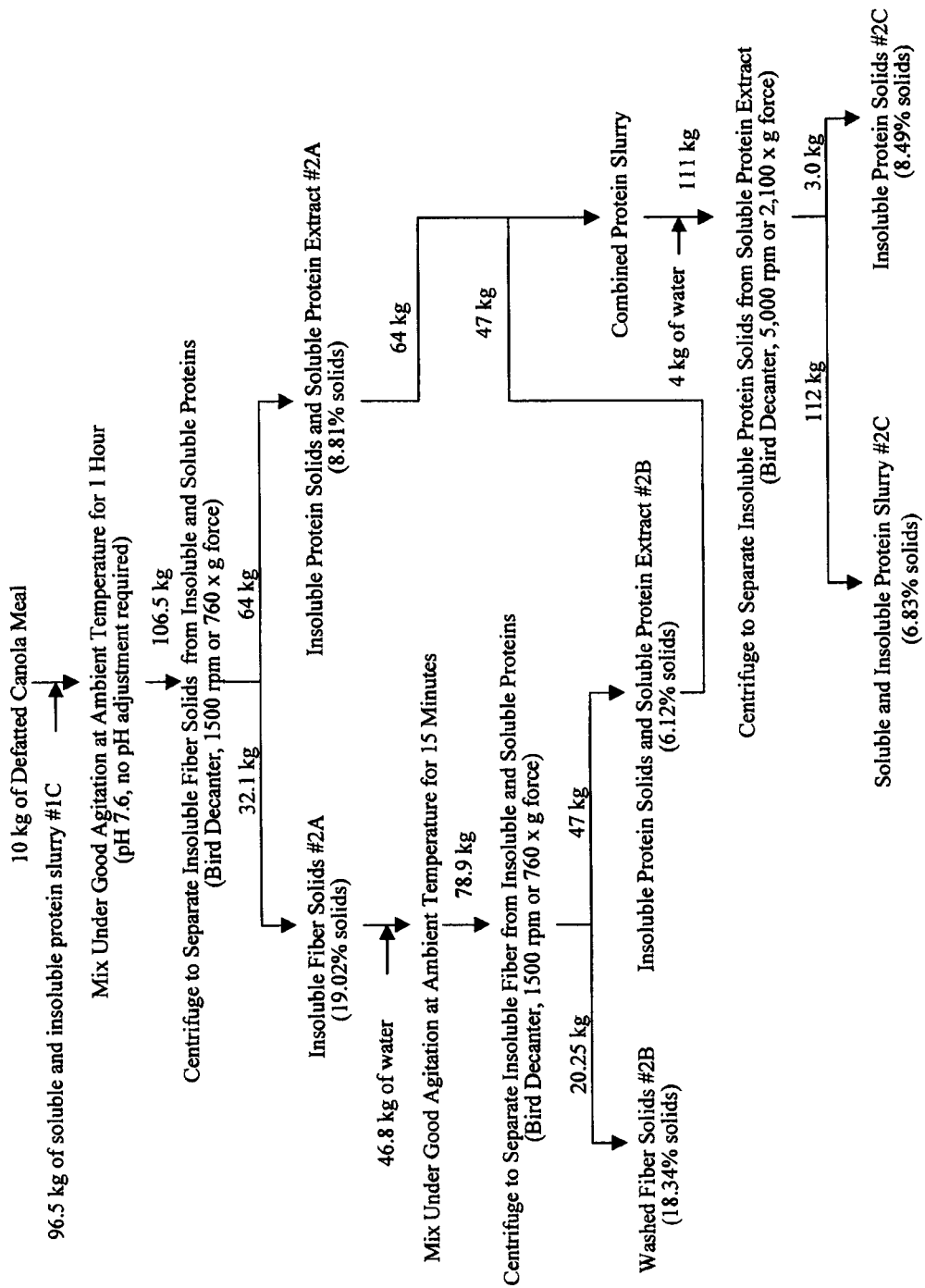
FIG. 28 is a schematic representation illustrating a first recycling of a protein fraction and a wet fiber removal process.

(b) Recycling of Protein Slurry Containing Soluble and Insoluble Protein Fractions A schematic flowchart for wet fiber separation and the 1$^{st}$ recycle is shown in FIG. 28. Approximately 10 kg of defatted meal was mixed with 96.5 kg of soluble and insoluble protein slurry #1C generated from the previous wet fiber separation process under homogeneous agitation for 1 hour. The pH of protein slurry was at 7.6 and no further pH adjustment was required. The canola meal slurry was centrifuged at ambient temperature using a Bird Decanter Centrifuge (Bird 6" Continuous Bowl Centrifuge, Bird Machine Company of Canada, Saskatoon, Saskatchewan) at 1,500 rpm bowl speed and a low pool depth. The canola meal slurry was pumped through the Bird Decanter at ambient temperature and a feed rate of 150 kg/hr to separate the coarse fiber solids from the soluble and insoluble protein fractions. Approximately 32.1 kg of wet fiber solids #2A containing 19.02% solids and 64 kg of protein slurry #2A containing soluble and insoluble proteins at 8.81% solids were produced, respectively.

The wet fiber solids #2A was mixed with 46.8 kg of water in a tank for 15 minutes, which was followed by centrifugation to separate the washed fiber solids #2B from the insoluble protein solids and soluble protein extract #2B at ambient temperature using the Bird Decanter at a bowl speed of 1,500 rpm and a feed rate of 150 kg/hr. Approximately 20.25 kg of washed fiber solids #2B containing 18.34% solids and 47 kg of insoluble and soluble protein slurry #2B containing 6.12% solids were produced.

The insoluble protein solids and soluble protein extract #2A and #2B were combined, which was followed by centrifugation using the Bird Decanter at 5,000 rpm to separate the insoluble protein solids #2C from the soluble and insoluble protein slurry #2C. Approximately 3.0 kg of insoluble protein solids #2C containing 8.49% solids and 112 kg of soluble and insoluble protein slurry #2C containing 6.83% solids were produced.

(c) Second Recycling

Figure 29:
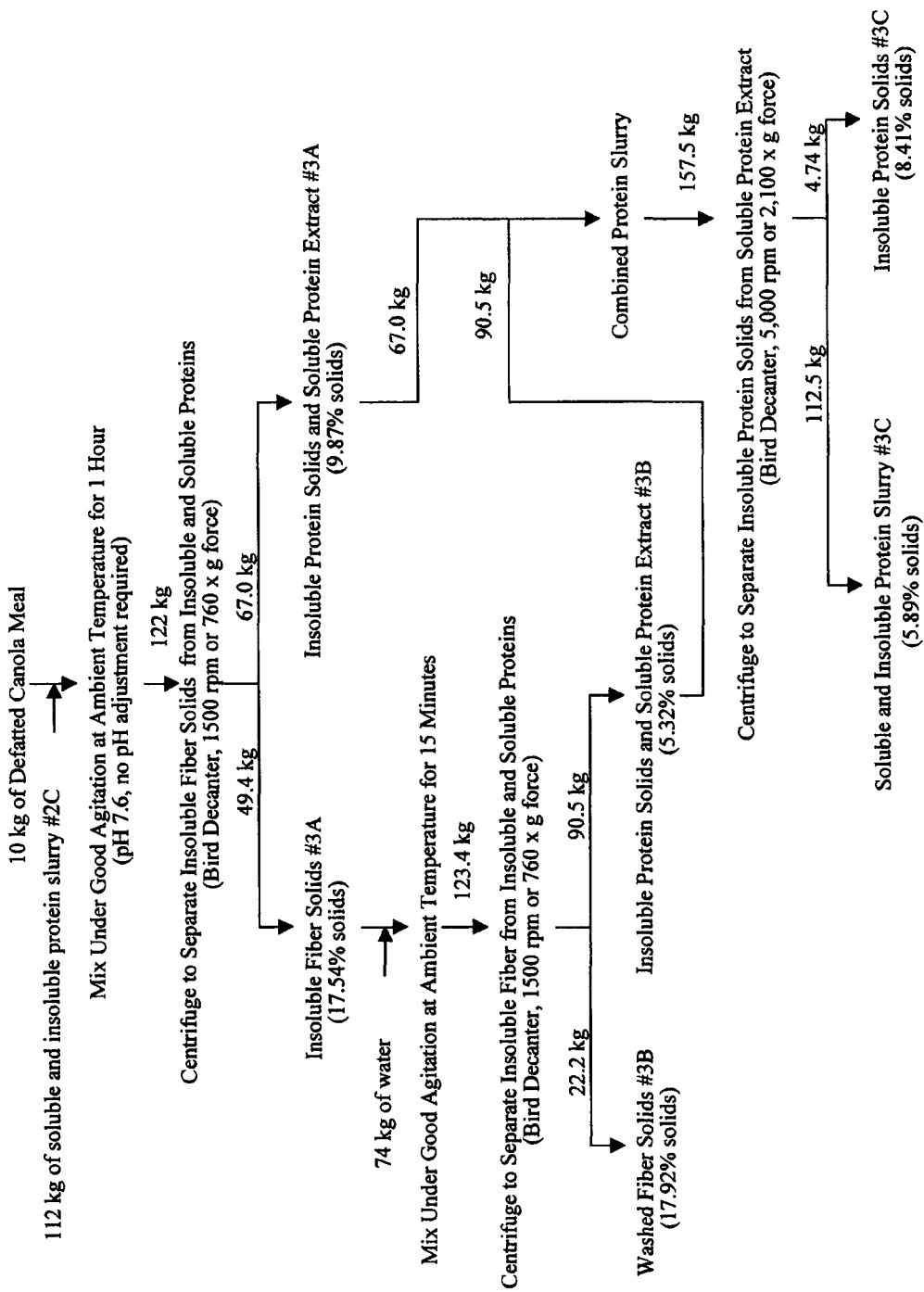
FIG. 29 is a schematic representation illustrating a second recycling of a protein fraction and a wet fiber removal process.

A schematic flowchart for wet fiber separation and the 2$^{nd}$ recycle is shown in FIG. 29. Approximately 10 kg of defatted meal was mixed with 112 kg of soluble and insoluble protein slurry #2C generated from the previous wet fiber separation process under homogeneous agitation for 1 hour. The pH of protein slurry was at 7.6 and no further pH adjustment was required. The canola meal slurry was centrifuged at ambient temperature using a Bird Decanter Centrifuge (Bird 6" Continuous Bowl Centrifuge, Bird Machine Company of Canada, Saskatoon, Saskatchewan) at 1,500 rpm bowl speed and a low pool depth. The canola meal slurry was pumped through the Bird Decanter at ambient temperature and a feed rate of 150 kg/hr to separate the coarse fiber solids from the soluble and insoluble protein fractions. Approximately 49.4 kg of wet fiber solids #3A containing 17.54% solids and 67.0 kg of protein slurry #3A containing soluble and insoluble proteins at 9.87% solids were produced, respectively.

The wet fiber solids #3A was mixed with 74 kg of water in a tank for 15 minutes, which was followed by centrifugation to separate the washed fiber solids #3B from the insoluble protein solids and soluble protein extract #3B at ambient temperature using the Bird Decanter at a bowl speed of 1,500 rpm and a feed rate of 150 kg/hr. Approximately 22.2 kg of washed fiber solids #3B containing 17.92% solids and 90.5 kg of insoluble and soluble protein slurry #3B containing 5.32% solids were produced.

The insoluble protein solids and soluble protein extract #3A and #3B were combined, which was followed by centrifugation using the Bird Decanter at 5,000 rpm to separate the insoluble protein solids #3C from the soluble and insoluble protein slurry #3C. Approximately 4.74 kg of insoluble protein solids #3C containing 8.41% solids and 112.5 kg of soluble and insoluble protein slurry #3C containing 5.89% solids were produced.

(d) Third Recycling

Figure 30:
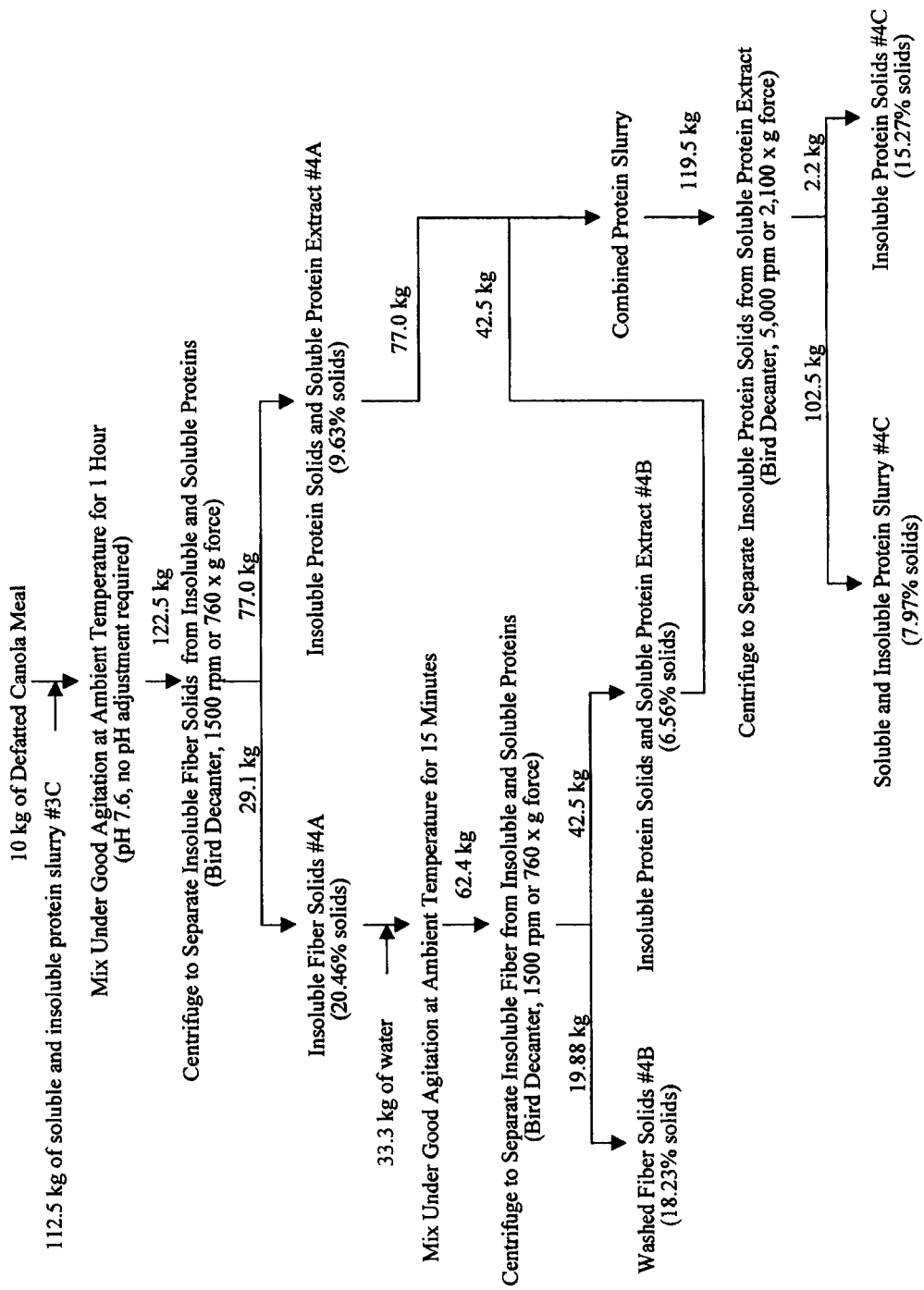
FIG. 30 is a schematic representation illustrating a third recycling of a protein fraction and a wet fiber removal process.

A schematic flowchart for wet fiber separation and the $3^{rd}$ recycle is shown in FIG. 30. Approximately 10 kg of defatted meal was mixed with 112.5 kg of soluble and insoluble protein slurry #3C generated from the previous wet fiber separation process under homogeneous agitation for 1 hour. The pH of protein slurry was at 7.6 and no further pH adjustment was required. The canola meal slurry was centrifuged at ambient temperature using a Bird Decanter Centrifuge (Bird 6" Continuous Bowl Centrifuge, Bird Machine Company of Canada, Saskatoon, Saskatchewan) at 1500 rpm bowl speed and a low pool depth. The canola meal slurry was pumped through the Bird Decanter at ambient temperature and a feed rate of 150 kg/hr to separate the coarse fiber solids from the soluble and insoluble protein fractions. Approximately 29.1 kg of wet fiber solids #4A containing 20.46% solids and 77.0 kg of protein slurry #4A containing soluble and insoluble proteins at 9.63% solids were produced, respectively.

The wet fiber solids #4A was mixed with 33.3 kg of water in a tank for 15 minutes, which was followed by centrifugation to separate the washed fiber solids #4B from the insoluble protein solids and soluble protein extract #4B at ambient temperature using the Bird Decanter at a bowl speed of 1,500 rpm and a feed rate of 150 kg/hr. Approximately 19.88 kg of washed fiber solids #4B containing 18.23% solids and 42.5 kg of insoluble and soluble protein slurry #4B containing 6.56% solids were produced.

The insoluble protein solids and soluble protein extract #4A and #4B were combined, which was followed by centrifugation using the Bird Decanter at 5,000 rpm to separate the insoluble protein solids #4C from the soluble and insoluble protein slurry #4C. Approximately 2.2 kg of insoluble protein solids #4C containing 15.27% solids and 102.5 kg of soluble and insoluble protein slurry #4C containing 7.97% solids were produced.

(e) Fourth Recycling

Figure 31:
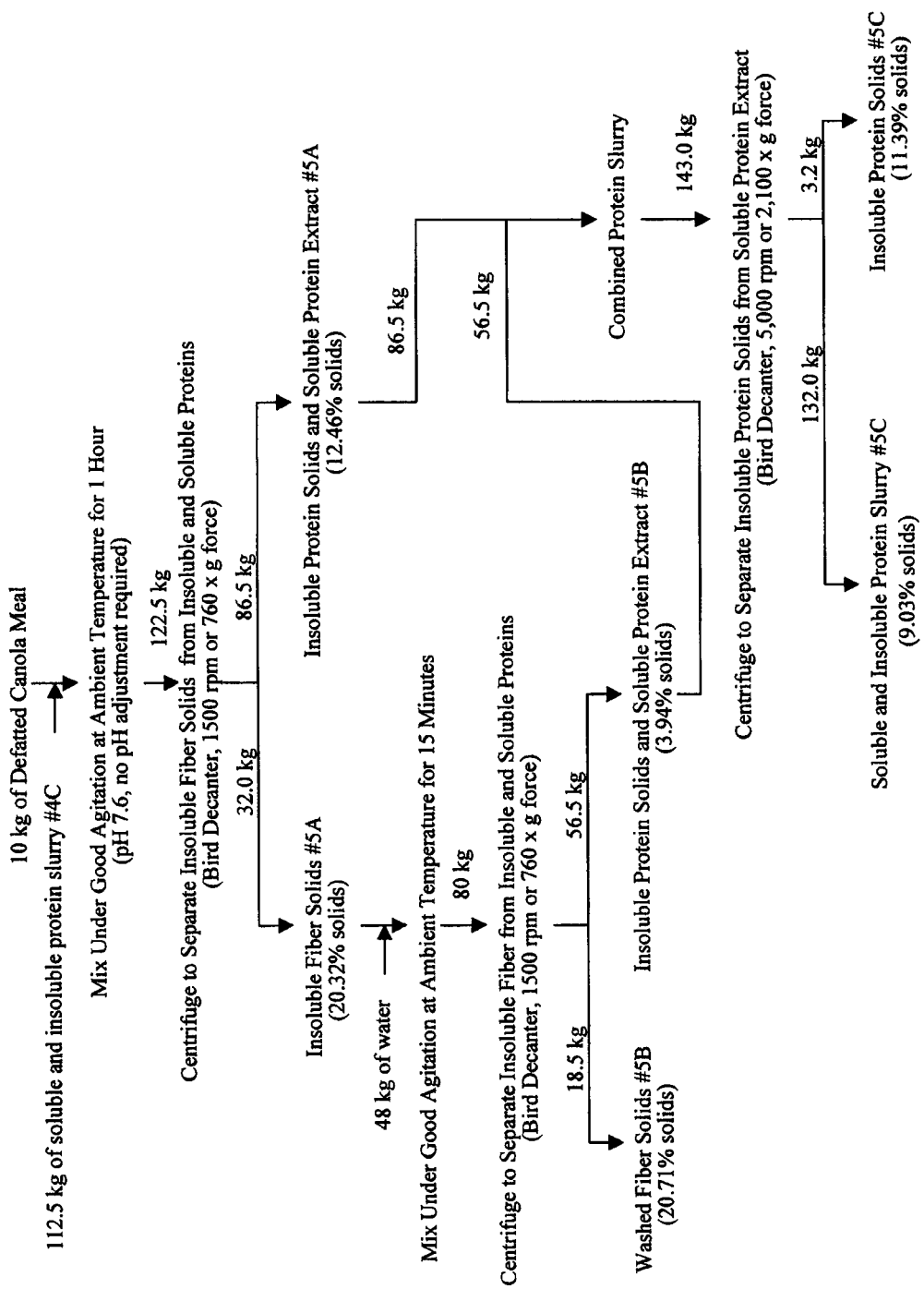
FIG. 31 is a schematic representation illustrating a fourth recycling of a protein fraction and a wet fiber removal process.

A schematic flowchart for wet fiber separation and the $4^{th}$ recycle is shown in FIG. 31. Approximately 10 kg of defatted meal was mixed with 112.5 kg of soluble and insoluble protein slurry #4C generated from the previous wet fiber separation process under homogeneous agitation for 1 hour. The pH of protein slurry was at 7.6 and no further pH adjustment was required. The canola meal slurry was centrifuged at ambient temperature using a Bird Decanter Centrifuge (Bird 6" Continuous Bowl Centrifuge, Bird Machine Company of Canada, Saskatoon, Saskatchewan) at 1,500 rpm bowl speed and a low pool depth. The canola meal slurry was pumped through the Bird Decanter at ambient temperature and a feed rate of 150 kg/hr to separate the coarse fiber solids from the soluble and insoluble protein fractions. Approximately 32.0 kg of wet fiber solids #5A containing 20.32% solids and 86.5 kg of protein slurry #5A containing soluble and insoluble proteins at 12.46% solids were produced, respectively.

The wet fiber solids #5A was mixed with 48 kg of water in a tank for 15 minutes, which was followed by centrifugation to separate the washed fiber solids #5B from the insoluble protein solids and soluble protein extract #5B at ambient temperature using the Bird Decanter at a bowl speed of 1,500 rpm and a feed rate of 150 kg/hr. Approximately 18.5 kg of washed fiber solids #5B containing 20.71% solids and 56.5 kg of insoluble and soluble protein slurry #5B containing 3.94% solids were produced.

The insoluble protein solids and soluble protein extract #5A and #5B were combined, which was followed by centrifugation using the Bird Decanter at 5,000 rpm to separate the insoluble protein solids #5C from the soluble and insoluble protein slurry #5C. Approximately 3.2 kg of insoluble protein solids #5C containing 11.39% solids and 132 kg of soluble and insoluble protein slurry #5C containing 9.03% solids were produced.

(f) Fifth Recycling

Figure 32:
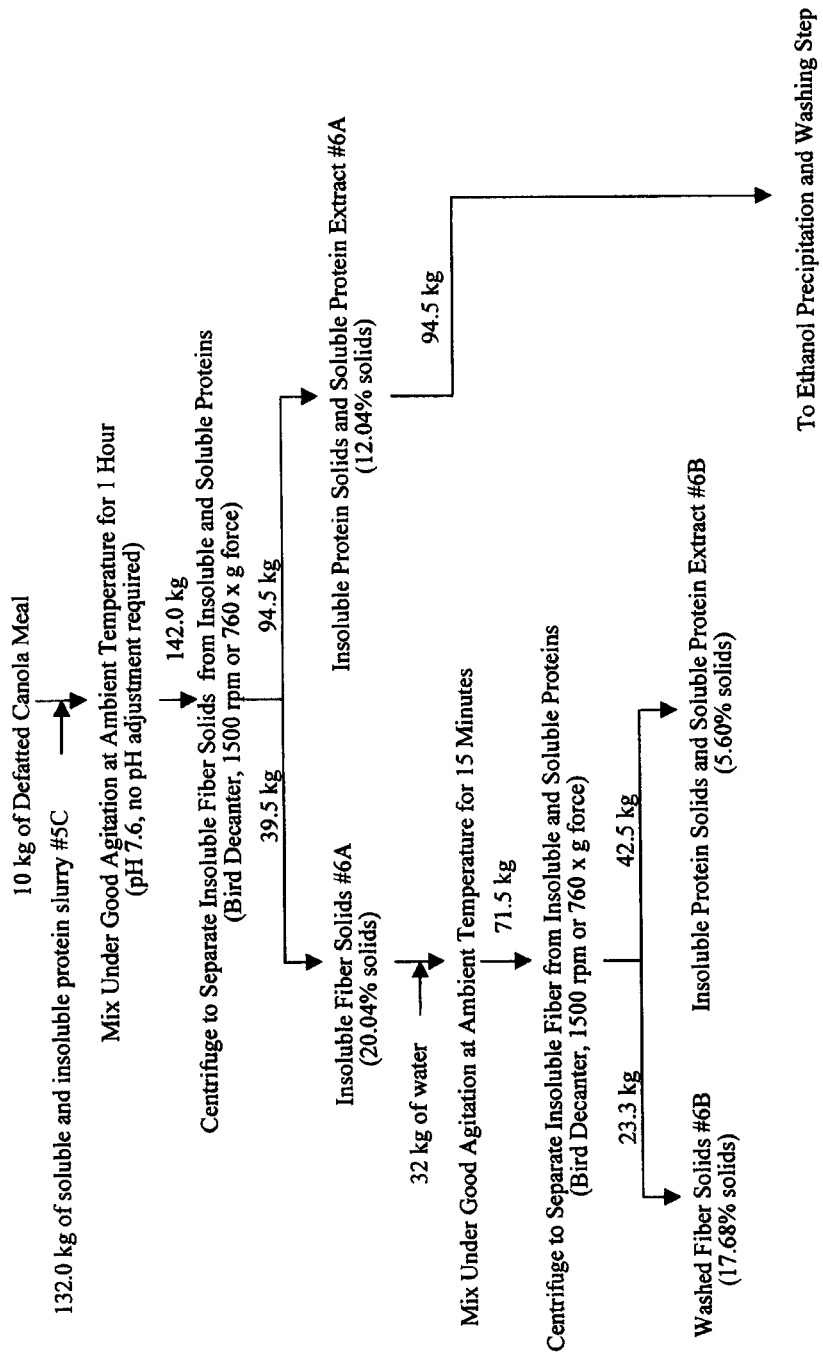
FIG. 32 is a schematic representation illustrating a fifth recycling of a protein fraction and a wet fiber removal process.

A schematic flowchart for wet fiber separation and the $5^{th}$ recycle is shown in FIG. 32. Approximately 10 kg of defatted meal was mixed with 132 kg of soluble and insoluble protein slurry #5C generated from the previous wet fiber separation process under homogeneous agitation for 1 hour. The pH of protein slurry was at 7.6 and no further pH adjustment was required. The canola meal slurry was centrifuged at ambient temperature using a Bird Decanter Centrifuge (Bird 6" Continuous Bowl Centrifuge, Bird Machine Company of Canada, Saskatoon, Saskatchewan) at 1,500 rpm bowl speed and a low pool depth. The canola meal slurry was pumped through the Bird Decanter at ambient temperature and a feed rate of 150 kg/hr to separate the coarse fiber solids from the soluble and insoluble protein fractions. Approximately 39.5 kg of wet fiber solids #6A containing 20.04% solids and 94.5 kg of protein slurry #6A containing soluble and insoluble proteins at 12.04% solids were produced, respectively.

The wet fiber solids #6A was mixed with 32 kg of water in a tank for 15 minutes, which was followed by centrifugation to separate the washed fiber solids #6B from the insoluble protein solids and soluble protein extract #6B at ambient temperature using the Bird Decanter at a bowl speed of 1,500 rpm and a feed rate of 150 kg/hr. Approximately 23.3 kg of washed fiber solids #6B containing 17.68% solids and 42.5 kg of insoluble and soluble protein slurry #6B containing 5.60% solids were produced.

(iii) Preparation of Canola Protein Concentrate from Recycled Protein Slurry

Figure 33:
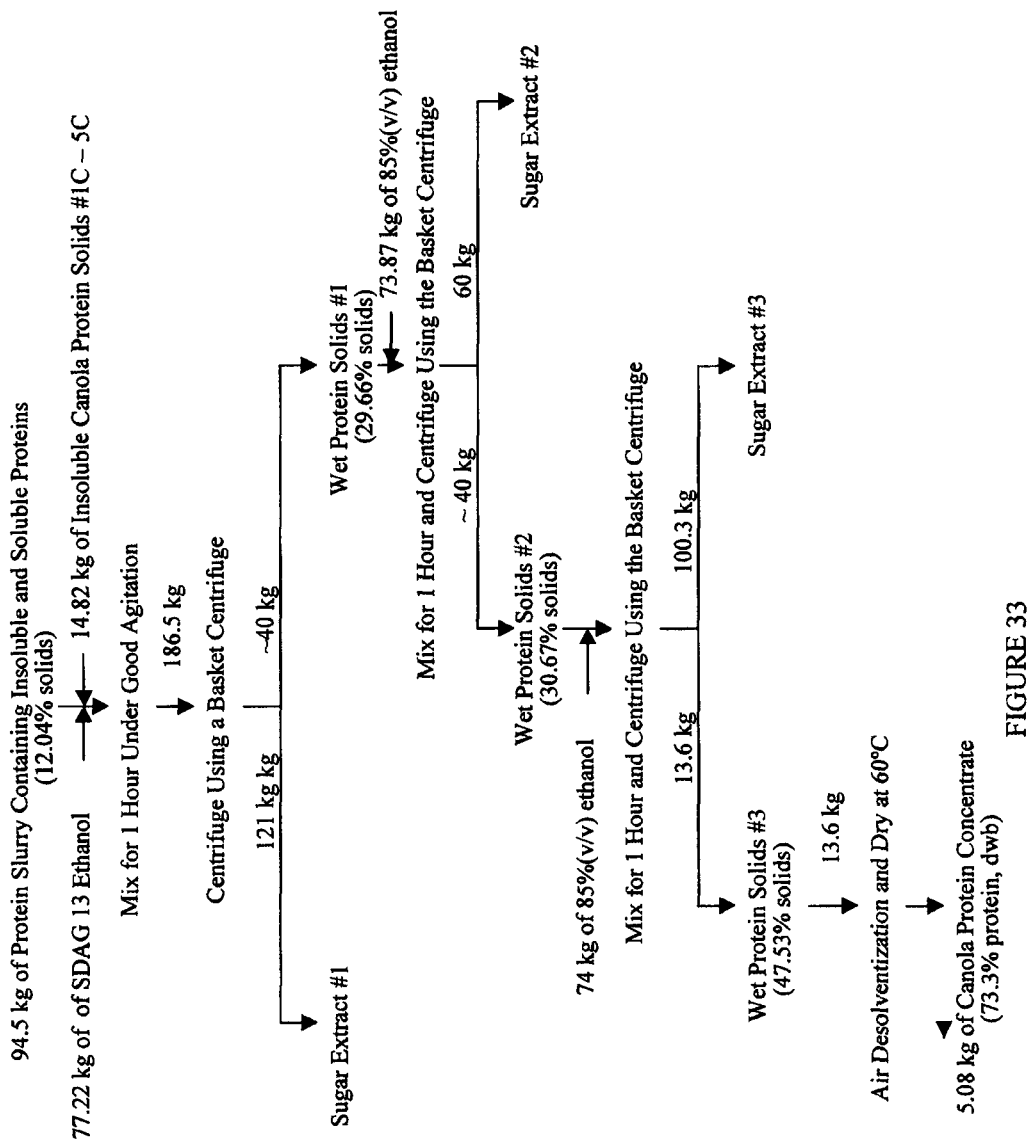
FIG. 33 is schematic representation illustrating a preparation of a protein concentrate produced by recycling a protein fraction.

A schematic flowchart for preparation of protein concentrate from the defatted meal slurry after the fiber removal is shown in FIG. 33. 94.5 kg of protein slurry containing soluble and insoluble proteins after the fiber removal and 14.82 kg of insoluble protein solids #1C-#5C were mixed with 77.22 kg of SDAG 13 denatured ethanol (containing 99% ethanol and 1% ethyl acetate) for 1 hour at room temperature. This was followed by centrifugation using a Basket Centrifuge (Tolhurst—26 in. Center-Slung, Ametek, Inc., East Moline, Ill., USA) to obtain 121 kg of sugar extract #1 and ~40 kg of wet protein solids #1 containing 29.66% solids. The wet protein solids (~40 kg) were mixed with 73.87 kg of 85% ethanol (v/v) for 1 hour at ambient temperature. This was again followed by centrifugation using the Basket Centrifuge to obtain 60 kg of sugar extract #2 and ~40 kg of wet protein solid #2 containing 30.67% solids. Finally, the wet protein solids (~40 kg) were mixed with 74 kg of 85% ethanol (v/v) for 1 hour at ambient temperature, which was followed by centrifugation using the Basket Centrifuge to obtain 100.3 kg of sugar extract #3 and 13.6 kg of wet protein solid #3 containing 47.53% solids. The wet protein solids #3 was air desolventized in a lab fume hood for 2 days, which was followed by drying at 60° C. in a forced air oven until the moisture content is below 7%. The protein concentrate contained 73.3% protein on a dry weight basis.

Discussion

As shown in Table 47, canola protein concentrate containing 73.3% protein (dwb) and 3.78% crude fiber (dwb) was produced from defatted canola meal (*B. juncea*) the wet fiber separation method based on the density and particle size difference between the insoluble fiber particles and the insoluble protein particles. In an embodiment, dry screening to prepare a protein enriched meal from defatted meal is not required, which increases the protein recovery yield in the protein concentrate.

As shown in Table 48, after the wet fiber separation by centrifugation, the protein slurry containing soluble and insoluble proteins is recycled to mix with the defatted meal before the fiber separation. The solid content of the protein slurry containing soluble and insoluble proteins was increased from 6.31% solids to 12.46% solids after 4 recycling trials. Higher solid content in the canola slurry did not affect the fiber separation by the wet fiber separation process. The protein content of the protein slurry containing insoluble and soluble proteins was increased while the crude fiber content remained at similar level with the increased in the solid content (Table 48). Interestingly, canola protein slurry #6A contained 57.6% protein (dwb) and 1.60% crude fiber (dwb) after the fiber separation and before ethanol precipitation. Canola protein concentrate containing 73.3% protein (dwb) and 3.78% crude fiber was produced. In an embodiment, the fiber separation by the decanter centrifuge based on the density difference results in a low crude fiber content in the protein slurry containing soluble and insoluble proteins after fiber separation and removal.

As shown in Table 49, the $1^{st}$ ethanol precipitation increased the protein content to 69.3% (dwb), the $1^{st}$ ethanol washing increased the protein content to 70.6% (dwb) and the $2^{nd}$ ethanol washing increased the protein content to 73.3% (dwb). In an embodiment, a one step ethanol precipitation is sufficient to produce a protein concentrate containing 70% protein (dwb) and a low fiber content comparable to soy protein concentrate. In another embodiment, a membrane filtration process is conducted on the protein slurry containing soluble and insoluble proteins at high solid content after fiber separation to concentrate and purify proteins before spray drying to produce protein concentrate containing 70% protein (dwb). In an embodiment, an ultrafiltration is utilized since the protein slurry at high solid content already has reasonable purity in terms of protein content.

In an embodiment, the increase in the solid content of the protein slurry containing soluble and insoluble proteins serves the purpose of reducing the processing volume and the amount of ethanol usage. This would reduce the size of the equipment, energy consumption, processing cost and capital investment.

Example 9

Figure 34:
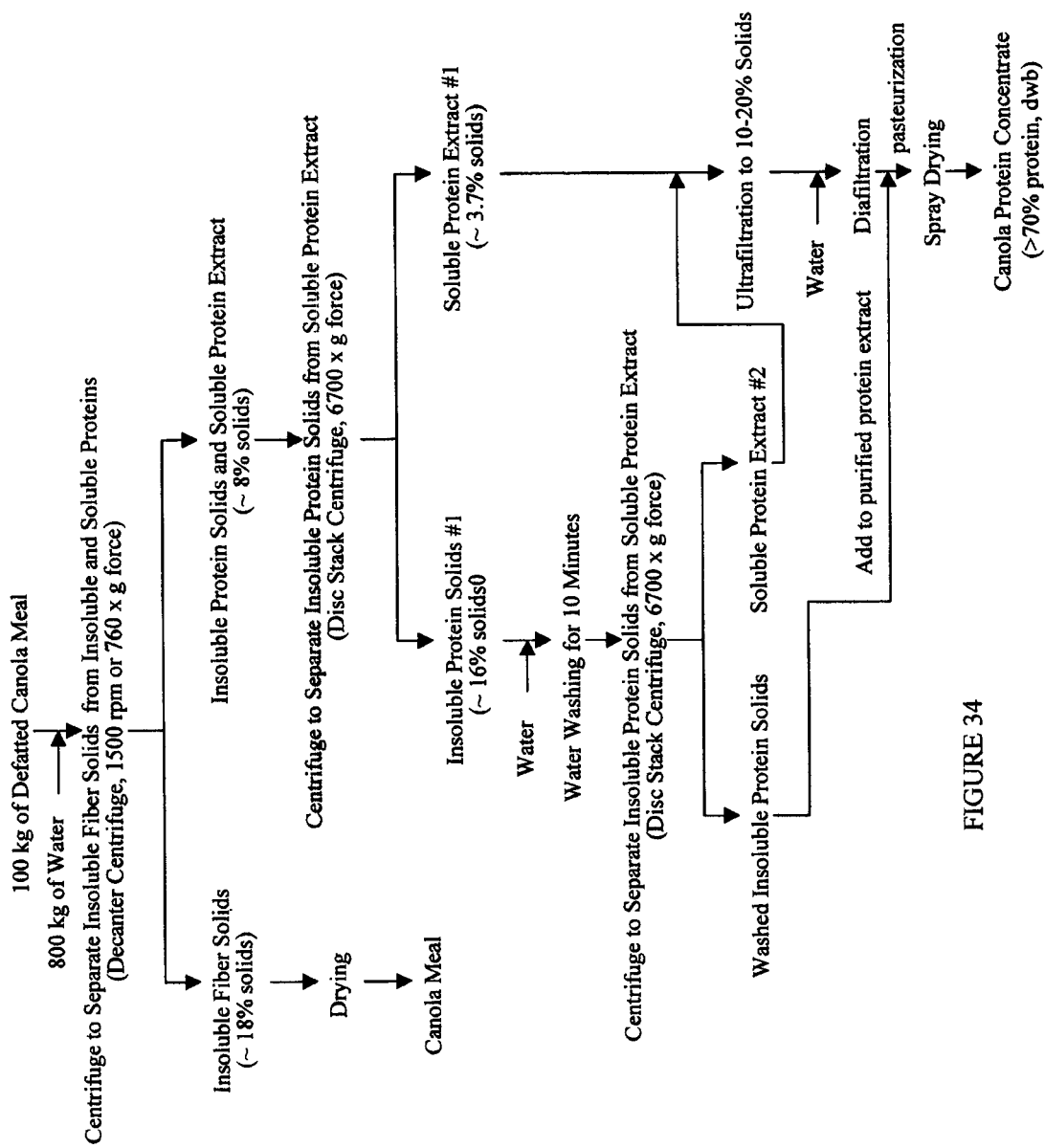
FIG. 34 is a schematic representation illustrating a preparation of a protein concentrate.

Hypothetical Example of Preparation of Canola Protein Concentrate Containing Greater than 70% Protein A schematic representation for the preparation of canola protein concentrate by membrane filtration is shown in FIG. 34. 100 kg of defatted meal is mixed with 800 kg of water at a ratio of 1 to 8 (by weight) under homogeneous agitation. This is followed by centrifugation at room temperature using a Decanter Centrifuge at 1500 rpm bowl speed and a low pool depth to separate the insoluble fiber solids from the protein slurry containing insoluble and soluble proteins. The protein slurry containing soluble and insoluble proteins after the fiber removal is centrifuged using a Disc Stack Centrifuge at ambient temperature to separate the soluble protein extract #1 from the insoluble protein solids #1. The insoluble protein solids #1 is mixed with water at a ratio of 1 to 2 by weight at ambient temperature for 0.5 hour under homogeneous agitation, which is followed by centrifugation using the Disc Stack Centrifuge to separate soluble protein extract #2 from the washed insoluble protein solids.

Soluble protein extracts #1 and #2 are combined and the combined extract is adjusted to pH 7.0 by addition of 11% NaOH solution if the pH is below 7, which is followed by concentration of the protein extract in the feed tank to 10-20% solids using a ultrafiltration membrane with a molecular weight cutoff of 10,000-100,000 daltons. The protein extract is pumped through the membrane unit while the retentate is recycled back to the feed tank and the permeate is collected in another tank.

Water is then added into the feed tank and diafiltration is conducted using the ultrafiltration membrane with a molecular weight cutoff of 10,000-100,000 daltons. The original volume of protein solution in the feed tank is held constant by adding water to make up for the removed permeate. The retentate is recycled back to the feed tank. Sufficient amount of water is used in the diafiltration process until the retentate contains 90% protein or higher on a dry weight basis.

The purified protein extract from ultrafiltration and diafiltration is mixed with the washed insoluble protein solids, which is followed by pasteurization (UV or heat). The pasteurized protein slurry containing soluble and insoluble proteins is spray dried into protein concentrate containing 70% protein or higher.

Example 10

Figure 35:
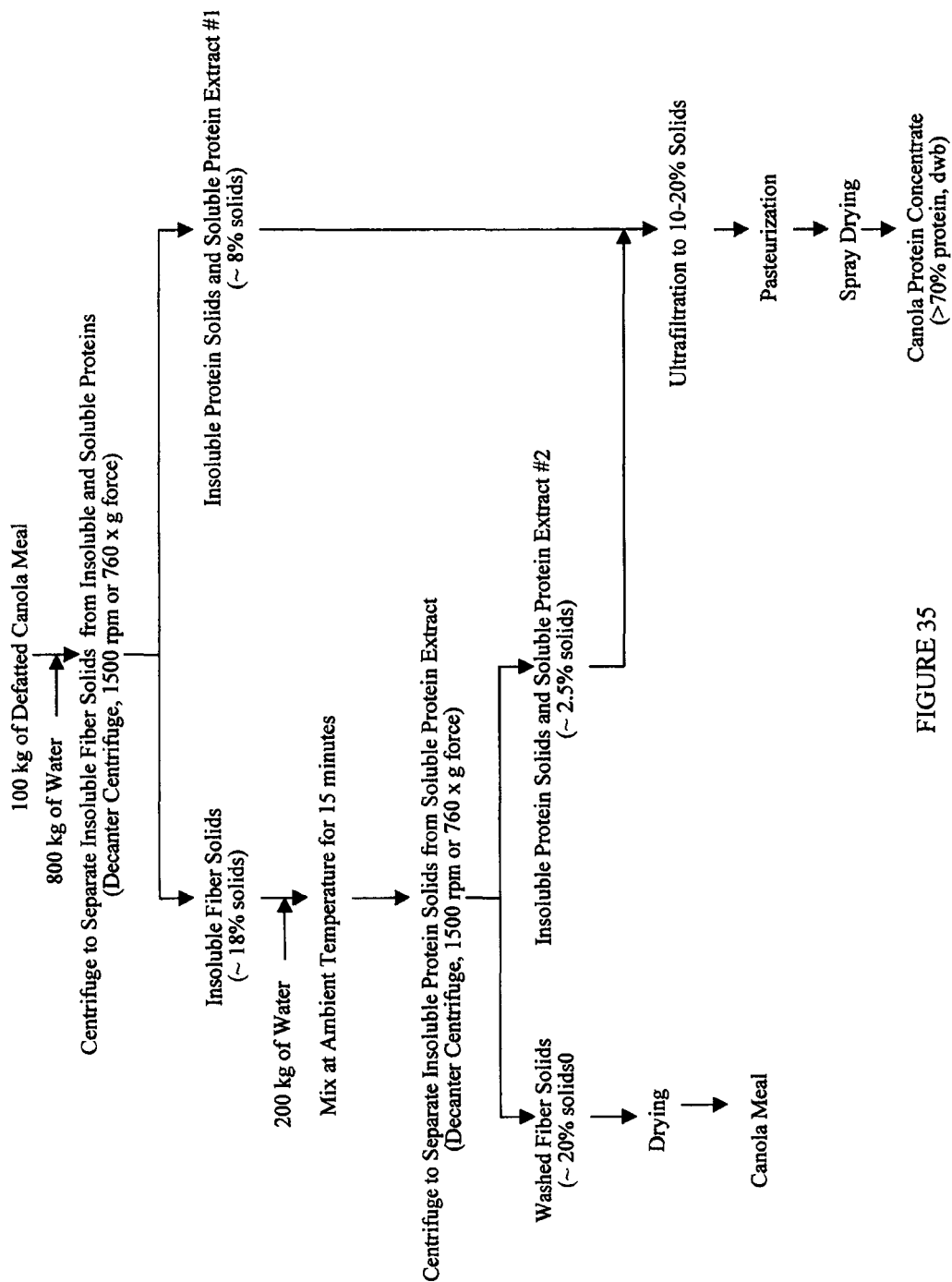
FIG. 35 is a schematic representation illustrating a preparation of a protein concentrate.

Hypothetical Example of Preparation of Canola Protein Concentrate Containing Greater than 70% Protein A schematic representation for preparation of a canola protein concentrate by membrane filtration is shown in FIG. 35. 100 kg of defatted meal is mixed with 800 kg of water at a ratio of 1 to 8 (by weight) under homogeneous agitation. This is followed by centrifugation at ambient temperature using a Decanter Centrifuge at 1500 rpm bowl speed and a low pool depth to separate the insoluble fiber solids from the protein slurry #1 containing insoluble and soluble proteins. The insoluble fiber solids are mixed with 200 kg of water for 15 minutes at ambient temperature, which is followed by centrifugation using the Decanter Centrifuge at 1500 rpm bowl speed and a low pool depth to separate the washed fiber solids from the protein slurry #2 containing insoluble and soluble proteins.

Protein slurries #1 and #2 are combined and the combined slurry is adjusted to pH 7.0 by addition of 11% NaOH solution if the pH is below 7, which is followed by concentration of the protein slurry in the feed tank to about 20% solids using a microfiltration membrane of 0.1-0.2 micron and an ultrafiltration membrane with a molecular weight cutoff of 10,000-100,000 daltons. The protein slurry is pumped through the membrane unit while the retentate is recycled back to the feed tank and the permeate is collected in another tank.

The purified protein slurry from the ultrafiltration process is pasteurized by UV or heat. The pasteurized protein slurry containing soluble and insoluble proteins is spray dried into protein concentrate containing 70% protein.

Prophetic Example 11

Protein Concentrate of About 70-75% Protein Fiber Hydrolysis and Ethanol Washing The process for preparation of protein-enriched meal is the same as that of Example 1. Approximately 1 kg of protein-enriched meal is mixed with 6 kg of water in a lab Eberbach Waring Blenderunder for 5 minutes to breakdown the insoluble protein and fiber particles. The protein slurry is added to a beaker and pH of the slurry is adjusted to 5±0.2 under good agitation using a magnetic stirrer. Approximately 0.5% cellulase or cellulase complex based on the weight of starting protein enriched meal is added to the protein slurry. The slurry is heated to 55-60° C. and held at this temperature range for 4 hours. After enzymatic reaction, 8 kg of 100% (v/v) ethanol is added to the protein slurry, which is followed by mixing for 0.5 hour at 55-60° C. The protein slurry is centrifuged at 4,000 g force for 15 minutes to separate the protein solids from the sugar extract. The sugar extract is concentrated and dried to produce a dried sugar and fraction. The protein solids are dried under vacuum to produce a protein concentrate containing 70-75% protein on a dry weight basis.

Prophetic Example 12

Protein Concentrate of ≧80% Protein and Protein Isolate of ≧90% Protein

Fiber Removal by Screening and Centrifugation 1,000 kg of canola seed at 7-10% moisture is conditioned at 80±5° C. for 30±10 minutes in a stack cooker, which is followed by pressing using a DeSmet mini press. Approximately 800 kg of pressed cake and 200 kg of pressed oil are produced. The pressed cake has a PDI (protein dispersibility index) of 30-35. The pressed cake is extracted with hexane at 55-60° C. for 1 hour using a Crown counter-current extractor at a ratio of hexane to cake of 2 to 1 by weight. The extracted meal is desolventized and dried at 50° C. for 5 hours under vacuum using a Littleford® dryer to a solvent residue of less than 500 ppm. Approximately 520 kg of extracted meal is produced.

The extracted meal is milled using a disc mill at a gap of 0.02" and the milled meal is screened through a 45 US mesh screen using a Rotary Vibratory Screen. Approximately 220 kg of protein enriched meal and 300 kg of fiber enriched meal are produced.

Approximately 220 kg of protein enriched meal is mixed with 2,200 kg of water under good agitation. The protein slurry is screened through a 40 mesh US screen at ambient temperature to remove some fiber. The slurry is adjusted to a pH of 7, which is followed by wet milling through a wet mill (Szego Mill) at ambient temperature. The slurry is centrifuged using a decanter (Bird Decanter) at ambient temperature to separate the rest of fiber from the soluble and insoluble proteins at a bowl speed of 1,500 rpm. The slurry of soluble and insoluble proteins is centrifuged again at ambient temperature to separate the soluble protein solution from the insoluble protein precipitates using a disc stack centrifuge (Westfalia® Desludger).

The insoluble protein precipitates are washed with water 2 times at ambient temperature, and the washed protein precipitates are separated from the washing liquid using a disc stack centrifuge at ambient temperature. The washed protein precipitates are mixed with 2 parts of water and pH of the slurry is adjusted to pH7 at ambient temperature. The slurry of protein precipitates is spray dried using a spray dryer at an inlet temperature of 190° C. and outlet temperature of 85° C. to a dried protein concentrate of 80-85% protein on a dry weight basis.

The soluble protein solution recovered from the centrifugation operations is heated to 45-50° C. before being passed through hollow fiber ultrafiltration cartridge membranes with a molecular weight cutoff of 10,000 daltons. The hollow fiber cartridges are fitted to a Millipore® ultrafiltration unit. The retentate was recycled back to the feed tank and the permeate is discarded. The ultrafiltration process is continued until the amount of protein solution in the feed tank is equal to 25% of its initial weight. After the ultrafiltration is completed, diafiltration is conducted at 45-50° C. using the same ultrafiltration unit which is fitted with the same hollow fiber cartridges. The original volume of protein solution in the feed tank is held constant by adding water to make up for the removed permeate. The retentate is recycled back to the feed tank. The amount of water received to maintain the original volume of protein solution is 3 times the original volume of protein solution. Finally, after all the water is added to the feed tank, the purified protein solution is adjusted to pH7 before it is spray dried into a dried protein isolate containing ≧90% protein on a dry weight basis using a spray dryer. The spray drying conditions are the same as those used for the protein concentrate.

Prophetic Example 13

Protein Concentrate of ≧80% Protein and Protein Isolate of ≧90% Protein

Fiber Hydrolysis by Cellulase or Cellulase Complex

The process for preparation of protein enriched meal from canola seed is the same as that of Prophetic Example 12.

Approximately 220 kg of protein enriched meal is mixed with 2,200 kg of water under good agitation. The protein slurry is screened through a 40 mesh US screen at ambient temperature to remove some fiber, which is followed by wet milling the protein slurry through a wet mill (Szego Mill) at ambient temperature. The protein slurry is centrifuged at ambient temperature to separate the soluble protein solution from the insoluble protein and fiber solids using a disc stack centrifuge (Westfalia® Desludger).

The insoluble solids are mixed with 3 parts of water, which is followed by pH adjustment to 5±0.2. Approximately 0.5% cellulase or cellulase complex based on the weight of starting protein enriched meal is added to the protein slurry. The slurry is heated to 55-60° C. and held at this temperature range for 4 hours. After enzymatic reaction, the insoluble protein solids are washed with water following the same process as outlined in Example 4 to produce a protein concentrate of ≧80% protein.

The process to produce protein isolate of ≧90% protein from the soluble protein solution is the same as that of Example 12.

TABLE 1

Heat Treatment Conditions

| Heat Treatment | Temperature (° C.) | Residence Time |
|---|---|---|
| 1 | 75 | 15 seconds |
| 2 | 80 | 15 seconds |
| 3 | 85 | 15 seconds |
| 4 | 85 | 15 seconds |
| 5 | 85 | 15 seconds |
| 6 | 90 | 15 seconds |
| Control | 95 | 30 minutes |

TABLE 2

Heat Treatment Conditions

| Heat Treatment | Temperature (° C.) | Time (second.) |
|---|---|---|
| 1 | 100 | 15 |
| 2 | 105 | 15 |
| 3 | 110 | 15 |
| 4 | 120 | 15 |
| 5 | 130 | 15 |

TABLE 3

Evaluation of Heat Treatments on Quality of Defatted Canola Meal (*B. juncea*)

| Heat Treatment Conditions | Moisture of Defatted Meal (%) | PDI of Defatted Meal | Protein of Defatted Meal (%, as is) | Oil of Defatted Meal (%, as is) |
|---|---|---|---|---|
| 75° C. for 15 Seconds. | 7.81 | 34.43 | 41.3 | 2.08 |
| 80° C. for 15 Seconds. | 7.30 | 34.17 | 43.2 | 1.54 |
| 85° C. for 15 Seconds | 11.56 | 31.55 | 41.3 | 4.03 |
| 90° C. for 15 Seconds | 7.54 | 31.98 | 43.0 | 1.29 |
| 95° C. for 15 Seconds | 7.82 | 31.97 | 41.9 | 1.47 |
| 100° C. for 15 Seconds | 7.50 | 30.33 | 40.2 | 1.74 |
| 105° C. for 15 Seconds | 7.79 | 29.32 | 39.0 | 1.99 |
| 110° C. for 15 Seconds | 7.67 | 27.82 | 37.7 | 1.64 |
| 120° C. for 15 Seconds | 7.11 | 23.10 | 33.7 | 1.58 |
| 130° C. for 15 Seconds | 7.19 | 18.20 | 28.6 | 1.66 |
| No Heat Treatment | 10.37 | 31.92 | 39.2 | 5.31 |
| Heat Treatment at 95° C. for 0.5 Hr. | 8.03 | 32.22 | 42.6 | 2.78 |

TABLE 4

Evaluation of Heat Treatment on the Sulphur Content of Pressed and Extracted Canola Oils (*B. juncea*)

| Heat Treatment Conditions | Sulphur in Pressed Oil (ppm) | Sulphur in butane/R134a Extracted Oil (ppm) | Sulphur in Methyl Pentane Extracted Oil (ppm) |
|---|---|---|---|
| 75° C. for 15 Seconds. | 21.5 | 99.3 | 222 |
| 80° C. for 15 Seconds. | 9.77 | 101 | 175 |
| 85° C. for 15 Seconds | 9.82 | 562 | 111 |
| 90° C. for 15 Seconds | 9.67 | 86.4 | 55.3 |
| 95° C. for 15 Seconds | 8.71 | 75.8 | 34.5 |
| 100° C. for 15 Seconds | 8.65 | 71.4 | not determined |
| 105° C. for 15 Seconds | 7.13 | 61.8 | not determined |
| 110° C. for 15 Seconds | 8.94 | 55.8 | not determined |
| 120° C. for 15 Seconds | 8.77 | 48.7 | not determined |
| 130° C. for 15 Seconds | 9.82 | 19.9 | not determined |
| No Heat Treatment | 46.9 | 303 | 205 |
| Heat Treatment at 95° C. for 0.5 Hr. | 41.8 | 254 | 98.3 |

TABLE 5

Evaluation of Heat Treatment on the FFA Content of Pressed and Extracted Canola Oils (*B. juncea*)

| Heat Treatment Conditions | FFA in Pressed Oil (%) | FFA in butane/R134a Extracted Oil (%) | FFA in Methyl Pentane Extracted Oil (%) |
|---|---|---|---|
| 75° C. for 15 Seconds. | 1.67 | 2.48 | 2.70 |
| 80° C. for 15 Seconds. | 1.70 | 2.35 | 2.40 |
| 85° C. for 15 Seconds | 1.67 | 2.61 | 2.48 |
| 90° C. for 15 Seconds | 1.65 | 2.06 | 2.39 |
| 95° C. for 15 Seconds | 1.60 | 2.22 | 2.38 |
| 100° C. for 15 Seconds | 1.26 | 2.07 | not determined |
| 105° C. for 15 Seconds | 1.38 | 2.12 | not determined |
| 110° C. for 15 Seconds | 1.23 | 2.13 | not determined |
| 120° C. for 15 Seconds | 1.37 | 1.94 | not determined |
| 130° C. for 15 Seconds | 1.33 | 2.15 | not determined |
| No Heat Treatment | 1.67 | 2.47 | 2.72 |
| Heat Treatment at 95° C. for 0.5 Hr. | 1.67 | 2.63 | 2.78 |

TABLE 6

Evaluation of Heat Treatment on the Phosphorus Content of Pressed and Extracted Canola Oils (*B. juncea*)

| Heat Treatment Conditions | Phosphorus in Pressed Oil (ppm) | Phosphorus in butane/R134a Extracted Oil ppm) | Phosphorus in Methyl Pentane Extracted Oil (ppm) |
|---|---|---|---|
| 75° C. for 15 Seconds. | not determined | 2.93 | 1020 |
| 80° C. for 15 Seconds. | not determined | 2.65 | 899 |
| 85° C. for 15 Seconds | not determined | 8.43 | 975 |
| 90° C. for 15 Seconds | not determined | 2.72 | 735 |
| 95° C. for 15 Seconds | not determined | 22.8 | 805 |
| 100° C. for 15 Seconds | 36.2 | not determined | not determined |
| 105° C. for 15 Seconds | 26.3 | not determined | not determined |
| 110° C. for 15 Seconds | 31.8 | not determined | not determined |
| 120° C. for 15 Seconds | 117 | not determined | not determined |
| 130° C. for 15 Seconds | 30.3 | not determined | not determined |
| No Heat Treatment | not determined | 4.25 | 962 |
| Heat Treatment at 95° C. for 0.5 Hr. | not determined | not determined | 875 |

TABLE 7

Analytical Results of Pressed Canola Cakes (*B. juncea*)

| Sample | Moisture of Press Cake (%) | Oil Content of Press Cake (%) |
|---|---|---|
| 75° C. for 15 Seconds. | 11.4 | 26.2 |
| 80° C. for 15 Seconds. | 10.4 | 27.6 |
| 85° C. for 15 Seconds | 10.2 | 24.4 |
| 90° C. for 15 Seconds | 9.00 | 27.9 |
| 95° C. for 15 Seconds | 9.46 | 26.9 |
| 100° C. for 15 Seconds | 8.20 | 28.0 |
| 105° C. for 15 Seconds | 7.60 | 22.7 |
| 110° C. for 15 Seconds | 9.01 | 23.5 |
| 120° C. for 15 Seconds | 8.60 | 37.7 |
| 130° C. for 15 Seconds | 6.15 | 22.1 |
| No Heat Treatment | 12.0 | 26.4 |
| Heat Treatment at 95° C. for 0.5 Hr. | 12.1 | 24.6 |

TABLE 8

Analysis of Defatted Meal, Protein-Enriched Meal and 65% Protein Concentrate

| Sample | Moisture (%) | Protein (%, dwb) | Ash (%, dwb) | Crude Fiber (%, dwb) | Oil (% dwb) | Carbohydrates (%, dwb) |
|---|---|---|---|---|---|---|
| Canola Seed (b. juncea) | 6.25 | 27.24 | 4.1 | 4.52 | 42.27 | 21.87 |
| Pressed Cake | 8.2 | 33.66 | 5.23 | 5.2 | 30.5 | 25.41 |
| Defatted Meal | 7.5 | 43.36 | 7.29 | 6.99 | 1.88 | 40.38 |
| Protein Enriched Meal | 6.76 | 52.44 | 7.47 | 4.37 | 1.56 | 34.16 |
| Fiber Enrich Meal | 7.47 | 43.01 | 6.94 | 9.83 | 2.44 | 37.78 |
| Protein Concentrate | 4.55 | 64.74 | 8.23 | 5.77 | 0.55 | 20.71 |
| Dried Sugar Fraction | 6.43 | 12.40 | 5.75 | 0.17 | 1.93 | 79.75 |

TABLE 9

Water Addition and Seed Weight for Each Batch of Moisture Adjustment and Mixing

| Batch | Weight of Canola Seed (Kg) | Amount of Water Added (kg) | Mixing Time (Min.) |
|---|---|---|---|
| 1 | 220.5 | 4.41 | 5 |
| 2 | 221.0 | 4.42 | 5 |
| 3 | 221.0 | 4.42 | 5 |
| 4 | 222.0 | 4.44 | 5 |
| 5 | 223.5 | 4.47 | 5 |
| 6 | 225.0 | 4.50 | 5 |
| 7 | 221.0 | 4.42 | 5 |
| 8 | 225.0 | 4.50 | 5 |
| 9 | 211.0 | 4.22 | 5 |
| 10 | 224.5 | 4.49 | 5 |
| 11 | 222.0 | 4.44 | 5 |
| 12 | 220.5 | 4.41 | 5 |
| 13 | 214.0 | 4.28 | 5 |
| 14 | 47.5 | 0.95 | 5 |
| Total | 2918.5 | 53.96 | |

TABLE 10

Mass Balance of Flaking and Pressing Trials

| Sample | Canola Seed (kg) | Flaked Seed (kg) | Press Cake (kg) | Press Oil (kg) | Ratio of Cake/Seed |
|---|---|---|---|---|---|
| Sample 1a | 300.5 | NA | 181.6 | 73.1 | 60.43 |
| Sample 1b | 2,676 | 2,676 | 1,566 | 872 | 58.52 |

TABLE 11

Results of Proximate Analysis for Canola Seed and Press Cakes

| | Canola Seed (moisture adjusted) | Sample 1a | Sample 1b |
|---|---|---|---|
| Moisture (%) | 8.12 | 7.62 | 10.33 |
| Protein (%, dwb$^a$) | 27.00 | 34.86 | 42.04 |
| Crude Oil (%, dwb$^a$) | 44.39 | 32.37 | 12.58 |
| Crude Fiber (%, dwb$^a$) | 4.75 | 5.3 | 7.00 |
| Ash (%, dwb$^a$) | 4.56 | 4.87 | 7.02 |

$^a$dwb = dry weight basis

TABLE 12

The Results of Screening Trials for Lab and Milled Canola Meals

| Screening Trial Milled Canola Meal | Sample 1e (%, w/w) | Sample 1f (%, w/w) |
|---|---|---|
| 1 | 57.23 | 42.76 |
| 2 | 47.05 | 52.94 |
| 3 | 42.33 | 57.66 |
| 4 | 49.49 | 50.51 |
| 5 | 49.29 | 50.71 |
| 6 | 43.96 | 56.04 |
| 7 | 46.89 | 53.11 |
| 8 | 47.16 | 52.84 |
| Average | 47.93 | 52.07 |
| Milling and Screening - Sample 2b | 42.85 | 57.15 |
| Milling and Screening - Sample 3b | 40.31 | 59.69 |
| Screening Trial - Sample 1 | 37.14 | 62.86 |

TABLE 13

Processing Conditions for Samples 1-3 of Press Cakes,
Extracted Meals, Fiber Enriched Meals and Protein Concentrates

| | Sample 1 | Sample 2 | Sample 3 |
|---|---|---|---|
| Canola Seed | *B. juncea* | *B. juncea* | *B. juncea* |
| Flaking | Yes | No | No |
| Temperature of Heat Treatment in Cooker | 75-96° C. | N/A | N/A |
| Residence Time in Cooker | 20 minutes | 30 minutes | 30 minutes |
| Press Cake Temperature | 68-79° C. | NA | NA |
| Extraction of Press Cake | Butane/R134a | Butane/R134a | Butane/R134a |
| Temperature for Milling and Screening of Defatted Meals | Room Temperature (23° C.) | Room Temperature (23° C.) | Room Temperature (23° C.) |
| Extraction of Protein Enriched Meals | Room Temperature (23° C.) 80% (v/v) ethanol Three Extractions (ratio of 1 to 6 by weight of meal to ethanol) | Room Temperature (23° C.) 80% (v/v) ethanol Three Extractions (ratio of 1 to 6 by weight of meal to ethanol) | Room Temperature (23° C.) 80% (v/v) ethanol Three Extractions (ratio of 1 to 6 by weight of meal to ethanol) |
| Temperature and Residence Time for Desolventization and Drying of Protein Concentrates | 54 ± 3° C. for 18 hours in a Vacuum Dryer | Room Temperature (23° C.) in a Fume Hood for 3 days 50° C. in a Vacuum Dryer for 15 Hours | Room Temperature (23° C.) in a Fume Hood for 3 days 50° C. in a Vacuum Dryer for 15 Hours |
| Milling and Screening | Room Temperature (23° C.) | Room Temperature (23° C.) | Room Temperature (23° C.) |

TABLE 14

Moisture and Oil Contents of Samples 1a-d

| Sample | Mass of Run | Moisture Content (%) | Crude Oil Content (%, dwb[a]) |
|---|---|---|---|
| Sample 1a | 1 kg | 9.32 | 26.81 |
| Sample 1c | 1 kg | 6.13 | 8.75 |
| Sample 1b | 1 kg | 8.58 | 15.12 |
| Sample 1d | 1 kg | 5.81 | 1.94 |
| Sample 1b | 9 kg | 8.00 | 27.83 |
| Sample 1d | 9 kg | 5.38 | 12.73 |

[a]dwb = dry weight basis

TABLE 15

Moisture and Oil Contents of Press Cake from Flaking Trial (Sample 1b)

| Sample | Mass of Run | Moisture Content (%) | Crude Oil Content (%, dwb[a]) |
|---|---|---|---|
| Sample 1b | 8.9 kg | 7.73 | 13.94 |
| Sample 1b | 8.9 kg | 7.25 | 14.00 |
| Sample 1b | 8.9 kg | 7.38 | 15.03 |
| Sample 1b | 8.9 kg | 7.22 | 17.68 |
| Sample 1b | 8.9 kg | 6.90 | 22.90 |
| Sample 1b | 8.9 kg | 7.05 | 19.68 |
| Sample 1b | 8.9 kg | 7.30 | 19.77 |
| Sample 1b | 8.9 kg | 7.70 | 19.92 |
| Sample 1b | 8.9 kg | 7.85 | 19.01 |
| Sample 1b | 8.9 kg | 8.02 | 14.68 |
| Flaked *Juncea* | NA | 9.13 | 13.76 |
| Press Cake Composite (Multiple Runs) | | | |
| Flaked *Juncea* | NA | 9.04 | 13.52 |
| Press Cake Composite (Multiple Runs) | | | |
| Sample 1b | 9 kg | 8.42 | 13.03 |
| Sample 1b | 9 kg | 8.26 | 13.04 |
| Sample 1b | 9 kg | 6.63 | 13.33 |
| Sample 1b | 8.9 kg | 8.32 | 13.46 |
| Sample 1b | 8.9 kg | 8.36 | 13.65 |
| Sample 1b | 8.9 kg | 8.35 | 13.73 |
| Sample 1b | 8.9 kg | 8.57 | 12.96 |
| Sample 1b | 8.9 kg | 8.58 | 12.92 |
| Sample 1b | 8.9 kg | 8.40 | 12.72 |
| Sample 1b | 8.9 kg | 8.00 | 13.06 |
| Sample 1b | 8.9 kg | 7.14 | 17.21 |
| Sample 1b | 8.9 kg | 7.29 | 16.80 |
| Sample 1b | 8.9 kg | 7.20 | 14.26 |
| Flaked *Juncea* | NA | 7.97 | 13.22 |
| Press Cake Composite (Multiple Runs) | | | |
| Flaked *Juncea* | NA | 8.49 | 14.38 |
| Press Cake Composite (Multiple Runs) | | | |

TABLE 15-continued

Moisture and Oil Contents of Press Cake from Flaking Trial (Sample 1b)

| Sample | Mass of Run | Moisture Content (%) | Crude Oil Content (%, dwb[a]) |
|---|---|---|---|
| Flaked *Juncea* Press Cake Composite (Multiple Runs) | NA | 8.09 | 14.07 |
| Flaked *Juncea* Press Cake Composite (Multiple Runs) | NA | 7.41 | 16.64 |
| Flaked *Juncea* Press Cake Composite (Multiple Runs) | NA | 7.95 | 14.92 |
| Flaked *Juncea* Press Cake Composite (Multiple Runs) | NA | 8.33 | 15.86 |
| Flaked *Juncea* Press Cake Composite (Multiple Runs) | NA | 7.1 | 14.90 |
| Flaked *Juncea* Press Cake Composite (Multiple Runs) | NA | 7.68 | 13.91 |
| Flaked *Juncea* Press Cake Composite (Multiple Runs) | NA | 8.47 | 14.18 |

[a]dwb = dry weight basis

TABLE 16

Moisture and Oil Contents of Sample 1d

| Sample | Mass of Run | Moisture Content (%) | Crude Oil Content (%, dwb[a]) |
|---|---|---|---|
| Sample 1d | 8.9 kg | 4.81 | 1.70 |
| Sample 1d | 8.9 kg | 4.14 | 1.76 |
| Sample 1d | 8.9 kg | 6.53 | 2.3 |
| Sample 1d | 8.9 kg | 6.44 | 2.45 |
| Sample 1d | 8.9 kg | 6.54 | 2.63 |
| Sample 1d | 8.9 kg | 6.18 | 1.89 |
| Sample 1d | 8.9 kg | 5.80 | 2.49 |
| Sample 1d | 8.9 kg | 6.33 | 2.93 |
| Sample 1d | 8.9 kg | 6.10 | 2.85 |
| Sample 1d | 8.9 kg | 6.02 | 2.14 |
| Sample 1d | 8.9 kg | 5.61 | 2.26 |
| Flaked *Juncea* Extracted Meal Composite (Multiple Runs) | — | 8.70 | 2.36 |
| Flaked *Juncea* Extracted Meal Composite (Multiple Runs) | — | 8.27 | 2.30 |
| Flaked *Juncea* Extracted Meal Composite (Multiple Runs) | 9 kg | 8.20 | 2.68 |
| Flaked *Juncea* Extracted Meal Composite (Multiple Runs) | 9 kg | 8.38 | 2.13 |
| Flaked *Juncea* Extracted Meal Composite (Multiple Runs) | 9 kg | 7.13 | 2.27 |
| Flaked *Juncea* Extracted Meal Composite (Multiple Runs) | 9 kg | 7.74 | 2.03 |
| Sample 1d | 9 kg | 6.44 | 2.63 |
| Sample 1d | 9 kg | 6.28 | 2.50 |
| Sample 1d | 9 kg | 6.54 | 3.13 |
| Flaked *Juncea* Extracted Meal Composite (Multiple Runs) | — | 7.40 | 2.79 |
| Flaked *Juncea* Extracted Meal Composite (Multiple Runs) | — | 7.79 | 2.51 |
| Flaked *Juncea* Extracted Meal Composite (Multiple Runs) | — | 8.18 | 2.47 |
| Flaked *Juncea* Extracted Meal Composite (Multiple Runs) | — | 6.46 | 2.44 |
| Flaked *Juncea* Extracted Meal Composite (Multiple Runs) | — | 6.84 | 2.78 |
| Flaked *Juncea* Extracted Meal Composite (Multiple Runs) | — | 8.03 | 1.87 |
| Flaked *Juncea* Extracted Meal Composite (Multiple Runs) | — | 6.70 | 2.70 |
| Flaked *Juncea* Extracted Meal Composite (Multiple Runs) | — | 6.39 | 1.79 |
| Flaked *Juncea* Extracted Meal Composite (Multiple Runs) | — | 7.06 | 2.02 |

[a]dwb = dry weight basis

TABLE 17

Results of Proximate Analysis for *Juncea* Seed and Samples 1b, 1d-g, 2a-d and 3a-d

| Sample | Moisture (%) | Protein (%, dwb[a]) | Crude Oil (%, dwb[a]) | Ash (%, dwb[a]) | Crude Fiber (%, dwb[a]) | PDI |
|---|---|---|---|---|---|---|
| Canola Seed (*B. juncea*) | 8.12 | 27.00 | 44.39 | 4.56 | 4.75 | 25.64 |
| Sample 1b | 10.33 | 42.04 | 12.58 | 7.02 | 7.00 | 28.78 |
| Sample 1d | 6.86 | 47.02 | 1.38 | 8.12 | 7.75 | 33.35 |
| Sample 2a | 6.56 | 49.98 | 0.92 | 7.12 | 7.63 | 33.04 |
| Sample 3a | 6.99 | 47.31 | 2.29 | 6.61 | 7.60 | 28.42 |
| Sample 1f | 6.18 | 46.10 | 2.48 | 6.86 | 8.28 | 31.91 |
| Sample 2c | 6.60 | 46.25 | 1.48 | 6.90 | 9.79 | 29.41 |
| Sample 3c | 6.73 | 44.39 | 3.18 | 6.45 | 8.60 | 29.33 |
| Sample 1e | 6.90 | 53.92 | 1.49 | 7.07 | 5.03 | — |
| Sample 2b | 6.16 | 54.77 | 0.51 | 7.06 | 5.49 | — |
| Sample 3b | 6.50 | 52.62 | 1.37 | 6.67 | 4.82 | — |
| Sample 1g | 5.51 | 65.80 | 0.41 | 8.03 | 7.16 | — |
| Sample 2d | 5.52 | 68.69 | 0.02 | 8.1 | 7.11 | — |
| Sample 3d | 5.32 | 69.60 | 0.31 | 7.68 | 6.37 | — |

[a]dwb = dry weight basis

TABLE 18

Yields of Protein Concentrates

| Sample | Weight of Protein Enriched Meal (kg) | Weight of Protein Concentrate (kg) | Yield of Protein Concentrate (%) |
|---|---|---|---|
| 1g | 412 (Sample 1e) | 248.3 | 60.27 |
| 2d | 1.5 (Sample 2b) | 1.1 | 73.33 |
| 3d | 3.9 (Sample 3b) | 2.38 | 61.03 |

TABLE 19

Analytical Results of Sample 2d

| | |
|---|---|
| Moisture | 4.86% (as is) |
| Gross Fat | 0.28% (as is) |
| Gross Protein | 65.0% (as is) |
| Gross Ash | 7.00% (as is) |
| Gross Fiber | 6.30% (as is) |
| Carbohydrate | 16.56% (as is) |
| Starch | 0.56% (as is) |
| Total Glucosinolate | 0.500 µmole/g |
| Phytic Acid | 732 (mg/kg) |
| Phytic Bounded Phosphorus | 206 (mg/kg) |

TABLE 20

Amino Acid Profile (Acid Hydrolysis) of Sample 2d

| | |
|---|---|
| Alanine | 3.18 (g/100 g) |
| Arginine | 4.89 (g/100 g) |
| Aspartic Acid | 5.74 (g/100 g) |
| Glutamic Acid | 10.6 (g/100 g) |
| Glycine | 3.67 (g/100 g) |
| Histidine | 1.82 (g/100 g) |
| Isoleucine | 2.84 (g/100 g) |
| Leucine | 5.23 (g/100 g) |
| Lysine | 3.28 (g/100 g) |
| Phenylalanine | 2.87 (g/100 g) |
| Proline | 3.30 (g/100 g) |
| Serine | 3.06 (g/100 g) |
| Threonine | 3.10 (g/100 g) |
| Tyrosine | 2.35 (g/100 g) |
| Valine | 3.46 (g/100 g) |
| Tryptophan | 0.927 (g/100 g) |
| Cystein + Cystine | 1.02 (g/100 g) |
| Methionine | 1.23 (g/100 g) |

TABLE 21

Glucosinolate Profile of Samples 1g, 2d and 3d on a Dry Weight Basis

| | Sample 1g | Sample 2d | Sample 3d |
|---|---|---|---|
| Total Glucosinolates (µmole/g) | 3.81 | 6.85 | 0.46 |
| allyl | — | 0.06 | — |
| 3-butenyl | 1.41 | 2.36 | 0.20 |
| 4-pentenyl | 0.06 | 0.11 | — |
| 2-OH-3-butenyl | — | 0.13 | — |
| 2-OH-4-pentenyl | — | — | — |
| CH3-thiopentenyl | — | — | — |
| phenylethyl | — | — | — |
| CH3-thiopentenyl | — | — | — |
| 3-CH3-indolyl | — | — | — |
| 4-OH-3-CH3-indolyl | 2.34 | 4.18 | 0.26 |
| Total Aliphatic Glucosinolates | 1.52 | 2.59 | 0.22 |

TABLE 22

Glucosinolate Profile of 1d, 2a and 3a on a Dry Weight Basis

| | Sample 1d | Sample 2a | Sample 3a |
|---|---|---|---|
| Total Glucosinolates (µmole/g) | 20.93 | 20.87 | 18.60 |
| allyl | 0.27 | 0.29 | 0.26 |
| 3-butenyl | 14.26 | 14.23 | 12.70 |
| 4-pentenyl | 0.84 | 0.83 | 0.72 |
| 2-OH-3-butenyl | 0.88 | 0.90 | 0.76 |
| 2-OH-4-pentenyl | — | — | — |
| CH3-thiopentenyl | 0.03 | 0.09 | — |
| phenylethyl | 0.18 | 0.19 | 0.14 |
| CH3-thiopentenyl | 0.05 | 0.05 | — |
| 3-CH3-indolyl | 0.11 | 0.11 | 0.13 |
| 4-OH-3-CH3-indolyl | 2.29 | 4.18 | 3.89 |
| Total Aliphatic Glucosinolates | 15.97 | 15.96 | 14.18 |

TABLE 23

Sinapine and Phytate Contents in Samples 1g, 2d and 3d and Samples 1d, 2a and 3a on an As Is Basis

| | Sample 1g | Sample 2d | Sample 3d |
|---|---|---|---|
| Sinapine (phenyl propanoid) % (as is) | 0.006 | 0.003 | 0.007 |
| Total Phytic Acid % (as is) | 3.18 | 2.71 ± 0.029 | 3.35 ± 0.039 |

| | Sample 1d | Sample 2a | Sample 3a |
|---|---|---|---|
| Sinapine (phenyl propanoid) % (as is) | 0.122 | 0.239 | 0.104 |
| Total Phytic Acid % (as is) | 2.53 ± 0.10 | 2.56 ± 0.15 | 2.59 ± 0.13 |

TABLE 24

Solvent Residues in 1, 2a and 2c Before Vacuum Drying

| Sample | Solvent Residues |
|---|---|
| 1 | Butane: 160 ppm and R134a: 435.2 ppm |
| 2a | Butane: 194 ppm and R134a: 1414.3 ppm |
| 2c | Butane: 178 ppm and R134a: 1049.3 ppm |

TABLE 25

Solvent Residues in Samples 1-3 after Desolventization and Drying in a Vacuum Dryer at 50° C. for 15 Hours.

| | Sample 1 | Sample 2 | Sample 3 |
|---|---|---|---|
| Sample 1d, 2a and 3a | Butane: <10 ppm R134a: <10 ppm | Butane: 16.8 ppm R134a: 41.5 ppm | Butane: 11 ppm R134a: <10 ppm |
| Sample 1f, 2c and 3c | Butane: <10 ppm R134a: <10 ppm | Butane: 15 ppm R134a: 41.7 ppm | Butane: <10 ppm R134a: <10 ppm |
| Sample 1g, 2d and 3d | Ethanol: 32.8 ppm Ethyl Acetate: <1.0 ppm Butane: <10 ppm R134a: <10 ppm | Ethanol: NA Ethyl Acetate: <1.0 ppm Butane: <10 ppm R134a: <10 ppm | Ethanol: 6.6 ppm Ethyl Acetate: <1.0 ppm Butane: <10 ppm R134a: <10 ppm |

TABLE 26

Results of the Proximate Analysis for Canola Seed, Canola Seed Press Cake, Defatted Meal, Protein Enriched Meal, Fiber Enriched Meal, Canola Protein Concentrate, Hydrolyzed Canola Protein Concentrate and Canola Protein Isolate.

| Sample | Moisture (%) | Protein (%, dwb$^a$) | Ash (%, dwb$^a$) | Oil (%, dwb$^a$) | Crude Fiber (%, dwb$^a$) |
|---|---|---|---|---|---|
| Canola Seed | 8.12 | 27.0 | 4.56 | 44.39 | 4.75 |
| Canola Seed Press cake | 10.33 | 42.0 | 7.02 | 12.58 | 7.00 |
| Defatted Meal | 6.86 | 47.0 | 8.12 | 1.38 | 7.75 |
| Protein Enriched Meal | 6.71 | 52.0 | 8.34 | 0.84 | 5.53 |
| Fiber Enriched Meal | 6.91 | 43.6 | 7.88 | 1.29 | 9.00 |
| Protein Concentrate | 6.14 | 70.6 | 10.5 | 0.11 | 4.88 |
| Hydrolyzed Protein Concentrate | 6.44 | 88.8 | 5.98 | 0.24 | 0.00 |
| Protein Isolate | 3.90 | 92.8 | 3.54 | 0.04 | 0.00 |

$^a$dwb = dry weight basis

TABLE 27

Results of Proximate Analysis on Samples for Production of Protein Concentrate Having About 70% Protein

| Sample | Solids (%) | Moisture (%) | Protein (%, dwb) | Ash (%, dwb) | Oil (%, dwb) | Crude Fiber (%, dwb) |
|---|---|---|---|---|---|---|
| Bird Decanter - Canola fiber 1$^{st}$ pass | 15.42 | 4.19 | 47.5 | 8.42 | 0.66 | 10.2 |
| Bird Decanter - Washed Canola fiber 2$^{nd}$ pass | 15.33 | 4.81 | 45.4 | — | 0.69 | 12.7 |
| Bird Decanter - Protein slurry after fiber removal | 8.26 | 10.3 | 52.4 | 10.16 | 0.06 | 3.20 |
| Bird Decanter - Protein slurry after fiber removal 2$^{nd}$ pass | 4.80 | 7.37 | 49.6 | 9.61 | 0.42 | 6.52 |
| Westfalia decanter - Protein solids #1 | 19.54 | 7.35 | 52.6 | 10.81 | 0.21 | 6.89 |
| Westfalia decanter - Protein Extract #1 | 3.75 | — | — | 7.29 | — | — |
| Westfalia decanter - Protein solids #2 | 15.74 | 6.59 | 48.4 | 11.49 | 0.14 | 9.92 |
| Westfalia decanter - Protein extract #2 | 1.65 | — | — | — | — | — |
| Disc stack centrifuge - Protein solids | 15.72 | — | — | — | — | — |
| Disc stack centrifuge - Clarified protein extract | 2.61 | — | — | — | — | — |
| Permeate - Ultrafiltration | 1.14 | — | — | — | — | — |
| Permeate - Diafiltration | 0.19 | | | | | |
| Protein retentate - Ultrafiltration (UF) | 13.17 | 6.90 | 90.4 | 2.14 | 0.12 | 0.00 |
| Protein retentate - Diafiltration (DF) | 3.40 | 1.34 | 92.4 | 2.65 | 0.01 | 0.03 |
| Protein isolate solution - UF and DF | 5.50 | — | — | — | — | — |
| Westfalia decanter - hydrolyzed protein extract 1 | 2.27 | — | 75.0 | — | — | — |
| Westfalia decanter - canola fiber solids #1 | 12.98 | 5.89 | 27.8 | 18.1 | 2.53 | 14.5 |
| Westfalia decanter - hydrolyzed protein extract 2 | 1.12 | — | 58.5 | — | — | — |
| Westfalia decanter - canola fiber solids - 2$^{nd}$ centrifuge | 11.74 | 5.84 | 19.6 | 18.8 | 2.28 | 21.4 |

TABLE 28

Amino Acid Profiles of Protein Concentrate, Hydrolyzed Protein Concentrate and Protein Isolate on a Dry Weight Basis

| Amino Acid | Protein Concentrate | Hydrolyzed Protein Concentrate | Protein Isolate |
|---|---|---|---|
| Aspartic Acid (%, dwb[a]) | 4.84 | 7.05 | 7.91 |
| Glutamic Acid (%, dwb[a]) | 12.25 | 15.71 | 17.48 |
| Serine (%, dwb[a]) | 3.61 | 4.63 | 4.45 |
| Glycine (%, dwb[a]) | 3.82 | 4.58 | 5.13 |
| Histidine (%, dwb[a]) | 1.71 | 2.20 | 2.19 |
| Arginine (%, dwb[a]) | 5.79 | 7.41 | 6.92 |
| Threonine (%, dwb[a]) | 3.18 | 4.35 | 3.74 |
| Alanine (%, dwb[a]) | 3.48 | 4.90 | 4.56 |
| Proline (%, dwb[a]) | 4.07 | 5.70 | 5.22 |
| Tyrosine (%, dwb[a]) | 2.77 | 5.10 | 3.28 |
| Valine (%, dwb[a]) | 3.79 | 4.77 | 4.95 |
| Methionine (%, dwb[a]) | 1.40 | 1.75 | 2.02 |
| Cystine (%, dwb[a]) | 1.17 | 1.46 | 1.55 |
| Isoleucine (%, dwb[a]) | 3.18 | 4.75 | 4.06 |
| Leucine (%, dwb[a]) | 5.76 | 6.38 | 7.36 |
| Phenylalanine (%, dwb) | 3.34 | 3.62 | 4.23 |
| Lysine (%, dwb[a]) | 3.77 | 5.55 | 4.10 |
| Tryptophan (%, dwb[a]) | 1.02 | 1.09 | 1.38 |
| Total Amino Acid (%, dwb[a]) | 68.95 | 91.00 | 90.53 |

[a]dwb = dry weight basis

TABLE 29

Amino Acid Profiles of Canola Protein Concentrate, Hydrolyzed Canola Protein Concentrate, Canola Protein Isolate, Soy Protein Isolate and Pea Protein Isolate on a Normalized Basis of Pure Protein

| Amino Acid | Canola Protein Concentrate | Hydrolyzed Canola Protein Concentrate | Canola Protein Isolate | Soy Protein Isolate | Pea Protein Isolate |
|---|---|---|---|---|---|
| Aspartic Acid (%) | 7.02 | 7.75 | 8.74 | 11.5 | 11.78 |
| Glutamic Acid (%) | 17.77 | 17.26 | 19.31 | 19.0 | 19.13 |
| Serine (%) | 5.24 | 5.09 | 4.92 | 5.2 | 5.28 |
| Glycine (%) | 5.54 | 5.03 | 5.67 | 4.1 | 3.86 |
| Histidine[a] (%) | 2.48 | 2.42 | 2.42 | 2.6 | 2.55 |
| Arginine (%) | 8.40 | 8.14 | 7.64 | 7.5 | 8.58 |
| Threonine[a] (%) | 4.61 | 4.78 | 4.13 | 3.8 | 3.68 |
| Alanine (%) | 5.05 | 5.39 | 5.04 | 4.2 | 4.15 |
| Proline (%) | 5.90 | 6.26 | 5.77 | 5.1 | 4.15 |
| Tyrosine (%) | 4.02 | 5.60 | 3.62 | 3.8 | 3.68 |
| Valine[a] (%) | 5.50 | 5.24 | 5.47 | 5.0 | 4.90 |
| Methionine[a] (%) | 2.03 | 1.92 | 2.23 | 1.3 | 1.13 |
| Cystine (%) | 1.70 | 1.60 | 1.71 | 1.3 | 1.04 |
| Isoleucine[a] (%) | 4.61 | 5.22 | 4.49 | 4.8 | 4.43 |
| Leucine[a] (%) | 8.35 | 7.01 | 8.13 | 8.1 | 8.20 |
| Phenylalanine[a] (%) | 4.84 | 3.98 | 4.67 | 5.2 | 5.29 |
| Lysine[a] (%) | 5.47 | 6.10 | 4.53 | 6.2 | 7.26 |
| Tryptophan[a] (%) | 1.49 | 1.20 | 1.52 | 1.3 | 0.94 |
| Total Amino Acid (%) | 100 | 100 | 100 | 100 | 100 |

[a]Nine essential amino acids.

TABLE 30

Essential Amino Acid Profiles of Canola Protein Concentrate, Hydrolyzed Canola Protein Concentrate, Canola Protein Isolate, Soy Protein Isolate and Pea Protein Isolate and Their Functions on Human Nutrition

| Amino Acid | Canola Protein Concentrate | Hydrolyzed Canola Protein Concentrate | Canola Protein Isolate | Soy Protein Isolate | Pea Protein Isolate | Specific Benefit and Impact on Human Nutrition |
|---|---|---|---|---|---|---|
| Histidine (%) | 2.48 | 2.42 | 2.42 | 2.6 | 2.55 | — |
| Threonine (%) | 4.61 | 4.78 | 4.13 | 3.8 | 3.68 | Brain Activity |
| Valine[a] (%) | 5.50 | 5.24 | 5.47 | 5.0 | 4.90 | Muscle Mass |
| Methionine (%) | 2.03 | 1.92 | 2.23 | 1.3 | 1.13 | Muscle Building, Antioxidant and Development of Appendages |
| Isoleucine (%) | 4.61 | 5.22 | 4.49 | 4.8 | 4.43 | Muscle Mass |
| Leucine (%) | 8.35 | 7.01 | 8.13 | 8.1 | 8.20 | Muscle Mass |
| Phenylalanine (%) | 4.84 | 3.98 | 4.67 | 5.2 | 5.29 | — |
| Lysine (%) | 5.47 | 6.10 | 4.53 | 6.2 | 7.26 | Growth |
| Tryptophan (%) | 1.49 | 1.20 | 1.52 | 1.3 | 0.94 | Sleep Aid and Anti-depression |

TABLE 31

Functional Properties of Canola Protein Isolate as Compared to Soy and Pea Protein Isolates

| Sample | Concentration of Protein Isolate (%, w/w) | Emulsifying Capacity at pH7 (%) | Emulsion Stability at pH7 (%) | Foaming Capacity at pH7 (%) | Foam Stability at pH7 (%) |
|---|---|---|---|---|---|
| Canola Protein Isolate | 0.5 | 58 | 55 | 352 | 18.5 |
|  | 1.0 | 66 | 60 | 389 | 26 |
| Soy Protein Isolate | 0.5 | 59 | 57 | 108 | 4.9 |
|  | 1.0 | 64 | 60 | 478 | 21 |
| Pea Protein Isolate | 0.5 | 57 | 52 | 24.4 | 7 |
|  | 1.0 | 62 | 58 | 202 | 7 |

TABLE 32

Functional Properties of Canola Protein Isolate

| Functional Property | Results and Comments |
|---|---|
| Emulsifying Capacity | Emulsifying capacity of 0.5% canola protein isolate solution was high, comparable to that of 5% native egg yolk. |

| Oil Content of Emulsion | Emulsion of Canola Protein Isolate |
|---|---|
| 50.0 | Stable |
| 60.0 | Stable |
| 70.0 | Stable |
| 72.5 | Stable |
| 75.0 | Stable |
| 77.5 | Instable |

Figure 36:
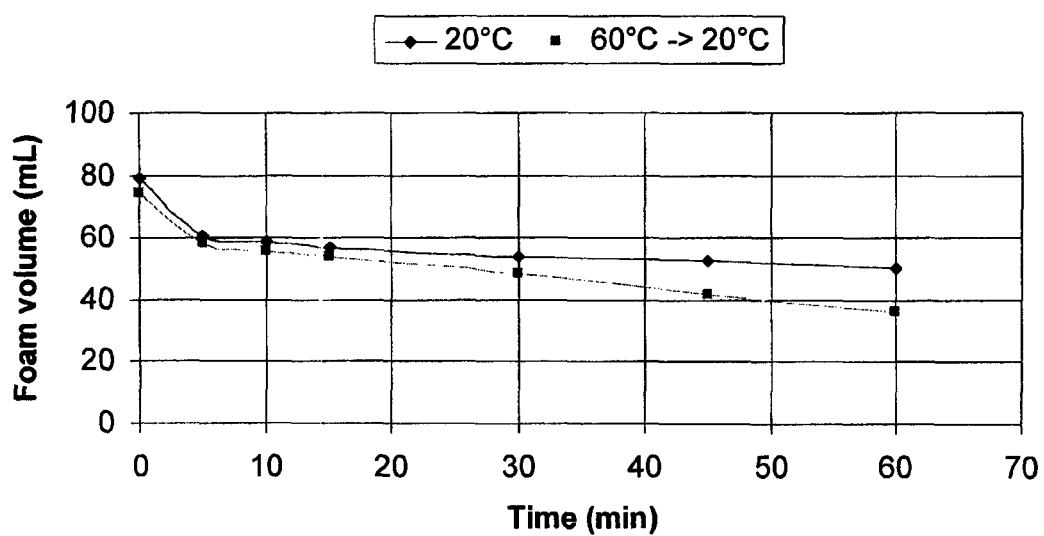
FIG. 36 is a graph showing the foam volume of a protein isolate produced in accordance with a process of the present disclosure.

| Functional Property | Results and Comments |
|---|---|
| Foaming and Foam Stability | Foaming properties of canola protein isolate were superior in comparison to whey protein isolate as shown in FIG. 36. |

| Time (min) | Foam Volume (mL) Whipping at 20° C. for 1 minute | Foam Volume (mL) Heated at 60° for 15 minutes and then cooled to 20° C., finally whipping at 20° C. for 1 minute |
|---|---|---|
| 0 | 80 | 75 |
| 5 | 61 | 59 |
| 10 | 60 | 58 |
| 15 | 58 | 56 |
| 30 | 53 | 50 |
| 45 | 52 | 42 |
| 60 | 50 | 38 |

Figure 37:
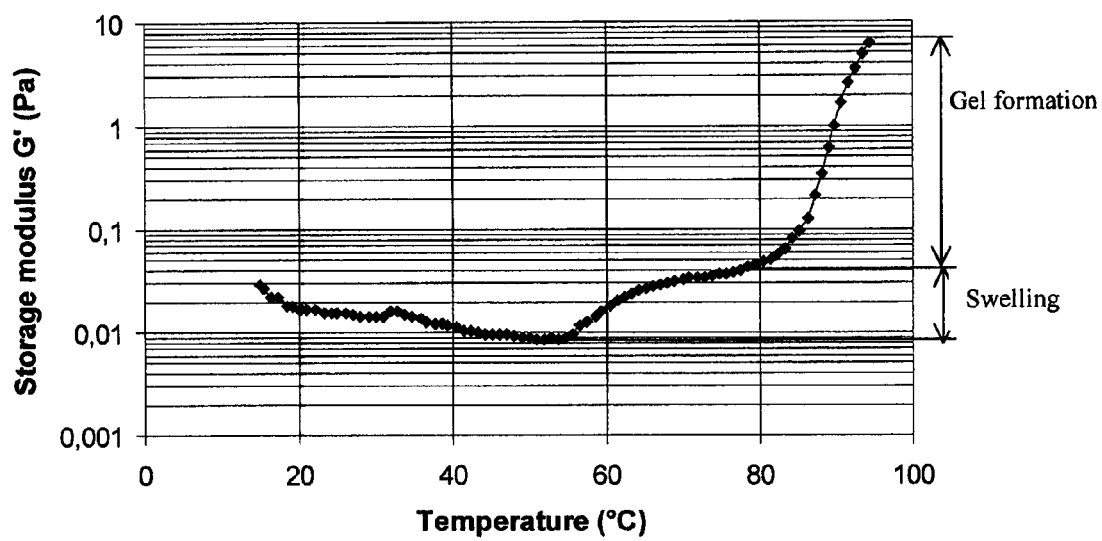
FIG. 37 is a graph showing the gel forming temperature of a protein isolate produced in accordance with a process of the present disclosure.
Figure 38:
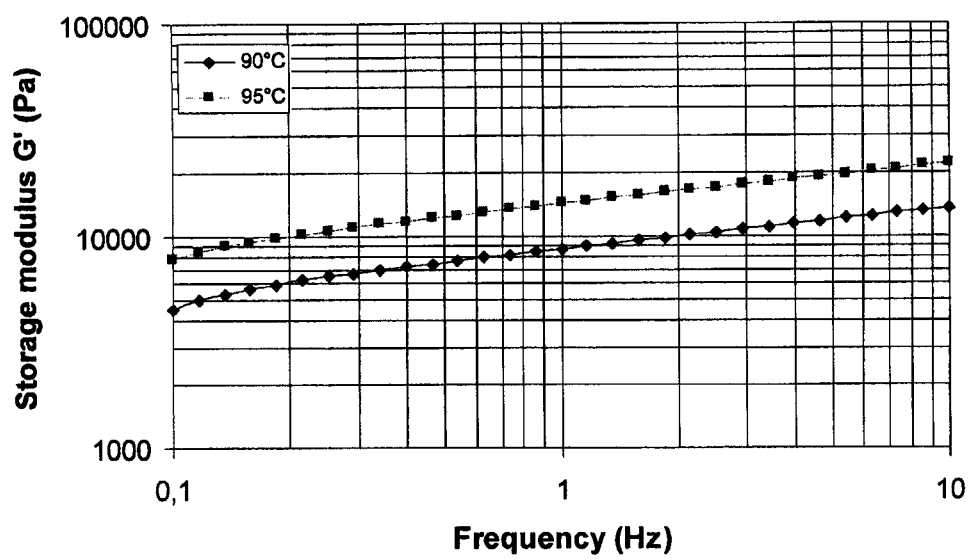
FIG. 38 is a graph showing the oscillation tests of gels of a protein isolate produced in accordance with a process of the present disclosure.
Figure 39:
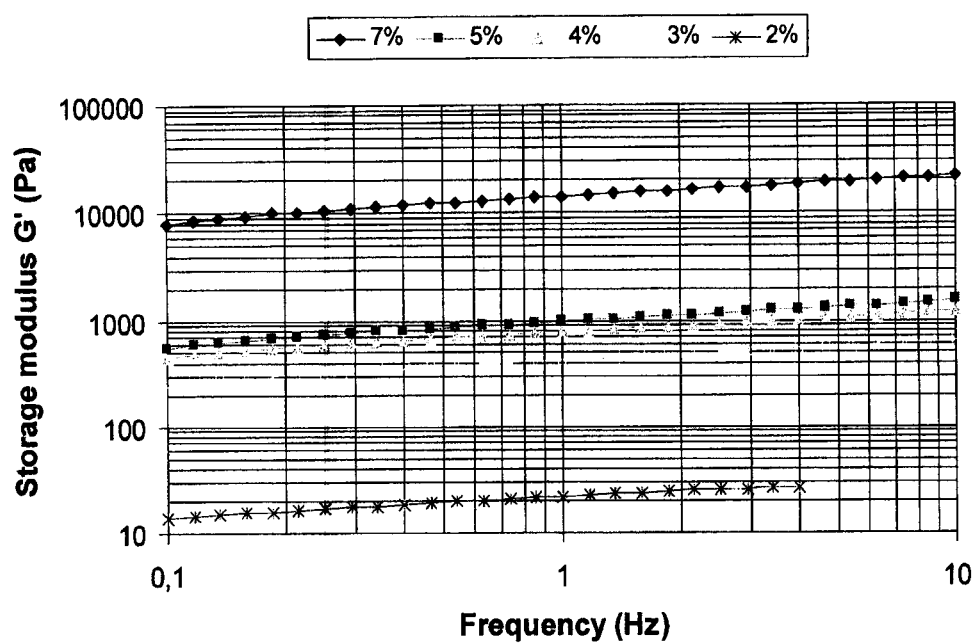
FIG. 39 is a graph showing the oscillation test of gels of different concentrations of a protein isolate produced in accordance with a process of the present disclosure.

| Functional Property | Results and Comments |
|---|---|
| Gel Formation and Gel Strength | Canola protein isolate required higher temperature for gel formation in comparison to whey protein isolate, as shown in FIGS. 37 and 38. Gel firmness of canola protein isolate was comparable to that of whey protein isolate and soy protein isolate gels at 5% protein content. For canola protein isolate, gels with 7% protein content were strong, gels with 3-5% content possessed a medium scaled strength, and gels with 2% protein content were very weak, as shown in FIG. 39. |
| Water Immobilization | Water immobilization of canola protein isolate gels was slightly lower than that of whey protein isolate gels. |

TABLE 33

Results of Solubility Tests on Canola, Pea and Soy Protein Isolate

| Test Method | Solubility Borate-phosphate buffer (12.20 g/L of $NaH_2PO_4 \cdot H_2O$ and 8.91 g/L of $Na_2B_4O_7 \cdot 10H_2O$) 1% concentration pH 6.7 39° C. 1 hour |
|---|---|
| Solubility of Canola Protein Isolate (%, w/w) (Obtained from Example 5(b)) | 99.81 |
| Solubility of Pea Protein Isolate (%, w/w) | 18.85 |
| Solubility of Soy Protein Isolate (%, w/w) | 25.21 |

TABLE 34

Anti-nutritional Factors of Canola Protein Isolate

| Anti-nutritional Factors | Content |
|---|---|
| Total Glucosinolate | 0.200 μmol/g |
| Erucic Acid | 0.1% of total fat (1.7% total fat) |
| Phytic Acid | <0.05% |
| Phytic Bounded Phosphorus | <0.01% |
| Allyl Isothiocyanate | <0.02% |

TABLE 35

Glucosinolates in *Juncea* Seed, Press Cake. BioExx Extracted Meal, Protein Enriched meal, Fiber Enriched Meal, Protein Concentrate, Hydrolyzed Protein Concentrate, and Protein Isolate

| Glucosinolates | *Juncea* Seed | Press Cake | BioExx Extracted Meal | Protein Enriched Meal |
|---|---|---|---|---|
| Allyl (μmoles/g) | 0.12 | 0.21 | 0.25 | 0.26 |
| 3-butenyl (μmoles/g) | 6.69 | 10.34 | 12.23 | 14.71 |
| 4-pentenyl (μmoles/g) | 0.46 | 0.72 | 0.85 | 0.99 |
| 2-OH-3-butenyl (μmoles/g) | 0.76 | 1.18 | 1.40 | 1.58 |
| CH3-thiobutenyl (μmoles/g) | 0 | 0.05 | 0.05 | 0.05 |
| Phenylethyl (μmoles/g) | 0.17 | 0.27 | 0.32 | 0.37 |
| 3-CH3-indolyl (μmoles/g) | 0.48 | 0.81 | 0.91 | 1.01 |
| 4-OH-3-CH3-indolyl (μmoles/g) | 2.11 | 2.95 | 3.56 | 4.20 |
| Total Aliphatics (μmoles/g) | 7.92 | 12.26 | 14.51 | 17.31 |

| Glucosinolates | Fiber Enriched Meal | Canola Protein Concentrate | Hydrolyzed Protein Concentrate | Canola Protein Isolate |
|---|---|---|---|---|
| Allyl (μmoles/g) | 0.21 | 0 | 0 | 0 |
| 3-butenyl (μmoles/g) | 12.64 | 0.11 | 0.23 | 0.17-0.41 |

TABLE 35-continued

Glucosinolates in *Juncea* Seed, Press Cake. BioExx Extracted Meal, Protein Enriched meal, Fiber Enriched Meal, Protein Concentrate, Hydrolyzed Protein Concentrate, and Protein Isolate

| | | | | |
|---|---|---|---|---|
| 4-pentenyl (µmoles/g) | 0.86 | 0 | 0 | 0 |
| 2-OH-3-butenyl (µmoles/g) | 1.53 | 0 | 0 | 0 |
| CH3-thiobutenyl (µmoles/g) | 0 | 0 | 0 | 0 |
| Phenylethyl (µmoles/g) | 0.33 | 0 | 0 | 0 |
| 3-CH3-indolyl (µmoles/g) | 0.91 | 0 | 0 | 0 |
| 4-OH-3-CH3-indolyl (µmoles/g) | 3.26 | 0 | 0 | 0 |
| Total Aliphatics (µmoles/g) | 15.05 | 0.11 | 0.23 | 0.17-0.41 |

TABLE 36

Results of Proximate Analysis for Defatted *Juncea* Meal, Protein Enriched Meal, Fiber Enriched Meal, Protein Concentrate and Hydrolyzed Canola Protein Concentrate

| Sample | Moisture (%) | Protein (%, dwb[a]) | Ash (%, dwb[a]) | Oil (%, dwb[a]) | Crude Fiber (%, dwb[a]) |
|---|---|---|---|---|---|
| Defatted *Juncea* Meal | 6.43 | 48.0 | 7.50 | 2.15 | 7.75 |
| Protein Enriched Meal | 5.92 | 51.5 | 7.71 | 1.23 | 5.48 |
| Fiber Enriched Meal | 6.12 | 45.0 | 7.42 | 2.33 | 8.86 |
| Protein Concentrate | 7.83 | 68.2 | 8.56 | 0.10 | 5.71 |
| Hydrolyzed Protein Concentrate | 8.69 | 82.0 | 5.84 | 0.11 | 0.12 |

[a] dwb = dry weight basis

TABLE 37

Results of Proximate Analysis of Ethanol Washed Protein Solids

| Sample | Solids (%) | Protein (%, dwb[a]) | Ash (%, dwb[a]) | Oil (%, dwb[a]) | Crude Fiber (%, dwb[a]) |
|---|---|---|---|---|---|
| Ethanol Washed Protein Solids #1 | 14.07 | 61.4 | 8.26 | 0.74 | 5.53 |
| Ethanol Washed Protein Solids #2 | 19.22 | 66.3 | 8.43 | 0.53 | 5.81 |
| Ethanol Washed Protein Solids #3 | 19.39 | 67.8 | 8.38 | 0.41 | 5.97 |
| Protein Concentrate | 92.17 | 68.2 | 8.56 | 0.10 | 5.71 |

[a] dwb = dry weight basis

TABLE 38

Protein Recovery Yield Through Protein Hydrolysis and Membrane Purification

| Sample | Weight (kg) | Solid Content (%) | Protein (%, dwb) | Protein Weight (kg, dwb) |
|---|---|---|---|---|
| Insoluble Fiber Solids | 126.3 | 13.91 | 46.0 | 8.08 |
| Soluble Hydrolyzed Protein Extract | 328 | 2.59 | 84.0 | 7.14 |
| Hydrolyzed Protein Retentate from UF | 47.7 | 1.36 | 39.8 | 0.26 |
| Hydrolyzed Protein Permeate | 540 | — | — | 6.88 |

TABLE 39

Results of Absorbance and Transmittance for Hydrolyzed Canola Protein concentrate, Soy and Pea Protein Isolate Solutions at 720 nm Wavelength

| Sample | Absorbance | Transmittance | Percent Transmittance |
|---|---|---|---|
| 1% Hydrolyzed Protein Concentrate Solution | 0.014 | 0.97 | 97 |
| 3% Hydrolyzed Protein Concentrate Solution | 0.053 | 0.89 | 89 |
| 5% Hydrolyzed Protein Concentrate Solution | 0.063 | 0.87 | 87 |
| 1% Soy Protein Isolate Solution | >3.8 | <0.00016 | <0.016 |
| 1% Pea Protein Isolate Solution | >3.8 | <0.00016 | <0.016 |

TABLE 40

Mass Balance Data for Crushing and Extraction of Regular and *Juncea* Canola Seeds

| 10 kg of Regular Canola Seed (*B. napus*) | 499 kg of *Juncea* Seed (*B. juncea*) |
|---|---|
| 6.32 kg of Press Cake | 278.9 kg of Press Cake |
| 3.26 kg of Press Oil | 138.1 kg of Press Oil |
| 5.02 kg of Defatted Meal | 8.23 kg of Defatted Meal from 10 kg of Press Cake |
| 1.76 kg of Protein Enriched Meal from 4.01 kg of Defatted Meal | 1.53 kg of Protein Enriched Meal from 3.52 kg of Defatted Meal |
| 2.24 kg of Fiber Enriched Meal from 4.01 kg of Defatted Meal | 1.84 kg of Fiber Enriched Meal from 3.52 kg of Defatted Meal |

TABLE 41

Mass Balance Data for the Wet Fiber Separation to Remove Fiber and Prepare Canola Protein Concentrates

| Regular Canola Protein Slurry (*B. napus*) | *Juncea* Protein Slurry (*B. juncea*) |
|---|---|
| 0.75 kg of Protein Enriched Meal | 1 kg of Protein Enriched Meal |
| 6 kg of Water | 8 kg of Water |
| 1.708 kg of Total Insoluble Wet Solids | 2.282 kg of Total Insoluble Wet Solids |
| 0.347 kg of Wet Fiber Solids | 0.431 kg of Wet Fiber Solids |
| 19.13 kg of Sugar Extract | 27.32 kg of Sugar Extract |
| 0.418 kg of Dried Protein Concentrate | 0.544 kg of Dried Protein Concentrate |

TABLE 42

Results of Proximate Analysis for Regular and *Juncea* Defatted Meals, and Protein and Fiber Enriched Meals

| Sample | Moisture (%) | Protein (%, dwb[a]) | Crude Oil (%, dwb[a]) | Ash (%, dwb[a]) | Crude Fiber (%, dwb[a]) |
|---|---|---|---|---|---|
| Defatted Regular Canola Meal | 7.11 | 46.8 | 1.04 | 7.35 | 9.90 |
| Defatted *Juncea* Meal | 7.18 | 48.7 | 0.87 | 7.48 | 7.44 |
| Protein Enriched Regular Canola Meal | 6.77 | 51.5 | 0.51 | 7.52 | 7.09 |
| Protein Enriched *Juncea* Meal | 6.54 | 52.8 | 0.34 | 7.55 | 5.36 |
| Fiber Enriched Regular Canola Meal | 7.03 | 43.9 | 1.61 | 7.09 | 13.3 |
| Fiber Enriched *Juncea* Meal | 6.73 | 45.6 | 1.06 | 7.12 | 9.71 |

[a]dwb = dry weight basis

TABLE 43

Results of Proximate Analysis for Regular and *Juncea* Protein Concentrates and Fiber Fraction from Wet Separation Process

| Sample | Moisture (%) | Protein (%, dwb[a]) | Crude Oil (%, dwb[a]) | Ash (%, dwb[a]) | Crude Fiber (%, dwb[a]) |
|---|---|---|---|---|---|
| Regular Canola Protein Concentrate | 5.26 | 66.9 | 0.21 | 7.83 | 7.30 |
| *Juncea* Canola Protein Concentrate | 3.90 | 71.2 | 0.13 | 7.99 | 5.96 |
| Regular Canola Fiber Fraction | 6.74 | 36.3 | 1.52 | 5.83 | 21.6 |
| *Juncea* Fiber Fraction | 5.68 | 48.2 | 1.41 | 7.91 | 11.49 |

[a]dwb = dry weight basis

TABLE 44

Amino Acid Profiles of Canola Protein Concentrates and Methyl Pentane Defatted Regular Canola and *Juncea* Meals on a Normalized Basis of Pure Protein.

| Amino Acid | Defatted Regular Canola Meal (*B. napus*) | Defatted *Juncea* Meal (*B. juncea*) | Regular Canola Protein Concentrate | *Juncea* Protein Concentrate |
|---|---|---|---|---|
| Aspartic Acid (%) | 6.86 | 7.55 | 6.75 | 7.17 |
| Glutamic Acid (%) | 18.93 | 19.00 | 19.27 | 18.78 |
| Serine (%) | 5.03 | 5.15 | 4.95 | 4.95 |
| Glycine (%) | 5.45 | 5.48 | 5.40 | 5.41 |
| Histidine[a] (%) | 2.77 | 2.21 | 2.39 | 2.39 |
| Arginine (%) | 7.78 | 7.71 | 7.29 | 8.22 |
| Threonine[a] (%) | 3.86 | 4.24 | 3.89 | 4.10 |
| Alanine (%) | 4.90 | 5.00 | 4.81 | 4.88 |
| Proline (%) | 7.15 | 6.47 | 6.80 | 6.27 |
| Tyrosine (%) | 3.62 | 3.66 | 3.79 | 3.96 |
| Valine[a] (%) | 5.45 | 5.30 | 5.28 | 5.22 |
| Methionine[a] (%) | 2.24 | 2.04 | 2.34 | 2.11 |
| Cystine (%) | 2.64 | 2.32 | 2.30 | 2.11 |
| Isoleucine[a] (%) | 3.88 | 4.18 | 3.96 | 4.08 |
| Leucine[a] (%) | 7.34 | 7.66 | 7.68 | 7.91 |
| Phenylalanine[a] (%) | 4.25 | 4.50 | 4.55 | 4.65 |
| Lysine[a] (%) | 6.73 | 6.26 | 6.96 | 6.27 |
| Tryptophan[a] (%) | 1.05 | 1.41 | 1.45 | 1.54 |
| Total Amino Acid (%) | 100 | 100 | 100 | 100 |

[a]Nine essential amino acids.

TABLE 45

Results of Solubility Test on Defatted Canola Meals, Protein Concentrates, and Commercial Samples of Soy and Pea Protein Isolates

| Test Method | Borate-phosphate buffer (12.20 g/L of $NaH_2PO_4 \cdot H_2O$ and 8.91 g/L of $Na_2B_4O_7 \cdot 10H_2O$), 1% concentration, pH 6.7, 39° C., 1 hour |
|---|---|
| Protein Solubility of Defatted Regular Canola Meal (*B. napus*) (%, w/w) | 31.48 |
| Protein Solubility of Defatted *Juncea* Meal (*B. juncea*) (%, w/w) | 30.36 |
| Protein Solubility of Regular Canola Protein Concentrate (%, w/w) | 36.76 |
| Protein Solubility of *Juncea* Protein Concentrate (%, w/w) | 32.27 |
| Protein Solubility of Commercial Soy Protein Isolate (%, w/w) | 22.90 |
| Protein Solubility of Commercial Pea Protein Isolate (%, w/w) | 15.93 |

TABLE 46

Results of Anti-nutritional Factors.

| Sample | Sinapine (%) | Betain (%) | Choline (%) | Phytate (IP5 & IP6) (%, as is) |
|---|---|---|---|---|
| Defatted Regular Canola Meal (*B. napus*) | 0.188 | 0.592 | 0.252 | 3.35 |
| Defatted *Juncea* Meal (*B. juncea*) | 0.784 | 0.385 | 0.214 | 3.24 |
| Regular Canola Protein Concentrate | 0.073 | 0.003 | 0.003 | 4.46 |
| *Juncea* Protein Concentrate | 0.050 | 0.001 | 0.004 | 4.67 |
| *Juncea* Protein Isolate | 0.105 | 0.004 | 0.051 | 1.01 |
| Soy Protein Isolate | 0.063 | 0.002 | 0.047 | 2.14 |
| Pea Protein Isolate | 0.058 | 0.004 | 0.010 | 2.43 |

TABLE 47

Results of Proximate Analysis for Defatted *Juncea* Meal and Protein Concentrate

| Sample | Moisture (%) | Protein (%, dwb$^a$) | Ash (%, dwb$^a$) | Oil (%, dwb$^a$) | Crude Fiber (%, dwb$^a$) |
|---|---|---|---|---|---|
| Defatted *Juncea* Meal | 6.43 | 48.0 | 7.50 | 2.15 | 7.75 |
| Canola Protein Concentrate | 5.02 | 73.3 | 9.44 | 0.51 | 3.78 |

$^a$dwb = dry weight basis

TABLE 48

Results of Proximate Analysis for Canola Protein Slurries Containing Soluble and Insoluble Proteins, Canola Fiber Solids, Washed Canola Fiber Solids and Insoluble Protein Solids

| Sample | Solids (%) | Protein (%, dwb$^a$) | Ash (%, dwb$^a$) | Oil (%, dwb$^a$) | Crude Fiber (%, dwb$^a$) |
|---|---|---|---|---|---|
| Insoluble Protein Solids and Soluble Protein Extract #1A | 6.31 | 52.6 | 8.84 | 0.61 | 1.38 |
| Insoluble Protein Solids and Soluble Protein Extract #2A | 8.81 | 55.4 | 9.06 | 0.29 | 3.32 |
| Insoluble Protein Solids and Soluble Protein Extract #3A | 9.87 | 55.0 | 8.91 | 0.39 | 1.94 |
| Insoluble Protein Solids and Soluble Protein Extract #4A | 9.63 | 55.5 | 8.71 | 0.39 | 1.44 |
| Insoluble Protein Solids and Soluble Protein Extract #5A | 12.46 | 54.4 | 7.1 | 0.38 | 1.93 |
| Insoluble Protein Solids and Soluble Protein Extract #6A | 12.04 | 57.6 | 8.86 | 1.01 | 1.60 |
| Insoluble Fiber Solids #1A | 16.65 | 44.9 | 6.97 | 2.85 | 9.58 |
| Insoluble Fiber Solids #2A | 19.02 | 45.1 | 7.35 | 3.22 | 10.23 |
| Insoluble Fiber Solids #3A | 17.54 | 46.6 | 7.79 | 2.34 | 8.04 |
| Insoluble Fiber Solids #4A | 20.46 | 43.4 | 7.10 | 3.17 | 10.64 |
| Insoluble Fiber Solids #5A | 20.32 | 44.4 | 7.46 | 2.29 | 9.17 |
| Insoluble Fiber Solids #6A | 20.04 | 44.8 | 7.38 | 3.22 | 10.16 |
| Insoluble Protein Solids and Soluble Protein Extract #1B | 1.90 | 49.1 | 12.05 | 0.45 | 0.48 |
| Insoluble Protein Solids and Soluble Protein Extract #2B | 6.12 | 52.9 | 9.14 | 0.46 | 2.00 |
| Insoluble Protein Solids and Soluble Protein Extract #3B | 5.32 | 55.5 | 10.64 | 0.68 | 2.72 |
| Insoluble Protein Solids and Soluble Protein Extract #4B | 6.56 | 50.8 | 9.15 | 0.49 | 1.75 |
| Insoluble Protein Solids and Soluble Protein Extract #5B | 3.94 | 51.2 | 10.0 | 0.19 | 0.19 |
| Insoluble Protein Solids and Soluble Protein Extract #6B | 5.60 | 56.8 | 10.05 | 1.53 | 1.35 |
| Washed Fiber Solids #1B | 17.28 | 43.1 | 5.45 | 3.08 | 14.23 |
| Washed Fiber Solids #2B | 18.34 | 43.0 | 6.01 | 3.52 | 12.93 |
| Washed Fiber Solids #3B | 17.92 | 43.8 | 6.33 | 3.69 | 13.19 |
| Washed Fiber Solids #4B | 18.23 | 41.6 | 6.46 | 3.39 | 14.09 |
| Washed Fiber Solids #5B | 20.71 | 40.9 | 6.20 | 4.26 | 13.97 |
| Washed Fiber Solids #6B | 17.68 | 41.0 | 6.26 | 3.90 | 10.6 |
| Soluble and Insoluble Protein Slurry #1C | 4.34 | 53.4 | 10.0 | 0.60 | 1.57 |
| Soluble and Insoluble Protein Slurry #2C | 6.83 | 53.2 | 9.66 | 0.43 | 2.20 |
| Soluble and Insoluble Protein Slurry #3C | 5.89 | 53.6 | 9.20 | 0.30 | 9.00 |
| Soluble and Insoluble Protein Slurry #4C | 7.97 | 53.4 | 8.98 | 0.29 | 1.17 |
| Soluble and Insoluble Protein Slurry #5C | 9.03 | 53.9 | 8.83 | 0.77 | 2.02 |
| Insoluble Protein Solids #1C | 10.57 | 44.2 | 6.20 | 2.52 | 12.74 |
| Insoluble Protein Solids #2C | 8.49 | 48.2 | 7.56 | 1.63 | 7.08 |
| Insoluble Protein Solids #3C | 8.41 | 49.1 | 7.51 | 1.72 | 6.80 |
| Insoluble Protein Solids #4C | 15.27 | 43.8 | 7.53 | 2.86 | 10.79 |
| Insoluble Protein Solids #5C | 11.39 | 50.0 | 7.65 | 2.19 | 4.98 |

$^a$dwb = dry weight basis

TABLE 49

Results of Proximate Analysis for Ethanol Precipitated and Washed Protein Solids

| Sample | Solids (%) | Protein (%, dwb$^a$) | Ash (%, dwb$^a$) | Oil (%, dwb$^a$) | Crude Fiber (%, dwb$^a$) |
|---|---|---|---|---|---|
| Ethanol Precipitated Protein Solids #1 | 29.66 | 69.3 | 8.90 | 0.76 | 4.76 |
| Ethanol Washed Protein Solids #2 | 30.67 | 70.6 | 9.17 | 0.60 | 4.10 |
| Ethanol Washed Protein Solids #3 | 47.53 | 73.3 | 9.44 | 0.51 | 3.78 |

$^a$dwb = dry weight basis

The invention claimed is:

1. An oilseed protein isolate comprising a protein content of at least 90% (w/w), wherein the protein isolate has a solubility of at least 85% (w/w) and comprises i) a first class of proteins having a molecular weight of about 60 kpa to about 80 kpa, the first class of proteins comprising about 60% to about 90% (w/w) of the oilseed isolate;

ii) a second class of proteins having a molecular weight of about 10 kpa to about 30 kpa, the second class of proteins comprising about 10% to about 30% (w/w) of the oilseed isolate; and iii) a third class of proteins having a molecular weight of less than about 10 kpa, the third class of proteins comprising about 2% to about 10% (w/w) of the oilseed isolate.

2. The oilseed protein isolate according to claim 1, wherein the oilseed protein isolate comprises
  i) a first class of proteins having a molecular weight of about 60 kpa to about 80 kpa, the first class of proteins comprising about 60% to about 70% (w/w) of the oilseed isolate;
  ii) a second class of proteins having a molecular weight of about 10 kpa to about 30 kpa, the second class of proteins comprising about 20% to about 30% (w/w) of the oilseed isolate; and
  iii) a third class of proteins having a molecular weight of less than about 10 kpa, the third class of proteins comprising about 5% to about 10% (w/w) of the oilseed isolate.

3. The oilseed protein isolate according claim 1, wherein the oilseed protein isolate comprises a canola, rapeseed, broccoli seed, mustard seed, flax seed, cotton seed, hemp seed, safflower seed, sesame seed or soybean oilseed protein isolate.

4. The oilseed protein isolate according to claim 1, wherein the oilseed protein isolate comprises a canola oilseed protein isolate.

5. The oilseed protein isolate according to claim 1, wherein the oilseed protein isolate has a threonine content of at least about 4.1% (w/w) and a valine content of at least about 5.1% (w/w).

6. An insoluble protein concentrate derived from the insoluble proteins in an oilseed precursor, said insoluble protein concentrate having a water insoluble protein content of about 65% to about 90% (w/w), wherein the water insoluble protein concentrate has a methionine content of at least 1.90% by weight and a cysteine content of at least 1.60% by weight of the total protein weight.

7. The oilseed protein concentrate according to claim 6, wherein the protein concentrate has a methionine content of at least 1.95% by weight of the total protein weight.

8. The oilseed protein concentrate according to claim 6, wherein the protein concentrate has a cysteine content of at least 1.65% by weight of the total protein weight.

9. The oilseed protein concentrate according to claim 6, wherein the protein concentrate further has a threonine content of at least 4.0% by weight, a valine content of at least 5.1% (w/w) and a leucine content of at least 8.25% (w/w) of the total protein weight.

10. The oilseed protein concentrate according to claim 6, wherein the protein concentrate has a glucosinolate content less than about 1 µmol/g of the total protein concentrate.

11. A process for the production of a protein concentrate and a protein isolate from seed meals selected from the group consisting of canola seed meal and rape seed meal, said seed meals comprising fiber, soluble protein and insoluble protein, comprising the steps of:
  i) mixing the seed meal with a solvent consisting essentially of water to form a mixture;
  ii) adjusting the pH of the mixture to about 7.0 to about 10.0;
  iii) separating the mixture to form a protein slurry substantially free of fiber and a fiber fraction substantially free of protein, wherein separating the mixture comprises centrifuging the mixture at a speed from about 1,000 rpm to about 2,000 rpm, or using gravity sedimentation, a gravity table or a hydrocyclone,
  wherein the protein slurry comprises
    a) substantially only soluble protein and
    b) substantially all of the only insoluble protein; and substantially all of the fiber is in the fiber fraction;
  iv) removing the separated fiber fraction from the mixture;
  v) separating the protein slurry into a soluble protein fraction and an insoluble protein fraction so as to provide, by steps i)-iv) above, three separated fractions comprising the fiber fraction, a soluble protein fraction and an insoluble protein fraction, the soluble protein fraction constituting an isolate and the insoluble protein fraction constituting a concentrate, and
  vi) optionally separating said isolate by membrane filtration to remove residual insoluble fractions from the isolate to form a protein isolate comprising having a greater concentration of the soluble proteins;
  vii) optionally drying the protein concentrate and the isolate.

12. The process according to claim 11, wherein the ratio of seed meal to water is about 1:3 to about 1:30 (w/w).

13. The process according to claim 11, wherein the protein slurry is subjected to centrifugation to separate the insoluble protein fraction from the soluble protein fraction.

14. A process for the production of protein isolate from a seed meal selected from the group consisting of canola meal and rapeseed meal, comprising:
  i) mixing the seed meal with water to form a mixture;
  ii) adjusting the pH of the mixture to about 7.0 to about 10.0;
  iii) subjecting the mixture to centrifuging performed at a speed selected from the range of about 1,000 rpm to about 2,000 rpm, or gravity sedimentation, a gravity table or a hydrocyclone, the operating conditions thereof selected to separate the fiber from the protein in the mixture to form a fiber fraction phase and a protein slurry substantially free of fiber, wherein the first protein slurry comprises
    a) a soluble protein fraction, and
    b) an insoluble protein fraction;
  such that substantially all of the soluble and insoluble protein is in the protein slurry and substantially all of the fiber is in the fiber fraction phase;
  iv) separating the fiber fraction phase from the protein slurry and the protein slurry into an-insoluble-protein fraction and a soluble protein fraction so as to provide, by steps i)-iv), three fractions comprising a fiber fraction, a soluble protein fraction and an insoluble protein fraction;
  v) processing the soluble protein fractions to recover therefrom a clarified soluble protein fraction and a residual solid protein fraction;
  vi) optionally adjusting the pH of the clarified soluble protein fraction to a pH of about 7;
  vii) separating the clarified soluble protein fraction by filtering to remove residual insoluble protein and provide a further clarified soluble protein fraction; and
  viii) optionally drying the further clarified soluble protein fraction.

15. The process according to claim 14, wherein the ratio of the seed meal to the water is about 1:3 to about 1:30 (w/w).

16. The process according to claim 14, wherein processing of the soluble protein fractions comprises centrifuging or filtering to recover therefrom the clarified soluble protein fraction and the residual insoluble protein fraction.

17. The process according to claim 16, wherein the filtering of the clarified soluble protein fraction comprises ultrafiltration.

18. The process according to claim 17, further comprising the step of filtering the clarified soluble protein fraction using a diafiltration apparatus.

19. The process according to claim 14, wherein the protein isolate comprises a protein content of greater than about 90% on a dry weight basis.

20. The oilseed protein concentrate according to claim 6, wherein the protein concentrate comprises less than 5% (w/w) of fiber.

* * * * *

UNITED STATES PATENT AND TRADEMARK OFFICE
CERTIFICATE OF CORRECTION

PATENT NO.         : 8,529,981 B2
APPLICATION NO.    : 12/467227
DATED              : September 10, 2013
INVENTOR(S)        : Qingnong Nelson Tang et al.

It is certified that error appears in the above-identified patent and that said Letters Patent is hereby corrected as shown below:

In the Claims:

Column 98, Claim 1, Line 56: after "about 60" please delete "kpa" and add --kDa-- and after "to about 80" please delete "kpa" and add --kDa--
Column 98, Claim 1, Line 60: after "about 10" please delete "kpa" and add --kDa-- and after "to about 30" please delete "kpa" and add --kDa--
Column 98, Claim 1, Line 65: after "less than about 10" please delete "kpa" and add --kDa--
Column 99, Claim 2, Line 4: after "about 60" please delete "kpa" and add --kDa-- and after "to about 80" please delete "kpa" and add --kDa--
Column 99, Claim 2, Line 8: after "about 10" please delete "kpa" and add --kDa-- and after "to about 30" please delete "kpa" and add --kDa--
Column 99, Claim 2, Line 12: after "less than about 10" please delete "kpa" and add --kDa--
Column 99, Claim 11, Line 65: after "b) substantially" please delete "all of the"
Column 100, Claim 14, Line 32: after "slurry substantially free of fiber, wherein the" please delete "first"

Signed and Sealed this
Twenty-ninth Day of October, 2013

Teresa Stanek Rea
*Deputy Director of the United States Patent and Trademark Office*